US011779584B2

(12) United States Patent
Niyikiza et al.

(10) Patent No.: US 11,779,584 B2
(45) Date of Patent: *Oct. 10, 2023

(54) ALPHA POLYGLUTAMATED PEMETREXED AND USES THEREOF

(71) Applicant: L.E.A.F. HOLDINGS GROUP LLC, Gulph Mills, PA (US)

(72) Inventors: Clet Niyikiza, Gulph Mills, PA (US); Victor Mandla Moyo, Ringoes, NJ (US)

(73) Assignee: L.E.A.F. HOLDINGS GROUP LLC, Gulph Mills, PA (US)

(*) Notice: Subject to any disclaimer, the term of this patent is extended or adjusted under 35 U.S.C. 154(b) by 57 days.

This patent is subject to a terminal disclaimer.

(21) Appl. No.: 16/967,212

(22) PCT Filed: Feb. 7, 2019

(86) PCT No.: PCT/US2019/016989
§ 371 (c)(1),
(2) Date: Aug. 4, 2020

(87) PCT Pub. No.: WO2019/157138
PCT Pub. Date: Aug. 15, 2019

(65) Prior Publication Data
US 2020/0360388 A1   Nov. 19, 2020

Related U.S. Application Data

(60) Provisional application No. 62/764,955, filed on Aug. 17, 2018, provisional application No. 62/764,943, filed on Aug. 17, 2018, provisional application No. 62/702,732, filed on Jul. 24, 2018, provisional application No. 62/702,561, filed on Jul. 24, 2018, provisional application No. 62/662,374, filed on Apr. 25, 2018, provisional application No. 62/630,629, filed on Feb. 14, 2018, provisional application No. 62/627,703, filed on Feb. 7, 2018, provisional application No. 62/627,741, filed on Feb. 7, 2018.

(51) Int. Cl.
| A61K 31/519 | (2006.01) |
| A61K 9/127 | (2006.01) |
| A61K 31/282 | (2006.01) |
| C07K 16/28 | (2006.01) |

(52) U.S. Cl.
CPC .......... *A61K 31/519* (2013.01); *A61K 9/1271* (2013.01); *A61K 31/282* (2013.01); *C07K 16/2818* (2013.01)

(58) Field of Classification Search
CPC .................................................. A61K 31/519
See application file for complete search history.

(56) References Cited

U.S. PATENT DOCUMENTS

| 4,584,375 | A | 4/1986 | Coward |
| 5,268,362 | A | 12/1993 | Akimoto et al. |
| 5,646,253 | A | 7/1997 | Wallace et al. |
| 5,912,251 | A | 6/1999 | Nair |
| 6,569,432 | B1 | 5/2003 | Israeli et al. |
| 7,053,065 | B2 | 5/2006 | Niyikiza et al. |
| 7,399,461 | B2 | 7/2008 | Heston et al. |
| 7,446,120 | B2 | 11/2008 | Gour et al. |
| 7,772,209 | B2 | 8/2010 | Niyikiza et al. |
| 8,466,111 | B2 | 6/2013 | Jansen et al. |
| 8,747,869 | B2 | 6/2014 | Irvine et al. |
| 9,207,238 | B2 | 12/2015 | Ando et al. |
| 9,261,509 | B2 | 2/2016 | Dervieux |
| 9,440,979 | B2 | 9/2016 | Lahiri et al. |
| 11,344,628 | B2* | 5/2022 | Niyikiza ............... A61K 45/06 |
| 11,534,498 | B2 | 12/2022 | Niyikiza et al. |
| 2001/0046533 | A1 | 11/2001 | Bailey et al. |
| 2003/0125302 | A1 | 7/2003 | Lu et al. |
| 2004/0001846 | A1 | 1/2004 | Israeli et al. |
| 2004/0175834 | A1 | 9/2004 | Dervieux et al. |
| 2005/0031679 | A1 | 2/2005 | Unger et al. |
| 2006/0063768 | A1 | 3/2006 | Mueller et al. |
| 2006/0067368 | A1 | 3/2006 | Ballester et al. |
| 2006/0111272 | A1 | 5/2006 | Roberts et al. |
| 2006/0160751 | A1 | 7/2006 | McGuire |
| 2006/0222696 | A1 | 10/2006 | Okada et al. |
| 2007/0116753 | A1 | 5/2007 | Hong et al. |
| 2007/0270431 | A1 | 11/2007 | Tabunoki et al. |

(Continued)

FOREIGN PATENT DOCUMENTS

| CN | 103040748 A | 4/2013 |
| RU | 2423114 C2 | 2/2011 |

(Continued)

OTHER PUBLICATIONS

Schultz, Progress in Drug Research, Birkhäuser Verlag, vol. 63, 2005, 275-303.*
Schwendener, Chapter 9, Liposomes in Biology and Medicine, Chapter 9, 117-128, 2007.*
Pignatello, Drug Delivery, 10:95-100, 2003.*
International Search Report for PCT/US2019/016989 dated Apr. 24, 2019, 4 pages.
Written Opinion of the ISA for PCT/US2019/016989 dated Apr. 24, 2019, 5 pages.
Assaraf, Y. G., et al., "Characterization of the Coexisting Multiple Mechanisms of Methotrexate Resistance in Mouse 3T6 R50 Fibroblasts," J. Biological Chemistry, 267(9):5776-5784 (1992).

(Continued)

*Primary Examiner* — Nizal S Chandrakumar
(74) *Attorney, Agent, or Firm* — Nixon & Vanderhye, PC

(57) ABSTRACT

The disclosure relates generally to alpha polyglutamated pemetrexed, formulations containing liposomes filled with alpha polyglutamated pemetrexed, methods of making the alpha polyglutamated pemetrexed and liposome containing formulations, and methods of using polyglutamated alpha polyglutamated pemetrexed and liposome containing formulations to treat hyperproliferative disorders (e.g., cancer) and disorders of the immune system (e.g., an autoimmune disease such as rheumatoid arthritis).

38 Claims, 18 Drawing Sheets

Specification includes a Sequence Listing.

(56) References Cited

U.S. PATENT DOCUMENTS

| | | |
|---|---|---|
| 2007/0280880 A1 | 12/2007 | Moser et al. |
| 2008/0214585 A1 | 9/2008 | Roberts et al. |
| 2008/0260812 A1 | 10/2008 | Matsuyama et al. |
| 2009/0155345 A1 | 6/2009 | Barenholz et al. |
| 2010/0203539 A1 | 8/2010 | Dervieux |
| 2010/0266709 A1 | 10/2010 | Hicks |
| 2011/0262948 A1 | 10/2011 | Dervieux et al. |
| 2011/0280932 A1 | 11/2011 | Garcia et al. |
| 2012/0077784 A1 | 3/2012 | Whitbourne |
| 2012/0142692 A1 | 6/2012 | Roberts et al. |
| 2013/0122096 A1 | 5/2013 | Shemi et al. |
| 2013/0165654 A1 | 6/2013 | Kadaboina et al. |
| 2013/0177570 A1 | 7/2013 | Low et al. |
| 2013/0259922 A1 | 10/2013 | Haas et al. |
| 2013/0324727 A1 | 12/2013 | Tarnchompoo et al. |
| 2014/0086939 A1 | 3/2014 | Karin et al. |
| 2014/0120157 A1 | 5/2014 | Chang et al. |
| 2015/0239956 A1 | 8/2015 | Koguma et al. |
| 2016/0228573 A1 | 8/2016 | Niyikiza et al. |
| 2018/0236098 A1 | 8/2018 | Niyikiza et al. |
| 2019/0224334 A1 | 7/2019 | Niyikiza et al. |
| 2020/0360388 A1 | 11/2020 | Niyikiza et al. |
| 2021/0038719 A1 | 2/2021 | Niyikiza et al. |
| 2021/0052592 A1 | 2/2021 | Niyikiza et al. |
| 2021/0128469 A1 | 5/2021 | Niyikiza et al. |
| 2021/0154196 A1 | 5/2021 | Niyikiza et al. |
| 2021/0161899 A1 | 6/2021 | Niyikiza et al. |
| 2021/0169887 A1 | 6/2021 | Niyikiza et al. |
| 2021/0220494 A1 | 7/2021 | Bradbury et al. |
| 2021/0338675 A1 | 11/2021 | Niyikiza et al. |
| 2022/0088219 A1 | 3/2022 | Niyikiza et al. |
| 2022/0088220 A1 | 3/2022 | Niyikiza et al. |
| 2022/0279831 A1 | 9/2022 | Perrin et al. |

FOREIGN PATENT DOCUMENTS

| | | | | |
|---|---|---|---|---|
| WO | WO-200002938 A2 | 1/2000 | | |
| WO | WO-2001005405 A1 | 1/2001 | | |
| WO | WO-200195884 A2 | 12/2001 | | |
| WO | WO-2005070465 A2 | 8/2005 | | |
| WO | WO-2005080431 A2 | 9/2005 | | |
| WO | WO-2005089767 A1 | 9/2005 | | |
| WO | WO-2011106528 A2 | 9/2005 | | |
| WO | WO-2006002049 A2 | 1/2006 | | |
| WO | 2006/029385 | 3/2006 | | |
| WO | WO 2006029385 | * | 3/2006 | .......... A61K 31/505 |
| WO | WO-2006029385 A2 | 3/2006 | | |
| WO | WO-2006074416 A1 | 7/2006 | | |
| WO | 2007/023243 | 3/2007 | | |
| WO | WO-2007023243 A2 | 3/2007 | | |
| WO | WO-2007098089 A2 | 8/2007 | | |
| WO | WO-2008030818 A2 | 3/2008 | | |
| WO | WO-2009153575 A1 | 12/2009 | | |
| WO | WO-2011150392 A1 | 12/2011 | | |
| WO | WO-2012037068 A1 | 3/2012 | | |
| WO | WO-2012118806 A1 | 3/2012 | | |
| WO | WO-2012061759 A2 | 5/2012 | | |
| WO | WO-2013008240 A2 | 1/2013 | | |
| WO | WO-2013012722 A1 | 1/2013 | | |
| WO | WO-2014046630 A1 | 3/2014 | | |
| WO | WO-2014186403 A2 | 11/2014 | | |
| WO | WO-2016025882 A2 | 2/2016 | | |
| WO | WO-2018031967 A1 | 2/2018 | | |
| WO | WO-2018031968 A1 | 2/2018 | | |
| WO | WO-2018031979 A1 | 2/2018 | | |
| WO | WO-2018031980 A1 | 2/2018 | | |
| WO | WO-2019094648 A1 | 5/2019 | | |
| WO | WO-2019157120 A1 | 8/2019 | | |
| WO | WO-2019157121 A1 | 8/2019 | | |
| WO | WO-2019157123 A1 | 8/2019 | | |
| WO | WO-2019157125 A1 | 8/2019 | | |
| WO | WO-2019157129 A1 | 8/2019 | | |
| WO | WO-2019157133 A1 | 8/2019 | | |
| WO | WO-2019157138 A1 | 8/2019 | | |
| WO | WO-2019157140 A1 | 8/2019 | | |
| WO | WO-2019157145 A1 | 8/2019 | | |
| WO | WO-2019157146 A1 | 8/2019 | | |
| WO | WO-2019157148 A1 | 8/2019 | | |
| WO | WO-2019160732 A1 | 8/2019 | | |
| WO | WO-2019160733 A1 | 8/2019 | | |
| WO | WO-2019160734 A1 | 8/2019 | | |
| WO | WO-2019160735 A1 | 8/2019 | | |
| WO | WO-2019160736 A1 | 8/2019 | | |
| WO | WO-2021026310 A1 | 2/2021 | | |

OTHER PUBLICATIONS

Banerjee, D., et al., "Molecular mechanisms of resistance to antifolates, a review," Acta Biochim Pol., 42(4):457-464 (1995).

Bertino, J. R., et al., "Resistance Mechanisms to Methotrexate in Tumors," Stem Cells, 14:5-9 (1996).

Bozzuto, G., et al., "Liposomes as nanomedical devices," Intl. J. Nanomed. 10:975-999 (2015).

Bulbake, U., et al., "Liposomal Formulations in Clinical Use: An Updated Review," Pharmaceutics, 9(12):1-33 (2017).

Chabner, B. A., et al., "Polyglutamation of Methotrexate Is Methotrexate a Prodrug?" Journal of Clinical Investigation, 76:907-912 (1985).

Chazal, M., et al., "Decreased Folylpolyglutamate Synthetase Activity in Tumors Resistant to Fluorouracil-Folinic Acid Treatment: Clinical Data," Clinical Cancer Research, 3:553-557 (1997).

Danenberg, P. V., et al., "Folates as adjuvants to anticancer agents: Chemical rationale and mechanism of action," Crit Rev. Oncol. Hematol., 106:118-131. (2016).

Delfino, R. T., et al., "Type 2 Antifolates in the Chemotherapy of falciparum Malaria," J. Braz. Chem. Soc., 13(6):727-741 (2002).

Deshpande, P., et al., "Current trends in the use of liposomes for tumor targeting," Nanomedicine (Lond), 8(9):1-32 (2013).

Desmoulin, S. K., et al., "The human proton-coupled folate transporter," Cancer Biology & Therapy, 13(14):1355-1373; (2012).

Faessel, H. M., et al., "Super in Vitro Synergy between Inhibitors of Dihydrofolate Reductase and Inhibitors of Other Folate-requiring Enzymes: The Critical Role of Polyglutamylation," Cancer Research, 58:3036-3050 (1998).

Fan, Y., et al., "Development of liposomal formulations: From concept to clinical investigations," Asian Journal of Pharmaceutical Sciences, 8(2):81-87 (2013).

Fouladi, F., et al., "Enzyme-Responsive Liposomes for the Delivery of Anticancer Drug," Bioconjug Chem., 19:28(4): 857-868 (2017).

Galivan, J., et al., "+-Fluoromethotrexate: Synthesis and biological activity of a potent inhibitor of dihydrofolate reductase with greatly diminished ability to form poly-y-glutamates," Proc. Natl. Acad. Sci. USA, (82):2598-2602 (1985).

Gonen, N., et al., "Antifolates in cancer therapy: Structure, activity and mechanisms of drug resistance," Drug Resistance Updates, 15:183-210 (2012).

Habeck L. L., et al., "A Novel Class of Monoglutamated Antifolates Exhibits Tight-binding Inhibition of Human Glycinamide Ribonucleotide Formyltransferase and Potent Activity against Solid Tumors," Cancer Research, 54:1021-1026 (1994).

Heath, T.D., et al., "Antibody-directed liposomes Determination of affinity constants for soluble and liposome-bound antifluorescein," Biochimica et Biophysica Acta (BBA)—Biomembranes, 770(2):148-158 (1984).

Jackman, A. L., et al., "Folate-based thymidylate synthase inhibitors as anticancer drugs," Annals of Oncology, 6:871-881 (1995).

Jansen, G., et al., "Folates in rheumatoid arthritis," Pteridines, 24(1): 21-26 (2013).

Kim, S., et al., "Gamma-glutamyl' hydrolase modulation and folate influence chemosensitivity of cancer cells to 5-fluorouracil and methotrexate," British Journal of Cancer, 109:2175-2188 (2013).

Kremer, J.M., "Toward a Better Understanding of Methotrexate," Arthritis and Rheumatism, 50(5):1370-1372 (2004).

Kuehl, M. et al., "Cytotoxicity, Uptake, Polyglutamate Formation, and Antileukemic Effects of 8-Deaza Analogues of Methotrexate and Aminopterin in Mice," Cancer Res. 48:1481-1488 (1988).

Ledermann, J. A., et al., "Targeting the folate receptor: diagnostic and therapeutic approaches to personalize cancer treatments," Annals of Oncology, 26:2034-2043 (2015).

(56) References Cited

OTHER PUBLICATIONS

Li, J., et al., "A review on phospholipids and their main applications in drug delivery systems," Asian Journal of Pharmaceutical Science, 10(2):81-98 (2015).
Lila, A. S., et al., "Liposomal Delivery Systems: Design Optimization and Current Applications," Biol. Pharm. Bull., 40:1-10 (2017).
Matherly, L. H., et al., "The Major Facilitative Folate Transporters Solute Carrier 19A1 and Solute Carrier 46A1: Biology and Role in Antifolate Chemotherapy of Cancer," Drug Metabolism and Disposition, 42:632-649 (2014).
McCloskey, D. E., et al., "Decreased Folylpolyglutamate Synthetase Activity as a Mechanism of Methotrexate Resistance in CCRF-CEM Human Leukemia Sublines," J. Biological Chemistry, 266(10):6181-6187 (1991).
Muhale, F., et al., "Systems pharmacology assessment of the 5-fluorouracil pathway," Pharmacogenomics, 12(3): 341-350 (2011).
Obeid, R., et al., "Is 5-methyltetrahydrofolate an alternative to folic acid for the prevention of neural tube defects?" J. Perinat. Med., 41(5): 469-483 (2013).
Pavlova, N., et al., "The Emerging Hallmarks of Cancer Metabolism," Cell Metab., 12;23(1):27-47 (2016).
Reeve, S. M., et al., "Charged Propargyl-Linked Antifolates Reveal Mechanisms of Antifolate Resistance and Inhibit Trimethoprim-Resistant MRSA Strains Possessing Clinically Relevant Mutations," J. Med. Chem., 59:6493-6500 (2016).
Rhee, M. S., et al., "Acquisition of Resistance to Antifolates Caused by Enhanced y-Glutamyl Hydrolase Activity," Cancer Research, 53:2227-2230 (1993).
Rots, M. G., et al., "Role of Folylpolyglutamate Synthetase and Folylpolyglutamate Hydrolase in Methotrexate Accumulation and Polyglutamylation in Childhood Leukemia," Blood, 93(5):1677-1683 (1999).
Samuels, L.S., et al., "Similar Differential for Total Polyglutamylation and Cytotoxicity among Various Folate Analogues in Human and Murine Tumor Cells in Vitro," Cancer Research, 45:1488-1495 (1985).
Ser, A., et al., "Targeting One Carbon Metabolism with an Antimetabolite Disrupts Pyrimidine Homeostasis and Induces Nucleotide Overflow," Cell Reports, 15(11): P2367-2376 (2016).
Shih, C., et al., "LY231514, a Pyrrolo[2,3-d]pyrimidine-based Antifolate That Inhibits Multiple Folate-requiring Enzymes," Cancer Research, 57:1116-1123 (1997).
Shimamoto, Y., et al., "Association between mRNA expression of chemotherapy-related genes and clinicopathological features in colorectal cancer: A large-scale population analysis," International Journal of Molecular Medicine, 37:319-328 (2016).
Shrestha, H., et al., "Lipid-Based Drug Delivery Systems," Journal of Pharmaceutics, 1-10 (2014).
Stathopoulos, G. P., et al., "Lipoplatin Formulation Review Article," Journal of Drug Delivery, 1-10 (2012).
Torchilin, V, P., "Recent Advances with Liposomes as Pharmaceutical Carriers," Nature Reviews Drug Discovery, 4:145-160 (2005).
Tsukioka, S., et al., "In vivo evidence for a significant role of folylpolyglutamate synthase in combined chemotherapy with oral fluoropyrimidine, UFT or S-1, and leucovorin," Oncology Reports 25:1407-1412 (2011).
Van Triest, B., et al., "Thymidylate Synthase Level as the Main Predictive Parameter for Sensitivity to 5-Fluorouracil, but not for Folate-based Thymidylate Synthase Inhibitors, in 13 Nonselected Colon Cancer Cell Lines," Clinical Cancer Research, 5:643-654 (1999).
Verma, M. S., "1,3-Beta-Glucans: Drug Delivery and Pharmacology," The Complex World of Polysaccharides, Chapter 21:551-572 (2012).
Visentin, M., et al., "The Antifolates," Hematol. Oncol. Clin. North Am., 26(3): 629-ix (2012).
Wagner, A. et al., "Liposome Technology for Industrial Purposes," Journal of Drug Delivery, vol. 2011, Article ID 591325, 9 pages (2011).
Whitehead, V. M., et al., "Accumulation of Methotrexate and Methotrexate Polyglutamates in Lymphoblasts at Diagnosis of Childhood Acute Lymphoblastic Leukemia: A Pilot Prognostic Factor Analysis," Blood, 76(1):44-49 (1990).
Wilson, M. R., et al., "Targeting Nonsquamous Non small Cell Lung Cancer via the Proton-Coupled Folate Transporter with 6-Substituted Pyrrolo [2,3-d]Pyrimidine Thienoyl Antifolates," Mol. Pharmacol., 89:425-434 (2016).
Wojtuszkiewicz, A., et al., "Methotrexate resistance in relation to treatment outcome in childhood acute lymphoblastic leukemia," J. Hematol Oncol., 8:61 (2015).
Molina, et al., "The role of Pemetrexed (Alimta®, LY231514) in Lung Cancer Therapy" Clinical Lung Cancer 5(1):21-27 (2003).
Tomsho, et al., "Concentration-dependent processivity of multiple glutamate ligations catalyzed by foly-poly-gamma-glutamate synthetase," Biochemistry 47(34):9040 (2008).
Tomsho et al., "Synthesis of (6R)- and (6S)-5,10-dideazatetrahydrofolate oligo-γ-glutamates: Kinetics of multiple glutamate ligations catalyzed by folylpoly-γ-glutamate synthetase," Org. Biomol Chem 3(18):3388-98 (2005).
Besson et al., "Effects of tetrahydrofolate polyglutamates on the kinetic parameters of serine hydroxymethyltransferase and glycine decarboxylase from pea leaf mitochondria," Biochem. J. (Pt 2):425 (1993).
Tsushima, T., et al., "Fluorine containing amino acids and their derivatives. 7. Synthesis and antitumor activity of α- and γ-substituted methotrexate analogs," Tetrahedron 44(77):5375 (1988).
Takimoto, C. H., et al., "New Antifolates in Clinical Development." vol. 9, Issue: 7 (1995).
Duch et al., "Biochemical and Cellular Pharmacology of 1843U89, a Novel Benzoquinazoline Inhibitor of Thymidylate Synthase," Cancer Research 53:810-818 (1993).
Matherly et al., "Enhanced Polyglutamylation of Aminopterin Relative to Methotrexate in the Ehrlich Ascites Tumor Cell in Vitro," Cancer Research 45:1073 (1985).
Fry et al., "Rapid formation of poly-v-glutamyl derivatives of methotrexate and their association with dihydrofolate reductase as assessed by high pressure liquid chromatography in the Ehrlich ascites tumor cell in vitro" J. Biol. Chem. 257(4):1980-1986 (1982).
Piper et al., "Syntheses of. alpha .- and. gamma .- substituted amides, peptides, and esters of methotrexate and their evaluation as inhibitors of folate metabolism" J. Med. Chem. 25( 2): 182-187 (1982).
Zwicke et al., "Utilizing the folate receptor for active targeting of cancer nanotherapeutics" Nano Reviews 3(1):18496 (2012).
Springer et al.,"Prodrugs of thymidylate synthase inhibitors potential for antibody directed enzyme prodrug therapy (ADEPT)", Anti-Cancer Drug Design, Oxford University Press, Basingstoke 11(8):625-636 (1996).
Anonymous, "Antifolate—Wikipedia" (Dec. 29, 2020), pp. 1-5, Retrieved from the Internet: URL:https://en.wikipedia.org/wiki/Antifolate [retrieved on Mar. 29, 2021].
Abolmaali et al., A review of therapeutic challenges and achievements of methotrexate delivery systems for treatment of cancer and rheumatoid arthritis Cancer Chemotherapy and Pharmacology 71:1115-1130 (2013).
Jackman et al., "ICI D1694, a Quinazoline Antifolate Thymidylate Synthase Inhibitor That Is a Potent Inhibitor of L1210 Tumor Cell Growth in Vitro and in Vivo: A New Agent for Clinical Study," Cancer Research 51:5579-5586 (1991).
Abraham et al., "Folate analogs. 33. Synthesis of folate and antifolate poly-.gamma.-glutamates by [(9-fluorenylmethoxy)oxy]carbonyl chemistry and biological evaluation of certain methotrexate polyglutamate polylysine conjugates as inhibitors of the growth of H35 hepatoma cells", J. Med. Chem. 33(2):711-717 (1990).
Pawelczak, K., et al., "Quinazoline Antifolates Inhibiting Thymidylate Synthase: Synthesis of Four Oligo(L-γ-glutamyl) Conjugates of N10-Propargyl-5,8-dideazafolic Acid and Their Enzyme Inhibition," J. Med. Chem, 32(1): 160-165 (1989).
Michalak et al., "Synthesis and 42-82 Physicochemical Characterization of the Impurities of Pemetrexed Disodium, an Anticancer Drug", Molecules, 20(6):10004-10031 (2015).

(56) References Cited

OTHER PUBLICATIONS

Meesters et al., "Assessment of intracellular methotrexate and methotrexate-polyglutamate metabolite concentrations in erythrocytes by ultrafast matrix-assisted laser desorption/ionization triple quadrupole tandem mass spectrometry", Rapid Comm. Mass Spec. 25(20):3063-3070 (2011).
Pitts et al., "Interaction energy analyses of folate analog binding to human dihydrofolate reductase: contribution of the antifolate substructural regions to complex stability", Drug Metabol Drug Interact. 16(2):99-121 (2000).
Schultz, R. M., "Preclinical development of Alimta (Pemetrexed, LY231514), a multitargeted antifolate", Progress in Drug Research, vol. 63, pp. 275-300. DOI: https://doi.org/10.1007/3-7643-7414-4_11, published in 2005.
Ng, K-Y. et al., "Liposome-dependent delivery of pteridine antifolates: a two-compartment growth inhibition assay for evaluating drug leakage and metabolism", BBA Biomembranes, vol. 981 (2), pp. 261-268. DOI: https://doi.org/10.1016/0005-2736(89)90036-9, published on Jun. 6, 1989.
Lachelt et al., Synthetic polyglutamylation of dual-functional MTX ligands for enhanced combined cytotoxicity of poly(I:C) nanoplexes, Molecular Pharmaceutics (118): 2631-2639 (2014).
Szabo et al., "Cell-penetrating conjugates of pentaglutamylated methotrexate as potential anticancer drugs against resistant tumor cells" European Journal of Medicinal Chemistry 115:361-368 (2016).
Ando et al."Advanced therapeutic approach for the treatment of malignant pleural mesothelioma via the intrapleural administration of liposomal pemetrexed" Journal of Controlled Release, 220(A): 29-36 (2015).
Khan et al., "Methotrexate: a detailed review on drug delivery and clinical aspects", Expert Opinion on Drug Delivery 9(2) 151-169 (2012).
Chattopadhyay et al., "Pemetrexed: biochemical and cellular pharmacology, mechanisms, and clinical applications", Molecular Cancer Therapeutics 6(2):404-417 (2007).
Schwedener, R., Liposomes in biology and medicine, University of Zurich, vol. 9, pp. 1-36 (2007).
Selim, A., et al., "Liposomal Delivery Systems: Design Optimization and Current Applications," Biol. Pharm. Bull. 40:1-10 (2017).
Shmeeda, H., et al., "Intracellular uptake and intracavitary targeting of folate-conjugated liposomes in a mouse lymphoma model with up-regulated folate receptors," Mol. Cancer Ther., 5(4):818-824 (2006).
Tseng, Y-L, et al., "Translocation of Liposomes into Cancer Cells by CellPenetrating Peptides Penetratin and Tat: A Kinetic and Efficacy Study," Mol. Pharmacol. 62:864-872 (2002).
Lehtinen, J., et al., "Pre-Targeting and Direct Immunotargeting of Liposomal Drug Carriers to Ovarian Carcinoma," PLOS One, 7(7):1-10 (2012).
Li, T., "A novel application of maleimide for advanced drug delivery: in vitro and in vivo evaluation of maleimide-modified pH-sensitive liposomes," Intl J. Nanomed.8:3855-3866 (2013).
Li, Y., "Self-assembly of multifunctional integrated nanoparticles loaded with a methotrexate-phospholipid complex: combining simplicity and efficacy in both targeting and anticancer effects," RSC Ad., 6:86717 (2016).
Paolino et al., "Gemcitabine-loaded PEGylated unilamellar liposomes vs GEMZAR®: Biodistribution, pharmacokinetic features and in vivo antitumor activity," J Controlled Release 144:144-150 (2010).
Pasut, G., et al., "Antitumoral activity of PEG-gemcitabine prodrugs targeted by folic acid," J. Controlled Rel. 127:239-248 (2008).
Varshochian, et al., "Utilizing liposomes and lipid nanoparticles to overcome challenges in breast cancer treatment," Clin. Lipidol. 9(5), 571-585 (2014).
Wibowo, A., et al., "Structures of human folate receptors reveal biological trafficking states and diversity in folate and antifolate recognition," PNAS 110(38):15180-15188 (2013).
Rhee, et al., "Glutamyl hydrolase and the multitargeted antifolate LY231514," Cancer Chemother. Pharmacol.,44:427-432 (1999).
Pignatello et al., "Effect of Liposomal Delivery on In Vitro Antitumor Activity of Lipophilic Conjugates of Methotrexate with Lipoamino Acids" Drug Delivery, 10:95-100 (2003).
Chan et al., Advances in Experimental Medicine and Biology, vol. 620,Biochem. J. (1986) 236, 193-200 (Printed in Great Britain) (2007).
Fiehn C: "The future of methotrexate therapy and other folate inhibitors", Zeitschrift fur Rheumatologie, Springer, DE, vol. 70, No. 2, Jan. 27, 2011 (Jan. 27, 2011), pp. 129-134, XP036030662, ISSN: 0340-1855, DOI: 10.1007/S00393-010-0688-Z.
Alexis F., et al: "Nanoparticle technologies for cancer therapy", Jan. 1, 2010 (Jan. 1, 2010, Drug Delivery in: Handbook of Experimental Pharmacology; vol. 197; pp. 55-86, ISSN 0171-2004; XP008182266.
Allegra et al., "Enhanced Inhibition of Thymidylate Synthase by Methotrexate Polyglutamates," J. Biological Chemistry, 260(17):9720-9726 (1985).
Beutel et al., "Phase I study of OSI-7904L, a novel liposomal thymidylate synthase inhibitor in patients with refractory solid tumors," Clinical Cancer Research 11, 5487-5495 (2005).
Boechat et al., "Methotrexate-loaded lipid-core nanocapsules are highly effective in the control of inflammation in synovial cells and a chronic arthritis model," Intl. J. Nanomed. 10:6603-6614 (2015).
Desjardins et al., "Pharmacokinetics, safety, and efficacy of a liposome encapsulated thymidylate synthase inhibitor, OSI-7904L [(S)-2-[5-[(1,2-dihydro-3-methyl-1-oxobenzo [f] quinazolin-9-yl)methyl]amino-1-oxo-2-isoindolynl]-glutaric acid] in mice," Journal of Pharmacology and Experimental Therapeutics, 309(3):894-902 (2004).
Baggot et al., "Inhibition of 5-aminoimidazole-4-carboxamide ribotide transformylase, adenosine deaminase and 5'-adenylate deaminase by polyglutamates of methotrexate and oxidized folates and by 5-aminoimidazole-4-carboxamide riboside and ribotide," Biochem. J., 236:193-200 (1986).
Jolivet et al., "Synthesis, Retention, and Biological Activity of Methotrexate Polyglutamates in Cultured Human Breast Cancer Cells," The Journal of Clinical Investigation, 70:351-360 (1982).
Tomsho et al., "Deazo analogs and folic acids as antitumor agents," Org. & Molecular Chemistry, 3(18):3388-3398 (2005).
Purcell et al., "Novel antifolate Drugs," Curr. Oncology Reports, Curr. Science, 5(2):114-125 (2003).
Database Biosis [Online] Biosciences Information Service, Philadelphia, PA, US; Jackman A L et al: "ICI D1694, a Quinazoline Antifolate Thymidylate Synthase Inhibitor That Is a Potent Inhibitor of L1210 Tumor Cell Growth in Vitro and in Vivo: A New Agent for Clinical Study", XP002341574, retrieved from BIOSIS Database accession No. PREV199293007206 abstract.
National Center for Biotechnology Information (2020). PubChem Compound Summary for CID 101607589. Retrieved Nov. 22, 2020 from https://pubchem.ncbi.nlm.nih.gov/compound/101607589.
National Center for Biotechnology Information (2020). PubChem Compound Summary for CID 102483590. Retrieved Nov. 22, 2020 from https://pubchem.ncbi.nlm.nih.gov/compound/101607589.
National Center for Biotechnology Information (2020). PubChem Compound Summary for CID 267606. Retrieved Nov. 22, 2020 from https://pubchem.ncbi.nlm.nih.gov/compound/101607589.
Eldin et al., "Liposomal Pemetrexed: Formulation, Characterization and in Vitro Cytotoxicity Studies for Effective Management of Malignant Pleural Mesothelioma," Biol. Pharm. Bull. 38: 461-469 (2015).
Paiardini et al., "Screening and In Vitro Testing of Antifolate Inhibitors of Human Cytosolic Serine Hydroxymethyltransferase," ChemMedChem. 10(3): 490-497 (2015); doi:10.1002/cmdc.201500028.
Piper et al., "Synthesis and antifolate activity of 5-methyl-5, 10-dideaza analogs of aminopterin and folic acid and an alternative synthesis of 5,10-dideazatetrahydrofolic acid, a potent inhibitor of glycinamide ribonucleotide formyltransferase," J. Med. Chem. 31(11):2164-9 (1988);doi: 10.1021/jm00119a018. PMID: 3184124.
Hobl et al., "A short-chain methotrexate polyglutamate as outcome parameter in rheumatoid arthritis patients receiving methotrexate," Clin. Exp. Rheum. 30:156-163 (2012).

(56) References Cited

OTHER PUBLICATIONS

Rosowsky et al., "Synthesis and in Vitro Antifolate Activity of Rotationally Restricted Aminopterin and Methotrexate Analogues," Medicinal Chemistry 47:6958-6963 (2004).

Sakamoto et al., "Folylpolyglutamate synthase and y-glutamyl hydrolase regulate leucovorin-enhanced 5-fluorouracil anticancer activity," Biochem. and Biophys. Res. Comm. 365(4):801-807 (2008), ISSN 0006-291X.

Sulciner et al., "Resolvins suppress tumor growth and enhance cancer therapy," Journal of Experimental Medicine, 215(1):115-1402 (2018).

Heinrich et al., "Comparison of the results obtained by ELISA and surface plasmon resonance for the determination of antibody affinity," Journal of Immunological Methods, 352:13-22 (2010).

Nagai et al., "Production of a High-affinity Monoclonal Antibody Reactive with Folate Receptors Alpha and Beta Monoclonal Antibodies in Immunodiagnosis and Immunotherapy," 34(3):181-190 (2015); doi.org/10.1089/mab.2014.0072.

Nair et al., "Synthesis and biological evaluation of poly-gamma.-glutamyl metabolites of 10-deazaaminopterin and 10-ethyl-10-deazaaminopterin," J. Med. Chem. 31:181-185 (1988).

Raz et al., "Folylpoly-γ-glutamate synthetase: A key determinant of folate homeostasis and antifolate resistance in cancer," Drug Resistance Updates, 28:43-64 (2016).

Langer et al., "Carboplatin and pemetrexed with or without pembrolizumab for advanced, non-squamous non-small-cell lung cancer: a randomised, phase 2 cohort of the open-label KEYNOTE-021 study," Lancet Oncol. 17:1497-1508 (2016).

Marchi et al., "Pralatrexate Pharmacology and Clinical Development," Clin. Cancer Res. 19(24):6657-6661 (2013).

\* cited by examiner $[NA^+]_n$ (n=2-4)

$[NA^+]_n$ (n=2-5)

$[NA^+]_n$ (n=2-6)

[NA+]n (n=2-7)

[NA+]n (n=3-8)

[NA+]n (n=3-9)

FIG. 1A  Pemetrexed
FIGS. 1B-N  Examples of Alpha Polyglutamate Derivatives of Pemetrexed Exemplary alpha polyglutamated pemetrexed molecules $$PMX - [glutamyl]_n$$

Wherein: at least one glutamyl is L-alpha glutamyl or D-alpha glutamyl, and wherein each of the other glutamyl groups (even in the same molecule) can be independently
D-alpha glutamyl,
L-alpha glutamyl, or
D-gamma glutamyl, and wherein
n = 4, 5, 2-10, 4-6, or >5

FIG. 1P  Exemplary Pemetrexed Derivatives n=1, 3, 4, 5, 6, 7

FIG. 1Q   Exemplary Pemetrexed Derivatives
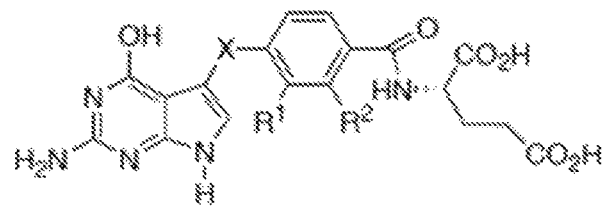
Wherein (a) X = C₂H₄, C₄H₈, C₆H₁₂, O(CH₂)₂O, or O(CH₂)₃O,
R¹ and R² = H, Cl, or R¹=Cl and R²=H,
(b) X= C₂H₄, R¹=Cl, R²=H,
(c) X= C₂H₄, R¹= R²=Cl,
(d) X= C₄H₈, R¹= R²=H,
(e) X= C₆H₁₂, R¹= R²=H,
(f) X= O(CH₂)₂O, R¹= R²=H,
(g) X= O(CH₂)₃O, R¹= R²=H
FIG. 1R
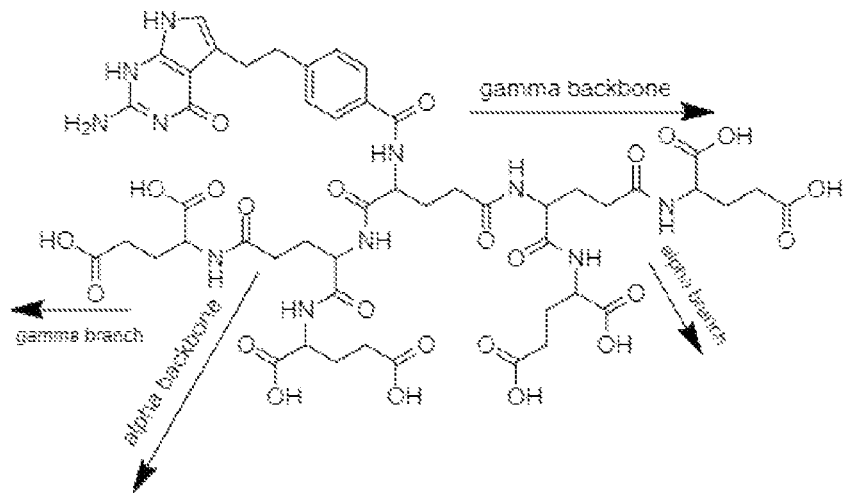
Principle for alpha / gamma glutamyl branching Gamma glutamyl backbone alpha glutamyl branches Alpha glutamyl backbone gamma glutamyl branches Alpha glutamyl backbone gamma glutamyl branches Formation and Disassociation of aG6 and Cisplatin with varying pH

SEQUENCE LISTING

```
<160> NUMBER OF SEQ ID NOS: 44

<210> SEQ ID NO 1
<211> LENGTH: 25
<212> TYPE: PRT
<213> ORGANISM: Artificial Sequence
<220> FEATURE:
<223> OTHER INFORMATION: synthetic construct

<400> SEQUENCE: 1

Arg Gln Ile Lys Ile Trp Phe Gln Asn Arg Arg Met Lys Trp Lys Lys
1               5                   10                  15

Arg Lys Lys Arg Arg Gln Arg Arg Arg
            20                  25

<210> SEQ ID NO 2
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
```

```
<222> LOCATION: (6)..(6)
<223> OTHER INFORMATION: Xaa can be any naturally occurring amino acid

<400> SEQUENCE: 2

Arg Lys Lys Arg Arg Xaa Arg Arg Gly Cys
1               5                   10

<210> SEQ ID NO 3
<211> LENGTH: 13
<212> TYPE: DNA
<213> ORGANISM: Artificial Sequence
<220> FEATURE:
<223> OTHER INFORMATION: synthetic construct

<400> SEQUENCE: 3
ccgccaagaa gcg                                                          13

<210> SEQ ID NO 4
<211> LENGTH: 100
<212> TYPE: DNA
<213> ORGANISM: Artificial Sequence
<220> FEATURE:
<223> OTHER INFORMATION: synthetic construct

<400> SEQUENCE: 4
gcgtgcacac gcgcgtagac ttccccgca agtcactcgt tagcccgcca agaagcgacc         60
cctccggggc gagctgagcg gcgtggcgcg ggggcgtcat                             100

<210> SEQ ID NO 5
<211> LENGTH: 101
<212> TYPE: DNA
<213> ORGANISM: Artificial Sequence
<220> FEATURE:
<223> OTHER INFORMATION: synthetic construct

<400> SEQUENCE: 5
acgtgcatac gcacgtagac attccccgct tcccactcca aagtccgcca agaagcgtat        60
cccgctgagc ggcgtggcgc gggggcgtca tccgtcagct c                          101

<210> SEQ ID NO 6
<211> LENGTH: 58
<212> TYPE: DNA
<213> ORGANISM: Artificial Sequence
<220> FEATURE:
<223> OTHER INFORMATION: synthetic construct

<400> SEQUENCE: 6
acttcccccg caagtcactc gttagcccgc caagaagcga cccctccggg gcgagctg         58

<210> SEQ ID NO 7
<211> LENGTH: 9
<212> TYPE: PRT
<213> ORGANISM: Artificial Sequence
<220> FEATURE:
<223> OTHER INFORMATION: synthetic construct

<400> SEQUENCE: 7

Arg Lys Lys Arg Arg Gln Arg Arg Arg
1               5

<210> SEQ ID NO 8
<211> LENGTH: 13
<212> TYPE: PRT
<213> ORGANISM: Artificial Sequence
<220> FEATURE:
```

```
<223> OTHER INFORMATION: synthetic construct

<400> SEQUENCE: 8

Gly Arg Lys Lys Arg Arg Gln Arg Arg Thr Pro Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic construct

<400> SEQUENCE: 9

Tyr Gly Arg Lys Lys Arg Arg Gln Arg Arg Arg
1               5                   10

<210> SEQ ID NO 10
<211> LENGTH: 15
<212> TYPE: PRT
<213> ORGANISM: Artificial Sequence
<220> FEATURE:
<223> OTHER INFORMATION: synthetic construct

<400> SEQUENCE: 10

Ala Ala Val Ala Leu Leu Pro Ala Val Leu Leu Ala Leu Leu Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic construct

<400> SEQUENCE: 11

Met Gly Leu Gly Leu His Leu Leu Val Leu Ala Ala Ala Leu Gln
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic construct

<400> SEQUENCE: 12

Gly Ala Leu Phe Leu Gly Phe Leu Gly Ala Ala Gly Ser Thr Met
1               5                   10                  15

<210> SEQ ID NO 13
<211> LENGTH: 21
<212> TYPE: PRT
<213> ORGANISM: Artificial Sequence
<220> FEATURE:
<223> OTHER INFORMATION: synthetic construct

<400> SEQUENCE: 13

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 14
<211> LENGTH: 16
<212> TYPE: PRT
```

```
<213> ORGANISM: Artificial Sequence
<220> FEATURE:
<223> OTHER INFORMATION: synthetic construct

<400> SEQUENCE: 14

Arg Val Ile Arg Val Trp Phe Gln Asn Lys Arg Cys Lys Asp Lys Lys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic construct

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 20
<212> TYPE: PRT
<213> ORGANISM: Artificial Sequence
<220> FEATURE:
<223> OTHER INFORMATION: synthetic construct

<400> SEQUENCE: 16

Gly Leu Phe Glu Ala Ile Ala Gly Phe Ile Glu Asn Gly Trp Glu Gly
1               5                   10                  15

Met Ile Asp Gly
            20

<210> SEQ ID NO 17
<211> LENGTH: 15
<212> TYPE: PRT
<213> ORGANISM: Artificial Sequence
<220> FEATURE:
<223> OTHER INFORMATION: synthetic construct

<400> SEQUENCE: 17

Gly Trp Thr Leu Asn Ser Ala Gly Tyr Leu Leu Gly Lys Ile Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetic construct

<400> SEQUENCE: 18

Arg Ser Gln Ser Arg Ser Arg Tyr Tyr Arg Gln Arg Gln Arg Ser
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: synthetic construct

<400> SEQUENCE: 19

Leu Ala Ile Pro Glu Gln Glu Tyr
1               5

<210> SEQ ID NO 20
```

```
<211> LENGTH: 8
<212> TYPE: PRT
<213> ORGANISM: Artificial Sequence
<220> FEATURE:
<223> OTHER INFORMATION: synthetic construct

<400> SEQUENCE: 20

Leu Gly Ile Ala Glu Gln Glu Tyr
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic construct

<400> SEQUENCE: 21

Leu Gly Ile Pro Ala Gln Glu Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic construct

<400> SEQUENCE: 22

Leu Gly Ile Pro Glu Ala Glu Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic construct

<400> SEQUENCE: 23

Leu Gly Ile Pro Glu Gln Ala Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct

<400> SEQUENCE: 24

Leu Gly Ile Ala Glu Ala Glu Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic construct

<400> SEQUENCE: 25

Leu Gly Ile Pro Glu Ala Ala Tyr
1               5

<210> SEQ ID NO 26
<211> LENGTH: 8
```

```
<212> TYPE: PRT
<213> ORGANISM: Artificial Sequence
<220> FEATURE:
<223> OTHER INFORMATION: synthetic construct

<400> SEQUENCE: 26

Leu Gly Ile Ala Glu Gln Ala Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic construct

<400> SEQUENCE: 27

Leu Gly Ile Ala Glu Ala Ala Tyr
1               5

<210> SEQ ID NO 28
<211> LENGTH: 18
<212> TYPE: PRT
<213> ORGANISM: Artificial Sequence
<220> FEATURE:
<223> OTHER INFORMATION: synthetic construct

<400> SEQUENCE: 28

Leu Leu Ile Ile Leu Arg Arg Arg Ile Arg Lys Gln Ala His Ala His
1               5                   10                  15

Ser Lys

<210> SEQ ID NO 29
<211> LENGTH: 12
<212> TYPE: PRT
<213> ORGANISM: Artificial Sequence
<220> FEATURE:
<223> OTHER INFORMATION: synthetic construct

<400> SEQUENCE: 29

Leu Lys Ala Leu Ala Ala Leu Ala Lys Lys Ile Leu
1               5                   10

<210> SEQ ID NO 30
<211> LENGTH: 18
<212> TYPE: PRT
<213> ORGANISM: Artificial Sequence
<220> FEATURE:
<223> OTHER INFORMATION: synthetic construct

<400> SEQUENCE: 30

Lys Leu Ala Leu Lys Leu Ala Leu Lys Ala Leu Lys Ala Ala Leu Lys
1               5                   10                  15

Leu Ala

<210> SEQ ID NO 31
<211> LENGTH: 21
<212> TYPE: PRT
<213> ORGANISM: Artificial Sequence
<220> FEATURE:
<223> OTHER INFORMATION: synthetic construct

<400> SEQUENCE: 31

Lys Glu Thr Trp Trp Glu Thr Trp Trp Thr Glu Trp Ser Gln Pro Lys
1               5                   10                  15
```

```
Lys Lys Arg Lys Val
            20

<210> SEQ ID NO 32
<211> LENGTH: 8
<212> TYPE: PRT
<213> ORGANISM: Artificial Sequence
<220> FEATURE:
<223> OTHER INFORMATION: synthetic construct

<400> SEQUENCE: 32

Asp His Gln Leu Asn Pro Ala Phe
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic construct

<400> SEQUENCE: 33

Asp Pro Lys Gly Asp Pro Lys Gly
1               5

<210> SEQ ID NO 34
<211> LENGTH: 18
<212> TYPE: PRT
<213> ORGANISM: Artificial Sequence
<220> FEATURE:
<223> OTHER INFORMATION: synthetic construct

<400> SEQUENCE: 34

Val Thr Val Thr Val Thr Val Thr Val Thr Gly Lys Gly Asp Pro Lys
1               5                   10                  15

Pro Asp

<210> SEQ ID NO 35
<211> LENGTH: 16
<212> TYPE: PRT
<213> ORGANISM: Artificial Sequence
<220> FEATURE:
<223> OTHER INFORMATION: synthetic construct

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: synthetic construct

<400> SEQUENCE: 36

Gly Arg Lys Lys Arg Arg Gln Arg Arg Arg Pro Pro Gln
1               5                   10

<210> SEQ ID NO 37
<211> LENGTH: 27
<212> TYPE: PRT
<213> ORGANISM: Artificial Sequence
<220> FEATURE:
<223> OTHER INFORMATION: synthetic construct

<400> SEQUENCE: 37
```

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 38
<211> LENGTH: 10
<212> TYPE: PRT
<213> ORGANISM: Artificial Sequence
<220> FEATURE:
<223> OTHER INFORMATION: synthetic construct

<400> SEQUENCE: 38

```
Gly Arg Lys Lys Arg Arg Gln Arg Arg Arg
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: synthetic construct

<400> SEQUENCE: 39

```
Arg Arg Arg Arg Arg Arg Arg
1               5
```

<210> SEQ ID NO 40
<211> LENGTH: 8
<212> TYPE: PRT
<213> ORGANISM: Artificial Sequence
<220> FEATURE:
<223> OTHER INFORMATION: synthetic construct

<400> SEQUENCE: 40

```
Arg Arg Arg Arg Arg Arg Arg Arg
1               5
```

<210> SEQ ID NO 41
<211> LENGTH: 9
<212> TYPE: PRT
<213> ORGANISM: Artificial Sequence
<220> FEATURE:
<223> OTHER INFORMATION: synthetic construct

<400> SEQUENCE: 41

```
Arg Arg Arg Arg Arg Arg Arg Arg Arg
1               5
```

<210> SEQ ID NO 42
<211> LENGTH: 10
<212> TYPE: PRT
<213> ORGANISM: Artificial Sequence
<220> FEATURE:
<223> OTHER INFORMATION: synthetic construct

<400> SEQUENCE: 42

```
Arg Arg Arg Arg Arg Arg Arg Arg Arg Arg
1               5                   10
```

<210> SEQ ID NO 43
<211> LENGTH: 10
<212> TYPE: PRT
<213> ORGANISM: Artificial Sequence
<220> FEATURE:
<223> OTHER INFORMATION: synthetic construct

```
<400> SEQUENCE: 43

Arg Arg Arg Arg Arg Arg Arg Arg Arg Arg
1               5                   10

<210> SEQ ID NO 44
<211> LENGTH: 33
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (33)..(33)
<223> OTHER INFORMATION: Xaa can be 2 to 15 Arg independently in the L
      and/or D form

<400> SEQUENCE: 44

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Xaa
```

ALPHA POLYGLUTAMATED PEMETREXED AND USES THEREOF

CROSS-REFERENCE TO RELATED APPLICATIONS

This application is the U.S. national phase of International Application No. PCT/US2019/016989 filed Feb. 7, 2019 which designated the U.S. and claims priority to U.S. Provisional Application No. 62/627,703 filed Feb. 7, 2018, U.S. Provisional Application No. 62/627,741 filed Feb. 7, 2018, U.S. Provisional Application No. 62/630,629 filed Feb. 14, 2018, U.S. Provisional Application No. 62/662,374 filed Apr. 25, 2018, U.S. Provisional Application No. 62/702,732 filed Jul. 24, 2018, U.S. Provisional Application No. 62/702,561 filed Jul. 24, 2018, U.S. Provisional Application No. 62/764,943 filed Aug. 17, 2018 and U.S. Provisional Application No. 62/764,955 filed Aug. 17, 2018, the entire contents of each of which are hereby incorporated by reference.

REFERENCE TO SEQUENCE LISTING SUBMITTED ELECTRONICALLY

The content of the electronically submitted sequence listing (Name: 6155_144_Sequence_Listing.txt; Size: 10.6 kilobytes; and Date of Creation: Aug. 3, 2020) filed with the application is incorporated herein by reference in its entirety.

BACKGROUND

This disclosure generally relates to alpha polyglutamated pemetrexed compositions, including delivery vehicles such as liposomes containing the alpha polyglutamated pemetrexed compositions, and methods of making and using the compositions to treat diseases including hyperproliferative diseases such as cancer, disorders of the immune system such as rheumatoid arthritis, and infectious diseases such as HIV and malaria.

Pemetrexed disodium is the active ingredient in antineoplastic products marketed under the trade name ALIMTA® (Eli Lilly and Company) and is also known by the chemical name L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate (molecular formula $C_{20}H_{19}N_5Na_2O_6 \cdot 7H_2O$) approved as a single agent for the treatment of locally advanced or metastatic non-small cell lung cancer, and in combination with cisplatin for the treatment of patients with malignant pleural mesothelioma. Pemetrexed has demonstrated activity in clinical trials in a variety of tumor types, including lung, breast, colon, mesothelioma, pancreatic, gastric, bladder, head and neck, and cervical cancer.

Folate is an essential cofactor that mediates the transfer of one-carbon units involved in nucleotide biosynthesis and DNA repair, the remethylation of homocysteine (Hcy), and the methylation of DNA, proteins, and lipids. The only circulating forms of folates in the blood are monoglutamates and folate monoglutamates are the only form of folate that is transported across the cell membrane—likewise, the monoglutamate form of polyglutamatable antifolates such as pemetrexed, are transported across the cell membrane. Once taken up into cells, intracellular folate is converted to polyglutamates by the enzyme folylpoly-gamma-glutamate synthetase (FPGS).

Pemetrexed is a multi-targeted antifolate agent that exerts its action by disrupting folate-dependent metabolic processes essential for cell homeostasis and replication. Pemetrexed inhibits three enzymes required in purine and pyrimidine biosynthesis—thymidylate synthase (TS), dihydrofolate reductase (DHFR), and glycinamide ribonucleotide formyl transferase (GARFTase). The inhibition of these enzymes suppresses de novo nucleotide biosynthesis and results in a disruption of cell homeostasis and an imbalance of purine and pyrimidine precursors that render cells incapable of undergoing accurate DNA replication and ultimately results in cell death.

Pemetrexed is transported into cells by the reduced folate carrier (RFC) system and folate receptors (FRs) $\alpha$ and $\beta$ and by Proton Coupled Folate Transporter (PCFT) that is generally most active in a lower pH environment. RFC is the main transporter of pemetrexed at physiologic pH and is ubiquitously expressed in both normal and diseased cells. Consequently, pemetrexed treatment often suffers from the dose-limiting toxicity that is a major obstacle in cancer chemotherapy. Once inside the cell, pemetrexed is polyglutamated by FPGS, which may add up to 6 L glutamyl groups in a L-gamma carboxyl group linkage to the pemetrexed. The L-gamma polyglutamation of pemetrexed by FPGS serves at least 2 main therapeutic purposes: (1) it greatly enhances pemetrexed affinity and inhibitory activity for several folate-dependent enzymes, including thymidylate synthase and GARFTase; and (2) it facilitates the accumulation of polyglutamated pemetrexed, which unlike pemetrexed (monoglutamate), is not easily transported out of cells by cell efflux pumps.

Pemetrexed acts during DNA and RNA synthesis, and consequently has a greater toxic effect on rapidly dividing cells such as malignant and myeloid cells. Myelosuppression is typically the dose-limiting toxicity of pemetrexed therapy and has limited the clinical applications of pemetrexed. Pretreatment with folic acid and vitamin B is now used to ameliorate the most frequent side effects associated with pemetrexed therapy that include bone marrow suppression, fatigue, and skin rash.

Resistance to pemetrexed therapy is typically associated with one or more of, (a) increased cell efflux pump activity, (b) increased thymidylate synthetase activity, (c) decreased folylpoly-gamma-glutamate synthetase (FPGS) activity, and (d) increased gamma-glutamyl hydrolase (GGH) activity, which cleaves gamma polyglutamate chains attached to folates and antifolates.

The challenge to the longstanding (>30 years) observation that higher-level polyglutamates of various antifolates have much greater potency compared to lower-level glutamates, has been that the scientific community has relied on the intracellular FPGS mediated mechanisms to convert the lower-level glutamates to their higher-level forms. The present inventions provide the means to deliver higher-level polyglutamate forms of antifolates directly into the cell, without having to rely on the cells' machinery to achieve this goal.

The provided alpha polyglutamated pemetrexed compositions deliver a strategy for overcoming the pharmacological challenges associated with the dose limiting toxicities and with treatment resistance associated with pemetrexed therapy. The provided methods deliver to cancer cells a novel alpha polyglutamated form of pemetrexed while (1) minimizing/reducing exposure to normal tissue cells, (2) optimizing/improving the cytotoxic effect of pemetrexed-based agents on cancer cells and (3) minimizing/reducing

BRIEF SUMMARY

This disclosure generally relates to novel alpha polyglutamated pemetrexed (PMX) compositions and methods of making and using the compositions to treat diseases including hyperproliferative diseases such as cancer, disorders of the immune system such as rheumatoid arthritis, and infectious diseases such as HIV and malaria.

In some embodiments, the disclosure provides:
[1] a composition comprising an alpha polyglutamated pemetrexed, wherein at least one glutamyl group has an alpha carboxyl group linkage;
[2] the composition of [1], wherein the alpha polyglutamated pemetrexed comprises 1-10 glutamyl groups having an alpha carboxyl group linkage;
[3] the composition of [1] or [2] wherein the alpha polyglutamated pemetrexed contains 4, 5, 6, 2-10, 4-6, or greater than 5, glutamyl groups;
[4] the composition according to any of [1]-[3], which comprises alpha tetraglutamated pemetrexed;
[5] the composition according to any of [1]-[3], which comprises alpha pentaglutamated pemetrexed;
[6] the composition according to any of [1]-[3], which comprises alpha hexaglutamated pemetrexed;
[7] the composition according to any of [1] to [6], wherein
  (a) two or more glutamyl groups have an alpha carboxyl group linkage,
  (b) each of the glutamyl groups other than the glutamyl group of pemetrexed has an alpha carboxyl group linkage; or
  (c) two or more glutamyl groups have a gamma carboxyl group linkage,
[8] the composition according to any of [1] to [6], wherein
  (a) each of the glutamyl groups other than the C-terminal glutamyl group or groups and the glutamyl group of pemetrexed has an alpha carboxyl group linkage; or
  (b) each of the glutamyl groups other than the C-terminal glutamyl group or groups has an alpha carboxyl group linkage;
[9] the composition according to any of [1]-[8], wherein at least one glutamyl group has both an alpha carboxyl group linkage and a gamma carboxyl group linkage;
[10] the composition according to any of [1]-[9], wherein:
  (a) at least 2 of the glutamyl groups of the alpha polyglutamated pemetrexed are in the L-form,
  (b) each of the glutamyl groups of the alpha polyglutamated pemetrexed is in the L-form,
  (c) at least 1 of the glutamyl groups of the alpha polyglutamated pemetrexed is in the D-form,
  (d) each of the glutamyl groups of the alpha polyglutamated pemetrexed other than the glutamyl group of pemetrexed is in the D-form, or
  (e) at least 2 of the glutamyl groups of the alpha polyglutamated pemetrexed are in the L-form and at least 1 of the glutamyl groups is in the D-form;
[11] the composition according to any of [1]-[10], wherein the polyglutamate is linear;
[12] the composition according to any of [1]-[10], wherein the polyglutamate is branched;
[13] a liposomal composition comprising the alpha polyglutamated pemetrexed according to any of [1]-[12] (Lp-αPPMX);
[14] the LαPP composition according to [13], wherein the alpha polyglutamated pemetrexed comprises glutamyl groups in the L-form having alpha carboxyl group linkages;
[15] the Lp-αPPMX composition according to [13] or [14], wherein each of the glutamyl groups of the alpha polyglutamated pemetrexed is in the L-form;
[16] the Lp-αPPMX composition of [13] or [14], wherein at least one of the glutamyl groups of the alpha polyglutamated pemetrexed is in the D-form;
[17] the Lp-αPPMX composition according to any of [13]-[16], wherein the liposome comprises an alpha polyglutamated pemetrexed containing 4, 5, 6, 2-10, 4-6, or more than 5, glutamyl groups;
[18] the Lp-αPPMX composition according to any of [13]-[17], wherein at least one of the glutamyl groups of the alpha polyglutamated pemetrexed has a gamma carboxyl group linkage;
[19] the composition according to any of [13]-[18], wherein at least one glutamyl group has both an alpha carboxyl group linkage and a gamma carboxyl group linkage;
[20] the composition according to any of [13]-[18], which contains 2, 3, 4, 5, 6, 2-10, 4-6, or more than 5, glutamyl groups that have both an alpha carboxyl group linkage and a gamma carboxyl group linkage;
[21] the Lp-αPPMX composition according to any of [13]-[19], wherein the liposome comprises an alpha polyglutamated pemetrexed containing alpha tetraglutamated pemetrexed, alpha pentaglutamated pemetrexed, or alpha hexaglutamated pemetrexed;
[22] the Lp-αPPMX composition according to any of [13]-[21], wherein the polyglutamate is linear or branched;
[23] the Lp-αPPMX composition according to any of [13]-[22], wherein the liposome is pegylated (PαLp-αPPMX);
[24] the Lp-αPPMX composition according to any of [13]-[23], wherein the liposomes comprise at least 1% weight by weight (w/w) of the alpha polyglutamated pemetrexed or wherein during the process of preparing the Lp-αPPMX, at least 1% of the starting material of alpha polyglutamated PMX is encapsulated (entrapped) in the Lp-αPPMX;
[25] the Lp-αPPMX composition according to any of [13]-[24], wherein the liposome has a diameter in the range of 20 nm to 500 nm or 20 nm to 200 nm;
[26] the Lp-αPPMX composition according to any of [13]-[25], wherein the liposome has a diameter in the range of 80 nm to 120 nm;
[27] the Lp-αPPMX composition according to any of [13]-[26], wherein the liposome is formed from liposomal components;
[28] the Lp-αPPMX composition according to [27], wherein the liposomal components comprise at least one of an anionic lipid and a neutral lipid;
[29] the Lp-αPPMX composition according to [27] or [28], wherein the liposomal components comprise at least one selected from the group consisting of: DSPE; DSPE-PEG; DSPE-PEG-maleimide; HSPC; HSPC-PEG; cholesterol; cholesterol-PEG; and cholesterol-maleimide;
[30] the Lp-αPPMX composition according to any of [27]-[29], wherein the liposomal components comprise at least one selected from the group consisting of: DSPE; DSPE-PEG; DSPE-PEG-FITC; DSPE-PEG-maleimide; cholesterol; and HSPC;

[31] the Lp-αPPMX composition according to any of [27]-[30], wherein one or more liposomal components further comprises a steric stabilizer;

[32] the Lp-αPPMX composition according to [31], wherein the steric stabilizer is at least one selected from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L-amino-acid-based polymer; oligoglycerol, copolymer containing polyethylene glycol and polypropylene oxide, Poloxamer 188, and polyvinyl alcohol;

[33] the Lp-αPPMX composition according to [32], wherein the steric stabilizer is PEG and the PEG has a number average molecular weight (Mn) of 200 to 5000 daltons;

[34] the Lp-αPPMX composition according to any of [13]-[33], wherein the liposome is anionic or neutral;

[35] the Lp-αPPMX composition according to any of [13]-[33], wherein the liposome has a zeta potential that is less than or equal to zero;

[36] the Lp-αPPMX composition according to any of [13]-[33], wherein the liposome has a zeta potential that is between 0 to −150 mV;

[37] the Lp-αPPMX composition according to any of [13]-[33], wherein the liposome has a zeta potential that is between −30 to −50 mV;

[38] the Lp-αPPMX composition according to any of [13]-[33], wherein the liposome is cationic;

[39] the Lp-αPPMX composition according to any of [13]-[38], wherein the liposome has an interior space comprising the alpha polyglutamated pemetrexed and an aqueous pharmaceutically acceptable carrier;

[40] the Lp-αPPMX composition of [39], wherein the pharmaceutically acceptable carrier comprises a tonicity agent such as dextrose, mannitol, glycerine, potassium chloride, sodium chloride, at a concentration of greater than 1%;

[41] the Lp-αPPMX composition of [39], wherein the aqueous pharmaceutically acceptable carrier is trehalose;

[42] the Lp-αPPMX composition of [41], wherein the pharmaceutically acceptable carrier comprises 5% to 20% weight of trehalose;

[43] the Lp-αPPMX composition according to any of [39]-[42], wherein the pharmaceutically acceptable carrier comprises 1% to 15 weight of dextrose;

[44] the Lp-αPPMX composition according to any of [39]-[43], wherein the interior space of the liposome comprises 5% dextrose suspended in an HEPES buffered solution;

[45] the Lp-αPPMX composition according to any of [39]-[44], wherein the pharmaceutically acceptable carrier comprises a buffer such as HEPES Buffered Saline (HBS) or similar, at a concentration of between 1 to 200 mM and a pH of between 2 to 8;

[46] the Lp-αPPMX composition according to any of [39]-[45], wherein the pharmaceutically acceptable carrier comprises a total concentration of sodium acetate and calcium acetate of between 50 mM to 500 mM;

[47] the Lp-αPPMX composition according to any of [13]-[46], wherein the interior space of the liposome has a pH of 5-8 or a

[61] the Lp-αPPMX composition according to any of [58]-[60], wherein the immunostimulatory agent and the detectable marker is the same;
[62] the Lp-αPPMX composition according to any of [58]-[61], further comprising a hapten;
[63] the Lp-αPPMX composition of [62], wherein the hapten comprises one or more of fluorescein or Beta 1, 6-glucan;
[64] the Lp-αPPMX composition according to any of [13]-[63], which further comprises in the interior space, the exterior space, or both the interior space and the exterior space at least one cryoprotectant selected from the group consisting of mannitol; trehalose; sorbitol; and sucrose;
[65] a targeted composition comprising the composition according to any of [1]-[64];
[66] an non-targeted composition comprising the composition according to any of [1]-[49];
[67] the Lp-αPPMX composition according to any of [13]-[66], which further comprises carboplatin and/or pembroluzumab;
[68] a pharmaceutical composition comprising the liposomal alpha polyglutamated pemetrexed composition according to any of [13]-[67];
[69] a pharmaceutical composition comprising alpha polyglutamated pemetrexed composition according to any of [1]-[7];
[70] the composition of any of [1]-[69], for use in the treatment of disease;
[71] use of the composition of any of [1]-[70], in the manufacture of a medicament for the treatment of disease;
[72] a method for treating or preventing disease in a subject needing such treatment or prevention, the method comprising administering the composition of any of [1]-[70] to the subject;
[73] a method for treating or preventing disease in a subject needing such treatment or prevention, the method comprising administering the liposomal alpha polyglutamated pemetrexed composition of any of [13]-[69] to the subject;
[74] a method of killing a hyperproliferative cell that comprises contacting a hyperproliferative cell with the composition of any of [1]-[69];
[75] a method of killing a hyperproliferative cell that comprises contacting a hyperproliferative cell with the liposomal alpha polyglutamated pemetrexed composition of any of [13]-[69];
[76] the method of [74] or [75], wherein the hyperproliferative cell is a cancer cell, a mammalian cell, and/or a human cell;
[77] a method for treating cancer that comprises administering an effective amount of the composition of any of [1]-[69] to a subject having or at risk of having cancer;
[78] a method for treating cancer that comprises administering an effective amount of the liposomal alpha polyglutamated pemetrexed composition of any of [13]-[68] to a subject having or at risk of having cancer;
[79] the method of [77] or [78], wherein the cancer is selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias;
[80] the method of [77] or [78], wherein the cancer is a member selected from the group consisting of: lung cancer, breast cancer, colon cancer, pancreatic cancer, gastric cancer, bladder cancer, head and neck cancer, ovarian cancer, and cervical cancer;
[81] the method of [77] or [78], wherein the cancer is wherein the cancer is mesothelioma or non-small cell lung carcinoma (NSCLC);
[82] the method of [77] or [78], wherein the cancer is a sarcoma such as osteosarcoma;
[83] a method for treating cancer that comprises administering an effective amount of the Lp-αPPMX composition of any of [50]-[66] to a subject having or at risk of having a cancer cell that expresses on its surface a folate receptor bound by the targeting moiety;
[84] a maintenance therapy comprising administering an effective amount of the composition of any of [1]-[69] to a subject that is undergoing or has undergone cancer therapy;
[85] a maintenance therapy comprising administering an effective amount of the liposomal alpha polyglutamated pemetrexed composition of any of [13]-[69] to a subject that is undergoing or has undergone cancer therapy;
[86] a method for treating a disorder of the immune system that comprises administering an effective amount of the composition of any of [1]-[69] to a subject having or at risk of having a disorder of the immune system;
[87] a method for treating a disorder of the immune system that comprises administering an effective amount of the liposomal alpha polyglutamated pemetrexed composition of any of [9]-[69] to a subject having or at risk of having a disorder of the immune system;
[88] a method for treating an infectious disease that comprises administering an effective amount of the composition of any of [1]-[69] to a subject having or at risk of having an infectious disease;
[89] a method for treating an infectious disease that comprises administering an effective amount of the liposomal alpha polyglutamated pemetrexed composition of any of [13]-[69] to a subject having or at risk of having an infectious disease;
[90] a method of delivering alpha polyglutamated pemetrexed to a tumor expressing a folate receptor on its surface, the method comprising: administering the Lp-αPPMX composition of any of [1]-[69] to a subject having the tumor in an amount to deliver a therapeutically effective dose of the alpha polyglutamated pemetrexed to the tumor;
[91] a method of preparing an alpha polyglutamated pemetrexed composition comprising the liposomal alpha polyglutamated pemetrexed composition of any of [13]-[69], the method comprising: forming a mixture comprising: liposomal components and alpha polyglutamated pemetrexed in solution; homogenizing the mixture to form liposomes in the solution; and processing the mixture to form liposomes containing alpha polyglutamated pemetrexed;
[92] a method of preparing an alpha polyglutamated pemetrexed composition comprising the liposomal alpha polyglutamated pemetrexed composition of any of [13]-[69], the method comprising: forming a mixture comprising: liposomal components and alpha polyglutamated pemetrexed in solution; and processing the mixture to form liposomes containing alpha polyglutamated pemetrexed;

[93] the method of [92], wherein the processing the mixture comprises homogenizing the mixture to form liposomes in the solution;

[94] a method of preparing the composition of any of [13]-[69] comprising the steps of: forming a mixture comprising: liposomal components and alpha polyglutamated pemetrexed in a solution; homogenizing the mixture to form liposomes in the solution; processing the mixture to form liposomes entrapping and/or encapsulating alpha polyglutamated pemetrexed; and providing the targeting moiety on a surface of the liposomes, the targeting moiety having the specific affinity for at least one of folate receptor alpha (FR-α), folate receptor beta (FR-β) and folate receptor delta (FR-δ);

[95] a method of preparing the composition of any of [50]-[69], comprising the steps of: forming a mixture comprising: liposomal components and alpha polyglutamated pemetrexed in a solution; processing the mixture to form liposomes entrapping and/or encapsulating alpha polyglutamated pemetrexed; and providing the targeting moiety on a surface of the liposomes, the targeting moiety having the specific affinity for at least one of folate receptor alpha (FR-α), folate receptor beta (FR-β) and folate receptor delta (FR-δ);

[96] the method of [95], wherein the processing step comprises homogenizing the mixture to form liposomes in the solution;

[97] the method according to any of [94] to [96], wherein the processing step includes one or more steps of: thin film hydration, extrusion, in-line mixing, ethanol injection technique, freezing-and-thawing technique, reverse-phase evaporation, dynamic high pressure microfluidization, microfluidic mixing, double emulsion, freeze-dried double emulsion, 3D printing, membrane contactor method, and stirring;

[98] the method according to any of [94] to [97], wherein said processing step includes one or more steps of modifying the size of the liposomes by one or more of steps of extrusion, high-pressure microfluidization, and/or sonication; and/or

[99] the method of any of [91] to [98], wherein at least 1% of the starting material of alpha polyglutamated PMX is encapsulated or entrapped in the Lp-αPPMX.

In some embodiments, the disclosure provides an alpha polyglutamated pemetrexed (αPPMX) composition wherein at least one of the glutamyl residues of the alpha polyglutamated pemetrexed is linked by its alpha carboxyl group. In some embodiments, the αPPMX contains 2-20, 2-15, 2-10, 2-5, or more than 5, glutamyl groups (including the glutamyl group in pemetrexed). In some embodiments, the αPPMX comprises two or more glutamyl groups in the L-form. In other embodiments, the αPPMX comprises a glutamyl group in the D-form. In further embodiments, the αPPMX comprises a glutamyl group in the D-form and two or more glutamyl groups in the L-form. In additional embodiments, the αPPMX comprises two or more glutamyl groups that have a gamma linkage. In some embodiments, at least one glutamyl group has both an alpha linkage and a gamma linkage.

In one embodiment, the αPPMX composition contains a chain of 3 glutamyl groups attached to the glutamyl group of pemetrexed (i.e., a tetraglutamated pemetrexed). In some embodiments, the tetraglutamated PMX comprises two or more glutamyl groups in the L-form. In other embodiments, the tetraglutamated PMX comprises a glutamyl group in the D-form. In further embodiments, the tetraglutamated PMX comprises a glutamyl group in the D-form and two or more glutamyl groups in the L-form. In additional embodiments, the tetraglutamated PMX comprises two or more glutamyl groups that have a gamma linkage.

In one embodiment, the αPPMX composition contains a chain of 4 glutamyl groups attached to the glutamyl group of pemetrexed (i.e., a pentaglutamated pemetrexed). In some embodiments, the pentaglutamated PMX comprises two or more glutamyl groups in the L-form. In other embodiments, the pentaglutamated PMX comprises a glutamyl group in the D-form. In further embodiments, the pentaglutamated PMX comprises a glutamyl group in the D-form and two or more glutamyl groups in the L-form. In additional embodiments, the pentaglutamated PMX comprises two or more glutamyl groups that have a gamma linkage.

In one embodiment, the αPPMX composition contains a chain of 5 glutamyl groups attached to the glutamyl group of pemetrexed (i.e., a hexaglutamated pemetrexed). In some embodiments, the hexaglutamated PMX comprises two or more glutamyl groups in the L-form. In other embodiments, the hexaglutamated PMX comprises a glutamyl group in the D-form. In further embodiments, the hexaglutamated PMX comprises a glutamyl group in the D-form and two or more glutamyl groups in the L-form. In additional embodiments, the hexaglutamated PMX comprises two or more glutamyl groups that have a gamma linkage.

In additional embodiments, the disclosure provides compositions containing delivery vehicles such as liposomes filled with (i.e., encapsulating) and/or otherwise associated with alpha polyglutamated pemetrexed, and methods of making and using the αPPMX filled/associated delivery vehicle compositions to deliver alpha polyglutamated pemetrexed to diseased (e.g., cancerous) and/or targeted cells. These compositions have uses that include but are not limited to treating diseases that include for example, hyperproliferative diseases such as cancer, disorders of the immune system such as rheumatoid arthritis, and infectious diseases such as HIV and malaria. The αPPMX filled/associated delivery vehicle compositions provide improvements to the efficacy and safety of delivering pemetrexed to cancer cells by providing the preferential delivery of a more cytotoxic payload (e.g., polyglutamated pemetrexed) compared to the cytotoxicity of pemetrexed administered in its monoglutamate state (PMX).

In additional embodiments, the disclosure provides a composition comprising a liposome encapsulating (filled with) alpha polyglutamated pemetrexed (Lp-αPPMX). In some embodiments, the alpha polyglutamated pemetrexed in the Lp-αPPMX contains 2-20, 2-15, 2-10, 2-5, or more than 20, glutamyl groups (including the glutamyl group in pemetrexed). In some embodiments, the alpha polyglutamated pemetrexed in the Lp-αPPMX comprises two or more glutamyl groups in the L-form. In other embodiments, the alpha polyglutamated pemetrexed in the Lp-αPPMX comprises a glutamyl group in the D-form. In further embodiments, the alpha polyglutamated pemetrexed in the Lp-αPPMX comprises a glutamyl group in the D-form and two or more glutamyl groups in the L-form. In additional embodiments, the alpha polyglutamated pemetrexed in the Lp-αPPMX comprises two or more glutamyl groups that have a gamma linkage. In additional embodiments, the alpha polyglutamated pemetrexed in the Lp-αPPMX comprises one or more glutamyl groups that have both an alpha linkage and a gamma linkage. In some embodiments, the alpha polyglutamated pemetrexed in the Lp-αPPMX comprises 2-10 glutamyl groups that have both an alpha linkage and a gamma linkage, or any range therein between. In some embodiments, the polyglutamate chain of the alpha polyglutamated pemetrexed is linear. In some embodiments, the polyglutamate chain of the alpha polyglutamated pemetrexed is branched.

In one embodiment, the Lp-αPPMX composition comprises an alpha polyglutamated PMX that contains a chain of 3 glutamyl groups attached to the glutamyl group of pemetrexed (i.e., tetraglutamated pemetrexed). In some embodiments, the tetraglutamated PMX comprises two or more glutamyl groups in the L-form. In other embodiments, the tetraglutamated PMX comprises a glutamyl group in the D-form. In further embodiments, the tetraglutamated PMX comprises a glutamyl group in the D-form and two or more glutamyl groups in the L-form. In additional embodiments, the tetraglutamated PMX comprises two or more glutamyl groups that have a gamma linkage. In some embodiments, the polyglutamate chain of the alpha polyglutamated pemetrexed is linear. In some embodiments, the polyglutamate chain of the alpha polyglutamated pemetrexed is branched.

In one embodiment, the Lp-αPPMX composition comprises an alpha polyglutamated PMX that contains a chain of 4 glutamyl groups attached to the glutamyl group of pemetrexed (i.e., pentaglutamated pemetrexed). In some embodiments, the pentaglutamated PMX comprises two or more glutamyl groups in the L-form. In other embodiments, the pentaglutamated PMX comprises a glutamyl group in the D-form. In further embodiments, the pentaglutamated PMX comprises a glutamyl group in the D-form and two or more glutamyl groups in the L-form. In additional embodiments, the pentaglutamated PMX comprises two or more glutamyl groups that have a gamma linkage. In some embodiments, the polyglutamate chain of the alpha polyglutamated pemetrexed is linear. In some embodiments, the polyglutamate chain of the alpha polyglutamated pemetrexed is branched.

In one embodiment, the Lp-αPPMX composition comprises an alpha polyglutamated PMX that contains a chain of 5 glutamyl groups attached to the glutamyl group of pemetrexed (i.e., hexaglutamated pemetrexed). In some embodiments, the hexaglutamated PMX comprises two or more glutamyl groups in the L-form. In other embodiments, the hexaglutamated PMX comprises a glutamyl group in the D-form. In further embodiments, the hexaglutamated PMX comprises a glutamyl group in the D-form and two or more glutamyl groups in the L-form. In additional embodiments, the hexaglutamated PMX comprises two or more glutamyl groups that have a gamma linkage. In some embodiments, the polyglutamate chain of the alpha polyglutamated pemetrexed is linear. In some embodiments, the polyglutamate chain of the alpha polyglutamated pemetrexed is branched.

In some embodiments, the Lp-αPPMX composition is cationic. In some embodiments, the Lp-αPPMX liposome is cationic and has a diameter in the range of 20 nm to 500 nm, 20 nm to 200 nm, 30 nm to 175 nm, or 50 nm to 150 nm, or any range therein between. In further embodiments, the Lp-αPPMX liposome is cationic and the composition has a diameter of 80 nm to 120 nm, or any range therein between. In some embodiments, the cationic Lp-αPPMX composition comprises at least 1%, 5%, 10%, 15%, 20%, 25%, 30%, 35, 40%, 45%, 50%, 55%, 60%, 65%, 70%, 75%, or more than 75%, w/w of the alpha polyglutamated PMX. In some embodiments, during the process of preparing the Lp-αPPMX, at least 1%, 5%, 10%, 15%, 20%, 25%, 30%, 35%, 40%, 45%, 50%, 55%, 60%, 65%, 70%, 75%, or more than 75%, of the starting material of alpha polyglutamated PMX is encapsulated (entrapped) in the cationic Lp-αPPMX. In additional embodiments, the alpha polyglutamated pemetrexed encapsulated by the liposome is in a HEPES buffered solution within the liposome.

In other embodiments, Lp-αPPMX composition is anionic or neutral. In some embodiments, the Lp-αPPMX composition is cationic. In some embodiments, the Lp-αPPMX liposome is anionic or neutral and has a diameter in the range of 20 nm to 500 nm, 20 nm to 200 nm, 30 nm to 175 nm, or 50 nm to 150 nm, or any range therein between. In further embodiments, the Lp-αPPMX liposome is anionic or neutral and the composition has a diameter in the range of 80 nm to 120 nm, or any range therein between. In some embodiments, the Lp-αPPMX liposome is anionic and has a diameter in the range of 20 nm to 500 nm, 20 nm to 200 nm, 30 nm to 175 nm, or 50 nm to 150 nm, or any range therein between. In further embodiments, the Lp-αPPMX liposome is anionic and the composition has a diameter of 80 nm to 120 nm, or any range therein between. In some embodiments, the Lp-αPPMX liposome is neutral and has a diameter in the range of 20 nm to 500 nm, 20 nm to 200 nm, 30 nm to 175 nm, or 50 nm to 150 nm, or any range therein between. In further embodiments, the Lp-αPPMX liposome is neutral and the composition has a diameter in the range of 80 nm to 120 nm, or any range therein between. In some embodiments, the anionic or neutral Lp-αPPMX composition comprises at least 1%, 5%, 10%, 15%, 20%, 25%, 30%, 35, 40%, 45%, 50%, 55%, 60%, 65%, 70%, 75%, or more than 75%, w/w of the alpha polyglutamated PMX. In some embodiments, during the process of preparing the Lp-αPPMX, at least 1%, 5%, 10%, 15%, 20%, 25%, 30%, 35%, 40%, 45%, 50%, 55%, 60%, 65%, 70%, 75%, or more than 75%, of the starting material of alpha polyglutamated PMX is encapsulated (entrapped) in the anionic or neutral Lp-αPPMX. In some embodiments, the anionic or neutral Lp-αPPMX composition comprises at least 1%, 5%, 10%, 15%, 20%, 25%, 30%, 35, 40%, 45%, 50%, 55%, 60%, 65%, 70%, 75%, or more than 75%, w/w of the alpha tetraglutamated PMX. In some embodiments, the anionic or neutral Lp-αPPMX composition comprises at least 1%, 5%, 10%, 15%, 20%, 25%, 30%, 35, 40%, 45%, 50%, 55%, 60%, 65%, 70%, 75%, or more than 75%, w/w of the alpha pentaglutamated PMX. In some embodiments, the anionic or neutral Lp-αPPMX composition comprises at least 1%, 5%, 10%, 15%, 20%, 25%, 30%, 35, 40%, 45%, 50%, 55%, 60%, 65%, 70%, 75%, or more than 75%, w/w of the alpha hexaglutamated PMX. In additional embodiments, the alpha polyglutamated pemetrexed encapsulated by the liposome is in a HEPES buffered solution within the liposome.

In additional embodiments, the liposomal alpha polyglutamated pemetrexed composition is pegylated (PLp-αPPMX).

In some embodiments, the liposomal alpha polyglutamated pemetrexed composition is non-targeted (NTLp-αPPMX). That is, the NTLp-αPPMX composition does not have specific affinity towards an epitope (e.g., an epitope on a surface antigen) expressed on the surface of a target cell of interest. In further embodiments, the non-targeted liposomal alpha polyglutamated pemetrexed composition is pegylated (NTPLp-αPPMX).

In other embodiments, the liposomal alpha polyglutamated pemetrexed composition is targeted (TLp-αPPMX). That is, the TLp-αPPMX composition contains a targeting moiety that has specific affinity for an epitope (surface antigen) on a target cell of interest. In some embodiments, the targeting moiety of the TLp-αPPMX or TPLp-αPPMX is not attached to the liposome through a covalent bond. In other embodiments, the targeting moiety of the TLp-αPPMX or TPLp-αPPMX is attached to one or both of a PEG and the exterior of the liposome. Targeted liposomal alpha polyglutamated pemetrexed compositions (TLp-αPPMX and TPLp-αPPMX) provide further improvements over the efficacy and safety profile of pemetrexed, by specifically delivering alpha polyglutamated (e.g., tetraglutamated, pentaglutamated and hexaglutamated) pemetrexed to target cells such as cancer cells. In further embodiments, the targeted liposomal alpha polyglutamated pemetrexed composition is pegylated (TPLp-αPPMX). Function of the targeting moiety of the TLp-αPPMX and/or TPLp-αPPMX compositions include but are not limited to, targeting the liposome to the target cell of interest in vivo or in vitro; interacting with the surface antigen for which the targeting moiety has specific affinity, and delivering the liposome payload (αPPMX) into the cell.

Suitable targeting moieties are known in the art and include, but are not limited to, antibodies, antigen-binding antibody fragments, scaffold proteins, polypeptides, and peptides. In some embodiments, the targeting moiety is a polypeptide. In further embodiments, the targeting moiety is a polypeptide that comprises at least 3, 5, 10, 15, 20, 30, 40, 50, or 100, amino acid residues. In some embodiments, the targeting moiety is an antibody or an antigen-binding antibody fragment. In further embodiments, the targeting moiety comprises one or more of an antibody, a humanized antibody, an antigen binding fragment of an antibody, a single chain antibody, a single-domain antibody, a bi-specific antibody, a synthetic antibody, a pegylated antibody, and a multimeric antibody. In some embodiments, the targeting moiety has specific affinity for an epitope that is preferentially expressed on a target cell such as a tumor cell, compared to normal or non-tumor cells. In some embodiments, the targeting moiety has specific affinity for an epitope on a tumor cell surface antigen that is present on a tumor cell but absent or inaccessible on a non-tumor cell. In some embodiments, the targeting moiety binds an epitope of interest with an equilibrium dissociation constant (Kd) in a range of $0.5 \times 10^{-10}$ to $10 \times 10^{-6}$ as determined using BIA-CORE® analysis.

In particular embodiments, the targeting moiety comprises a polypeptide that specifically binds a folate receptor. In some embodiments, the targeting moiety is an antibody or an antigen-binding antibody fragment. In some embodiments, the folate receptor bound by the targeting moiety is one or more folate receptors selected from the group consisting of: folate receptor alpha (FR-α, FOLR1), folate receptor beta (FR-β, FOLR2), and folate receptor delta (FR-δ, FOLR4). In some embodiments, the folate receptor bound by the targeting moiety is folate receptor alpha (FR-α). In some embodiments, the folate receptor bound by the targeting moiety is folate receptor beta (FR-β). In some embodiments, the targeting moiety specifically binds FR-α and FR-β.

In additional embodiments, the liposome αPPMX composition comprises one or more of an immunostimulatory agent, a detectable marker, and a maleimide, disposed on at least one of the PEG and the exterior of the liposome. In some embodiments, the liposome αPPMX composition (e.g., Lp-αPPMX, PLp-αPPMX, NTLp-αPPMX, NTPLp-αPPMX, TLp-αPPMX, or TPLp-αPPMX) is cationic. In other embodiments, the liposome αPPMX composition (e.g., Lp-αPPMX, PLp-αPPMX, NTLp-αPPMX, NTPLp-αPPMX, TLp-αPPMX or TPLp-αPPMX) is anionic or neutral. In additional embodiments, the liposomeofthelipo-some αPPMX composition (e.g., Lp-αPPMX, PLp-αPPMX, NTLp-αPPMX, NTPLp-αPPMX, TLp-αPPMX or TPLp-αPPMX) has a diameter in the range of 20 nm to 500 nm, or any range therein between. In further embodiments, the liposome of the liposome αPPMX composition has a diameter in the range of 80 nm to 120 nm, or any range therein between. In some embodiments, the liposome αPPMX composition is pegylated (e.g., PLp-αPPMX, NTPLp-αPPMX, or TPLp-αPPMX). In some embodiments, the liposome αPPMX composition is targeted (e.g., TLp-αPPMX or TPLp-αPPMX). In further embodiments, the liposome αPPMX composition is pegylated and targeted (e.g., TPLp-αPPMX). In some embodiments, the liposome αPPMX composition comprises alpha polyglutamated pemetrexed that contains 4, 5, 6, 2-10, 4-6, or more than 5, glutamyl groups. In some embodiments, the liposome αPPMX composition comprises alpha tetraglutamated pemetrexed. In some embodiments, the liposome αPPMX composition comprises alpha pentaglutamated pemetrexed. In other embodiments, the liposome αPPMX composition comprises alpha hexaglutamated pemetrexed.

In some embodiments, the liposome compositions comprise of alpha polyglutamated pemetrexed that contains 4, 5, 6, 2-10, 4-6, or more than 5, glutamyl groups and at least 1%, 5%, 10%, 15%, 20%, 25%, 30%, 35%, 40%, 45%, 50%, 55%, 60%, 65%, 70%, 75%, or more than 75%, w/w of the alpha polyglutamated PMX. In some embodiments, the Lp-αPPMX composition comprises alpha polyglutamated pemetrexed that contains 4, 5, 6, 2-10, 4-6, or more than 5, glutamyl groups and 1%-98.5% w/w of the alpha polyglutamated PMX. In some embodiments, the liposomes comprise alpha polyglutamated pemetrexed that contains 4, 5, 6, 2-10, 4-6, or more than 5, glutamyl groups and wherein during the process of preparing the Lp-αPPMX, at least 1%, 5%, 10%, 15%, 20%, 25%, 30%, 35%, 40%, 45%, 50%, 55%, 60%, 65%, 70%, 75%, or more than 75% of the starting material of alpha polyglutamated PMX is encapsulated (entrapped) in the Lp-αPPMX.

In some embodiments, the liposome compositions comprise of alpha tetraglutamated pemetrexed and at least 1%, 5%, 10%, 15%, 20%, 25%, 30%, 35%, 40%, 45%, 50%, 55%, 60%, 65%, 70%, 75%, or more than 75%, w/w of the alpha tetraglutamated PMX. In some embodiments, the Lp-αPPMX composition comprises alpha tetraglutamated pemetrexed and 1%-98.5% w/w of the alpha tetraglutamated PMX. In some embodiments, the liposomes comprise alpha tetraglutamated pemetrexed and wherein during the process of preparing the Lp-αPPMX, at least 1%, 5%, 10%, 15%, 20%, 25%, 30%, 35%, 40%, 45%, 50%, 55%, 60%, 65%, 70%, 75%, or more than 75% of the starting material of alpha tetraglutamated PMX is encapsulated (entrapped) in the Lp-αPPMX.

In some embodiments, the liposome compositions comprise of alpha pentaglutamated pemetrexed and at least 1%, 5%, 10%, 15%, 20%, 25%, 30%, 35%, 40%, 45%, 50%, 55%, 60%, 65%, 70%, 75%, or more than 75%, w/w of the alpha pentaglutamated PMX. In some embodiments, the Lp-αPPMX composition comprises alpha pentaglutamated pemetrexed and 1%-98.5% w/w of the alpha pentaglutamated PMX. In some embodiments, the liposomes comprise alpha pentaglutamated pemetrexed and wherein during the process of preparing the Lp-αPPMX, at least 1%, 5%, 10%, 15%, 20%, 25%, 30%, 35%, 40%, 45%, 50%, 55%, 60%, 65%, 70%, 75%, or more than 75% of the starting material of alpha pentaglutamated PMX is encapsulated (entrapped) in the Lp-αPPMX. In some embodiments, the liposome compositions comprise of alpha hexaglutamated pemetrexed and at least 1%, 5%, 10%, 15%, 20%, 25%, 30%, 35%, 40%, 45%, 50%, 55%, 60%, 65%, 70%, 75%, or more than 75%, w/w of the alpha hexaglutamated PMX. In some embodiments, the Lp-αPPMX composition comprises alpha hexaglutamated pemetrexed and 1%-98.5% w/w of the alpha hexaglutamated PMX. In some embodiments, the liposomes comprise alpha hexaglutamated pemetrexed and wherein during the process of preparing the Lp-αPPMX, at least 1%, 5%, 10%, 15%, 20%, 25%, 30%, 35%, 40%, 45%, 50%, 55%, 60%, 65%, 70%, 75%, or more than 75% of the starting material of alpha pentaglutamated PMX is encapsulated (entrapped) in the Lp-αPPMX.

Liposomal compositions comprising liposomes encapsulating αPPMX are also provided. In some embodiments, the liposomal composition comprises a pegylated αPPMX composition. In some embodiments, the liposomal composition comprises a αPPMX composition that is linked to or otherwise associated with a targeting moiety. In further embodiments, the liposomal composition comprises a αPPMX composition that is pegylated and linked to or otherwise associated with a targeting moiety. In some embodiments, the liposomal composition comprises αPPMX that contains 4, 5, 6, 2-10, 4-6, or more than 5, glutamyl groups. In some embodiments, the liposomal composition comprises alpha tetraglutamated pemetrexed. In some embodiments, the liposomal composition comprises alpha pentaglutamated pemetrexed. In other embodiments, the liposomal composition comprises alpha hexaglutamated pemetrexed.

In some embodiments, the liposomal composition comprises a liposome αPPMX (e.g., Lp-αPPMX, PLp-αPPMX, NTLp-αPPMX, NTPLp-αPPMX, TLp-αPPMX, and TPLp-αPPMX). In some embodiments, the liposome αPPMX is pegylated (e.g., NTPLp-αPPMX, and TPLp-αPPMX). In some embodiments, the liposome αPPMX comprises a targeting moiety that has a specific affinity for an epitope of antigen on the surface of a target cell of interest such as a cancer cell (e.g., TLp-αPPMX or TPLp-αPPMX)). In further embodiments, the liposomal composition comprises a liposome αPPMX that is pegylated and further comprises a targeting moiety that has a specific affinity for an epitope of antigen on the surface of a target cell of interest such as a cancer cell (e.g., TPLp-αPPMX). In some embodiments, the liposomal composition comprises a liposome αPPMX that is cationic. In other embodiments, the liposomal composition comprises a liposome αPPMX that is anionic or neutral. In additional embodiments, the liposomal composition comprises a liposome αPPMX that has a diameter in the range of 20 nm to 500 nm, 20 nm to 200 nm, or any range therein between. In further embodiments, the liposome αPPMX has a diameter in the range of 80 nm to 120 nm, or any range therein between.

Pharmaceutical compositions comprising alpha polyglutamated pemetrexed (αPPMX) including delivery vehicles such as liposome αPPMX are also provided. In some embodiments, the pharmaceutical composition comprises a pegylated αPPMX composition. In some embodiments, the pharmaceutical composition comprise a αPPMX composition that is linked to or otherwise associated with a targeting moiety. In further embodiments, the pharmaceutical composition comprise a αPPMX composition that is pegylated and linked to or otherwise associated with a targeting moiety. In some embodiments, the pharmaceutical composition comprises αPPMX that contains 4, 5, 6, 2-10, 4-6, or more than 5, glutamyl groups. In some embodiments, the pharmaceutical composition comprises alpha tetraglutamated pemetrexed. In some embodiments, the pharmaceutical composition comprises alpha pentaglutamated pemetrexed. In other embodiments, the pharmaceutical composition comprises alpha hexaglutamated pemetrexed.

In some embodiments, the pharmaceutical compositions comprise a liposome αPPMX (e.g., Lp-αPPMX, PLp-αPPMX, NTLp-αPPMX, NTPLp-αPPMX, TLp-αPPMX, and TPLp-αPPMX). In some embodiments, the liposome αPPMX composition is pegylated (e.g., NTPLp-αPPMX, and TPLp-αPPMX). In some embodiments, the liposome αPPMX comprises a targeting moiety that has a specific affinity for an epitope of antigen on the surface of a target cell of interest such as a cancer cell (e.g., TLp-αPPMX or TPLp-αPPMX)). In further embodiments, the pharmaceutical composition comprises a liposome αPPMX composition that is pegylated and further comprises a targeting moiety that has a specific affinity for an epitope of antigen on the surface of a target cell of interest such as a cancer cell (e.g., TPLp-αPPMX). In some embodiments, the pharmaceutical composition comprises a liposome αPPMX that is cationic. In other embodiments, the pharmaceutical composition comprises a liposome αPPMX that is anionic or neutral. In additional embodiments, the pharmaceutical composition comprises a liposome αPPMX that has a diameter in the range of 20 nm to 500 nm or 20 nm to 500 nm, or any range therein between. In further embodiments, the liposome αPPMX composition has a diameter in the range of 80 nm to 120 nm, or any range therein between.

In additional embodiments, the disclosure provides a method of killing a cell that comprises contacting the cell with a composition comprising an alpha polyglutamated pemetrexed (αPPMX) composition. In some embodiments, the contacted cell is a mammalian cell. In further embodiments, the contacted cell is a human cell. In some embodiments, the contacted cell is a hyperproliferative cell. In further embodiments, the hyperproliferative cell is a cancer cell. In further embodiments, the contacted cancer cell is a primary cell or a cell from a cell line obtained/derived from a cancer selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. In some embodiments, the method is performed in vivo. In other embodiments, the method is performed in vitro. In some embodiments, the αPPMX contains 4, 5, 6, 2-10, 4-6, or more than 5, glutamyl groups. In some embodiments, the αPPMX composition comprises alpha tetraglutamated pemetrexed. In some embodiments, the αPPMX composition comprises alpha pentaglutamated pemetrexed. In other embodiments, the αPPMX composition comprises alpha hexaglutamated pemetrexed.

In additional embodiments, the disclosure provides a method of killing a cell that comprises contacting the cell with a liposome containing alpha polyglutamated pemetrexed (i.e., an Lp-αPPMX such as, PLp-αPPMX, NTLp-αPPMX, NTPLp-αPPMX, TLp-αPPMX or TPLp-αPPMX). In some embodiments, the contacted cell is a mammalian cell. In further embodiments, the contacted cell is a human cell. In some embodiments, the contacted cell is a hyperproliferative cell. In further embodiments, the contacted hyperproliferative cell is a cancer cell. In further embodiments, the cancer cell is a primary cell or a cell from a cell line obtained/obtained/derived from a cancer selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. In some embodiments, the method is performed in vivo. In other embodiments, the method is performed in vitro. In some embodiments, the liposome contains a αPPMX containing 4, 5, 6, 2-10, 4-6, or more than 5, glutamyl groups. In some embodiments, the liposome contains alpha tetraglutamated pemetrexed. In some embodiments, the liposome contains alpha pentaglutamated pemetrexed. In other embodiments, the liposome contains alpha hexaglutamated pemetrexed.

In additional embodiments, the disclosure provides a method for treating cancer that comprises administering an effective amount of a delivery vehicle (e.g., an immunoconjugate or liposome) comprising alpha polyglutamated pemetrexed to a subject having or at risk of having cancer. In some embodiments, the delivery vehicle is an antibody-containing immunoconjugate (comprising e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX). In some embodiments, the administered delivery vehicle is pegylated. In some embodiments, the administered delivery vehicle is not pegylated. In additional embodiments, the administered delivery vehicle comprises a targeting moiety that has a specific affinity for an epitope of antigen on the surface of a cancer cell. In additional embodiments, the delivery vehicle comprises a targeting moiety that specifically binds a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA1, EphA2, EphA3, EphA4, EphA5, EphA6, EphA7, EphA8, EphB1, EphB2, EphB3, EphB4, EphB6, an integrin (e.g., integrign αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle comprises a targeting moiety that specifically binds a cell surface antigen(s) derived from, or determined to be expressed on, a specific subject's cancer (tumor) such as a neoantigen. In some embodiments, the targeting moiety specifically binds a cell surface antigen(s) derived from or determined to be expressed on a specific subject's tumor such as a neoantigen. In some embodiments, the targeting moiety is an antibody or an antigen binding antibody fragment. In some embodiments, the administered delivery vehicle comprises αPPMX containing 4, 5, 6, 2-10, 4-6, or more than 5, glutamyl groups. In some embodiments, the administered delivery vehicle comprises alpha tetraglutamated pemetrexed. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In further embodiments, the administered delivery vehicle comprises L and D alpha polyglutamated pemetrexed. In some embodiments, the cancer is selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. In some embodiments, the cancer is lung cancer (e.g., NSCLC or mesothelioma). In some embodiments, the cancer is breast cancer (e.g., HER2++ or triple negative breast cancer). In some embodiments, the cancer is colorectal cancer. In some embodiments, the cancer is ovarian cancer. In some embodiments, the cancer is endometrial cancer. In some embodiments, the cancer is pancreatic cancer. In some embodiments, the cancer is liver cancer. In some embodiments, the cancer is head and neck cancer. In some embodiments, the cancer is osteosarcoma.

In additional embodiments, the disclosure provides a method for treating cancer that comprises administering an effective amount of a liposome comprising alpha polyglutamated pemetrexed (e.g., an Lp-αPPMX such as, PLp-αPPMX, NTLp-αPPMX, NTPLp-αPPMX, TLp-αPPMX, or TPLp-αPPMX) to a subject having or at risk of having cancer. In some embodiments, the liposome is pegylated. In some embodiments, the liposome is not pegylated. In additional embodiments, the liposome comprises a targeting moiety that has a specific affinity for an epitope of antigen on the surface of a cancer cell. In additional embodiments, the liposome comprises a targeting moiety that specifically binds a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. This also includes the use of cancer stem cell targeting moieties such as those targeting CD34, CD133 and CD44, CD138, and CD15. In some embodiments, the liposome comprises a targeting moiety that specifically binds a cell surface antigen(s) derived from or determined to be expressed on a specific subject's tumor such as a neoantigen. In some embodiments, the targeting moiety is an antibody or an antigen binding antibody fragment. In some embodiments, the liposome comprises αPPMX containing 4, 5, 6, 2-10, 4-6, or more than 5, glutamyl groups. In some embodiments, the liposome comprises alpha tetraglutamated pemetrexed. In some embodiments, the liposome comprises alpha pentaglutamated pemetrexed. In other embodiments, the liposome comprises alpha hexaglutamated pemetrexed. In some embodiments, the liposome comprises L alpha polyglutamated pemetrexed. In some embodiments, liposome comprises D alpha polyglutamated pemetrexed. In some embodiments, the liposome comprises L and D alpha polyglutamated pemetrexed. In some embodiments, the cancer is selected from the group consisting of: lung (e.g., non-small lung cancer), pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, and a hematologic malignancy (e.g., a leukemia or lymphoma). In some embodiments, the cancer is lung cancer (e.g., NSCLC or mesothelioma). In some embodiments, the cancer is breast cancer (e.g., HER2++ or triple negative breast cancer). In some embodiments, the cancer is colorectal cancer. In some embodiments, the cancer is ovarian cancer. In some embodiments, the cancer is endometrial cancer. In some embodiments, the cancer is pancreatic cancer. In some embodiments, the cancer is liver cancer. In some embodiments, the cancer is head and neck cancer. In some embodiments, the cancer is osteosarcoma.

In additional embodiments, the disclosure provides a method for treating cancer that comprises administering to a subject having or at risk of having cancer, an effective amount of a liposomal composition comprising a liposome that comprises alpha polyglutamated pemetrexed and a targeting moiety that has a specific affinity for an epitope of antigen on the surface of the cancer. In some embodiments, the liposome comprises a targeting moiety that specifically binds a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrign αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the administered liposome comprises a targeting moiety that specifically binds a cell surface antigen(s) derived from, or determined to be expressed on, a specific subject's tumor such as a neoantigen. In some embodiments, the administered liposomal composition comprises pegylated liposomes (e.g., TPLp-αPPMX). In some embodiments, the administered liposomal composition comprises liposomes that are not pegylated. In some embodiments, liposomes of the administered liposomal composition comprise a αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprise alpha hexaglutamated pemetrexed. In some embodiments, the liposomal composition is administered to treat a cancer selected from the group consisting of: lung cancer (e.g., non-small cell), pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, leukemia, lymphoma, and other B cell malignancies, myeloma and other plasma cell dysplasias or dyscrasias. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma.

In additional embodiments, the disclosure provides a method for treating cancer that comprises administering an effective amount of a liposomal composition to a subject having or at risk of having a cancer that expresses folate receptor on its cell surface, wherein the liposomal composition comprises liposomes that comprise (a) alpha polyglutamated pemetrexed (αPPMX) and (b) a targeting moiety that has specific binding affinity for a folate receptor. In some embodiments, the targeting moiety has specific binding affinity for folate receptor alpha (FR-α), folate receptor beta (FR-β), and/or folate receptor delta (FR-δ). In some embodiments, the targeting moiety has a specific binding affinity for folate receptor alpha (FR-α) and folate receptor beta (FR-β). In some embodiments, the administered liposomal composition comprises pegylated liposomes (e.g., TPLp-αPPMX). In some embodiments, the administered liposomal composition comprises liposomes that are not pegylated. In some embodiments, liposomes of the administered liposomal composition comprises an αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprises alpha hexaglutamated pemetrexed. In some embodiments, the liposomal composition is administered to treat a cancer selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma.

In additional embodiments, the disclosure provides a method for cancer maintenance therapy that comprises administering an effective amount of a liposomal composition comprising liposomes that contain alpha polyglutamated pemetrexed (Lp-αPPMX) to a subject that is undergoing or has undergone cancer therapy. In some embodiments, the administered liposomal composition is a PLp-αPPMX, NTLp-αPPMX, NTPLp-αPPMX, TLp-αPPMX or TPLp-αPPMX. In some embodiments, the administered liposomal composition comprises pegylated liposomes (e.g., PLp-αPPMX, NTPLp-αPPMX, or TPLp-αPPMX). In some embodiments, the administered liposomal composition comprises targeted liposomes (e.g., TLp-αPPMX or TPLp-αPPMX). In some embodiments, the administered liposomal composition comprises liposomes that are pegylated and targeted (e.g., TPLp-αPPMX). In some embodiments, liposomes of the administered liposomal composition comprises alpha polyglutamated pemetrexed that contains 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprise alpha hexaglutamated pemetrexed.

In additional embodiments, the disclosure provides a method for treating a disorder of the immune system that comprises administering an effective amount of a liposomal composition comprising liposomes that contain alpha polyglutamated pemetrexed (e.g., Lp-αPPMX, PLp-αPPMX, NTLp-αPPMX, NTPLp-αPPMX, TLp-αPPMX or TPLp-αPPMX) to a subject having or at risk of having a disorder of the immune system. In some embodiments, the liposomal composition is administered to treat an autoimmune disease. In a further embodiment, the liposomal composition is administered to treat rheumatoid arthritis. In some embodiments, the administered liposomal composition comprises pegylated liposomes (e.g., PLp-αPPMX, NTPLp-αPPMX, or TPLp-αPPMX). In some embodiments, the administered liposomal composition comprises targeted liposomes (e.g., TLp-αPPMX or TPLp-αPPMX) that contain a targeting moiety having a specific affinity for a surface antigen on a target cell of interest (e.g., an immune cell). In further embodiments, the administered liposomal composition comprises liposomes that are pegylated and targeted (e.g., TPLp-αPPMX)). In some embodiments, liposomes of the administered liposomal composition comprise alpha pentaglutamated pemetrexed that contains 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprise alpha hexaglutamated pemetrexed.

The disclosure also provides a method of delivering alpha polyglutamated pemetrexed to a tumor cancer cell that comprises: administering to a subject having the tumor, a composition comprising alpha polyglutamated pemetrexed (L-αPPMX) and a targeting moiety that has a specific binding affinity for an epitope on a surface antigen on the tumor cell or cancer cell. In some embodiments, the administered targeting moiety is associated with a delivery vehicle. In some embodiments, the delivery vehicle is an antibody or an antigen binding fragment of an antibody. In further embodiments, the delivery vehicle is a liposome. In further embodiments, the antibody, antigen-binding antibody fragment, or liposome is pegylated liposomes (e.g., TPLp-αPPMX). In some embodiments, the administered composition comprises alpha polyglutamated pemetrexed that contains 4, 5, 6, 2-10, 4-6, or more than 5, glutamyl groups. In some embodiments, the administered composition comprises alpha tetraglutamated pemetrexed. In some embodiments, the administered composition comprises alpha pentaglutamated pemetrexed. In other embodiments, the administered composition comprises alpha hexaglutamated pemetrexed.

In additional embodiments, the disclosure provides a method of preparing a liposomal composition that comprises a liposomal alpha polyglutamated pemetrexed (αPPMX) composition, the method comprising: forming a mixture comprising: liposomal components and a polyglutamated pemetrexed in solution; homogenizing the mixture to form liposomes in the solution; and processing the mixture to form liposomes containing polyglutamated pemetrexed. In some embodiments, the alpha polyglutamated pemetrexed contains 4, 5, 6, 2-10, 4-6, or more than 5, glutamyl groups. In some embodiments, the polyglutamated pemetrexed composition comprises alpha tetraglutamated pemetrexed. In some embodiments, the polyglutamated pemetrexed composition comprises alpha pentaglutamated pemetrexed. In other embodiments, the polyglutamated pemetrexed composition comprises alpha hexaglutamated pemetrexed.

In one embodiment, the disclosure provides a kit comprising an alpha polyglutamated pemetrexed composition or and/or αPPMX delivery vehicles such as liposomes containing αPPMX and αPPMX immunoconjugates (e.g., ADCs) described herein.

BRIEF DESCRIPTION OF THE DRAWINGS/FIGURES

FIGS. 1A-1L show chemical formulas of pemetrexed (FIG. 1A), exemplary alpha pemetrexed alpha polyglutamates, pemetrexed diglutamate (FIG. 1B), pemetrexed triglutamate (FIGS. 1C and 1D), pemetrexed tetraglutamate (FIGS. 1E and 1F), pemetrexed pentaglutamates (FIGS. 1G and 1H), pemetrexed hexaglutamates (FIGS. 1I and 1J), pemetrexed heptaglutamate (FIGS. 1K and 1L), pemetrexed octaglutamates (FIGS. 1M and 1N), exemplary alpha pemetrexed polyglutamates (FIG. 1O), and exemplary pemetrexed analogs (FIGS. 1P and 1Q). FIGS. 1R-1U FIGS. 1R-1U present depictions of exemplary branched pemetrexed polyglutamate structures, including a branched polyglutamate having a gamma glutamyl backbone and alpha glutamyl branches (FIG. 1S) and a branched polyglutamate having an alpha glutamyl backbone and gamma glutamyl branches (FIG. 1T).

FIG. 2 presents the relative potency of liposomal pemetrexed alpha-L hexaglutamate (liposomal aG6) and its mirror image, liposomal alpha-D hexaglutamate (liposomal aDG6) relative to pemetrexed following exposure of the cancer cell lines SW620 (CRC), HT-29 (colon cancer), H1806 (triple negative breast cancer), OAW28 (ovarian cancer), H292 (NSCLC, adenocarcinoma subtype), and H2342 (NSCLC, adenocarcinoma subtype), over 48 hours.

FIG. 3 presents an example dose response relationship of free pemetrexed L-gamma hexaglutamate (gG6), liposomal pemetrexed L-gamma hexaglutamate (liposomal gG6), pemetrexed, and folate receptor alpha targeting antibody (FR1Ab) liposomal pemetrexed L-gamma hexaglutamate (liposomal gG6-FR1Ab) in the NCI H2342 non-small cell lung cancer (NSCLC), adenocarcinoma subtype depicted as the percentage of viable cells after 48 hours of treatment. Folate receptor alpha targeted liposomes containing alpha polyglutamated pemetrexed are expected to also be successful in targeting and reducing the viability of NCI H2342 non-small cell lung cancer cells.

FIG. 4 presents an example dose response relationship of free pemetrexed L-gamma hexaglutamate (gG6), liposomal pemetrexed L-gamma hexaglutamate (liposomal gG6), pemetrexed, and folate receptor alpha targeting antibody (FR1Ab) liposomal pemetrexed L-gamma hexaglutamate (liposomal gG6-FR1Ab) in the HT-29 (colon cancer) at 48 hours. Folate receptor alpha targeted liposomes containing alpha polyglutamated pemetrexed are expected to also be successful in targeting and reducing the viability of HT-29 (colon cancer) cells.

FIG. 5 presents the treatment effect on HCC1806 triple negative breast cancer cells following exposure of liposomal pemetrexed alpha-L hexaglutamate (Lps Hexa aG6), liposomal pemetrexed alpha-D hexaglutamate (Lps Hexa aDG6), and to pemetrexed over 48 hours.

FIG. 6 presents the treatment effect on OAW28 ovarian cancer cells following exposure of liposomal pemetrexed alpha-L hexaglutamate (Lps Hexa aG6), liposomal pemetrexed alpha-D hexaglutamate (Lps Hexa aDG6), and to pemetrexed over 48 hours.

FIG. 7 presents the treatment effect on H292 non-small cell lung cancer cells following exposure of liposomal pemetrexed alpha-L hexaglutamate (Lps Hexa aG6), liposomal pemetrexed alpha-D hexaglutamate (Lps Hexa aDG6), as compared to pemetrexed over 48 hours.

FIG. 8 presents the treatment effect on H292 non-small cell lung cancer cells following exposure of various dose levels ranging from 16 to 128 nM of liposomal pemetrexed alpha-L hexaglutamate (Liposomal aG6), liposomal pemetrexed alpha-D hexaglutamate (Liposomal aDG6), and pemetrexed over 48 hours. At each of the tested dose ranges, the liposomal pemetrexed aG6 formulation is superior to inhibiting H292 non-small cell lung cancer cells compared to pemetrexed.

FIG. 9 presents the treatment effect on HCC1806 triple negative breast cancer cells following exposure of various dose levels ranging from 16 to 128 nM of liposomal pemetrexed alpha-L hexaglutamate (Liposomal aG6), liposomal pemetrexed alpha-D hexaglutamate (Liposomal aDG6), and pemetrexed over 48 hours. At each of the tested doses, the liposomal pemetrexed aG6 formulation is superior to pemetrexed in inhibiting HCC1806 triple negative breast cancer cells.

FIG. 10 presents the treatment effect on OAW28 ovarian cancer cells of liposomal pemetrexed alpha-L hexaglutamate (Liposomal aG6), liposomal alpha-D hexaglutamate (Liposomal aDG6), and pemetrexed following exposure over 48 hours following exposure over a range of concentrations. At the dose of 128 nM, pemetrexed appears to more effective than the Liposomal pemetrexed aG6 liposomal formulation, whereas the liposomal formulation at the dose of 32 nM and 64 nM has a better treatment effect than pemetrexed; at 16 nM the Liposomal pemetrexed aG6 treatment effect is similar in to pemetrexed.

Figure 13:
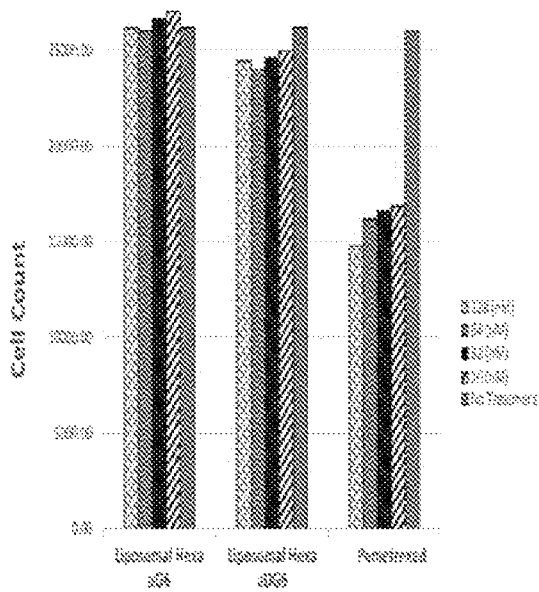

FIG. 13 shows the effect of liposomal pemetrexed alpha-L hexaglutamate (liposomal aG6), liposomal pemetrexed alpha-D hexaglutamate (liposomal aDG6), and pemetrexed on AML12 liver cells following exposure over 48 hours at 16 nM, 32 nM, and 64 nM, and 128 nM of the corresponding agent. Strikingly, there does not appear to be any toxicity to the AML12 liver cells following treatment with a liposomal pemetrexed aG6 at any of the liposomal agents at the dose levels tested. In contrast, pemetrexed treatment results in a reduction in the AML12 liver cell counts of approximately 40% at all doses studied.

Figure 14:
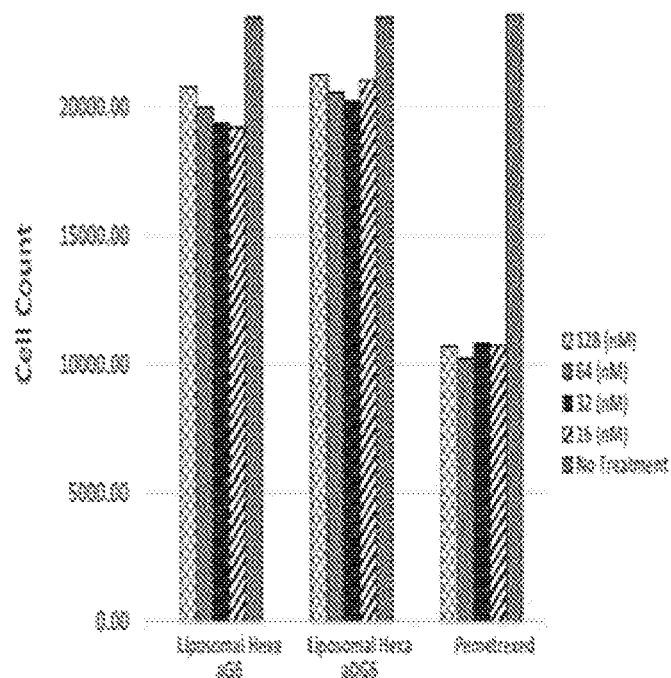

FIG. 14 shows the effect of liposomal pemetrexed alpha-L hexaglutamate (liposomal aG6), liposomal pemetrexed alpha-D hexaglutamate (liposomal aDG6), and pemetrexed on CCD841 colon epithelium cells following exposure over 48 hours at 16 nM, 32 nM, and 64 nM, and 128 nM, of the corresponding agent. At all of the concentrations tested, pemetrexed leads to approximately a ≥50% decrease in the number of CCD841 colon epithelium cells compared to approximately a 20% or less decrease in cell number after treatment with each of the liposome compositions tested.

Figure 15:
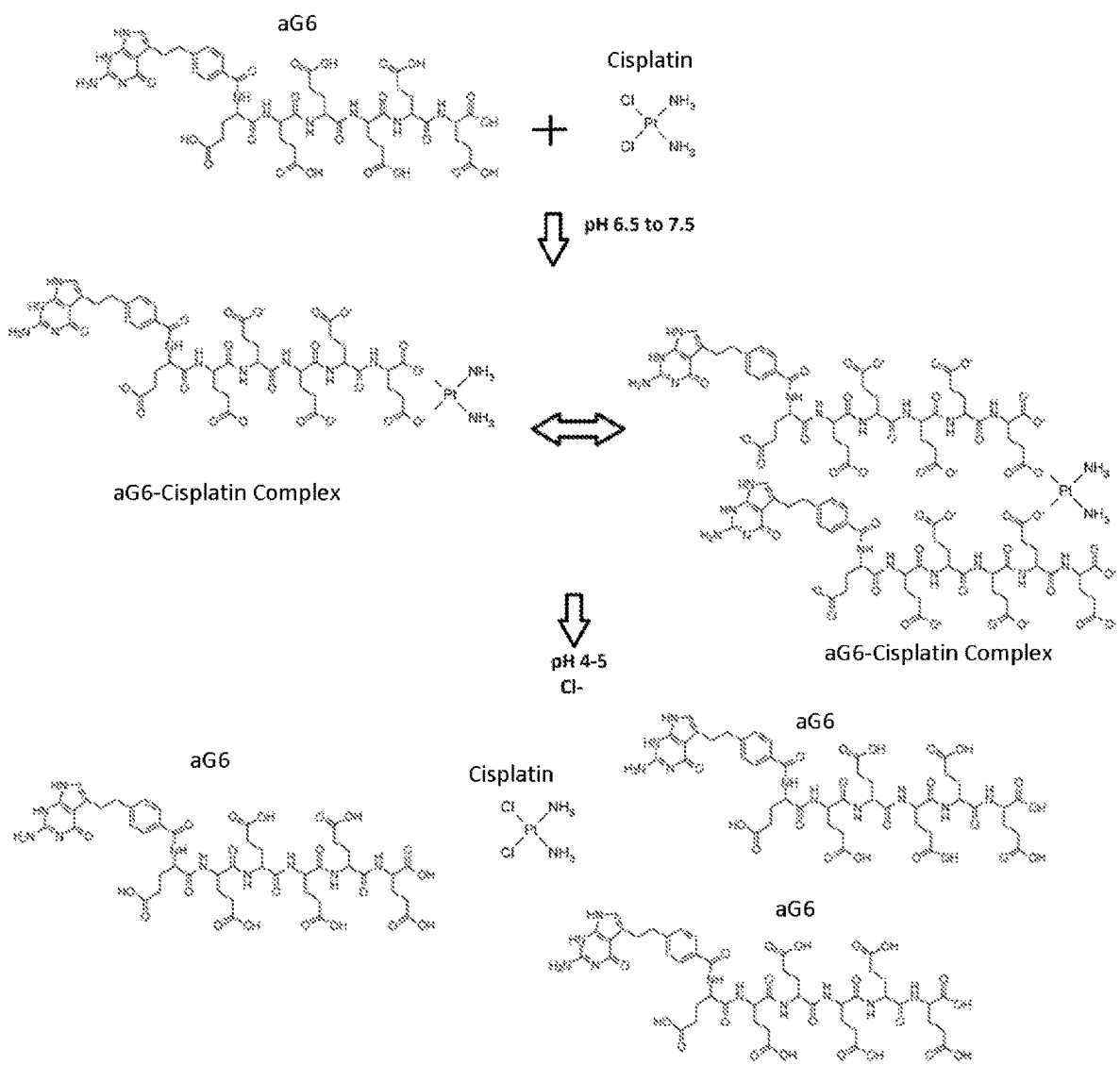

FIG. 15 depicts the structure of polyglutamate antifolate, Cisplatin (CDDP) and two potential aG6-Cisplatin complexes. The pH dependent formation of the interstrand and/or instrastrand coordination between the carboxyl groups of the polyglutamated antifolate and cisplatin is likely to disassemble into individual molecules of aG6 and cisplatin upon encountering acidic pH of lysosomes (pH 4-5) and presence of chloride ions inside the cells.

Figure 16:
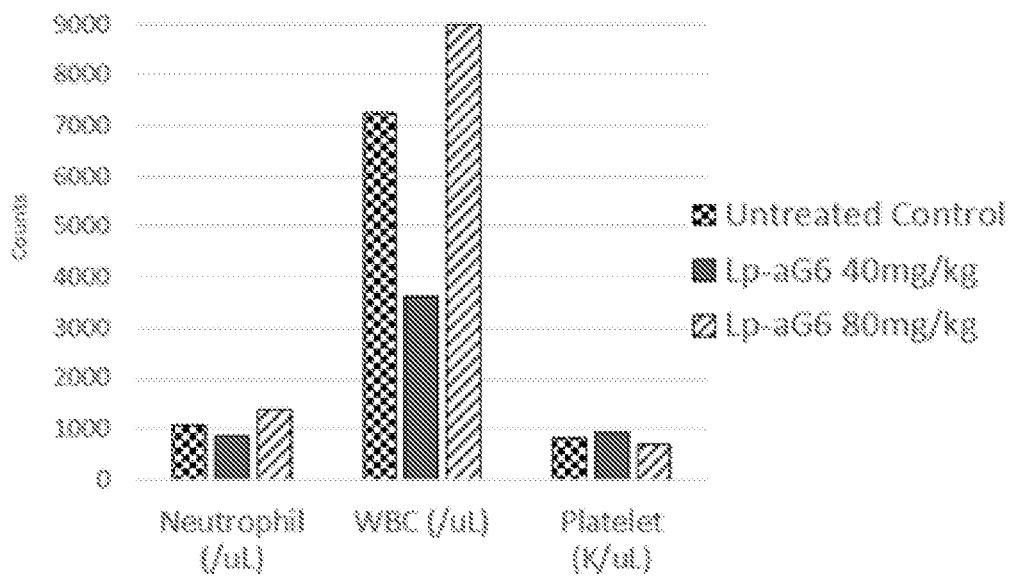

FIG. 16 presents the effects of liposomal aG6 treatment of mice with 40 mg/kg and 80 mg/kg given once weekly for 4 weeks upon the hematologic parameters: white blood cell (WBC) counts, neutrophil counts and as platelet counts. No appreciable decrease in mean neutrophil, mean white blood cell or mean platelet counts was observed.

Figure 17:
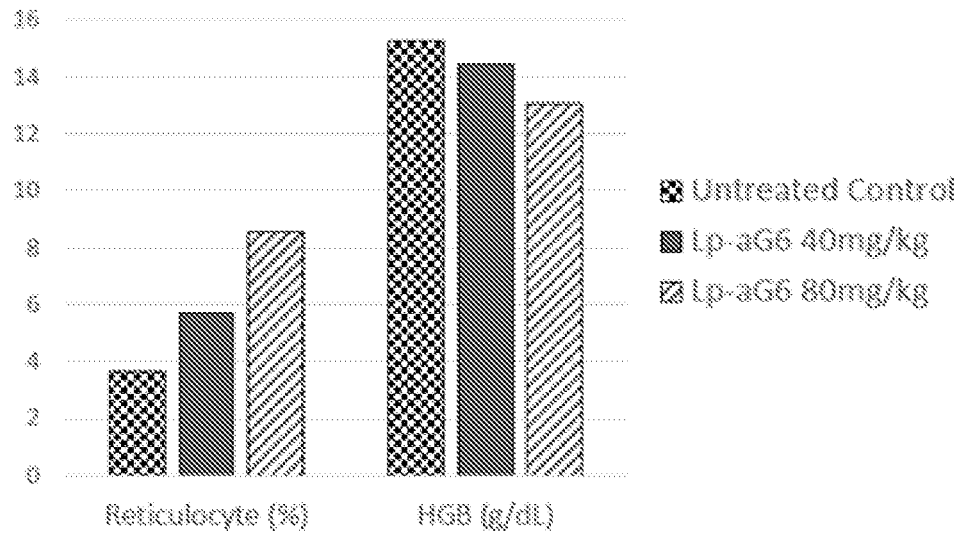
Figure 18:
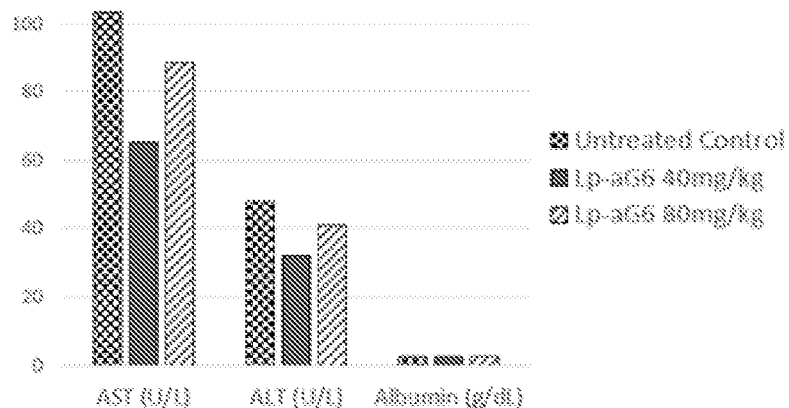

FIG. 17 presents the effects of liposomal aG6 treatment of mice with 40 mg/kg and 80 mg/kg given once weekly for 4 weeks upon hemoglobin and reticulocyte indices. There is a minimal decrease in mean hemoglobin concentrations at the higher dose level. In parallel there is a slight increase in mean reticulocytosis indices FIG. 18 presents the effects of liposomal aG6 treatment of mice with 40 mg/kg and 80 mg/kg given once weekly for 4 weeks upon hepatic markers including serum aspartate transaminase (AST) and serum alanine transaminase (ALT) along with serum albumin. There was no appreciable increases in liver transaminases mean AST or mean ALT levels and there was no observed change in mean albumin levels.

Figure 19:
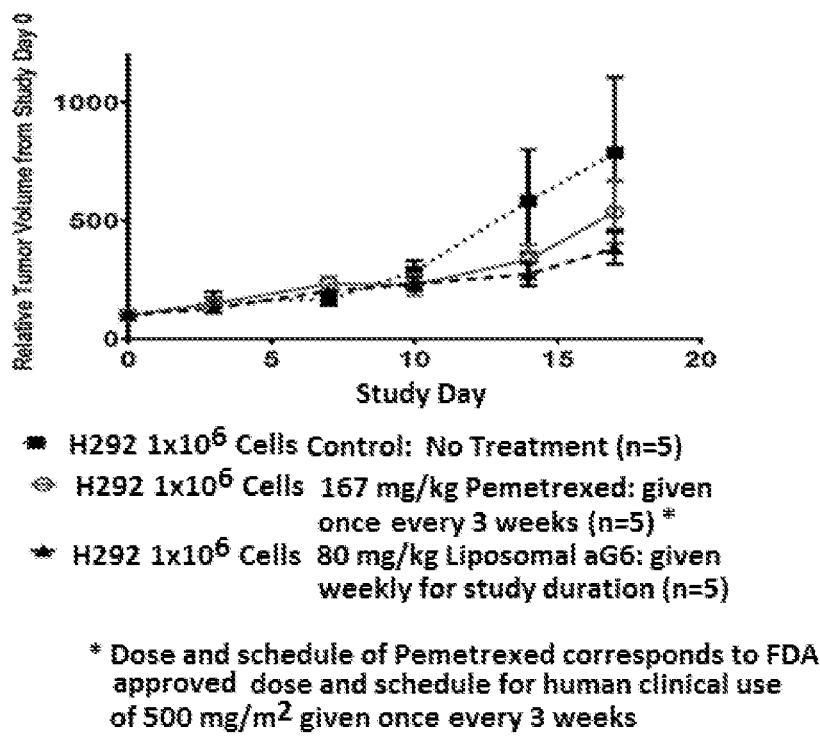

FIG. 19 presents the relative tumor volume of immunodeficient female Nu/J mice (6-8 weeks old) inoculated with NCI-H292 (Non-Small Cell Lung Cancer) cells and administered control, pemetrexed, and Liposomal aG6 intravenously at 167 mg/kg once every three weeks. As can be seen from these preliminary data, liposomal aG6 provides reduced tumor control compared to pemetrexed.

Figure 20:
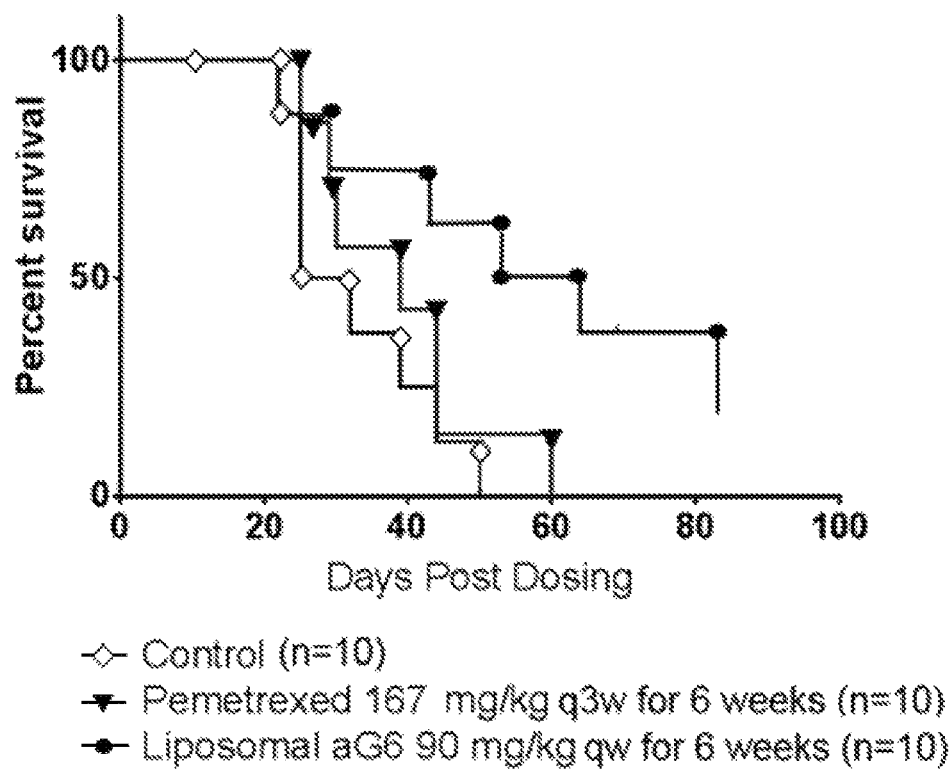

FIG. 20 presents the results of a liposomal pemetrexed alpha-L hexaglutamate (Liposomal aG6) treatment survival study in a NSCLC (H292) xenograft model. The survival curve of mice (10) dosed intravenously with 90 mg/kg Liposomal aG6 once a week for four weeks (90 mg/kg subQ weekly for 6 weeks) is depicted with a solid circle. The survival curve of mice (10) dosed with pemetrexed (167 mg/kg intravenously every three weeks for 6 weeks) is depicted with a solid triangle. The dose of 167 mg/kg of pemetrexed in mice is equivalent to a dose of 500 mg/m² in humans. The survival curve of control mice (10) is depicted with an open diamond.

Figure 21A:
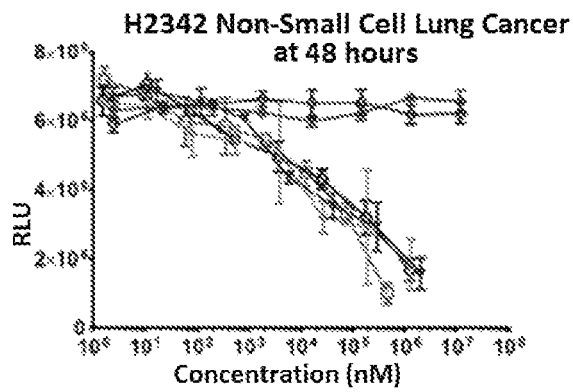
Figure 21D:
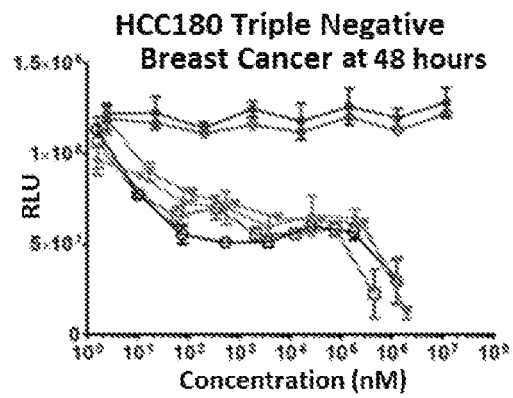
Figure 21B:
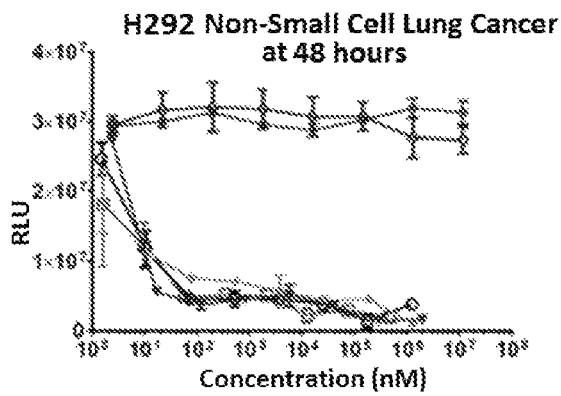
Figure 21E:
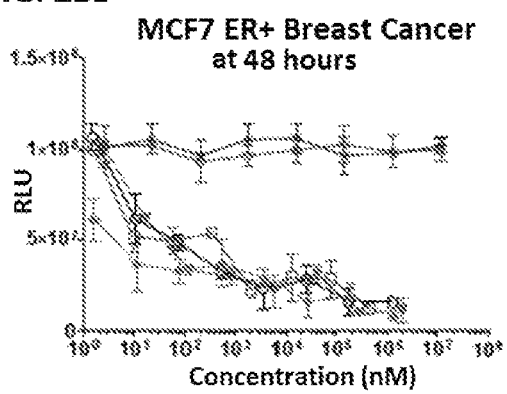
Figure 21C:
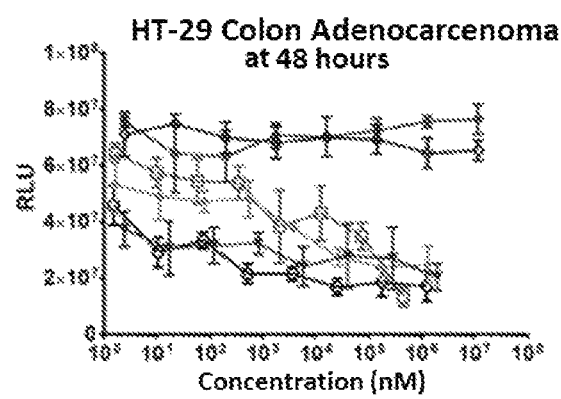
Figure 21F:
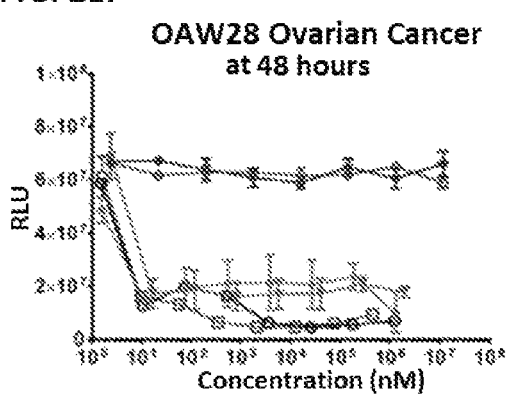

FIGS. 21A-F present the dose response relationship of liposomal pemetrexed alpha-L triglutamate (Liposomal aG3), liposomal pemetrexed alpha-L pentaglutamate (Liposomal aG5), liposomal pemetrexed alpha-L octaglutamate (Liposomal aG7), and a combination of liposomal pemetrexed alpha-L hexaglutamate (aG6) and alpha-L dodecaglutamate (aG12) (Liposomal aG6 and aG12), over 48 hours on H2342 (NSCLC, adenocarcinoma subtype)(FIG. 21A), H292 (NSCLC, adenocarcinoma subtype)(FIG. 21B), HT-29 (colon cancer)(FIG. 21C), HCC1806 (triple negative breast cancer)(FIG. 21D), MCF7 (ER+ breast cancer)(FIG. 21E), and OAW28 (ovarian cancer)(FIG. 21F). Cell viability was determined by CellTiter-Glo® (CTG) luminescent cell viability assay essentially as described in Example 1. As shown in all cell lines, the potency of each of the polyglutamated pemetrexed liposomal compositions well exceeded that of the liposomal vehicle and empty liposome controls.

DETAILED DESCRIPTION

The disclosure generally relates to novel alpha polyglutamated pemetrexed compositions. The compositions provide advances over prior treatments of hyperproliferative diseases such as cancer. Methods of making, delivering and using the alpha polyglutamated pemetrexed compositions are also provided. The alpha polyglutamated compositions have uses that include but are not limited to treating or preventing hyperproliferative diseases such as cancer, disorders of the immune system such as rheumatoid arthritis, and infectious diseases such as HIV and malaria.

I. Definitions

Unless defined otherwise, all technical and scientific terms used herein have the same meaning as commonly understood by one of ordinary skill in the art to which the disclosure pertains.

It is understood that wherever embodiments, are described herein with the language "comprising" otherwise analogous embodiments, described in terms of "containing" "consisting of" and/or "consisting essentially of" are also provided. However, when used in the claims as transitional phrases, each should be interpreted separately and in the appropriate legal and factual context (e.g., in claims, the transitional phrase "comprising" is considered more of an open-ended phrase while "consisting of" is more exclusive and "consisting essentially of" achieves a middle ground).

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

Unless indicated otherwise, the terms "pemetrexed" and "PMX" are used interchangeably to include a salt, acid and and/or free base form of pemetrexed (e.g., pemetrexed disodium). Compositions containing a PMX salt may further contain any of a variety of cations, such as $Na^+$, $Mg^{2+}$, $K^+$, $NH_4^+$, and/or $Ca^{2+}$. In particular embodiments, the salts are pharmaceutically acceptable salts. In additional particular embodiments, the PMX salt contains $Na^+$. Pemetrexed, may also be referred to as ALIMTA®, LY231514, MTA, by the chemical name N-[4-2-(2-Amino-4,7-dihydro-4-oxo-1H-pyrrolo[2,3-d]pyrimidin-5-yl)ethyl]benzoyl]-1-glutamic acid, or L-Glutamic acid, N-[4-[2-(2-amino-4,7-dihydro-4-oxo-1H-pyrrolo[2,3-c]pyramid-in-5-yl)ethyl]benzoyl]-, disodium salt, heptahydrate. Pemetrexed contains one L-gamma glutamyl group, and is therefore considered to be monoglutamated for the purpose of this disclosure.

The terms "polyglutamate", polyglutamated", or variations thereof, refer to a composition comprising at least one chain of 2 or more linked glutamyl groups. Polyglutamate chains can be linear or branched. Linear polyglutamate chains can contain for example, glutamyl groups containing either an alpha carboxyl group or a gamma carboxyl group linkage. Branched polyglutamate chains can comprise for example, one or more glutamyl groups that contain both an alpha carboxyl group and a gamma carboxyl group linkage to other glutamyl groups, thereby providing a branch point of the polyglutamate. Exemplary branched polyglutamates are depicted in FIGS. 1R-1U. Polyglutamate chains comprise an N-terminal glutamyl group and one or more C-terminal glutamyl groups. The N-terminal glutamyl group of a polyglutamate chain is not linked to another glutamyl group via its amine group, but is linked to one or more glutamyl group via its carboxylic acid group. In some embodiments, the N-terminal glutamyl group of a polyglutamated-pemetrexed is the glutamyl group of pemetrexed. The C-terminal glutamyl group or groups of a polyglutamate chain are linked to another glutamyl group via their amine group, but are not linked to another glutamyl group via their carboxylic acid group.

The terms "polyglutamated-pemetrexed", "polyglutamated-PMX", "PMX-PG", "PPMX" and iterations thereof, are used interchangeably herein to refer to a pemetrexed composition that comprises at least one glutamyl group in addition to the glutamyl group of pemetrexed (i.e., PMX-$PG_n$, wherein n≥1). Reference to the number of glutamyl groups in an αPPMX (PMX-PG) herein takes into account the glutamyl group of pemetrexed. For example, a PMX-PG composition containing 5 glutamyl residues in addition to the glutamyl group of PMX is referred to herein as hexaglutamated pemetrexed or pemetrexed hexaglutamate.

The terms "alpha glutamyl group", "alpha glutamate", and "alpha linkage" as they relate to the linkage of a glutamyl group, refers to a glutamyl group that contains an alpha carboxyl group linkage. In some embodiments, the alpha linkage is an amide bond between the alpha carboxyl group of one glutamyl group and a second glutamyl group. The alpha linkage can be between a glutamyl group and the glutamyl group of pemetrexed, or between the glutamyl group and a second glutamyl group that is not present in pemetrexed, such as a glutamyl group within a polyglutamate chain attached to pemetrexed.

The terms "gamma glutamyl group", "gamma glutamate", and "gamma linkage", as they relate to the linkage of a glutamyl group, refers to a glutamyl group that contains a gamma carboxyl group linkage. As discussed herein, once Pemetrexed enters the cell, it is polyglutamated by the enzyme folylpoly-gamma-glutamate synthetase (FPGS), which adds L glutamyl groups serially to the gamma carboxyl group of the glutamate within pemetrexed. Consequently, alpha polyglutamated pemetrexed compositions are not formed within cells during pemetrexed therapy. In some embodiments, the gamma linkage is an amide bond between the gamma carboxyl group of one glutamyl group and a second glutamyl group. The gamma linkage can be between a glutamyl group and the glutamyl group of pemetrexed, or between the glutamyl group and a second glutamyl group that is not present in pemetrexed, such as a glutamyl group within a polyglutamate chain attached to pemetrexed. In some embodiments, the gamma linkage refers to the amide bond of the glutamyl group in pemetrexed. Reference to gamma linkages are inclusive of gamma linkage of the glutamyl group in pemetrexed unless it is expressly stated or is unambiguously clear from the context that such is not intended.

Unless indicated otherwise, the terms "alpha polyglutamated pemetrexed", αPPMX", "alpha-PMX-PG", and iterations thereof, are used interchangeably herein to refer to a polyglutamated-pemetrexed composition that comprises at least one glutamyl group that contains an alpha linkage. For example, a pentaglutamated-PMX composition wherein the $2^{nd}$ glutamyl group has an alpha linkage, but each of the other glutamyl groups has a gamma linkage, is considered to be an alpha-PMX-PG for the purposes of this disclosure. In some embodiments, each of the glutamyl groups of the PMX-PG other than the glutamyl group of PMX, have an alpha linkage (e.g., PMX-$PG_n$, wherein n=5 and wherein each of $G_1$, $G_2$, $G_3$, $G_4$, and $G_5$, have an alpha linkage). In some embodiments, each of the glutamyl groups of the PMX-PG other than the C-terminal glutamyl group or groups and the glutamyl group of PMX, has an alpha linkage (e.g., PMX-$PG_n$, wherein n=5 and wherein each of $G_1$, $G_2$, $G_3$, and $G_4$, have an alpha linkage). In some embodiments, each of the glutamyl groups of the PMX-PG other than the C-terminal glutamyl group or groups, has an alpha linkage (e.g., PMX-$PG_n$, wherein n=5 and wherein each of the glutamyl group of PMX and $G_1$, $G_2$, $G_3$, and $G_4$, have an alpha linkage).

As use herein, the term "isolated" refers to a composition which is in a form not found in nature. Isolated alpha polyglutamated compositions include those which have been purified to a degree that they are no longer in a form in which they are found in nature. In some embodiments, an alpha polyglutamated pemetrexed which is isolated is substantially pure. Isolated compositions will be free or substantially free of material with which they are naturally associated such as other cellular components such as proteins and nucleic acids with which they may potentially be found in nature, or the environment in which they are prepared (e.g., cell culture). The alpha polyglutamated compositions may be formulated with diluents or adjuvants and still for practical purposes be isolated—for example, the alpha polyglutamated compositions will normally be mixed with pharmaceutically acceptable carriers or diluents when used in diagnosis or therapy. In some embodiments, the isolated alpha polyglutamated compositions (e.g., alpha polyglutamates and delivery vehicles such as liposomes containing the alpha polyglutamate contain less than 1% or less than 0.1% undesired DNA or protein content. In some embodiments, the alpha polyglutamate compositions (e.g., alpha polyglutamate and delivery vehicles such as liposomes containing the alpha polyglutamate) are "isolated."

The term "targeting moiety" is used herein to refer to a molecule that provides an enhanced affinity for a selected target, e.g., a cell, cell type, tissue, organ, region of the body, or a compartment, e.g., a cellular, tissue or organ compartment. The targeting moiety can comprise a wide variety of entities. Targeting moieties can include naturally occurring molecules, or recombinant or synthetic molecules. In some embodiments, the targeting moiety is an antibody, antigen-binding antibody fragment, bispecific antibody or other antibody-based molecule or compound. In some embodiments, the targeting moiety is an aptamer, avimer, a receptor-binding ligand, a nucleic acid, a biotin-avidin binding pair, a peptide, protein, carbohydrate, lipid, vitamin, toxin, a component of a microorganism, a hormone, a receptor ligand or any derivative thereof. Other targeting moieties are known in the art and are encompassed by the disclosure.

The terms "specific affinity" or "specifically binds" mean that a targeting moiety such as an antibody or antigen binding antibody fragment, reacts or associates more frequently, more rapidly, with greater duration, with greater affinity, or with some combination of the above to the epitope, protein, or target molecule than with alternative substances, including proteins unrelated to the target epitope. Because of the sequence identity between homologous proteins in different species, specific affinity can, in several embodiments, include a binding agent that recognizes a protein or target in more than one species. Likewise, because of homology within certain regions of polypeptide sequences of different proteins, the term "specific affinity" or "specifically binds" can include a binding agent that recognizes more than one protein or target. It is understood that, in certain embodiments, a targeting moiety that specifically binds a first target may or may not specifically bind a second target. As such, "specific affinity" does not necessarily require (although it can include) exclusive binding, e.g., binding to a single target. Thus, a targeting moiety may, in certain embodiments, specifically bind more than one target. In certain embodiments, multiple targets may be bound by the same targeting moiety.

The term "epitope" refers to that portion of an antigen capable of being recognized and specifically bound by a targeting moiety (i.e., binding moiety) such as an antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Expressions like "binding affinity for a target", "binding to a target" and analogous expressions known in the art refer to a property of a targeting moiety which may be directly measured through the determination of the affinity constants, e.g., the amount of targeting moiety that associates and dissociates at a given antigen concentration. Different methods can be used to characterize the molecular interaction, such as, but not limited to, competition analysis, equilibrium analysis and microcalorimetric analysis, and real-time interaction analysis based on surface plasmon resonance interaction (for example using a BIACORE® instrument). These methods are well-known to the skilled person and are described, for example, in Neri et al., Tibtech 14:465-470 (1996), and Jansson et al., J. Biol. Chem. 272:8189-8197 (1997).

The term "delivery vehicle" refers generally to any compositions that acts to assist, promote or facilitate entry of alpha polyglutamated pemetrexed into a cell. Such delivery vehicles are known in the art and include, but are not limited to, liposomes, liposphere, polymers (e.g., polymer-conjugates), peptides, proteins such as antibodies (e.g., immunoconjugates, such as Antibody Drug Conjugates (ADCs)) and antigen binding antibody fragments and derivatives thereof), cellular components, cyclic oligosaccharides (e.g., cyclodextrins), micelles, microparticles (e.g., microspheres), nanoparticles (e.g., lipid nanoparticles, biodegradable nanoparticles, and core-shell nanoparticles), hydrogels, lipoprotein particles, viral sequences, viral material, or lipid or liposome formulations, and combinations thereof. The delivery vehicle can be linked directly or indirectly to a targeting moiety. In some examples, the targeting moiety is selected from among a macromolecule, a protein, a peptide, a monoclonal antibody or a fatty acid lipid.

A "subject" refers to a human or vertebrate mammal including but not limited to a dog, cat, horse, goat and primate, e.g., monkey. Thus, the invention can also be used to treat diseases or conditions in non-human subjects. For instance, cancer is one of the leading causes of death in companion animals (i.e., cats and dogs). In some embodiments, of the invention, the subject is a human. In this disclosure, the term "subject" and "patient" is used interchangeably and has the same meaning. It is preferred generally that a maximum dose be used, that is, the highest safe dose according to sound medical judgment.

As used herein an "effective amount" refers to a dosage of an agent sufficient to provide a medically desirable result. The effective amount will vary with the desired outcome, the particular condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. An "effective amount" can be determined empirically and in a routine manner, in relation to the stated purpose. In the case of cancer, the effective amount of an agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), the response rates (RR), duration of response, and/or quality of life.

The terms "hyperproliferative disorder", "proliferative disease", and "proliferative disorder", are used interchangeably herein to pertain to an unwanted or uncontrolled cellular proliferation of excessive or abnormal cells which is undesired, such as, neoplastic or hyperplastic growth, whether in vitro or in vivo. In some embodiments, the proliferative disease is cancer or tumor disease (including benign or cancerous) and/or any metastases, wherever the cancer, tumor and/or the metastasis is located. In some embodiments, the proliferative disease is a benign or malignant tumor. In some embodiments, the proliferative disease is a non-cancerous disease. In some embodiments, the proliferative disease is a hyperproliferative condition such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

"Cancer," "tumor," or "malignancy" are used as synonymous terms and refer to any of a number of diseases that are characterized by uncontrolled, abnormal proliferation of cells, the ability of affected cells to spread locally or through the bloodstream and lymphatic system to other parts of the body (metastasize) as well as any of a number of characteristic structural and/or molecular features. "Tumor," as used herein refers to all neoplastic cell growth and proliferation, whether malignant or benign, and all pre-cancerous and cancerous cells and tissues. A "cancerous tumor," or "malignant cell" is understood as a cell having specific structural properties, lacking differentiation and being capable of invasion and metastasis. A cancer that can be treated using a αPPMX composition provided herein includes without limitation, a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. Other types of cancer and tumors that may be treated using a αPPMX composition are described herein or otherwise known in the art. The terms "cancer," "cancerous," "cell proliferative disorder," "proliferative disorder," and "tumor" are not mutually exclusive as referred to herein.

Terms such as "treating," or "treatment," or "to treat" refer to both (a) therapeutic measures that cure, slow down, lessen symptoms of, and/or halt progression of a diagnosed pathologic condition or disorder and (b) prophylactic or preventative measures that prevent and/or slow the development of a targeted disease or condition. Thus, subjects in need of treatment include those already with the cancer, disorder or disease; those at risk of having the cancer or condition; and those in whom the infection or condition is to be prevented. Subjects are identified as "having or at risk of having" cancer, an infectious disease, a disorder of the immune system, a hyperproliferative disease, or another disease or disorder referred to herein using well-known medical and diagnostic techniques. In certain embodiments, a subject is successfully "treated" according to the methods provided herein if the subject shows, e.g., total, partial, or transient amelioration or elimination of a symptom associated with the disease or condition (e.g., cancer, rheumatoid arthritis). In specific embodiments, the terms treating," or "treatment," or "to treat" refer to the amelioration of at least one measurable physical parameter of a proliferative disorder, such as growth of a tumor, not necessarily discernible by the patient. In other embodiments, the terms treating," or "treatment," or "to treat" refer to the inhibition of the progression of a proliferative disorder, either physically by, e.g., stabilization of a discernible symptom, physiologically by, e.g., stabilization of a physical parameter, or both. In other embodiments, the terms treating," or "treatment," or "to treat" refer to the reduction or stabilization of tumor size, tumor cell proliferation or survival, or cancerous cell count. Treatment can be with an α-PPMX composition, alone or in combination with an additional therapeutic agent.

"Subject" and "patient," and "animal" are used interchangeably and refer to mammals such as human patients and non-human primates, as well as experimental animals such as rabbits, rats, and mice, and other animals. Animals include all vertebrates, e.g., mammals and non-mammals, such as chickens, amphibians, and reptiles. "Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and other members of the class Mammalia known in the art. In a particular embodiment, the patient is a human.

"Treatment of a proliferative disorder" is used herein to include maintaining or decreasing tumor size, inducing tumor regression (either partial or complete), inhibiting tumor growth, and/or increasing the life span of a subject having the proliferative disorder. In one embodiment, the proliferative disorder is a solid tumor. Such tumors include, for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma. In one embodiment, the proliferative disorder is a hematologic malignancy. Such hematologic malignancies include for example, a leukemia, a lymphoma and other B cell malignancies, myeloma and other plasma cell dysplasias or dyscrasias.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "therapeutic agent" is used herein to refer to an agent or a derivative thereof that can interact with a hyperproliferative cell such as a cancer cell or an immune cell, thereby reducing the proliferative status of the cell and/or killing the cell. Examples of therapeutic agents include, but are not limited to, chemotherapeutic agents, cytotoxic agents, platinum-based agents (e.g., cisplatin, carboplatin, oxaliplatin), taxanes (e.g., TAXOL®), etoposide, alkylating agents (e.g., cyclophosphamide, ifosamide), metabolic antagonists (e.g., methotrexate (MTX), 5-fluorouracil gemcitabine, or derivatives thereof), antitumor antibiotics (e.g., mitomycin, doxorubicin), plant-derived antitumor agents (e.g., vincristine, vindesine, TAXOL®). Such agents may further include, but are not limited to, the anticancer agents trimetrexate, temozolomide, raltitrexed, S-(4-Nitrobenzyl)-6-thioinosine (NBMPR), 6-benzyguanidine (6-BG), bis-chloronitrosourea (BCNU) and camptothecin, or a therapeutic derivative of any thereof. Additional examples of therapeutic agents that may be suitable for use in accordance with the disclosed methods include, without limitation, anti-restenosis, pro- or anti-proliferative, anti-inflammatory, anti-neoplastic, antimitotic, anti-platelet, anticoagulant, antifibrin, antithrombin, cytostatic, antibiotic and other anti-infective agents, anti-enzymatic, anti-metabolic, angiogenic, cytoprotective, angiotensin converting enzyme (ACE) inhibiting, angiotensin II receptor antagonizing and/or cardioprotective agents. "Therapeutic agents" also refer to salts, acids, and free based forms of the above agents.

As used herein, the term "chemotherapeutic agent" when used in relation to cancer therapy, refers to any agent that results in the death of cancer cells or inhibits the growth or spread of cancer cells. Examples of such chemotherapeutic agents include alkylating agents, antibiotics, antimetabolitic agents, plant-derived agents, and hormones. In some embodiments, the chemotherapeutic agent is cisplatin. In some embodiments, the chemotherapeutic agent is carboplatin. In some embodiments, the chemotherapeutic agent is oxaliplatin. In other embodiments, the chemotherapeutic agent is gemcitabine. In other embodiments, the chemotherapeutic agent is doxorubicin.

The term "antimetabolite" is used herein to refer to a therapeutic agent that inhibits the utilization of a metabolite or a prodrug thereof. Examples of antimetabolites include methotrexate, pemetrexed, 5-fluorouracil, 5-fluorouracil prodrugs such as capecitabine, 5-fluorodeoxyuridine monophosphate, cytarabine, cytarabine prodrugs such as nelarabine, 5-azacytidine, gemcitabine, mercaptopurine, thioguanine, azathioprine, adenosine, pentostatin, erythrohydroxynonyladenine, and cladribine. Anti-metabolites useful for practicing the disclosed methods include nucleoside analogs, including a purine or pyrimidine analogs. In some embodiments, the alpha polyglutamated pemetrexed compositions are used in combination with an antimetabolite selection from the group consisting of fluoropyrimidine 5-fluorouracil, 5-fluoro-2'-deoxycytidine, cytarabine, gemcitabine, troxacitabine, decitabine, Azacytidine, pseudoisocytidine, Zebularine, Ancitabine, Fazarabine, 6-azacytidine, capecitabine, $N^4$-octadecyl-cytarabine, elaidic acid cytarabine, fludarabine, cladribine, clofarabine, nelarabine, forodesine, and pentostatin, or a derivative thereof. In one example, the nucleoside analog is a substrate for a nucleoside deaminase that is adenosine deaminase or cytidine deaminase. In some examples, the nucleoside analog is selected from among fludarabine, cytarabine, gemcitabine, decitabine and azacytidine or derivatives thereof. In certain embodiments, the antimetabolite is 5-fluorouracil.

As used herein, a "taxane" is an anti-cancer agent that interferes with or disrupts microtubule stability, formation and/or function. Taxane agents include paclitaxel and docetaxel as well as derivatives thereof, wherein the derivatives function against microtubules by the same mode of action as the taxane from which they are derived. In certain embodiments, the taxane is paclitaxel or docetaxel, or a pharmaceutically acceptable salt, acid, or derivative of paclitaxel or docetaxel. In certain embodiments, the taxane is paclitaxel (TAXOL®), docetaxel (TAXOTERE®), albumin-bound paclitaxel (nab-paclitaxel; ABRAXANE®), DHA-paclitaxel, or PG-paclitaxel.

The term "pharmaceutically-acceptable carrier" and "pharmaceutically acceptable carrier" refers to an ingredient in a pharmaceutical formulation, other than an active ingredient, which is nontoxic to a subject. A pharmaceutically acceptable carrier includes, but is not limited to, a buffer, carrier, excipient, stabilizer, diluent, or preservative. Pharmaceutically-acceptable carriers can include for example, one or more compatible solid or liquid filler, diluents or encapsulating substances which are suitable for administration to a human or other subject.

This disclosure generally relates novel alpha polyglutamated pemetrexed (PMX) compositions and methods of making and using the compositions to treat diseases including hyperproliferative diseases such as cancer, disorders of the immune system such as rheumatoid arthritis, and infectious diseases such as HIV and malaria.

In some embodiments, the disclosure provides:
[1] a composition comprising an alpha polyglutamated pemetrexed, wherein at least one glutamyl group has an alpha carboxyl group linkage;
[2] the composition of [1], wherein the alpha polyglutamated pemetrexed comprises 1-10 glutamyl groups having an alpha carboxyl group linkage;
[3] the composition according to any of [1]-[2], wherein the alpha polyglutamated pemetrexed contains 4, 5, 6, 2-10, 4-6, or greater than 5, glutamyl groups;
[4] the composition according to any of [1]-[3], which comprises alpha tetraglutamated pemetrexed;
[5] the composition according to any of [1]-[3], which comprises alpha pentaglutamated pemetrexed;
[6] the composition according to any of [1]-[3], which comprises alpha hexaglutamated pemetrexed;
[7] the composition according to any of [1] to [6], wherein
  (a) two or more glutamyl groups have an alpha carboxyl group linkage,
  (b) each of the glutamyl groups other than the glutamyl group of pemetrexed has an alpha carboxyl group linkage; or
  (c) two or more glutamyl groups have a gamma carboxyl group linkage;
[8] the composition according to any of [1] to [6], wherein
  (a) each of the glutamyl groups other than the C-terminal glutamyl group or groups and the glutamyl group of pemetrexed has an alpha carboxyl group linkage; or
  (b) each of the glutamyl groups other than the C-terminal glutamyl group or groups has an alpha carboxyl group linkage;
[9] the composition according to any of [1]-[8], wherein at least one glutamyl group has both an alpha carboxyl group linkage and a gamma carboxyl group linkage;
[10] The composition according to any of [1]-[9], wherein:
  (a) at least 2 of the glutamyl groups of the alpha polyglutamated pemetrexed are in the L-form,
  (b) each of the glutamyl groups of the alpha polyglutamated pemetrexed is in the L-form,
  (c) at least 1 of the glutamyl groups of the alpha polyglutamated pemetrexed is in the D-form,
  (d) each of the glutamyl groups of the alpha polyglutamated pemetrexed other than the glutamyl group of pemetrexed is in the D-form, or
  (e) at least 2 of the glutamyl groups of the alpha polyglutamated pemetrexed are in the L-form and at least 1 of the glutamyl groups is in the D-form;
[11] the composition according to any of [1]-[10], wherein the polyglutamate is linear;
[12] the composition according to any of [1]-[10], wherein the polyglutamate is branched;
[13] a liposomal composition comprising the alpha polyglutamated pemetrexed according to any of [1]-[12] (Lp-αPPMX);
[14] the LαPP composition according to [13], wherein the alpha polyglutamated pemetrexed comprises glutamyl groups in the L-form having alpha carboxyl group linkages;
[15] the Lp-αPPMX composition according to [13] or [14], wherein each of the glutamyl groups of the alpha polyglutamated pemetrexed is in the L-form;
[16] the Lp-αPPMX composition of [13] or [14], wherein at least one of the glutamyl groups of the alpha polyglutamated pemetrexed is in the D-form;
[17] the Lp-αPPMX composition according to any of [13]-[16], wherein the liposome comprises an alpha polyglutamated pemetrexed containing 4, 5, 6, 2-10, 4-6, or more than 5, glutamyl groups;
[18] the Lp-αPPMX composition according to any of [13]-[17], wherein at least one of the glutamyl groups of the alpha polyglutamated pemetrexed has a gamma carboxyl group linkage;

[19] the composition according to any of [13]-[18], wherein at least one glutamyl group has both an alpha carboxyl group linkage and a gamma carboxyl group linkage;

[20] the composition according to any of [13]-[18], which contains 2, 3, 4, 5, 6, 2-10, 4-6, or more than 5, glutamyl groups that have both an alpha carboxyl group linkage and a gamma carboxyl group linkage;

[21] the Lp-αPPMX composition according to any of [13]-[20], wherein the liposome comprises an alpha polyglutamated pemetrexed containing alpha tetraglutamated pemetrexed, alpha pentaglutamated pemetrexed, or alpha hexaglutamated pemetrexed;

[22] the Lp-αPPMX composition according to any of [13]-[21], wherein the polyglutamate is linear or branched;

[23] the Lp-αPPMX composition according to any of [13]-[22], wherein the liposome is pegylated (PαLp-αPPMX);

[24] the Lp-αPPMX composition according to any of [13]-[23], wherein the liposomes comprise at least 1% weight by weight (w/w) of the alpha polyglutamated pemetrexed or wherein during the process of preparing the Lp-αPPMX, at least 1% of the starting material of alpha polyglutamated PMX is encapsulated (entrapped) in the Lp-αPPMX;

[25] the Lp-αPPMX composition according to any of [13]-[24], wherein the liposome has a diameter in the range of 20 nm to 500 nm or 20 nm to 200 nm;

[26] the Lp-αPPMX composition according to any of [13]-[25], wherein the liposome has a diameter in the range of 80 nm to 120 nm;

[27] the Lp-αPPMX composition according to any of [13]-[26], wherein the liposome is formed from liposomal components;

[28] the Lp-αPPMX composition according to [27], wherein the liposomal components comprise at least one of an anionic lipid and a neutral lipid;

[29] the Lp-αPPMX composition according to [27] or [28], wherein the liposomal components comprise at least one selected from the group consisting of: DSPE; DSPE-PEG; DSPE-PEG-maleimide; HSPC; HSPC-PEG; cholesterol; cholesterol-PEG; and cholesterol-maleimide;

[30] the Lp-αPPMX composition according to any of [27]-[29], wherein the liposomal components comprise at least one selected from the group consisting of: DSPE; DSPE-PEG; DSPE-PEG-FITC; DSPE-PEG-maleimide; cholesterol; and HSPC;

[31] the Lp-αPPMX composition according to any of [27]-[30], wherein one or more liposomal components further comprises a steric stabilizer;

[32] the Lp-αPPMX composition according to [31], wherein the steric stabilizer is at least one selected from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L-amino-acid-based polymer; oligoglycerol, copolymer containing polyethylene glycol and polypropylene oxide, Poloxamer 188, and polyvinyl alcohol;

[33] the Lp-αPPMX composition according to [32], wherein the steric stabilizer is PEG and the PEG has a number average molecular weight (Mn) of 200 to 5000 daltons;

[34] the Lp-αPPMX composition according to any of [13]-[33], wherein the liposome is anionic or neutral;

[35] the Lp-αPPMX composition according to any of [13]-[33], wherein the liposome has a zeta potential that is less than or equal to zero;

[36] the Lp-αPPMX composition according to any of [13]-[33], wherein the liposome has a zeta potential that is between 0 to −150 mV;

[37] the Lp-αPPMX composition according to any of [13]-[33], wherein the liposome has a zeta potential that is between −30 to −50 mV;

[38] the Lp-αPPMX composition according to any of [13]-[33], wherein the liposome is cationic;

[39] the Lp-αPPMX composition according to any of [13]-[38], wherein the liposome has an interior space comprising the alpha polyglutamated pemetrexed and an aqueous pharmaceutically acceptable carrier;

[40] the Lp-αPPMX composition of [39], wherein the pharmaceutically acceptable carrier comprises a tonicity agent such as dextrose, mannitol, glycerine, potassium chloride, sodium chloride, at a concentration of greater than 1%;

[41] the Lp-αPPMX composition of [39], wherein the aqueous pharmaceutically acceptable carrier is trehalose;

[42] the Lp-αPPMX composition of [41], wherein the pharmaceutically acceptable carrier comprises 5% to 20% weight of trehalose;

[43] the Lp-αPPMX composition according to any of [39]-[42], wherein the pharmaceutically acceptable carrier comprises 1% to 15 weight of dextrose;

[44] the Lp-αPPMX composition according to any of [39]-[43], wherein the interior space of the liposome comprises 5% dextrose suspended in an HEPES buffered solution;

[45] the Lp-αPPMX composition according to any of [39]-[44], wherein the pharmaceutically acceptable carrier comprises a buffer such as HEPES Buffered Saline (HBS) or similar, at a concentration of between 1 to 200 mM and a pH of between 2 to 8;

[46] the Lp-αPPMX composition according to any of [39]-[45], wherein the pharmaceutically acceptable carrier comprises a total concentration of sodium acetate and calcium acetate of between 50 mM to 500 mM;

[47] the Lp-αPPMX composition according to any of [13]-[46], wherein the interior space of the liposome has a pH of 5-8 or a pH of 6-7, or any range therein between;

[48] the Lp-αPPMX composition according to any of [13]-[47], wherein the liposome comprises less than 500,000 or less than 200,000 molecules of the alpha polyglutamated pemetrexed;

[49] the Lp-αPPMX composition according to any of [13]-[48], wherein the liposome comprises between 10 to 100,000 molecules of the alpha polyglutamated pemetrexed, or any range therein between;

[50] the Lp-αPPMX composition according to any of [13]-[49], which further comprises a targeting moiety and wherein the targeting moiety has a specific affinity for a surface antigen on a target cell of interest;

[51] the Lp-αPPMX composition according to [50], wherein the targeting moiety is attached to one or both of a PEG and the exterior of the liposome, optionally wherein targeting moiety is attached to one or both of the PEG and the exterior of the liposome by a covalent bond;

[52] the Lp-αPPMX composition of [50] or [51], wherein the targeting moiety is a polypeptide;

[53] the Lp-αPPMX composition according to any of [50]-[52], wherein the targeting moiety is an antibody or an antigen binding fragment of an antibody;

[54] the Lp-αPPMX composition according to any of [50]-[53], wherein the targeting moiety binds the surface antigen with an equilibrium dissociation constant (Kd) in a range of $0.5 \times 10^{-10}$ to $10 \times 10^{-6}$ as determined using BIACORE® analysis;

[55] the Lp-αPPMX composition according to any of [50]-[55], wherein the targeting moiety specifically binds one or more folate receptors selected from the group consisting of: folate receptor alpha (FR-α), folate receptor beta (FR-β), and folate receptor delta (FR-δ);

[56] the Lp-αPPMX composition according to any of [50]-[56], wherein the targeting moiety comprises one or more selected from the group consisting of: an antibody, a humanized antibody, an antigen binding fragment of an antibody, a single chain antibody, a single-domain antibody, a bi-specific antibody, a synthetic antibody, a pegylated antibody, and a multimeric antibody;

[57] the Lp-αPPMX composition according to any of [50]-[56], wherein each pegylated liposome comprises from 1 to 1000 or 30-200 targeting moieties;

[58] the Lp-αPPMX composition according to any of [58], further comprising one or more of an immunostimulatory agent, a detectable marker and a maleimide, wherein the immunostimulatory agent, the detectable marker or the maleimide is attached to said PEG or the exterior of the liposome;

[59] the Lp-αPPMX composition according to any of [39]-[58], wherein immunostimulating agent is at least one selected from the group consisting of: a protein immunostimulating agent; a nucleic acid immunostimulating agent; a chemical immunostimulating agent; a hapten; and an adjuvant;

[60] the Lp-αPPMX composition of [58] or [59], wherein the immunostimulating agent is at least one selected from the group consisting of: a fluorescein; a fluorescein isothiocyanate (FITC); a DNP; a beta glucan; a beta-1,3-glucan; a beta-1,6-glucan; a resolvin (e.g., a Resolvin D such as $D_{n-6DPA}$ or $D_{n-3DPA}$, a Resolvin E, or a T series resolvin); and a Toll-like receptor (TLR) modulating agent such as, an oxidized low-density lipoprotein (e.g., OXPAC, PGPC), and an eritoran lipid (e.g., E5564);

[61] the Lp-αPPMX composition according to any of [58]-[60], wherein the immunostimulatory agent and the detectable marker is the same;

[62] the Lp-αPPMX composition according to any of [58]-[61], further comprising a hapten;

[63] the Lp-αPPMX composition of [62], wherein the hapten comprises one or more of fluorescein or Beta 1,6-glucan;

[64] the Lp-αPPMX composition according to any of [13]-[63], which further comprises in the interior space, the exterior space, or both the interior space and the exterior space at least one cryoprotectant selected from the group consisting of mannitol; trehalose; sorbitol; and sucrose;

[65] a targeted composition comprising the composition according to any of [1]-[64];

[66] an non-targeted composition comprising the composition according to any of [1]-[49];

[67] The Lp-αPPMX composition according to any of [13]-[66], which further comprises carboplatin and/or pembroluzumab;

[68] a pharmaceutical composition comprising the liposomal alpha polyglutamated pemetrexed composition according to any of [13]-[67];

[69] a pharmaceutical composition comprising alpha polyglutamated pemetrexed composition according to any of [1]-[8];

[70] the composition of any of [1]-[69], for use in the treatment of disease;

[71] use of the composition of any of [1]-[70], in the manufacture of a medicament for the treatment of disease;

[72] a method for treating or preventing disease in a subject needing such treatment or prevention, the method comprising administering the composition of any of [1]-[70] to the subject;

[73] a method for treating or preventing disease in a subject needing such treatment or prevention, the method comprising administering the liposomal alpha polyglutamated pemetrexed composition of any of [13]-[69] to the subject;

[74] a method of killing a hyperproliferative cell that comprises contacting a hyperproliferative cell with the composition of any of [1]-[69];

[75] a method of killing a hyperproliferative cell that comprises contacting a hyperproliferative cell with the liposomal alpha polyglutamated pemetrexed composition of any of [13]-[69];

[76] the method of [74] or [75], wherein the hyperproliferative cell is a cancer cell, a mammalian cell, and/or a human cell;

[77] a method for treating cancer that comprises administering an effective amount of the composition of any of [1]-[69] to a subject having or at risk of having cancer;

[78] a method for treating cancer that comprises administering an effective amount of the liposomal alpha polyglutamated pemetrexed composition of any of [13]-[68] to a subject having or at risk of having cancer;

[79] the method of [77] or [78], wherein the cancer is selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dyscrasias;

[80] the method of [77] or [78], wherein the cancer is a member selected from the group consisting of: lung cancer, breast cancer, colon cancer, pancreatic cancer, gastric cancer, bladder cancer, head and neck cancer, ovarian cancer, and cervical cancer;

[81] the method of [77] or [78], wherein the cancer is wherein the cancer is mesothelioma or non-small cell lung carcinoma (NSCLC);

[82] the method of [77] or [78], wherein the cancer is a sarcoma such as osteosarcoma;

[83] a method for treating cancer that comprises administering an effective amount of the Lp-αPPMX composition of any of [50]-[66] to a subject having or at risk of having a cancer cell that expresses on its surface a folate receptor bound by the targeting moiety;

[84] a maintenance therapy comprising administering an effective amount of the composition of any of [1]-[69] to a subject that is undergoing or has undergone cancer therapy;

[85] a maintenance therapy comprising administering an effective amount of the liposomal alpha polyglutamated pemetrexed composition of any of [13]-[69] to a subject that is undergoing or has undergone cancer therapy;

[86] a method for treating a disorder of the immune system that comprises administering an effective amount of the composition of any of [1]-[69] to a subject having or at risk of having a disorder of the immune system;

[87] a method for treating a disorder of the immune system that comprises administering an effective amount of the liposomal alpha polyglutamated pemetrexed composition of any of [9]-[69] to a subject having or at risk of having a disorder of the immune system;

[88] a method for treating an infectious disease that comprises administering an effective amount of the composition of any of [1]-[69] to a subject having or at risk of having an infectious disease;

[89] a method for treating an infectious disease that comprises administering an effective amount of the liposomal alpha polyglutamated pemetrexed composition of any of [13]-[69] to a subject having or at risk of having an infectious disease;

[90] a method of delivering alpha polyglutamated pemetrexed to a tumor expressing a folate receptor on its surface, the method comprising: administering the Lp-αPPMX composition of any of [1]-[69] to a subject having the tumor in an amount to deliver a therapeutically effective dose of the alpha polyglutamated pemetrexed to the tumor;

[91] a method of preparing an alpha polyglutamated pemetrexed composition comprising the liposomal alpha polyglutamated pemetrexed composition of any of [13]-[69], the method comprising: forming a mixture comprising: liposomal components and alpha polyglutamated pemetrexed in solution; homogenizing the mixture to form liposomes in the solution; and processing the mixture to form liposomes containing alpha polyglutamated pemetrexed;

[92] a method of preparing an alpha polyglutamated pemetrexed composition comprising the liposomal alpha polyglutamated pemetrexed composition of any of [13]-[69], the method comprising: forming a mixture comprising: liposomal components and alpha polyglutamated pemetrexed in solution; and processing the mixture to form liposomes containing alpha polyglutamated pemetrexed;

[93] the method of [92], wherein the processing the mixture comprises homogenizing the mixture to form liposomes in the solution;

[94] a method of preparing the composition of any of [13]-[69] comprising the steps of: forming a mixture comprising: liposomal components and alpha polyglutamated pemetrexed in a solution; homogenizing the mixture to form liposomes in the solution; processing the mixture to form liposomes entrapping and/or encapsulating alpha polyglutamated pemetrexed; and providing the targeting moiety on a surface of the liposomes, the targeting moiety having the specific affinity for at least one of folate receptor alpha (FR-α), folate receptor beta (FR-β) and folate receptor delta (FR-δ);

[95] a method of preparing the composition of any of [50]-[69], comprising the steps of: forming a mixture comprising: liposomal components and alpha polyglutamated pemetrexed in a solution; processing the mixture to form liposomes entrapping and/or encapsulating alpha polyglutamated pemetrexed; and providing the targeting moiety on a surface of the liposomes, the targeting moiety having the specific affinity for at least one of folate receptor alpha (FR-α), folate receptor beta (FR-β) and folate receptor delta (FR-δ);

[96] The method of [95], wherein the processing step comprises homogenizing the mixture to form liposomes in the solution;

[97] the method according to any of [94] to [96], wherein the processing step includes one or more steps of: thin film hydration, extrusion, in-line mixing, ethanol injection technique, freezing-and-thawing technique, reverse-phase evaporation, dynamic high pressure microfluidization, microfluidic mixing, double emulsion, freeze-dried double emulsion, 3D printing, membrane contactor method, and stirring;

[98] the method according to any of [94] to [97], wherein said processing step includes one or more steps of modifying the size of the liposomes by one or more of steps of extrusion, high-pressure microfluidization, and/or sonication; and/or

[99] the method of any of [91] to [98], wherein at least 1% of the starting material of alpha polyglutamated PMX is encapsulated or entrapped in the Lp-αPPMX.

II. Alpha Polyglutamated Pemetrexed (αPPMX)

The disclosure generally relates alpha polyglutamated pemetrexed (αPPMX) compositions. The αPPMX compositions comprise at least one glutamyl group having an alpha linkage. These compositions are structurally distinct from the L-gamma polyglutamated forms of pemetrexed (LαPPMX) that are produced by the enzyme folylpoly-gamma-glutamate synthetase (FPGS) in cells during pemetrexed therapy.

In some embodiments, the αPPMX composition contains 2-20, 2-15, 2-10, 2-5, or more than 5, glutamyl groups (including the glutamyl group in pemetrexed). In some embodiments, each of the glutamyl groups in the αPPMX other than the glutamyl group of pemetrexed, have an alpha linkage. In some embodiments, each of the glutamyl groups in the αPPMX other than the C-terminal glutamyl group or groups and the glutamyl group of pemetrexed, has an alpha linkage. In some embodiments, each of the glutamyl groups in the αPPMX other than the C-terminal glutamyl group or groups has an alpha linkage. In some embodiments, 2 or more of the glutamyl groups in the αPPMX have a gamma linkage. In some embodiments, at least one glutamyl group of the alpha polyglutamated pemetrexed has both an alpha carboxyl group linkage and a gamma carboxyl group linkage. In some embodiments, each of the glutamyl groups in the αPPMX is in the L-form. In some embodiments, each of the glutamyl groups in the αPPMX other than the glutamyl group of pemetrexed, is in the D-form. In some embodiments, the αPPMX comprises two or more glutamyl groups in the L-form and one or more glutamyl groups in the D-form. In some embodiments, the polyglutamate chain of the αPPMX is linear (not branched). In some embodiments, the polyglutamate chain of the αPPMX is branched.

In some embodiments, the alpha polyglutamated pemetrexed is diglutamated. That is, the alpha polyglutamated pemetrexed contains 1 additional glutamyl group in addition to the glutamyl group of pemetrexed (αPMX-PG$_1$), and the additional glutamyl group is linked to the glutamyl group in pemetrexed through an alpha linkage. In some embodiments, each of the glutamyl groups of the alpha diglutamated pemetrexed is in the L-form. In other embodiments, the alpha diglutamated PMX comprises a glutamyl group in the D-form.

In some embodiments, the alpha polyglutamated pemetrexed is triglutamated. That is, the alpha polyglutamated pemetrexed contains 2 additional glutamyl groups in addition to the glutamyl group of pemetrexed (αPMX-PG$_2$). In some embodiments, each of the 2 additional glutamyl groups have an alpha linkage. In other embodiments, one of the 2 additional glutamyl groups have an alpha linkage and the other glutamyl group has a gamma linkage. In some embodiments, one of the 2 additional glutamyl groups has an alpha linkage. In some embodiments, one of the 2 additional glutamyl groups has a gamma linkage. In some embodiments, two of the three glutamyl groups have an alpha linkage. In other embodiments, one of the three glutamyl groups has an alpha linkage and another glutamyl group has a gamma linkage. In some embodiments, one glutamyl group has both an alpha linkage and a gamma linkage. In some embodiments, each of the glutamyl groups of the alpha triglutamated pemetrexed is in the L-form. In other embodiments, the alpha triglutamated PMX comprises a glutamyl group in the D-form. In further embodiments, each of the glutamyl groups of the alpha triglutamated pemetrexed other than the glutamyl group of pemetrexed, is in the D-form. In additional embodiments, the triglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is tetraglutamated and thus contains 3 additional glutamyl groups in addition to the glutamyl group in pemetrexed (αPMX-PG$_3$). In some embodiments, each of the 3 additional glutamyl groups have an alpha linkage. In other embodiments, 1 or 2 of the 3 additional glutamyl groups have an alpha linkage and the remaining 2 or 1 glutamyl groups, respectively, have a gamma linkage. In some embodiments, 2 of the 3 additional glutamyl groups have an alpha linkage. In other embodiments, one of the 3 additional glutamyl groups has an alpha linkage and another additional glutamyl group has a gamma linkage. In other embodiments, one of the 3 additional glutamyl groups has an alpha linkage and a gamma linkage. In other embodiments, three of the four glutamyl groups have an alpha linkage. In some embodiments, at least one glutamyl group has both an alpha linkage and a gamma linkage. In some embodiments, the alpha tetraglutamated PMX comprises two or more glutamyl groups in the L-form. In further embodiments, each of the glutamyl groups of the alpha tetraglutamated pemetrexed is in the L-form. In other embodiments, the alpha tetraglutamated PMX comprises a glutamyl group in the D-form. In further embodiments, each of the glutamyl groups of the alpha tetraglutamated pemetrexed other than the glutamyl group of pemetrexed, is in the D-form. In additional embodiments, the tetraglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is pentaglutamated (αPMX-PG$_4$) and contains a chain of 4 additional glutamyl groups attached to the glutamyl group of pemetrexed. In some embodiments, each of the 4 additional glutamyl groups in the chain have an alpha linkage. In some embodiments, each of the 4 additional glutamyl groups in the chain other than the C-terminal glutamyl group or groups have an alpha linkage. In other embodiments, 1, 2, or 3, of the 4 additional glutamyl groups have an alpha linkage and the remaining 3, 2, or 1, glutamyl groups, respectively, are linked to a glutamyl group of the molecule through a gamma linkage. In other embodiments, 1 or 2 of the 4 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 5 glutamyl groups has both an alpha linkage and a gamma linkage. In some embodiments, each of the 5 glutamyl groups in the chain other than the C-terminal glutamyl group or groups have an alpha linkage. In some embodiments, the alpha pentaglutamated PMX comprises two or more glutamyl groups in the L-form. In further embodiments, each of the glutamyl groups of the alpha pentaglutamated pemetrexed is in the L-form. In other embodiments, the alpha pentaglutamated PMX comprises a glutamyl group in the D-form. In further embodiments, each of the glutamyl groups of the alpha pentaglutamated pemetrexed other than the glutamyl group of pemetrexed, is in the D-form. In additional embodiments, the pentaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is hexaglutamated (αPMX-PG$_5$) and contains a chain of 5 additional glutamyl groups attached to the glutamyl group of pemetrexed. In some embodiments, each of the 5 additional glutamyl groups in the chain have an alpha linkage. In some embodiments, each of the 5 additional glutamyl groups in the chain other than the C-terminal glutamyl group or groups have an alpha linkage. In some embodiments, 4 of the 5 additional glutamyl groups in the chain have an alpha linkage. In other embodiments, 1, 2, 3, or 4, of the 5 additional glutamyl groups are linked to a glutamyl group of the molecule through an alpha linkage and the remaining 4, 3, 2, or 1, glutamyl groups, respectively, are linked to a glutamyl group of the molecule through a gamma linkage. In other embodiments, 1, 2, 3, or 4 of the 5 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 6 glutamyl groups has both an alpha linkage and a gamma linkage. In some embodiments, each of the 6 glutamyl groups other than the C-terminal glutamyl group or groups have an alpha linkage. In some embodiments, 5 of the 6 glutamyl groups have an alpha linkage. In some embodiments, the alpha hexaglutamated PMX comprises two or more glutamyl groups in the L-form. In further embodiments, each of the glutamyl groups of the alpha hexaglutamated pemetrexed is in the L-form. In other embodiments, the alpha hexaglutamated PMX comprises a glutamyl group in the D-form. In further embodiments, each of the glutamyl groups of the alpha hexaglutamated pemetrexed other than the glutamyl group of pemetrexed, is in the D-form. In additional embodiments, the hexaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is heptaglutamated ($\alpha$PMX-PG$_6$) and thus contains a chain of 6 additional glutamyl groups attached to the glutamyl group of pemetrexed. In some embodiments, each of the 6 additional glutamyl groups have an alpha linkage. In some embodiments, each of the 6 additional glutamyl groups in the chain other than the C-terminal glutamyl group or groups have an alpha linkage. In some embodiments, 5 of the 6 additional glutamyl groups in the chain have an alpha linkage. In other embodiments, 1, 2, 3, 4, or 5, of the 6 additional glutamyl groups have an alpha linkage and the remaining 5, 4, 3, 2, or 1, glutamyl groups, respectively, have a gamma linkage. In other embodiments, 1, 2, 3, 4, or 5 of the 6 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 7 glutamyl groups has both an alpha linkage and a gamma linkage. In some embodiments, each of the 7 glutamyl groups other than the C-terminal glutamyl group or groups have an alpha linkage. In some embodiments, 6 of the 7 glutamyl groups have an alpha linkage. In some embodiments, the alpha heptaglutamated PMX comprises two or more glutamyl groups in the L-form. In further embodiments, each of the glutamyl groups of the alpha heptaglutamated pemetrexed is in the L-form. In other embodiments, the alpha heptaglutamated PMX comprises a glutamyl group in the D-form. In further embodiments, each of the glutamyl groups of the alpha heptaglutamated pemetrexed other than the glutamyl group of pemetrexed, is in the D-form. In additional embodiments, the heptaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is octaglutamated ($\alpha$PMX-PG) and thus contains a chain of 7 additional glutamyl groups attached to the glutamyl group of pemetrexed. In some embodiments, each of the 7 additional glutamyl groups in the chain other than the C-terminal glutamyl group or groups have an alpha linkage. In some embodiments, 6 of the 7 additional glutamyl groups in the chain have an alpha linkage. In some embodiments, each of the 7 additional glutamyl groups have an alpha linkage. In other embodiments, 1, 2, 3, 4, 5, or 6, of the 7 additional glutamyl groups have an alpha linkage and the remaining 6, 5, 4, 3, 2, or 1, glutamyl groups, respectively, have a gamma linkage. In other embodiments, 1, 2, 3, 4, 5, or 6 of the 7 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 8 glutamyl groups has both an alpha linkage and a gamma linkage. In some embodiments, each of the 8 glutamyl groups other than the C-terminal glutamyl group or groups have an alpha linkage. In some embodiments, 7 of the 8 glutamyl groups have an alpha linkage. In some embodiments, the alpha octaglutamated PMX comprises two or more glutamyl groups in the L-form. In further embodiments, each of the glutamyl groups of the alpha octaglutamated pemetrexed is in the L-form. In other embodiments, the alpha octaglutamated PMX comprises a glutamyl group in the D-form. In further embodiments, each of the glutamyl groups of the alpha octaglutamated pemetrexed other than the glutamyl group of pemetrexed, is in the D-form. In additional embodiments, the octaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is nonaglutamated ($\alpha$PMX-PG$_8$) and contains a chain of 8 additional glutamyl groups attached to the glutamyl group of pemetrexed. In some embodiments, each of the 8 additional glutamyl groups in the chain other than the C-terminal glutamyl group or groups have an alpha linkage. In some embodiments, 7 of the 8 additional glutamyl groups in the chain have an alpha linkage. In some embodiments, each of the 8 additional glutamyl groups have an alpha linkage. In other embodiments, 1, 2, 3, 4, 5, 6, or 7, of the 8 additional glutamyl groups have an alpha linkage and the remaining 7, 6, 5, 4, 3, 2, or 1, glutamyl groups, respectively, have a gamma linkage. In other embodiments, 1, 2, 3, 4, 5, 6, or 7 of the 8 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 9 glutamyl groups has both an alpha linkage and a gamma linkage. In some embodiments, each of the 9 glutamyl groups other than the C-terminal glutamyl group or groups have an alpha linkage. In some embodiments, 8 of the 9 glutamyl groups have an alpha linkage. In some embodiments, the alpha nonaglutamated PMX comprises two or more glutamyl groups in the L-form. In further embodiments, each of the glutamyl groups of the alpha nonaglutamated pemetrexed is in the L-form. In other embodiments, the alpha nonaglutamated PMX comprises a glutamyl group in the D-form. In further embodiments, each of the glutamyl groups of the alpha nonaglutamated pemetrexed other than the glutamyl group of pemetrexed, is in the D-form. In additional embodiments, the nonaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is decaglutamated ($\alpha$PMX-PG$_9$) (i.e., contains a chain of 9 additional glutamyl groups attached to the glutamyl group of pemetrexed). In some embodiments, each of the 9 additional glutamyl groups have an alpha linkage. In some embodiments, each of the 9 additional glutamyl groups in the chain other than the C-terminal glutamyl group or groups have an alpha linkage. In some embodiments, 8 of the 9 additional glutamyl groups in the chain have an alpha linkage. In other embodiments, 1, 2, 3, 4, 5, 6, 7, or 8, of the 9 additional glutamyl groups have an alpha linkage and the remaining 8, 7, 6, 5, 4, 3, 2, or 1, glutamyl groups, respectively, have a gamma linkage. In other embodiments, 1, 2, 3, 4, 5, 6, 7, or 8 of the 9 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 10 glutamyl groups has both an alpha linkage and a gamma linkage. In some embodiments, each of the 10 glutamyl groups other than the C-terminal glutamyl group or groups have an alpha linkage. In some embodiments, 9 of the 10 glutamyl groups have an alpha linkage. In some embodiments, the alpha decaglutamated PMX comprises two or more glutamyl groups in the L-form. In further embodiments, each of the glutamyl groups of the alpha decaglutamated pemetrexed is in the L-form. In other embodiments, the alpha decaglutamated PMX comprises a glutamyl group in the D-form. In further embodiments, each of the glutamyl groups of the alpha decaglutamated pemetrexed other than the glutamyl group of pemetrexed, is in the D-form. In additional embodiments, the decaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is undecaglutamated (αPMX-PG$_{10}$). In some embodiments, each of the 10 additional glutamyl groups have an alpha linkage. In some embodiments, each of the 10 additional glutamyl groups in the chain other than the C-terminal glutamyl group or groups have an alpha linkage. In some embodiments, 9 of the 10 additional glutamyl groups in the chain have an alpha linkage. In other embodiments, 1, 2, 3, 4, 5, 6, 7, 8, or 9, of the 10 additional glutamyl groups have an alpha linkage and the remaining 9, 8, 7, 6, 5, 4, 3, 2, or 1, glutamyl groups, respectively, have a gamma linkage. In other embodiments, 1, 2, 3, 4, 5, 6, 7, 8, or 9 of the 10 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 11 glutamyl groups has both an alpha linkage and a gamma linkage. In some embodiments, each of the 11 glutamyl groups other than the C-terminal glutamyl group or groups have an alpha linkage. In some embodiments, 10 of the 11 glutamyl groups have an alpha linkage. In some embodiments, the alpha undecaglutamated PMX comprises two or more glutamyl groups in the L-form. In further embodiments, each of the glutamyl groups of the alpha undecaglutamated pemetrexed is in the L-form. In other embodiments, the alpha undecaglutamated PMX comprises a D glutamyl group. In further embodiments, each of the glutamyl groups of the alpha undecaglutamated pemetrexed other than the glutamyl group of pemetrexed, is in the D-form. In additional embodiments, the undecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is dodecaglutamated (αPMX-PG$_{11}$). In some embodiments, each of the 11 additional glutamyl groups have an alpha linkage. In some embodiments, each of the 11 additional glutamyl groups in the chain other than the C-terminal glutamyl group or groups have an alpha linkage. In some embodiments, 10 of the 11 additional glutamyl groups in the chain have an alpha linkage. In other embodiments, 1, 2, 3, 4, 5, 6, 7, 8, 9, or 10, of the 11, additional glutamyl groups have an alpha linkage and the remaining 10, 9, 8, 7, 6, 5, 4, 3, 2, or 1, glutamyl groups, respectively, have a gamma linkage. In other embodiments, 1, 2, 3, 4, 5, 6, 7, 8, 9, or 10 of the 11 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 12 glutamyl groups has both an alpha linkage and a gamma linkage. In some embodiments, each of the 12 glutamyl groups other than the C-terminal glutamyl group or groups have an alpha linkage. In some embodiments, 11 of the 12 glutamyl groups have an alpha linkage. In some embodiments, the alpha dodecaglutamated PMX comprises two or more glutamyl groups in the L-form. In further embodiments, each of the glutamyl groups of the alpha dodecaglutamated pemetrexed is in the L-form. In other embodiments, the alpha dodecaglutamated PMX comprises a glutamyl group in the D-form. In further embodiments, each of the glutamyl groups of the alpha dodecaglutamated pemetrexed other than the glutamyl group of pemetrexed, is in the D-form. In additional embodiments, the dodecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is triskaidecaglutamated (αPMX-PG$_{12}$). In some embodiments, each of the 12 additional glutamyl groups have an alpha linkage. In some embodiments, each of the 12 additional glutamyl groups in the chain other than the C-terminal glutamyl group or groups have an alpha linkage. In some embodiments, 11 of the 12 additional glutamyl groups in the chain have an alpha linkage. In other embodiments, 1, 2, 3, 4, 5, 6, 7, 8, 9, 10, or 11, of the 12 additional glutamyl groups have an alpha linkage and the remaining 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, or 11 of the 12 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 13 glutamyl groups has both an alpha linkage and a gamma linkage. In some embodiments, each of the 13 glutamyl groups other than the C-terminal glutamyl group or groups have an alpha linkage. In some embodiments, 12 of the 13 glutamyl groups have an alpha linkage. In some embodiments, the alpha triskaidecaglutamated PMX comprises two or more glutamyl groups in the L-form. In further embodiments, each of the glutamyl groups of the alpha triskaidecaglutamated pemetrexed is in the L-form. In other embodiments, the alpha triskaidecaglutamated PMX comprises a glutamyl group in the D-form. In further embodiments, each of the glutamyl groups of the alpha triskaidecaglutamated pemetrexed other than the glutamyl group of pemetrexed, is in the D-form. In additional embodiments, the triskaidecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is tetradecaglutamated (αPMX-PG$_3$). In some embodiments, each of the 13 additional glutamyl groups have an alpha linkage. In some embodiments, each of the 13 additional glutamyl groups in the chain other than the C-terminal glutamyl group or groups have an alpha linkage. In some embodiments, 12 of the 13 additional glutamyl groups in the chain have an alpha linkage. In other embodiments, 1, 2, 3, 4, 5, 6, 7, 8, 9, 10, 11, or 12, of the 13 additional glutamyl groups have an alpha linkage and the remaining 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, or 12 of the 13 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 14 glutamyl groups has both an alpha linkage and a gamma linkage. In some embodiments, each of the 14 glutamyl groups other than the C-terminal glutamyl group or groups have an alpha linkage. In some embodiments, 13 of the 14 glutamyl groups have an alpha linkage. In some embodiments, the alpha tetradecaglutamated PMX comprises two or more glutamyl groups in the L-form. In further embodiments, each of the glutamyl groups of the alpha tetradecaglutamated pemetrexed is in the L-form. In other embodiments, the alpha tetradecaglutamated PMX comprises a glutamyl group in the D-form. In further embodiments, each of the glutamyl groups of the alpha tetradecaglutamated pemetrexed other than the glutamyl group of pemetrexed, is in the D-form. In additional embodiments, the tetradecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is pentadecaglutamated ($\alpha$PMX-PG$_{14}$). In some embodiments, each of the 14 additional glutamyl groups have an alpha linkage. In some embodiments, each of the 14 additional glutamyl groups in the chain other than the C-terminal glutamyl group or groups have an alpha linkage. In some embodiments, 13 of the 14 additional glutamyl groups in the chain have an alpha linkage. In other embodiments, 1, 2, 3, 4, 5, 6, 7, 8, 9, 10, 11, 12, or 13, of the 14 additional glutamyl groups have an alpha linkage and the remaining 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, or 13 of the 14 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 15 glutamyl groups has both an alpha linkage and a gamma linkage. In some embodiments, each of the 15 glutamyl groups other than the C-terminal glutamyl group or groups have an alpha linkage. In some embodiments, 14 of the 15 glutamyl groups have an alpha linkage. In some embodiments, the alpha pentadecaglutamated PMX comprises two or more glutamyl groups in the L-form. In further embodiments, each of the glutamyl groups of the alpha pentadecaglutamated pemetrexed is in the L-form. In other embodiments, the alpha pentadecaglutamated PMX comprises a glutamyl group in the D-form. In further embodiments, each of the glutamyl groups of the alpha pentadecaglutamated pemetrexed other than the glutamyl group of pemetrexed, is in the D-form. In additional embodiments, the pentadecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is hexadecaglutamated ($\alpha$PMX-PG$_{15}$). In some embodiments, each of the 15 additional glutamyl groups have an alpha linkage. In some embodiments, each of the 15 additional glutamyl groups in the chain other than the C-terminal glutamyl group or groups have an alpha linkage. In some embodiments, 14 of the 15 additional glutamyl groups in the chain have an alpha linkage. In other embodiments, 1, 2, 3, 4, 5, 6, 7, 8, 9, 10, 11, 12, 13, or 14, of the 15 additional glutamyl groups have an alpha linkage and the remaining 14, 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, 13, or 14 of the 15 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 16 glutamyl groups has both an alpha linkage and a gamma linkage. In some embodiments, each of the 16 glutamyl groups other than the C-terminal glutamyl group or groups have an alpha linkage. In some embodiments, 15 of the 16 glutamyl groups have an alpha linkage. In some embodiments, the alpha hexadecaglutamated PMX comprises two or more glutamyl groups in the L-form. In further embodiments, each of the glutamyl groups of the alpha hexadecaglutamated pemetrexed is in the L-form. In other embodiments, the alpha hexadecaglutamated PMX comprises a glutamyl group in the D-form. In further embodiments, each of the glutamyl groups of the alpha hexadecaglutamated pemetrexed other than the glutamyl group of pemetrexed, is in the D-form. In additional embodiments, the hexadecaglutamated PMX comprises a glutamyl group in the D-form and two or more glutamyl groups in the L-form. In some embodiments, the polyglutamate chain is linear. In other embodiments, the polyglutamate chain is branched.

In other embodiments, the alpha polyglutamated pemetrexed is heptadecaglutamated ($\alpha$PMX-PG$_{16}$). In some embodiments, each of the 16 additional glutamyl groups have an alpha linkage. In some embodiments, each of the 16 additional glutamyl groups in the chain other than the C-terminal glutamyl group or groups have an alpha linkage. In some embodiments, 15 of the 16 additional glutamyl groups in the chain have an alpha linkage. In other embodiments, 1, 2, 3, 4, 5, 6, 7, 8, 9, 10, 11, 12, 13, 14, or 15, of the 16, additional glutamyl groups have an alpha linkage and the remaining 15, 14, 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, 13, 14, or 15 of the 16 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 17 glutamyl groups has both an alpha linkage and a gamma linkage. In some embodiments, each of the 17 glutamyl groups other than the C-terminal glutamyl group or groups have an alpha linkage. In some embodiments, 16 of the 17 glutamyl groups have an alpha linkage. In some embodiments, the alpha heptadecaglutamated PMX comprises two or more glutamyl groups in the L-form. In further embodiments, each of the glutamyl groups of the alpha heptadecaglutamated pemetrexed is in the L-form. In other embodiments, the alpha heptadecaglutamated PMX comprises a D glutamyl group. In further embodiments, each of the glutamyl groups of the alpha heptadecaglutamated pemetrexed other than the glutamyl group of pemetrexed, is in the D-form. In additional embodiments, the heptadecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is octadecaglutamated ($\alpha$PMX-PG$_{17}$). In some embodiments, each of the 17 additional glutamyl groups have an alpha linkage. In some embodiments, each of the 17 additional glutamyl groups in the chain other than the C-terminal glutamyl group or groups have an alpha linkage. In some embodiments, 16 of the 17 additional glutamyl groups in the chain have an alpha linkage. In other embodiments, 1, 2, 3, 4, 5, 6, 7, 8, 9, 10, 11, 12, 13, 14, 15, or 16, of the 17 additional glutamyl groups have an alpha linkage and the remaining 16, 15, 14, 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, 13, 14, 15, or 16 of the 17 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 18 glutamyl groups has both an alpha linkage and a gamma linkage. In some embodiments, each of the 18 glutamyl groups other than the C-terminal glutamyl group or groups have an alpha linkage. In some embodiments, 17 of the 18 glutamyl groups have an alpha linkage. In some embodiments, the alpha octadecaglutamated PMX comprises two or more glutamyl groups in the L-form. In further embodiments, each of the glutamyl groups of the alpha octadecaglutamated pemetrexed is in the L-form. In other embodiments, the alpha octadecaglutamated PMX comprises a glutamyl group in the D-form. In further embodiments, each of the glutamyl groups of the alpha octadecaglutamated pemetrexed other than the glutamyl group of pemetrexed, is in the D-form. In additional embodiments, the octadecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is enneadecaglutamated ($\alpha$PMX-PG$_{18}$). In some embodiments, each of the 18 additional glutamyl groups have an alpha linkage. In some embodiments, each of the 18 additional glutamyl groups in the chain other than the C-terminal glutamyl group or groups have an alpha linkage. In some embodiments, 17 of the 18 additional glutamyl groups in the chain have an alpha linkage. In other embodiments, 1, 2, 3, 4, 5, 6, 7, 8, 9, 10, 11, 12, 13, 14, 15, 16, or 17, of the 18 additional glutamyl groups have an alpha linkage and the remaining 17, 16, 15, 14, 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, 13, 14, 15, 16, or 17 of the 18 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 19 glutamyl groups has both an alpha linkage and a gamma linkage. In some embodiments, each of the 19 glutamyl groups other than the C-terminal glutamyl group or groups have an alpha linkage. In some embodiments, 18 of the 19 glutamyl groups have an alpha linkage. In some embodiments, the alpha enneadecaglutamated PMX comprises two or more glutamyl groups in the L-form. In further embodiments, each of the glutamyl groups of the alpha enneadecaglutamated pemetrexed is in the L-form. In other embodiments, the alpha enneadecaglutamated PMX comprises a D glutamyl group. In further embodiments, each of the glutamyl groups of the alpha enneadecaglutamated pemetrexed other than the glutamyl group of pemetrexed, is in the D-form. In additional embodiments, the enneadecaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is icosiglutamated ($\alpha$PMX-PG$_{19}$). In some embodiments, each of the 19 additional glutamyl groups have an alpha linkage. In some embodiments, each of the 19 additional glutamyl groups in the chain other than the C-terminal glutamyl group or groups have an alpha linkage. In some embodiments, 18 of the 19 additional glutamyl groups in the chain have an alpha linkage. In other embodiments, 1, 2, 3, 4, 5, 6, 7, 8, 9, 10, 11, 12, 13, 14, 15, 16, 17, or 18, of the 19 additional glutamyl groups have an alpha linkage and the remaining 18, 17, 16, 15, 14, 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, 13, 14, 15, 16, 17, or 18 of the 19 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 20 glutamyl groups has both an alpha linkage and a gamma linkage. In some embodiments, each of the 20 glutamyl groups other than the C-terminal glutamyl group or groups have an alpha linkage. In some embodiments, 19 of the 20 glutamyl groups have an alpha linkage. In some embodiments, the alpha icosiglutamated PMX comprises two or more glutamyl groups in the L-form. In further embodiments, each of the glutamyl groups of the alpha icosiglutamated pemetrexed is in the L-form. In other embodiments, the alpha icosiglutamated PMX comprises a glutamyl group in the D-form. In further embodiments, each of the glutamyl groups of the alpha icosiglutamated pemetrexed other than the glutamyl group of pemetrexed, is in the D-form. In additional embodiments, the icosiglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed is icosikaihenaglutamated ($\alpha$PMX-PG$_{20}$). In some embodiments, each of the 20 additional glutamyl groups have an alpha linkage. In some embodiments, each of the 20 additional glutamyl groups in the chain other than the C-terminal glutamyl group or groups have an alpha linkage. In some embodiments, 19 of the 20 additional glutamyl groups in the chain have an alpha linkage. In other embodiments, 1, 2, 3, 4, 5, 6, 7, 8, 9, 10, 11, 12, 13, 14, 15, 16, 17, 18, or 19, of the 20 additional glutamyl groups have an alpha linkage and the remaining 19, 18, 17, 16, 15, 14, 13, 12, 11, 10, 9, 8, 7, 6, 5, 4, 3, 2, or 1, glutamyl groups, respectively, have a gamma linkage. In other embodiments, 1, 2, 3, 4, 5, 6, 7, 8, 9, 10, 11, 12, 13, 14, 15, 16, 17, 18, or 19 of the 20 additional glutamyl groups have an alpha linkage and the remaining non-C-terminal glutamyl groups are linked to a glutamyl group of the molecule through a gamma linkage. In some embodiments, at least one additional glutamyl group has both an alpha linkage and a gamma linkage. In some embodiments, at least one of the 21 glutamyl groups has both an alpha linkage and a gamma linkage. In some embodiments, each of the 21 glutamyl groups other than the C-terminal glutamyl group or groups have an alpha linkage. In some embodiments, 20 of the 21 glutamyl groups have an alpha linkage. In some embodiments, the alpha icosikaihenaglutamated PMX comprises two or more glutamyl groups in the L-form. In further embodiments, each of the glutamyl groups of the alpha icosikaihenaglutamated pemetrexed is in the L-form. In other embodiments, the alpha icosikaihenaglutamated PMX comprises a glutamyl group in the D-form. In further embodiments, each of the glutamyl groups of the alpha icosikaihenaglutamated pemetrexed other than the glutamyl group of pemetrexed, is in the D-form. In additional embodiments, the icosikaihenaglutamated PMX comprises a glutamyl group in the D-form and two or more glutamyl groups in the L-form. In some embodiments, the polyglutamate chain is linear. In other embodiments, the polyglutamate chain is branched.

In some embodiments, the alpha polyglutamated pemetrexed contains a chain of 4-7 glutamyl groups attached to pemetrexed (i.e., αPMX-PGn, wherein n=4-7) and each of the 4-7 attached glutamyl groups have an alpha linkage. In some embodiments, the alpha polyglutamated pemetrexed contains a chain of 4-7 glutamyl groups attached to pemetrexed (i.e., αPMX-PGn, wherein n=4-7) and each of the 4-7 attached glutamyl groups other than the C-terminal glutamyl group or groups has an alpha linkage. In some embodiments, each of the 4-7 attached glutamyl groups is in the L-form. In other embodiments, each of the 4-7 attached glutamyl groups is in the D-form. In other embodiments, the 4-7 attached glutamyl groups are in the L-form and the D-form. In some embodiments, the polyglutamate chain is linear. In other embodiments, the polyglutamate chain is branched.

In one embodiment, the alpha polyglutamated pemetrexed is tetraglutamated and each of the 3 glutamyl groups in the polyglutamate chain attached to the pemetrexed contains an alpha linkage. In one embodiment, the alpha polyglutamated pemetrexed is tetraglutamated and each of the 3 glutamyl groups in the polyglutamate chain attached to the pemetrexed other than the C-terminal glutamyl group or groups contains an alpha linkage. In some embodiments, each of the 4 glutamyl groups is in the L-form. In some embodiments, each of the glutamyl groups in the alpha tetraglutamated pemetrexed other than the glutamyl group of pemetrexed, is in the D-form. In other embodiments, at least two glutamyl groups in the alpha tetraglutamate pemetrexed are in the L-form and at least one glutamyl group is in the D-form. In some embodiments, the polyglutamate chain is linear. In other embodiments, the polyglutamate chain is branched.

In one embodiment, the alpha polyglutamated pemetrexed is pentaglutamated and each of the 4 glutamyl groups in the polyglutamate chain attached to the pemetrexed contains an alpha linkage. In one embodiment, the alpha polyglutamated pemetrexed is pentaglutamated and each of the 4 glutamyl groups in the polyglutamate chain attached to the pemetrexed other than the C-terminal glutamyl group or groups contains an alpha linkage. In some embodiments, each of the 4 glutamyl groups is in the L-form. In some embodiments, each of the glutamyl groups in the alpha pentaglutamated pemetrexed other than the glutamyl group of pemetrexed, is in the D-form. In other embodiments, at least two glutamyl groups in the alpha pentaglutamated pemetrexed are in the L-form and at least one glutamyl group is in the D-form. In some embodiments, the polyglutamate chain is linear. In other embodiments, the polyglutamate chain is branched.

In one embodiment, the alpha polyglutamated pemetrexed is hexaglutamated and each of the 5 glutamyl groups in the polyglutamate chain attached to the pemetrexed contains an alpha linkage. In one embodiment, the alpha polyglutamated pemetrexed is hexaglutamated and each of the 5 glutamyl groups in the polyglutamate chain attached to the pemetrexed other than the C-terminal glutamyl group or groups contains an alpha linkage. In some embodiments, each of the 5 glutamyl groups is in the L-form. In some embodiments, each of the glutamyl groups in the alpha hexaglutamated pemetrexed other than the glutamyl group of pemetrexed, is in the D-form. In other embodiments, at least two glutamyl groups in the alpha hexaglutamated pemetrexed are in the L-form and at least one glutamyl group is in the D-form. In some embodiments, the polyglutamate chain is linear. In other embodiments, the polyglutamate chain is branched.

In another embodiment, the alpha polyglutamated pemetrexed is heptaglutamated and each of the 6 glutamyl groups in the polyglutamate chain attached to the pemetrexed contains an alpha linkage. In another embodiment, the alpha polyglutamated pemetrexed is heptaglutamated and each of the 6 glutamyl groups in the polyglutamate chain attached to the pemetrexed other than the C-terminal glutamyl group or groups contains an alpha linkage. In some embodiments, each of the 6 glutamyl groups is in the L-form. In some embodiments, each of the glutamyl groups in the alpha heptaglutamated pemetrexed other than the glutamyl group of pemetrexed, is in the D-form. In other embodiments, at least two glutamyl groups in the alpha heptaglutamated pemetrexed are in the L-form and at least one glutamyl group is in the D-form. In some embodiments, the polyglutamate chain is linear. In other embodiments, the polyglutamate chain is branched.

In some embodiments, the alpha polyglutamated pemetrexed (αPPMX) contains a total of 1-15, 1-10, 2-15, 2-10, 3-15, 3-10, 3-6, 3-5, 4-10, 4-7, or 4-6, glutamyl groups including the glutamyl group in pemetrexed, or any range therein between. In some embodiments, each of the glutamyl groups in the αPPMX other than the glutamyl group of pemetrexed have an alpha linkage. In some embodiments, each of the glutamyl groups in the αPPMX other than the C-terminal glutamyl group or groups and the glutamyl group of pemetrexed has an alpha linkage. In some embodiments, each of the glutamyl groups in the αPPMX other than the C-terminal glutamyl group or groups has an alpha linkage. In some embodiments, 1, 2, 3, 4, 5, 6, 7, 8, 9, 10, 11, 12, 13, or 14, of the glutamyl groups in the αPPMX have an alpha linkage. In some embodiments, the αPPMX comprises glutamyl groups in the L-form and the D-form. In further embodiments, 1, 2, 3, 4, 5, 6, 7, 8, 9, 10, 11, 12, 13, or 14, of the glutamyl groups in the αPPMX have an alpha linkage and 13, 12, 11, 10, 9, 8, 7, 6, 5, 4, 3, 2, 1, or none, of the glutamyl groups, respectively, has a gamma linkage. In some embodiments, each of the glutamyl groups in the polyglutamate structure of the polyglutamated pemetrexed is in the L-form. In some embodiments, each of the glutamyl groups in the αPPMX other than the glutamyl group of pemetrexed is in the D-form. In one embodiment, 1, 2, 3, 4, 5, 6, 7, 8, 9, 10, 11, 12, 13, 14, or 15, of the glutamyl groups in the αPPMX is in the L-form. In another embodiment, 1, 2, 3, 4, 5, 6, 7, 8, 9, 10, 11, 12, 13, or 14, of the glutamyl groups in the αPPMX is in the D-form. In some embodiments, the polyglutamate chain is linear. In other embodiments, the polyglutamate chain is branched.

In some embodiments, the alpha polyglutamated pemetrexed (αPPMX) contains a total of 2-20, 2-15, 2-10, 2-5, glutamyl groups including the glutamyl group in pemetrexed, or any range therein between. In some embodiments, each of the glutamyl groups in the αPPMX other than the glutamyl group of pemetrexed, have an alpha linkage. In some embodiments, each of the glutamyl groups in the αPPMX other than the C-terminal glutamyl group or groups and the glutamyl group of pemetrexed has an alpha linkage. In some embodiments, each of the glutamyl groups in the αPPMX other than the C-terminal glutamyl group or groups has an alpha linkage. In other embodiments, 1, 2, 3, 4, 5, 6, 7, 8, 9, 10, 11, 12, 13, 14, 15, 16, 17, 18, or 19, of the glutamyl groups have an alpha linkage. In some embodiments, the αPPMX contains two or more glutamyl groups having a gamma linkage. In further embodiments, 1, 2, 3, 4, 5, 6, 7, 8, 9, 10, 11, 12, 13, 14, 15, 16, 17, 18, or 19, of the glutamyl groups in the αPPMX other than the glutamyl group of pemetrexed have an alpha linkage and 19, 18, 17, 16, 15, 14, 13, 12, 11, 10, 9, 8, 7, 6, 5, 4, 3, 2, 1, or none, of the glutamyl groups, respectively, has a gamma linkage. In some embodiments, each of the glutamyl groups in the αPPMX is in the L-form. In some embodiments, each of the glutamyl groups in the αPPMX other than the glutamyl group of pemetrexed is in the D-form. In one embodiment, 1, 2, 3, 4, 5, 6, 7, 8, 9, 10, 11, 12, 13, 14, 15, 16, 17, 18, 19, or 20, of the glutamyl groups in the αPPMX are in the L-form. In another embodiment, 1, 2, 3, 4, 5, 6, 7, 8, 9, 10, 11, 12, 13, 14, 15, 16, 17, 18, or 19, glutamyl groups in the αPPMX is in the D-form.

In some embodiments, the alpha polyglutamated pemetrexed contains a total of 1, 2, 3, 4, 5, 6, 7, 8, 9, 10, 11, 12, 13, 14, or 15, glutamyl groups in addition to the glutamyl group in pemetrexed). In further embodiments, 1, 2, 3, 4, 5, 6, 7, 8, 9, 10, 11, 12, 13, 14, or 15, of the additional glutamyl groups have an alpha linkage. In additional embodiments, 14, 13, 12, 11, 10, 9, 8, 7, 6, 5, 4, 3, 2, or 1, of the glutamyl groups in the alpha polyglutamated pemetrexed have a gamma linkage. In some embodiments, at least one glutamyl group has both an alpha linkage and a gamma linkage. In some embodiments, the glutamyl group in pemetrexed has an alpha linkage. In some embodiments, the glutamyl group in pemetrexed has both an alpha linkage and a gamma linkage.

In some embodiments, a total of 1, 2, 3, 4, 5, 6, 7, 8, 9, 10, 11, 12, 13, 14, or 15, glutamyl groups in the alpha polyglutamated pemetrexed are in the L-form, the D-form, or in the L-form and the D-form. In some embodiments, each of the glutamyl groups of the alpha polyglutamated pemetrexed is in the L-form. In other embodiments, each of the glutamyl groups of the alpha polyglutamated pemetrexed other than the glutamyl group of pemetrexed is in the D-form. In alternative embodiments, at least two of the glutamyl groups in the alpha polyglutamated pemetrexed are in the L-form and at least one of the glutamyl groups in the alpha polyglutamated pemetrexed is in the D-form. In some embodiments, 1, 2, 3, 4, 5, 6, 7, 8, 9, 10, 11, 12, 13, 14, 15 or 16, glutamyl groups in the alpha polyglutamated pemetrexed are in the L-form. In other embodiments, 1, 2, 3, 4, 5, 6, 7, 8, 9, 10, 11, 12, 13, or 14, glutamyl groups in the alpha polyglutamated pemetrexed are in the D-form.

In additional embodiments, the alpha polyglutamated pemetrexed contains 20-100, 20-75, 20-50, 20-40, 20-30, 20-25, or more than 100, alpha glutamyl groups, or any range therein between. In some embodiments, each of the glutamyl groups of the alpha polyglutamated pemetrexed is in the L-form. In other embodiments, each of the glutamyl groups of the alpha polyglutamated pemetrexed other than the glutamyl group of pemetrexed is in the D-form. In alternative embodiments, at least two of the glutamyl groups in the alpha polyglutamated pemetrexed are in the L-form and at least one of the glutamyl groups in the alpha polyglutamated pemetrexed is in the D-form In additional embodiments, the provided compositions comprise an alpha polyglutamated pemetrexed that contains 1, 2, 3, 4, 5, 6, 7, 8, 9, 1-10, or 1-20, glutamyl groups that have alpha linkages. In some embodiments, the alpha polyglutamated pemetrexed contains 1, 2, 3, 4, 5, 6, 7, 8, 9, 1-10, or 1-20, glutamyl groups in the L-form. In some embodiments, the alpha polyglutamated pemetrexed contains 0, 1, 2, 3, 4, 5, 6, 7, 8, 9, 1-10, or 1-20, glutamyl groups in the D-form. In some embodiments, the alpha polyglutamated pemetrexed contains 1, 2, 3, 4, 5, 6, 7, 8, 9, 1-10, or 1-20, glutamyl groups in the L-form and 0, 1, 2, 3, 4, 5, 6, 7, 8, 9, or 1-10 or 1-20, glutamyl groups in the D-form. In other embodiments, the alpha polyglutamated pemetrexed contains at least 1 glutamyl group that has both an alpha linkage and a gamma linkage. In some embodiments, the alpha polyglutamated pemetrexed contains 1, 2, 3, 4, 5, 6, 7, 8, 9, 1-10, or more than 10 glutamyl groups that have both an alpha linkage and a gamma linkage.

In some embodiments, the alpha-polyglutamated pemetrexed contains a least 1 glutamyl group having an alpha linkage and contains 2, 3, 4, 5, 6, 7, 8, 9, 1-10, 1-20, or more, glutamyl groups having a gamma linkage. For example, in some embodiments, the alpha polyglutamated pemetrexed contains 1, 2, 3, 4, 5, 6, 7, 8, 9, or 1-10, L-alpha glutamyl group linkages and further contains 1, 2, 3, 4, 5, 6, 7, 8, 9, or 1-10, L-gamma glutamyl group linkages. In some further embodiments, the alpha polyglutamated pemetrexed contains 1, 2, 3, 4, 5, 6, 7, 8, 9, or 1-10, L-alpha glutamyl group linkages and further contains 1, 2, 3, 4, 5, 6, 7, 8, 9, or 1-10, D-gamma glutamyl group linkages. In additional further embodiments, the alpha polyglutamated pemetrexed contains 1, 2, 3, 4, 5, 6, 7, 8, 9, or 1-10, D-alpha glutamyl group linkages and further contains 1, 2, 3, 4, 5, 6, 7, 8, 9, or 1-10, D-gamma glutamyl group linkages. In other further embodiments, the alpha polyglutamated pemetrexed contains 1, 2, 3, 4, 5, 6, 7, 8, 9, or 1-10, D-gamma glutamyl group linkages and further contains 1, 2, 3, 4, 5, 6, or 1-10, L-gamma glutamyl group linkages. In other embodiments, the alpha polyglutamated pemetrexed contains at least 1 glutamyl group that has both an alpha linkage and a gamma linkage. In some embodiments, the alpha polyglutamated pemetrexed contains 1, 2, 3, 4, 5, 6, 7, 8, 9, 1-10, or more than 10, glutamyl groups that have both an alpha linkage and a gamma linkage.

In some embodiments, the alpha polyglutamated pemetrexed composition provided herein is capable of accepting one or more additional glutamyl groups, that is the composition is able to act as a substrate for by FPGS (folylpolyglutamate synthetase). Reagents and assays and reagents for determining the ability of an alpha polyglutamated pemetrexed composition to act as a substrate for FPGS (e.g., human FPGS, or rat liver FPGS) are readily available and can routinely be performed.

In some embodiments, the rate of uptake of naked alpha PPMX compositions disclosed herein (e.g., alpha PPMX that is not associated with a delivery vehicle) by hepatic cells is significantly reduced compared to the uptake rate of pemetrexed under physiologic conditions. In some embodiments, the rate of hepatic cell uptake of the naked alpha PPMX composition is less than 30%, 20%, 15%, or 10% compared to the rate of pemetrexed. In further embodiments, the rate of the efflux (transport out) of alpha PPMX compositions disclosed herein from hepatic-cells occurs at a rate that is significantly reduced compared to pemetrexed (e.g., less than 30%, 20%, 15%, or 10%) compared to the rate of pemetrexed.

In some embodiments, an alpha polyglutamated pemetrexed composition provided herein is more cytotoxic to hyperproliferative cells than pemetrexed. In some embodiments the hyperproliferative cells are cancer cells. In some embodiments, the hyperproliferative cells are colorectal carcinoma cells, colon cancer cells, breast cancer cells, or ovarian cancer cells. In some embodiments, the cancer cells are mesothelioma cells or non-small cell lung carcinoma cells. In some embodiments, cytotoxicity is measured in an in vitro assay. In some embodiments, the alpha polyglutamated pemetrexed is a hexaglutamated pemetrexed.

In some embodiments, an alpha polyglutamated pemetrexed composition provided herein has lower toxic side effects than pemetrexed. In some embodiments, the alpha polyglutamated pemetrexed composition provided herein is less toxic to non-hyperproliferative cells than pemetrexed. In some embodiments, the alpha polyglutamated pemetrexed composition provided herein is less toxic to neutrophils, liver cells, or to colon epithelium cells than pemetrexed. In some embodiments, the neutrophils human neutrophils, differentiating human neutrophils, or neutrophils differentiated from CD34+ cells. In some embodiments, the liver cells are AML12 liver cells. In some embodiments, the colon epithelium cells are CCD841 colon epithelium cells. In some embodiments, the toxicity is measured in an in vitro assay. In some embodiments, the alpha polyglutamated pemetrexed is a hexaglutamated pemetrexed.

In some embodiments, an alpha polyglutamated pemetrexed composition provided herein has lower toxic side effects than pemetrexed. In some embodiments, an alpha polyglutamated pemetrexed composition provided herein causes fewer or less severe toxic side effects in an vivo assay than pemetrexed. In some embodiments, the in vivo assay is an in vivo murine model. In some embodiments, an alpha polyglutamated pemetrexed composition provided herein causes fewer or less severe hematological or hepatic toxic side effects than pemetrexed. In some embodiments, hematological side effects are assessed by measuring mean neutrophil, mean white blood cell or mean platelet counts. In some embodiments, hepatic toxic side effects are assessed by measuring serum aspartate transaminase (AST), serum alanine transaminase (ALT), and/or serum albumin levels. In some embodiments, the in vivo assay comprises administering 40 mg/kg or 80 mg/kg of the alpha polyglutamated pemetrexed composition once weekly for 4 weeks. In some embodiments, the alpha polyglutamated pemetrexed is a hexaglutamated pemetrexed.

In some embodiments, treatment with an alpha polyglutamated pemetrexed composition provided herein does not induce significant hematological or hepatic toxic side effects in an in vivo murine model. In some embodiments, hematological side effects are assessed by measuring mean neutrophil, mean white blood cell or mean platelet counts. In some embodiments, hepatic toxic side effects are assessed by measuring serum aspartate transaminase (AST), serum alanine transaminase (ALT), and/or serum albumin levels. In some embodiments, an alpha polyglutamated pemetrexed composition provided herein does not significantly decrease mean neutrophil, mean white blood cell or mean platelet counts. In some embodiments, an alpha polyglutamated pemetrexed composition provided herein does not significantly increase serum aspartate transaminase (AST) and serum alanine transaminase (ALT) levels. In some embodiments, an alpha polyglutamated pemetrexed composition provided herein does not significantly decrease serum albumin levels. In some embodiments, the in vivo assay comprises administering 40 mg/kg or 80 mg/kg of the alpha polyglutamated pemetrexed composition once weekly for 4 weeks. In some embodiments, the alpha polyglutamated pemetrexed is a hexaglutamated pemetrexed.

In some embodiments, the alpha polyglutamated pemetrexed compositions do not contain a fluorine atom. In some embodiments, the alpha polyglutamated pemetrexed compositions do not contain a 4-fluoroglutamyl group.

Alpha polyglutamated pemetrexed (a PPMX) compositions and their uses are further disclosed in each of U.S. Appl. Nos. 62/374,458, 15/675,695, 15/675,701, and 62/583,432; and Intl. Appl. Nos. PCT/US2017/046666, and PCT/US2017/046667, the contents of each of which is herein incorporated by reference in its entirety.

A. Polyglutamated Pemetrexed Analogs and Derivatives

Figure 1A:
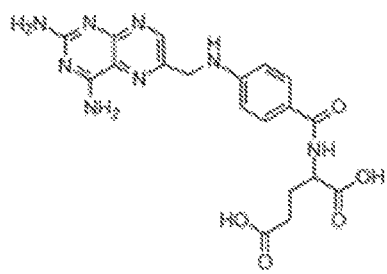
Figure 1B:
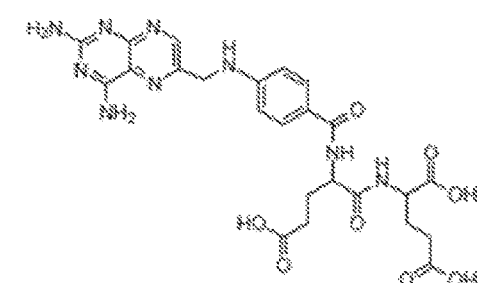
Figure 1C:
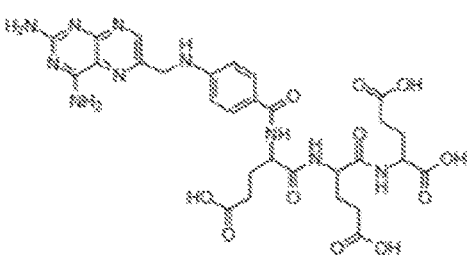
Figure 1D:
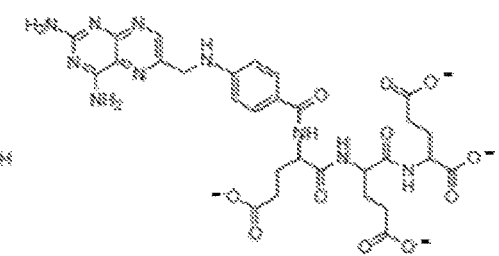
Figure 1E:
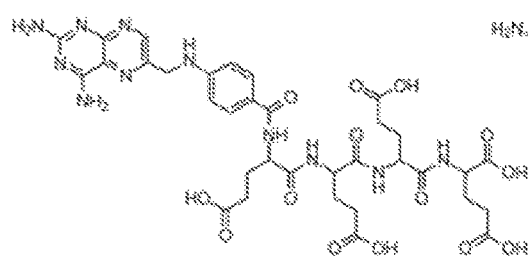
Figure 1F:
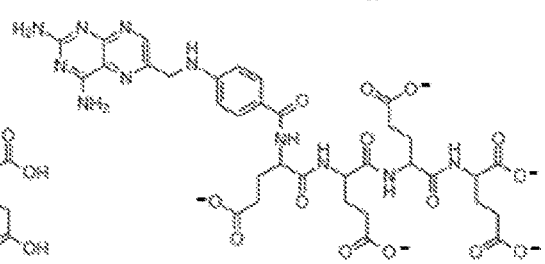
Figure 1H:
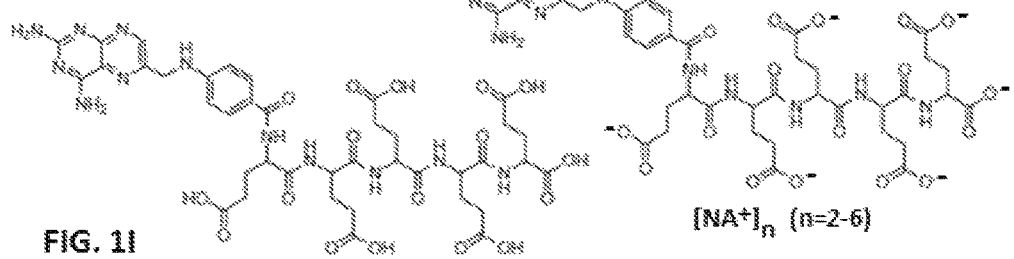
Figure 1G:
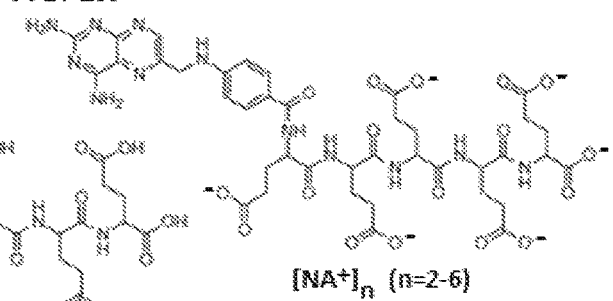
Figure 1I:
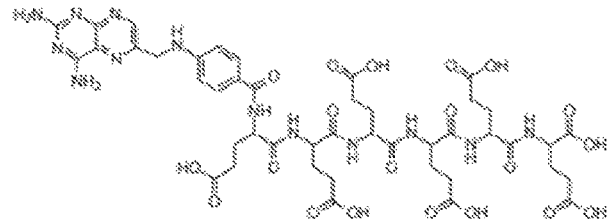
Figure 1J:
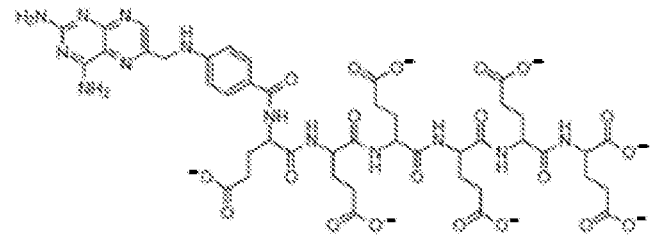
Figure 1K:
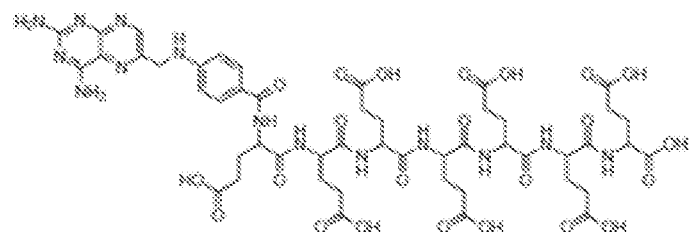
Figure 1L:
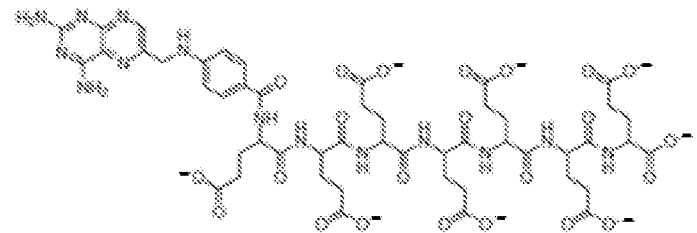
Figure 1M:
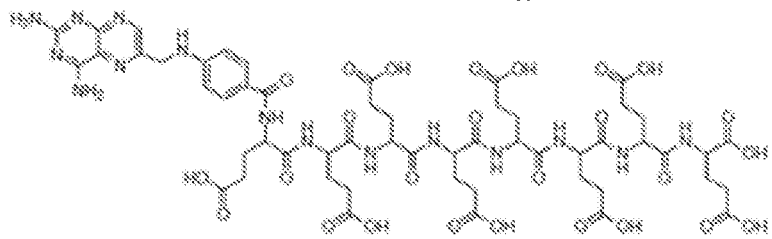
Figure 1N:
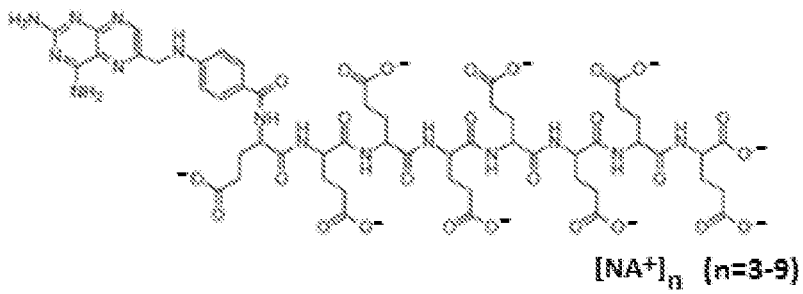
Figure 1O:
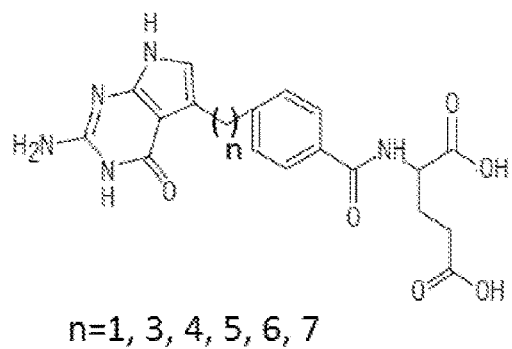
Figure 1S:
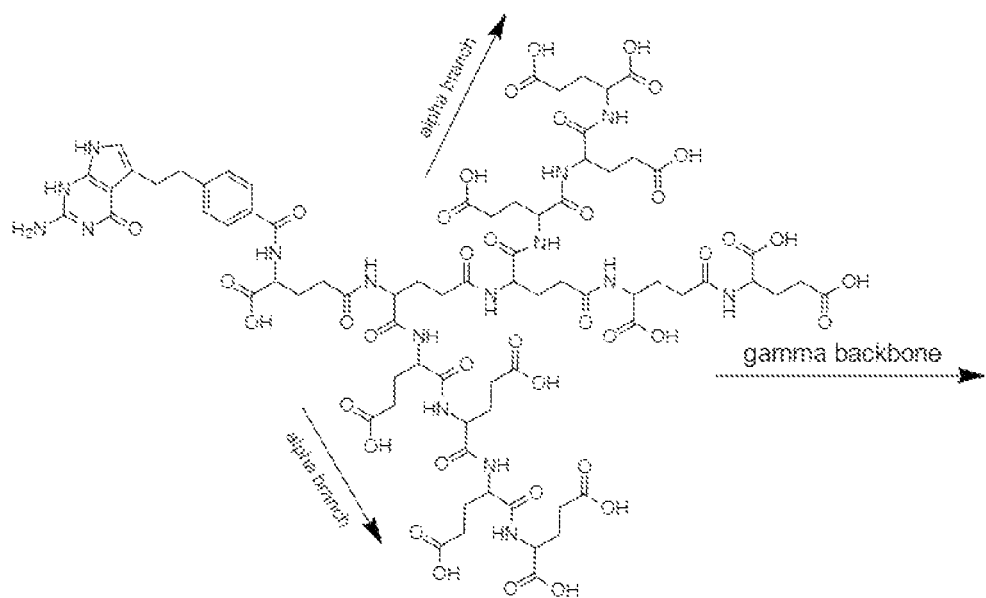
Figure 1T:
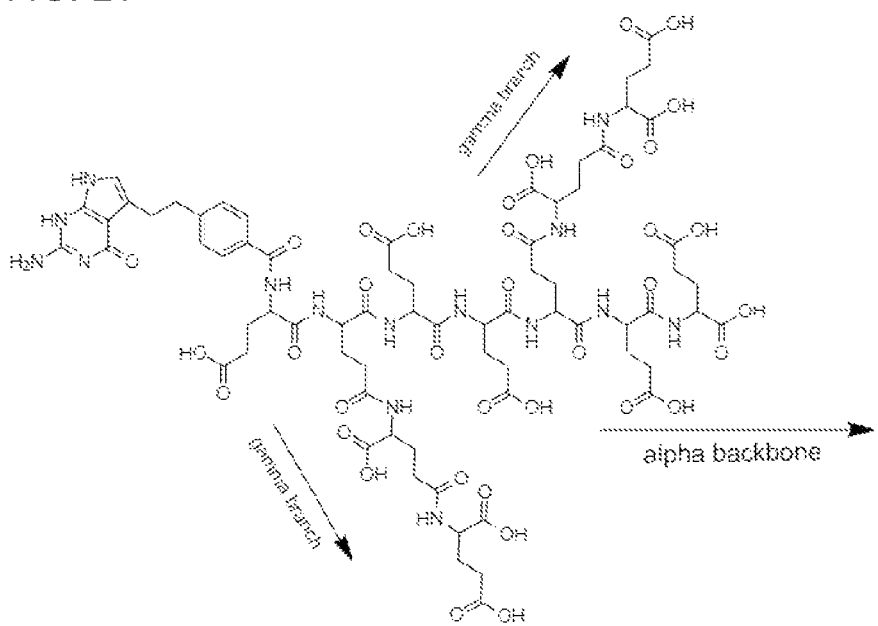
Figure 1U:
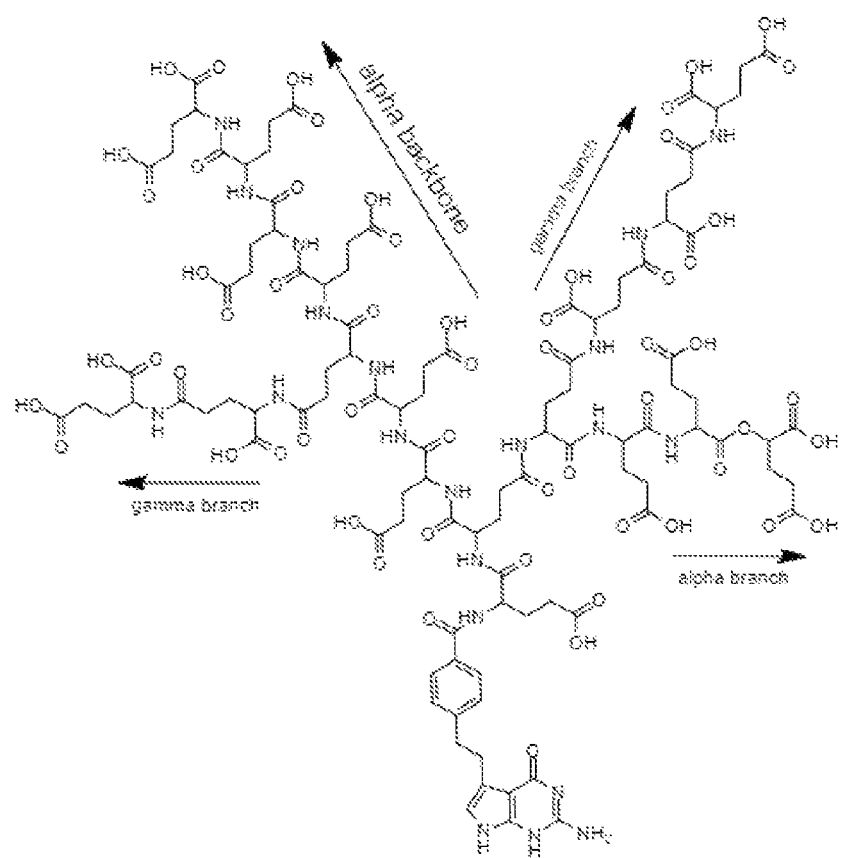

The disclosure also encompasses alpha polyglutamated pemetrexed derivatives and analogs. The compositions and methods disclosed herein are envisioned to apply to any and every known derivative or analog of pemetrexed that is polyglutamated. In some embodiments the polyglutamated pemetrexed analog or derivative composition prepared and used according to the disclosed compositions and methods is depicted in FIGS. 1I-1J. In some embodiments the analog corresponds to a modified form of pemetrexed wherein the glutamyl group of pemetrexed is not linked to the remainder of pemetrexed molecule through a gamma peptide linkage. In some embodiments, the analog is a variant form of pemetrexed wherein the glutamyl group of pemetrexed in in the D-form. In some embodiments, the polyglutamated form of pemetrexed, or polyglutamated pemetrexed analog or derivative is not fluor.

In additional embodiments, the alpha polyglutamated pemetrexed derivative or analog has a variant polyglutamate chain. In some embodiments the polyglutamate chain contains one or more natural or synthetic residues other than glutamate. In some embodiments the polyglutamate chain contains one or more glutamyl groups that do not contain an amide linkage. In other embodiments, one or more of the glutamyl groups of the polyglutamate chain is derivatized.

B. PMX-PG Synthesis

The pemetrexed polyglutamate compositions provided herein may be obtained by following synthetic procedures known in the art. Procedures for synthesizing pemetrexed (including different pharmaceutically acceptable salts or acids (e.g., pemetrexed disodium) and crystalline and amorphous forms) and intermediates for synthesizing pemetrexed include but are not limited to those described in U.S. Pat. Nos. 8,507,508, 8,362,245, 7,138,521, 6,262,262, 6,066,732, 5,416,211, 5,344,932; U.S. Appl. Publ. No. US2013/0165654 A1; European Pat. Nos. EP 0905128, EP 2882753 B1, EP 0905128 and EP 2409978 B1; Intl. Appl. Publ. Nos. WO 2014/024164 A1, WO 2012/056285 A1, WO 2008/021410 A1, and WO 2001/14379 A2, and Barnett et al., Org. Proc Res & Develop. 3:184-188 (1999), Taylor et al., J. Org. Chem. 68:9938-9947 (2003), Taylor et al., Tetrahedron Lett. 40:4023 (1999); Barnett et al., Org. Proc. Res. & Develop. 3:184-188 (1999) and Kjell et al., Org. Proc. Res. Dev. 9:738 (2005).

The addition of glutamyl residues to the glutamyl residues of pemetrexed can be accomplished using synthetic procedures known in the art. In some embodiments, glutamyl residues are added serially to the glutamyl residue of pemetrexed. In additional embodiments, polyglutamates are added to the glutamyl reside of pemetrexed using "click chemistry" methods or other bioconjugate chemistries known to those in the art. Alternatively a peptide of glutamyl residues can be generated of the desired length and added to a precursor of pemetrexed which does not have a glutamyl residue. The peptide can be produced using synthetic procedures known in the art. In some embodiments, an initial glutamyl residue is bonded to wang resin and additional glutamyl residues are added serially via solid phase peptide synthesis using F-moc chemistry. After the final glutamyl residue is added the pemetrexed precursor is coupled to the peptide and the molecule is cleaved from the resin.

C. Pemetrexed-PG Complexes

The inventors have surprisingly found that polyglutamated pemetrexed (αPPMX) is able to form complexes with other compositions including therapeutic agents, including cytotoxic compounds such as platinum-based compounds. Accordingly, in some embodiments, the disclosure provides a complex of a αPPMX (e.g., a αPPMX disclosed herein) and a therapeutic agent or a salt or acid thereof.

In some embodiments, the αPPMX/complex comprise αPPMX and a therapeutic agent. In some embodiments, the therapeutic agent is a cytotoxic compound such as a chemotherapeutic agent. In further embodiments, the αPPMX/complex contains a platinum-based drug such as platinum-based chemotherapeutic agent (e.g., cisplatin, carboplatin and oxaliplatin). In other embodiments, the αPPMX/complex contains a taxane-based chemotherapeutic agent (e.g., paclitaxel and docetaxel). In other embodiments, the αPPMX/complex contains a cyclodextrin. In further embodiments, the αPPMX/complex is encapsulated in a liposome In some embodiments, the disclosure provides a composition comprising a complex of a αPPMX and a therapeutic agent or a salt or acid thereof. In further embodiments, the αPPMX/therapeutic agent complex comprises one or more αPPMX containing 2-150, 2-100, 2-75, 2-50, 2-24, 2-30, 2-20, 2-19, 2-15, 2-10, or 2-5, glutamyl groups. In some embodiments, the αPPMX/therapeutic agent complex comprises one or more αPPMX containing 3-10, 3-9, 3-8, or 3-7, glutamyl groups, or any range therein between. In other embodiments, the αPPMX/therapeutic agent complex comprises one or more αPPMX containing 4-10, 4-9, 4-8, 4-7, 4-6, or 4-5, glutamyl groups, or any range therein between. In one particular embodiment, the complex comprises one or more αPPMX containing 3-10 glutamyl groups. In further embodiments, the αPPMX/therapeutic agent complex comprises one or more αPPMX containing 3-7 glutamyl groups. In another embodiment, the αPPMX/therapeutic agent complex comprises one or more αPPMX containing 5 glutamyl groups. In another embodiment, the αPPMX/therapeutic agent complex comprises one or more αPPMX containing 6 glutamyl groups. In some embodiments, the therapeutic agent is a cytotoxic compound or a salt or acid thereof. In a further embodiment, the therapeutic agent is a chemotherapeutic agent or a salt or acid thereof. In another embodiment, the therapeutic agent is a platinum-based drug. In another embodiment, the therapeutic agent is a taxane-based drug. In additional embodiments, the molar ratio of αPPMX/therapeutic agent in the complex is in the range 1-10:1. In some embodiments, the molar ratio of αPPMX/therapeutic agent in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/therapeutic agent in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the αPPMX/therapeutic agent complex is encapsulated in a liposome (e.g., as described herein or otherwise known in the art).

In an alternative embodiment, the αPPMX complex comprises αPPMX and cyclodextrin. In some embodiments, the molar ratio of αPPMX (e.g., αPPMX salt)/cyclodextrin in the complex is in the range 1-20:1, or any range therein between. In some embodiments, the molar ratio of αPPMX/cyclodextrin in the complex is in the range 1-10:1, or any range therein between. In further embodiments, the molar ratio of αPPMX/cyclodextrin in the complex is in the range 2-8:1, or any range therein between. In some embodiments, the molar ratio of αPPMX/cyclodextrin in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In other embodiments, the molar ratio of αPPMX/cyclodextrin in the complex is in the range 1:1-20, 1:1-10, or 1:2-8, or any range therein between. In some embodiments, the molar ratio of αPPMX/cyclodextrin in the complex is: 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the αPPMX/cyclodextrin complex is encapsulated in a liposome (e.g., as described herein or otherwise known in the art).

In some embodiments, the disclosure provides a composition comprising a αPPMX/platinum-based chemotherapeutic agent complex. In some embodiments, the platinum-based chemotherapeutic agent is selected from the group consisting of: cisplatin, carboplatin, and oxaliplatin, or a salt or acid thereof. In other embodiments, the αPPMX/platinum-based chemotherapeutic agent complex comprises an analog of a cisplatin, carboplatin, oxaliplatin, or a salt or acid thereof. In some embodiments, the molar ratio of αPPMX/platinum-based agent in the complex is in the range 1-20:1, or any range therein between. In some embodiments, the molar ratio of αPPMX/platinum-based agent in the complex is in the range 1-10:1, or any range therein between. In further embodiments, the molar ratio of αPPMX/platinum-based agent in the complex is in the range 2-8:1, or any range therein between. In some embodiments, the molar ratio of αPPMX/platinum-based agent in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In other embodiments, the molar ratio of αPPMX/platinum-based chemotherapeutic agent in the complex is in the range 1:1-20, 1:1-10, or 1:2-8, or any range therein between. In some embodiments, the molar ratio of αPPMX/platinum-based agent in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX//platinum-based agent complex is encapsulated in a liposome (e.g., as described herein or otherwise known in the art).

In additional embodiments, the αPPMX/platinum-based chemotherapeutic agent complex comprises an analog of a cisplatin, carboplatin, oxaliplatin, or a salt or acid thereof. In some embodiments, the molar ratio of αPPMX/platinum-based analog in the complex is in the range 1-20:1, or any range therein between. In some embodiments, the molar ratio of αPPMX/platinum-based analog in the complex is in the range 1-10:1, or any range therein between. In further embodiments, the molar ratio of αPPMX/platinum-based agent in the complex is in the range 2-8:1, or any range therein between. In some embodiments, the molar ratio of αPPMX/platinum-based analog in the complex is 11:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/platinum-based agent in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/platinum-based analog complex is encapsulated in a liposome (e.g., as described herein or otherwise known in the art).

In further embodiments, the disclosure provides a complex containing αPPMX and cisplatin or a salt or acid thereof. In some embodiments, the molar ratio of αPPMX/cisplatin (or cisplatin salt or acid) in the complex is in the range 1-20:1, or any range therein between. In some embodiments, the molar ratio of αPPMX/cisplatin (or cisplatin salt or acid) in the complex is in the range 1-10:1, or any range therein between. In further embodiments, the molar ratio of αPPMX/cisplatin (or cisplatin salt or acid) in the complex is in the range 2-8:1, or any range therein between. In some embodiments, the molar ratio of αPPMX/cisplatin (or cisplatin salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/cisplatin (or cisplatin salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX//cisplatin (or cisplatin salt or acid) complex is encapsulated in a liposome (e.g., as described herein or otherwise known in the art).

In another embodiment, the disclosure provides a complex containing αPPMX and carboplatin or a salt or acid thereof. In some embodiments, the molar ratio of αPPMX/carboplatin (or carboplatin salt or acid) in the complex is in the range 1-20:1, or any range therein between. In further embodiments, the molar ratio of αPPMX/carboplatin (or carboplatin salt or acid) in the complex is in the range 1-10:1, or any range therein between. In further embodiments, the molar ratio of αPPMX/carboplatin (or carboplatin salt or acid) in the complex is in the range 2-8:1, or any range therein between. In some embodiments, the molar ratio of αPPMX/carboplatin (or carboplatin salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/cyclodextrin in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/carboplatin (or carboplatin salt or acid) complex is encapsulated in a liposome (e.g., as described herein or otherwise known in the art).

In another embodiment, the disclosure provides a complex containing αPPMX and oxaliplatin, or a salt or acid thereof. In some embodiments, the molar ratio of αPPMX/oxaliplatin (or oxaliplatin salt or acid) in the complex is in the range 1-20:1, or any range therein between. In further embodiments, the molar ratio of αPPMX/oxaliplatin (or oxaliplatin salt or acid) in the complex is in the range 1-10:1, or any range therein between. In further embodiments, the molar ratio of αPPMX/oxaliplatin (or oxaliplatin salt or acid) in the complex is in the range 2-8:1, or any range therein between. In some embodiments, the molar ratio of αPPMX/oxaliplatin (or oxaliplatin salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/oxaliplatin (or oxaliplatin salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/oxaliplatin (or oxaliplatin salt or acid) complex is encapsulated in a liposome (e.g., as described herein or otherwise known in the art).

In additional embodiments, the disclosure provides a complex comprising αPPMX and a platinum-based chemotherapeutic agent (platinum) selected from the group consisting of: nedaplatin, heptaplatin, lobaplatin, stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM216, NK121, CI973, DWA 2114R, NDDP, and dedaplatin, or a salt or acid thereof. In other embodiments, the αPPMX/platinum-based chemotherapeutic agent complex comprises an analog of nedaplatin, heptaplatin, lobaplatin, stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM216, NK121, CI973, DWA 2114R, NDDP, or dedaplatin, or a salt or acid thereof. In some embodiments, the molar ratio of αPPMX/platinum (or platinum salt or acid) in the complex is in the range 1-20:1, or any range therein between. In further embodiments, the molar ratio of αPPMX/platinum (or platinum salt or acid) in the complex is in the range 1-10:1, or any range therein between. In further embodiments, the molar ratio of αPPMX/platinum (or platinum salt or acid) in the complex is in the range 2-8:1, or any range therein between. In some embodiments, the molar ratio of αPPMX/platinum (or platinum salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/platinum (or platinum salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/platinum (or salt or acid or analog thereof) complex is encapsulated in a liposome (e.g., as described herein or otherwise known in the art).

In some embodiments, the disclosure provides a composition comprising a αPPMX/taxane-based chemotherapeutic agent (taxane) complex. In some embodiments, the taxane-based chemotherapeutic agent is selected from the group consisting of: paclitaxel (PTX), docetaxel (DTX), larotaxel (LTX), and cabazitaxel (CTX), or a salt or acid thereof. In some embodiments, the molar ratio of αPPMX/taxane-based agent in the complex is in the range 1-20:1, or any range therein between. In further embodiments, the molar ratio of αPPMX/taxane (or taxane salt or acid) in the complex is in the range 1-10:1, or any range therein between. In further embodiments, the molar ratio of αPPMX/taxane (or taxane salt or acid) in the complex is in the range 2-8:1, or any range therein between. In some embodiments, the molar ratio of αPPMX/taxane (or taxane salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/taxane (or taxane salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/ taxane-based agent complex is encapsulated in a liposome (e.g., as described herein or otherwise known in the art).

In additional embodiments, the disclosure provides a complex comprising αPPMX and paclitaxel (PTX), or a salt or acid thereof. In other embodiments, the αPPMX/taxane-based chemotherapeutic agent complex comprises an analog of paclitaxel (PTX), or a salt or acid thereof. In some embodiments, the molar ratio of αPPMX/paclitaxel (or paclitaxel salt or acid) in the complex is in the range 1-20:1, or any range therein between. In further embodiments, the molar ratio of αPPMX/paclitaxel (or paclitaxel salt or acid) in the complex is in the range 1-10:1, or any range therein between. In further embodiments, the molar ratio of αPPMX/paclitaxel (or paclitaxel salt or acid) in the complex is in the range 2-8:1, or any range therein between. In some embodiments, the molar ratio of αPPMX/paclitaxel (or paclitaxel salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/paclitaxel (or paclitaxel salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/paclitaxel (or paclitaxel salt or acid) complex is encapsulated in a liposome (e.g., as described herein or otherwise known in the art).

In additional embodiments, the disclosure provides a complex comprising αPPMX and docetaxel (DTX), or a salt or acid thereof. In other embodiments, the αPPMX/taxane-based chemotherapeutic agent complex comprises an analog of docetaxel (DTX), or a salt or acid thereof. In some embodiments, the molar ratio of αPPMX/docetaxel (or docetaxel salt or acid) in the complex is in the range 1-20:1, or any range therein between. In some embodiments, the molar ratio of αPPMX/docetaxel (or docetaxel salt or acid) in the complex is in the range 1-10:1, or any range therein between. In further embodiments, the molar ratio of αPPMX/docetaxel (or docetaxel salt or acid) in the complex is in the range 2-8:1, or any range therein between. In some embodiments, the molar ratio of αPPMX/docetaxel (or docetaxel salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/docetaxel (or docetaxel salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/docetaxel (or docetaxel salt or acid) complex is encapsulated in a liposome (e.g., as described herein or otherwise known in the art).

In additional embodiments, the disclosure provides a complex comprising αPPMX and larotaxel (LTX), or a salt or acid thereof. In other embodiments, the αPPMX/taxane-based chemotherapeutic agent complex comprises an analog of larotaxel (LTX), or a salt or acid thereof. In some embodiments, the molar ratio of αPPMX/larotaxel (or larotaxel salt or acid) in the complex is in the range 1-20:1, or any range therein between. In further embodiments, the molar ratio of αPPMX/larotaxel (or larotaxel salt or acid) in the complex is in the range 1-10:1, or any range therein between. In further embodiments, the molar ratio of αPPMX/larotaxel (or larotaxel salt or acid) in the complex is in the range 2-8:1, or any range therein between. In some embodiments, the molar ratio of αPPMX/larotaxel (or larotaxel salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/larotaxel (or larotaxel salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/larotaxel (or larotaxel salt or acid) complex is encapsulated in a liposome (e.g., as described herein or otherwise known in the art).

In additional embodiments, the disclosure provides a complex comprising αPPMX and cabazitaxel (CTX), or a salt or acid thereof. In other embodiments, the αPPMX/taxane-based chemotherapeutic agent complex comprises an analog of cabazitaxel (CTX), or a salt or acid thereof. In some embodiments, the molar ratio of αPPMX/cabazitaxel (or cabazitaxel salt or acid) in the complex is in the range 1-20:1, or any range therein between. In further embodiments, the molar ratio of αPPMX/cabazitaxel (or cabazitaxel salt or acid) in the complex is in the range 1-10:1, or any range therein between. In further embodiments, the molar ratio of αPPMX/cabazitaxel (or cabazitaxel salt or acid) in the complex is in the range 2-8:1, or any range therein between. In some embodiments, the molar ratio of αPPMX/cabazitaxel (or cabazitaxel salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/cabazitaxel (or cabazitaxel salt or acid) in the complex is: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/cabazitaxel (or cabazitaxel salt or acid) complex is encapsulated in a liposome (e.g., as described herein or otherwise known in the art).

In additional embodiments, the disclosure provides a complex comprising αPPMX and another anti-metabolite, or a salt or acid thereof. An anti-metabolite is a chemical with a structure that is similar to a metabolite required for normal biochemical reactions, yet different enough to interfere with one or more normal functions of cells, such as cell division. In some embodiments, the disclosure provides a complex comprising αPPMX and pemetrexed (PMX), or a salt or acid thereof. In some embodiments, the disclosure provides a complex comprising αPPMX and an anti-metabolite selected from the group consisting of, gemcitabine, fluorouracil, capecitabine, an antifolate (e.g., methotrexate, raltitrexed), tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salt or acids, acids, or derivatives of any of these. In some embodiments, the molar ratio of αPPMX/anti-metabolite (or anti-metabolite salt or acid) in the complex is in the range 1-20:1, or any range therein between. In further embodiments, the molar ratio of αPPMX/anti-metabolite (or anti-metabolite salt or acid) in the complex is in the range 1-10:1, or any range therein between. In further embodiments, the molar ratio of αPPMX/anti-metabolite (or anti-metabolite salt or acid) in the complex is in the range 2-8:1, or any range therein between. In some embodiments, the molar ratio of αPPMX/anti-metabolite (or anti-metabolite salt or acid) in the complex is 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In some embodiments, the molar ratio of αPPMX/anti-metabolite (or anti-metabolite salt or acid) in the complex is 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In additional embodiments, the αPPMX/antimetabolite (or anti-metabolite salt or acid) complex is encapsulated in a liposome (e.g., as described herein or otherwise known in the art).

In additional embodiments, the disclosure provides a complex of αPPMX (e.g., an αPPMX disclosed herein) and a cyclodextrin. Cyclodextrins (CDs) are groups of cyclic oligosaccharides which have been shown to improve physicochemical properties of many drugs through formation of complexes. CDs are cyclic oligosaccharides composed of several D-glucose units linked by α-(1,4) bonds. This cyclic configuration provides a hydrophobic internal cavity and gives the CDs a truncated cone shape. Many hydroxyl groups are situated on the edges of the ring which make the CDs both lipophilic and soluble in water. As a result, CDs are able to form complexes with a wide variety of hydrophobic agents, and thus change the physical-chemical properties of these complexed agents.

The terms "cyclodextrin" or "CD" unless otherwise specified herein, refer generally to a parent or derivatized cyclic oligosaccharide containing a variable number of (α-1,4)-linked D-glucopyranoside units that is able to form a complex with a pemetrexed-PG. Each cyclodextrin glucopyranoside subunit has secondary hydroxyl groups at the 2 and 3 positions and a primary hydroxyl group at the 6-position. The terms "parent," "underivatized," or "inert," cyclodextrin refer to a cyclodextrin containing D-glucopyranoside units having the basic formula $C_6H_{12}O_6$ and a glucose structure without any additional chemical substitutions (e.g., α-cyclodextrin consisting of 6 D-glucopyranoside units, a β-cyclodextrin consisting of 7 D-glucopyranoside units, and a γ-cyclodextrin cyclodextrin consisting of 8 D-glucopyranoside units). The physical and chemical properties of a parent cyclodextrin can be modified by derivatizing the hydroxyl groups with other functional groups. Any substance located within the cyclodextrin internal phase is said to be "complexed" with the cyclodextrin, or to have formed a complex (inclusion complex) with the cyclodextrin.

As used herein, there are no particular limitations on the cyclodextrin component of the αPPMX/cyclodextrin complexes so long as the cyclodextrins can form complexes with the αPPMX. In particular embodiments, the cyclodextrins have been derivatized to bear ionizable (e.g., weakly basic and/or weakly acidic) functional groups to facilitate complex formation with αPPMX and/or liposome encapsulation.

Modifications of the hydroxyl groups of cyclodextrins, such as those facing away from the cyclodextrin interior phase, with ionizable chemical groups is known to facilitate the loading of cyclodextrins and therapeutic agents complexed with the cyclodextrins. In some embodiments, the cyclodextrin of the αPPMX/cyclodextrin complex has at least 2, 3, 4, 5, 6, 6, 7, 8, 9, or 10, hydroxyl group substituted with an ionizable chemical group. The term "charged cyclodextrin" refers to a cyclodextrin having one or more of its hydroxyl groups substituted with a charged moiety. Such a moiety can itself be a charged group or it can comprise an organic moiety (e.g., a $C_1$-$C_6$ alkyl or $C_1$-$C_6$ alkyl ether moiety) substituted with one or more charged moieties.

In some embodiments, the "ionizable" or "charged" moieties of a CD derivative are weakly ionizable. Weakly ionizable moieties are those that are either weakly basic or weakly acidic. Weakly basic functional groups (W) have a pKa of between about 6.0-9.0, 6.5-8.5, 7.0-8.0, 7.5-8.0, and any range in between inclusive according to CH3-W. Similarly, weakly acidic functional groups (X) have a log dissociation constant (pKa) of between about 3.0-7.0, 4.0-6.5, 4.5-6.5, 5.0-6.0, 5.0-5.5, and any range in between inclusive according to CH3-X. Representative anionic moieties include, without limitation, carboxylate, carboxymethyl, succinyl, sulfonyl, phosphate, sulfoalkyl ether, sulphate carbonate, thiocarbonate, dithiocarbonate, phosphate, phosphonate, sulfonate, nitrate, and borate groups. Representative cationic moieties include, without limitation, amino, guanidine, and quarternary ammonium groups.

In another embodiment, the derivatized cyclodextrin is a "polyanion" or "polycation." A polyanion is a derivatized cyclodextrin having more than one negatively charged group resulting in net a negative ionic charge of more than two units. A polycation is a derivatized cyclodextrin having more than one positively charged group resulting in net positive ionic charger of more than two units.

In another embodiment, the derivatized cyclodextrin is a "chargeable amphiphile." By "chargeable" is meant that the amphiphile has a pK in the range pH 4 to pH 8 or 8.5. A chargeable amphiphile may therefore be a weak acid or base. By "amphoteric" herein is meant a derivatized cyclodextrin having a ionizable groups of both anionic and cationic character wherein: (a) at least one, and optionally both, of the cation and anionic amphiphiles is chargeable, having at least one charged group with a pK between 4 and 8 to 8.5, (b) the cationic charge prevails at pH 4, and (c) the anionic charge prevails at pH 8 to 8.5.

In some embodiments, the "ionizable" or "charged" derivatized cyclodextrin as a whole, whether polyionic, amphiphilic, or otherwise, are weakly ionizable (i.e., have a pKai of between about 4.0-8.5, 4.5-8.0, 5.0-7.5, 5.5-7.0, 6.0-6.5, and any range in between inclusive).

Any one, some, or all hydroxyl groups of any one, some or all α-D-glucopyranoside units of a cyclodextrin can be modified to an ionizable chemical group as described herein. Since each cyclodextrin hydroxyl group differs in chemical reactivity, reaction with a modifying moiety can produce an amorphous mixture of positional and optical isomers. Alternatively, certain chemistry can allow for pre-modified α-D-glucopyranoside units to be reacted to form uniform products.

The aggregate substitution that occurs for cyclodextrin derivatives in a mixture is described by a term referred to as the degree of substitution. For example, a 6-ethylenediamino-β-cyclodextrin with a degree of substitution of seven would be composed of a distribution of isomers of 6-ethylenediamino-β-cyclodextrin in which the average number of ethylenediamino groups per 6-ethylenediamino-β-cyclodextrin molecule is seven. The degree of substitution for a cyclodextrin derivative mixture can routinely be determined using mass spectrometry or nuclear magnetic resonance spectroscopy.

In one embodiment, at least one hydroxyl moieties facing away from the cyclodextrin interior is substituted with an ionizable chemical group. For example, the C2, C3, C6, C2 and C3, C2 and C6, C3 and C6, and all three of C2-C3-C6 hydroxyls of at least one α-D-glucopyranoside unit are substituted with an ionizable chemical group. Any such combination of hydroxyls can similarly be combined with at least two, three, four, five, six, seven, eight, nine, ten, eleven, up to all of the alpha-D-glucopyranoside units in the modified cyclodextrin as well as in combination with any degree of substitution described herein. One such derivative is a sulfoalkyl ether cyclodextrin (SAE-CD). Sulfobutyl ether derivatives of beta cyclodextrin (SBE-β-CD) have been demonstrated to have significantly improved aqueous solubility compared to the parent cyclodextrin.

Additional cyclodextrin derivatives that may be complexed with therapeutic agents in the disclosed liposome compositions include sugammadex or Org-25969, in which the 6-hydroxy groups on γ-CD have been replaced by carboxythio acetate ether linkages, and hydroxybutenyl-β-CD. Alternative forms of cyclodextrin include: 2,6-Di-O-methyl-β-CD (DIMEB), 2-hydroxylpropyl-3-cyclodextrin (HP-β-CD), randomly methylated-β-cyclodextrin (RAMEB), sulfobutyl ether β-cyclodextrin (SBE-β-CD), and sulfobutylether-γ-cyclodextrin (SBEγCD), sulfobutylated beta-cyclodextrin sodium salt, (2-Hydroxypropyl)-alpha-cyclodextrin, (2-Hydroxypropyl)-beta-cyclodextrin, (2-Hydroxypropyl)-γ-cyclodextrin, 2,6-di-O-methyl)-beta-cyclodextrin (DIMEB-50 Heptakis), 2,3,6-tri-O-methyl)-beta-cyclodextrin (TRIMEB Heptakis), methyl-beta-cyclodextrin, octakis (6-deoxy-6-iodo)-γ-cyclodexrin, and, octakis (6-deoxy-6-bromo)-gamma-cyclodexrin.

In some embodiments, the cyclodextrin(s) has a high solubility in water in order to facilitate entrapment of a larger amount of the cyclodextrin in the liposome internal phase. In some embodiments, the water solubility of the cyclodextrin is at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL or higher. In some embodiments, the water solubility of the cyclodextrin(s) is within a range of 10-150 mg/mL, 20-100 mg/mL 20-75 mg/mL, and any range in between inclusive.

In some embodiments, a large association constant between the cyclodextrin and the αPPMX and/or other therapeutic agent complexed with cyclodextrin is preferable and can be obtained by selecting the number of glucose units in the cyclodextrin based on the size of the therapeutic agent (see, for example, Albers et al., Crit. Rev. Therap. Drug Carrier Syst. 12:311-337 (1995); Stella et al., Toxicol. Pathol. 36:30-42 (2008). When the association constant depends on pH, the cyclodextrin can be selected such that the association constant becomes large at the pH of the liposome internal phase. As a result, the solubility (nominal solubility) of the therapeutic agent in the presence of cyclodextrin can be further improved. In some embodiments, the association constant of the cyclodextrin with the therapeutic agent is 100, 200, 300, 400, 500, 600, 700, 800, 900, 1,000, or higher. In some embodiments, the association constant of the cyclodextrin with the therapeutic agent is in the range 100-1, 200, 200-1,000, 300-750, and any range therein between.

In some embodiments, the cyclodextrin of the αPPMX/cyclodextrin complex and/or cyclodextrin/therapeutic agent complex is underivatized.

In some embodiments, the cyclodextrin of the αPPMX/cyclodextrin complex and/or cyclodextrin/therapeutic agent complex is derivatized. In further embodiments, the cyclodextrin derivative of the complex has the structure of Formula I:

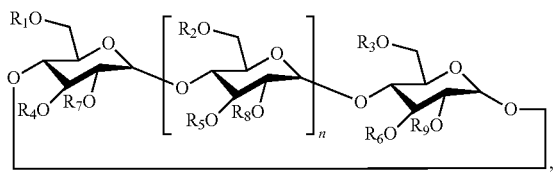

wherein: n is 4, 5, or 6;
wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene (e.g., $C_1$-$C_8$-(alkylene)-$SO_3^-$ group).

In some embodiments, the cyclodextrin derivative of the αPPMX/cyclodextrin complex and/or cyclodextrin/therapeutic agent complex has the structure of formula II:

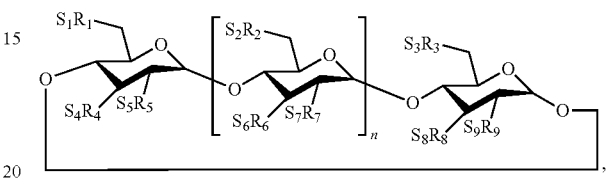

wherein: n is 4, 5, or 6;
wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3$— group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a pharmaceutically acceptable cation. In further embodiments, the pharmaceutically acceptable cation is selected from: an alkali metal such as $Li^+$, $Na^+$, or $K^+$; an alkaline earth metal such as $Ca^{+2}$, or $Mg^{+2}$ and ammonium ions and amine cations such as the cations of (C1-C6)-alkylamines, piperidine, pyrazine, (C1-C6)-alkanolamine and (C4-C8)-cycloalkanolamine. In some embodiments, at least one of R1 and R2 is independently a —O—(C2-C6 alkylene)-$SO_3$— group that is a —O—$(CH_2)_m SO3$- group, wherein m is 2 to 6, preferably 2 to 4, (e.g., —O—CH2CH2CH2SO3- or —O—CH2CH2CH2CH2SO3-); and $S_1$, $S_2$, $S_3$, $S_4$, $S_5$, $S_6$, $S_7$, $S_8$, and $S_9$ are each, independently, H or a pharmaceutically cation which includes for example, alkali metals (e.g., $Li^+$, $Na^+$, $K^+$) alkaline earth metals (e.g., $Ca^{+2}$, $Mg^{+2}$), ammonium ions and amine cations such as the cations of (C1-C6)-alkylamines, piperidine, pyrazine, ($C_1$-$C_6$)-alkanol-amine and ($C_4$-$C_8$)-cycloalkanolamine.

In some embodiments, a cyclodextrin derivative of the αPPMX/cyclodextrin complex and/or cyclodextrin/therapeutic agent complex is a cyclodextrin disclosed in U.S. Pat. Nos. 6,133,248, 5,874,418, 6,046,177, 5,376,645, 5,134,127, 7,034,013, 6,869,939; and Intl. Appl. Publ. No. WO 02005/117911, the contents each of which is herein incorporated by reference in its priority.

In some embodiments, the cyclodextrin derivative of the αPPMX/cyclodextrin complex and/or cyclodextrin/therapeutic agent complex is a sulfoalkyl ether cyclodextrin. In some embodiments, the cyclodextrin derivative of complex is a sulfobutyl ether-3-cyclodextrin such as CAPTISOL® (CyDex Pharma. Inc., Lenexa, Kansas. Methods for preparing sulfobutyl ether-3-cyclodextrin and other sulfoalkyl ether cyclodextrins are known in the art.

In some embodiments, the cyclodextrin derivative in of the αPPMX/cyclodextrin complex and/or cyclodextrin/therapeutic agent complex is a compound of Formula III:

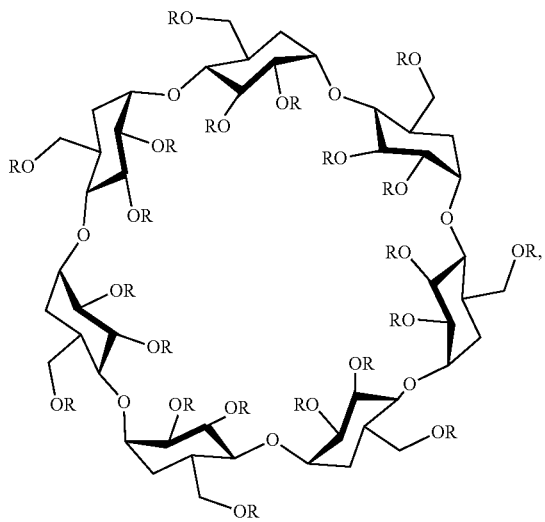

wherein R equals:
(a) $(H)_{21-x}$ or $(—(CH_2)_4—SO_3Na)x$, and x=1.0-10.0, 1.0-5.0, 6.0-7.0, or 8.0-10.0;
(b) $(H)_{21-x}$ or $(—CH_2CH(OH)CH_3)x$, and x=1.0-10.0, 1.0-5.0, 6.0-7.0, or 8.0-10.0;
(c) $(H)_{21-x}$ or (sulfoalkyl ethers)x, and x=1.0-10.0, 1.0-5.0, 6.0-7.0, or 8.0-10.0; or
(d) $(H)_{21-x}$ or $(—(CH_2)_4—SO_3Na)x$, and x=1.0-10.0, 1.0-5.0, 6.0-7.0, or 8.0-10.0.

In additional embodiments, the αPPMX/cyclodextrin complex and/or cyclodextrin/therapeutic agent complex is encapsulated in a liposome (e.g., as described herein or otherwise known in the art).

III. αPPMX Delivery Vehicles

In alternative embodiments, the disclosure provides αPPMX delivery systems and their use to deliver a payload of αPPMX to a cell or cells in vitro or in vivo. In some embodiments, αPPMX is complexed with or incorporated into a delivery vehicle. Such delivery vehicles are known in the art and include, but are not limited to, liposomes, lipospheres, polymers, peptides, proteins, antibodies (e.g., ADCs such as Antibody-αPPMX conjugates), cellular components, cyclic oligosaccharides (e.g., cyclodextrins), nanoparticles (e.g., lipid nanoparticles, biodegradable nanoparticles, and core-shell nanoparticles), lipoprotein particles, and combinations thereof. In particular embodiments, the delivery vehicle is a liposome. In other particular embodiments, the delivery vehicle is an antibody or an antigen binding antibody fragment.

A. Liposomes

In some embodiments, the disclosure provides liposomal compositions that comprise a liposome encapsulating (i.e., filled with) an alpha polyglutamated pemetrexed (e.g., an αPPMX disclosed herein). In some embodiments, a liposome in the liposomal composition comprises a αPPMX containing 4, 5, 6, 2-10, 4-6, or more than 5, glutamyl groups (including the glutamyl group in pemetrexed). In some embodiments, the alpha polyglutamated pemetrexed in the Lp-αPPMX comprises two or more glutamyl groups in the L-form. In other embodiments, the alpha polyglutamated pemetrexed in the Lp-αPPMX comprises a glutamyl group in the D-form. In further embodiments, the alpha polyglutamated pemetrexed in the Lp-αPPMX comprises a glutamyl group in the D-form and two or more glutamyl groups in the L-form. In additional embodiments, the alpha polyglutamated pemetrexed in the Lp-αPPMX comprises two or more glutamyl groups that have a gamma carboxyl linkage. In some embodiments, the alpha polyglutamated pemetrexed in the Lp-αPPMX comprises at least one glutamyl group that has both an alpha carboxyl linkage and a gamma carboxyl linkage. In some embodiments, the liposomal composition comprises a liposome comprising a α pentaglutamated PMX. In further embodiments, the liposome comprises an L-α pentaglutamated PMX, a D-α pentaglutamated PMX, or an L- and D-α pentaglutamated PMX. In some embodiments, the liposomal composition comprises a liposome comprising a α hexaglutamated PMX (Lp-αPPMX). In further embodiments, the liposome comprises an L-α hexaglutamated PMX, a D-α hexaglutamated PMX, or an L- and D-α hexaglutamated PMX. In some embodiments, the liposomal composition comprises a liposome that is anionic or neutral. In some embodiments, the liposomal composition comprises a liposome that is cationic. In some embodiments, the Lp-αPPMX composition is unpegylated. In some embodiments, the Lp-αPPMX composition is non-targeted (NTLp-αPPMX). In other embodiments, the Lp-αPPMX composition is targeted (TLp-αPPMX). In some embodiments, the liposomal composition comprises a liposome having a diameter in the range of 20 nm to 500 nm, or any range therein between. In some embodiments, the liposomal composition comprises a liposome having a diameter in the range of 20 nm to 400 nm, or any range therein between. In some embodiments, the liposomal composition comprises a liposome having a diameter in the range of 20 nm to 300 nm, or any range therein between. In some embodiments, the liposomal composition comprises a liposome having a diameter in the range of 20 nm to 200 nm, or any range therein between. In further embodiments, the liposomal composition comprises a liposome having a diameter in the range of 20 nm to 150 nm, or any range therein between. In further embodiments, the liposomal composition comprises a liposome having a diameter in the range of 80 nm to 120 nm, or any range therein between. In additional embodiments, 30-70%, 30-60%, or 30-50% w/w alpha polyglutamated pemetrexed, or any range therein between, is encapsulated (entrapped) in the Lp-αPPMX. In some embodiments, at least 1%, 5%, 10%, 15%, 20%, 25%, 30%, 35%, 40%, 45%, 50%, 55%, 60%, 65%, 70%, 75% or more than 75%, alpha polyglutamated pemetrexed, is encapsulated in the Lp-αPPMX during the process of preparing the liposomes.

In some embodiments, the provided liposomes further comprise an immunostimulatory agent, a detectable marker, or both disposed on its exterior. The immunostimulatory agent or detectable marker can be ionically bonded or covalently bonded to an exterior of the liposome, including, for example, optionally to a steric stabilizer component of the liposome.

The terms "immunostimulatory agents", also known as "immunostimulants", and "immunostimulators", refer to substances that stimulate an immune (including a preexisting immune response) by inducing activation or increasing activity of any of the components of the immune system. These immunostimulatory agents can include one or more of a hapten, an adjuvant, a protein immunostimulating agent, a nucleic acid immunostimulating agent, and a chemical immunostimulating agent. Many adjuvants contain a substance designed to stimulate immune responses, such as lipid A, *Bordetella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; IFN-gamma, IFN-alpha, FLT3-ligand; and immunostimulatory antibodies (e.g., anti-CTLA-4, anti-CD28, anti-CD3. Cytokines, such as GM-CSF, interleukin-2, -7, -12, and -15, and other like growth factors, can also be used as adjuvants. In a preferred embodiment, the immunostimulant can be at least one selected from the group consisting of fluorescein, DNP, beta glucan, beta-1,3-glucan, beta-1,6-glucan. In an additional preferred embodiment, the immunostimulant is a Toll-like receptor (TLR) modulating agent. In further embodiments, the Toll-like receptor (TLR) modulating agent is one or more of: an oxidized low-density lipoprotein (e.g., OXPAC, PGPC), an eritoran lipid (e.g., E5564), and a resolvin. In some embodiments, the liposomes comprise fluorescein isothiocyanate (FITC) which, based on our experiments, surprisingly serves as both an immunostimulant and a detectable marker.

In some embodiments, the liposomes comprise a detectable marker. A detectable marker may, for example, include, at least, a radioisotope, a fluorescent compound, a bioluminescent compound, chemiluminescent compound, a metal chelator, an enzyme, a dye, an ink, a magnetic compound, a biocatalyst or a pigment that is detectable by any suitable means known in the art, e.g., magnetic resonance imaging (MRI), optical imaging, fluorescent/luminescent imaging, and/or nuclear imaging techniques.

In some embodiments, the immunostimulatory agent and/or detectable marker is attached to the exterior by co-incubating it with the liposome. For example, the immunostimulatory agent and/or detectable marker may be associated with the liposomal membrane by hydrophobic interactions or by an ionic bond such as an avidin/biotin bond or a metal chelation bond (e.g., Ni-NTA). Alternatively, the immunostimulatory agent or detectable marker may be covalently bonded to the exterior of the liposome such as, for example, by being covalently bonded to a liposomal component or to the steric stabilizer which is the PEG.

In some embodiments, the liposomes further comprise an agent that increases the uptake of liposomes into a cellular compartment of interest including the cytosol.

In some embodiments, the liposomes comprise a mitochondrial-targeting agent. In some embodiments, the liposomes comprise triphenylphosphonium (TPP). Methods and mechanisms for surface functionalizing liposomes with TPP are known in the art (e.g., attaching TPP to the lipid anchor via a peg spacer group and modifying TPP with a stearyl group (stearyl triphenylphosphonium (STPP)). In some embodiments, the liposomes comprise high-density octa-arginine. In some embodiments, the liposomes comprise sphingomyelin and/or a sphingomyelin metabolite. Sphingomyelin metabolite used to formulate the liposomes of the present invention can include, for example ceramide, sphingosine or sphingosine 1-phosphate. In some embodiments, the liposomes comprise Rhodamine 123. In some embodiments, the liposomes comprise, a mitochondria penetrating peptide. In some embodiments, the liposomes comprise, a mitochondria penetrating agent selected from the group consisting of: a mitofusin peptide, a mitochondrial targeting signal peptide, Antennapedia helix III homeodomain cell-penetrating peptide (ANT) (e.g., comprising RQIKIWFQNRRMKWKKRKKRRQRRR (SEQ ID NO:1), RKKRRXR RRGC where X is any natural or non-natural amino acid (SEQ ID NO:2), CCGCCAAGAAGCG (SEQ ID NO:3), GCGTGCACACGCGCGTAGACTTCCCCC GCAAGTCACTCGTTAGCCCGC-CAAGAAGCGACCCCTCCGGGGCGAGCTGAGCGG CGTGGCGCGGGGGCGTCAT (SEQ ID NO:4), ACGTG-CATACGCACGTAGACATTCCC CGCTTCCCACTC-CAAAGTCCGCCAAGAAGCGTATCCCGCT-GAGCGGCGTGGCGC GGGGGCGTCATCCGTCAGCTC (SEQ ID NO:5), or ACTTCCCCCGCAAGTCACTCGT TAGCCCGC-CAAGAAGCGACCCCTCCGGGGCGAGCTG (SEQ ID NO:6)), or a mitochondrial penetrating fragment thereof.

In some embodiments, liposomes in the provided liposome compositions comprise a mitochondria penetrating agent selected from the group: a guanidine-rich peptoid, tetraguanidinium, triguanidinium, diguanidinium, monoguanidinium, a guanidine-rich polycarbamate, a beta-oligoarginine, a proline-rich dendrimer, and a phosphonium salt (e.g., methyltriphenyl-phosphonium and/or tetraphenylphosphonium).

In some embodiments, liposomes in the provided liposome compositions comprise sphingomyelin and/or stearyl-octa-arginine. In some embodiments, the liposomes comprise sphingomyelin and/or stearyl-octa-arginine. In some embodiments, the liposomes comprise DOPE, sphingomyelin, stearyl-octa-arginine sphingomyelin and stearyl-octa-arginine. In some embodiments, the liposomes comprise DOPE, sphingomyelin, stearyl-octa-arginine sphingomyelin and stearyl-octa-arginine at a molar ratio of 9:2:1. In some embodiments, the liposomes comprise the MITO-Porter® system or a variant thereof.

In some embodiments, liposomes in the provided liposome compositions comprise an agent such as a cell penetrating agent that that facilitates delivery of the liposome across a cell membrane and provides the liposome with the ability to bypass the endocytic pathway and the harsh environment of lysosomes. Cell penetrating agents are known in the art and can routinely be used and adapted for manufacture and use of the provided liposome compositions. In some embodiments, the cell penetrating/lysosome bypassing agent is chloroquine. In some embodiments, the cell penetrating agent is a cell penetrating peptide. In some embodiments, liposomes in the provided liposome compositions comprise a cell penetrating agent selected from the group: RKKRRQRRR (SEQ ID NO:7), GRKKRRQRRRTPQ (SEQ ID NO:8), YGRKKRRQRRR (SEQ ID NO:9), AAVAL LPAVLLALLA (SEQ ID NO:10), MGLGLHLLVLAAALQ (SEQ ID NO:11), GALFL GFL-GAAGSTM (SEQ ID NO:12), AGYLLGKINLKA-LAALAKKIL (SEQ ID NO:13), RVIRVWFQNKRCKDKK (SEQ ID NO:14), RQIKIWFQNRRMKWKK (SEQ ID NO:15), GLFEAIAGFIENGWEGMIDG (SEQ ID NO:16), GWTLNSAGYLLGKIN (SEQ ID NO:17), RSQSRSRYYRQRQRS (SEQ ID NO:18), LAIPEQEY (SEQ ID NO:19), LGIAEQEY (SEQ ID NO:20), LGI-PAQEY (SEQ ID NO:21), LGIPEAEY (SEQ ID NO:22), LGIPEQAY (SEQ ID NO:23), LGIAEAEY (SEQ ID NO:24), LGIPEAAY (SEQ ID NO:25), LGIAEQAY (SEQ ID NO:26), LGIAEAAY (SEQ ID NO:27), LLIILRR-RIRKQAHAHSK (SEQ ID NO:28), LKALAALAKKIL (SEQ ID NO:29), KLALKLALKALKAALKLA (SEQ ID NO:30), KETWWETWWTEWSQPKKKRKV (SEQ ID NO:31), DHQLNPAF (SEQ ID NO:32), DPKGDPKG (SEQ ID NO:33), VTVTVTVTVTGKGDPKPD (SEQ ID NO:34), RQIKIWFQNRRMKWKK (SEQ ID NO:35), GRKKRRQRRRPPQ (SEQ ID NO:36), GWTLN-SAGYLLGKINLKALAAL AKKIL (SEQ ID NO:37), GRKKRRQRRR (SEQ ID NO:38), RRRRRRR (SEQ ID NO:39), RRRRRRRR (SEQ ID NO:40), RRRRRRRRR (SEQ ID NO:41), RRRRRRRR RR (SEQ ID NO:42), RRRRRRRRRRR (SEQ ID NO:43), and YTIWMPEN-PRPGT PCDIFTNSRGKRASNGGG G(R)n wherein n=2-15 R in the L- and/or D-form (SEQ ID NO:44), or a cell permeating fragment thereof.

As discussed above, the liposomes may comprise a steric stabilizer that can increase their longevity in circulation. For those embodiments, which incorporate a steric stabilizer, the steric stabilizer may be at least one member selected from the group consisting of polyethylene glycol (PEG), poly-L-lysine (PLL), monosialoganglioside (GM1), poly(vinyl pyrrolidone) (PVP), poly(acrylamide) (PAA), poly(2-methyl-2-oxazoline), poly(2-ethyl-2-oxazoline), phosphatidyl polyglycerol, poly[N-(2-hydroxypropyl) methacrylamide], amphi-philic poly-N-vinylpyrrolidones, L-amino-acid-based polymer, oligoglycerol, copolymer containing polyethylene glycol and polypropylene oxide, Poloxamer 188, and polyvinyl alcohol. In some embodiments, the steric stabilizer or the population of steric stabilizer is PEG. In one embodiment, the steric stabilizer is a PEG. In a further embodiment, the PEG has a number average molecular weight (Mn) of 200 to 5000 daltons. These PEG(s) can be of any structure such as linear, branched, star or comb structure and are commercially available.

In some embodiments, the liposomal composition comprises a pegylated liposome (PLp-αPPMX). In some embodiments, a pegylated liposome in the liposomal composition comprises a αPPMX containing 4, 5, 6, 2-10, 4-6, or more than 5, glutamyl groups. In some embodiments, the alpha polyglutamated pemetrexed in the Lp-αPPMX comprises two or more glutamyl groups in the L-form. In other embodiments, the alpha polyglutamated pemetrexed in the Lp-αPPMX comprises a glutamyl group in the D-form. In further embodiments, the alpha polyglutamated pemetrexed in the Lp-αPPMX comprises a glutamyl group in the D-form and two or more glutamyl groups in the L-form. In additional embodiments, the alpha polyglutamated pemetrexed in the Lp-αPPMX comprises two or more glutamyl groups that have a gamma linkage. In some embodiments, at least one glutamyl group has both an alpha linkage and a gamma linkage. In some embodiments, the liposomal composition comprises a pegylated liposome comprising an α pentaglutamated PMX. In further embodiments, the liposome comprises an L-α pentaglutamated PMX, a D-α pentaglutamated PMX, or an L- and D-α pentaglutamated PMX. In some embodiments, the liposomal composition comprises a pegylated liposome comprising an α hexaglutamated PMX. In further embodiments, the liposome comprises an L-α hexaglutamated PMX, a D-α hexaglutamated PMX, or an L- and D-α hexaglutamated PMX. In some embodiments, the liposomal composition comprises a pegylated liposome that is anionic or neutral. In some embodiments, the liposomal composition comprises a pegylated liposome that is cationic. In some embodiments, the PLp-αPPMX composition is non-targeted (NTPLp-αPPMX). In other embodiments, the PLp-αPPMX composition is targeted (TPLp-αPPMX). In additional embodiments, the liposomal composition comprises a pegylated liposome that comprises 30-70%, 30-60%, or 30-50% liposome entrapped alpha polyglutamated pemetrexed, or any range therein between. In some embodiments, at least 1%, 5%, 10%, 15%, 20%, 25%, 30%, 35%, 40%, 45%, 50%, 55%, 60%, 65%, 70%, 75%, or more than 75%, w/w of the alpha polyglutamated pemetrexed is encapsulated (entrapped) in the PLp-αPPMX. In some embodiments, the liposomal composition comprises a pegylated liposome having a diameter in the range of 20 nm to 500 nm. In some embodiments, the liposomal composition comprises a pegylated liposome having a diameter in the range of 20 nm to 200 nm. In further embodiments, the liposomal composition comprises a pegylated liposome having a diameter in the range of 80 nm to 120 nm.

In some embodiments, greater than 30%, 40%, 50%, 60%, 70%, 80% or 90% of the polyglutamated pemetrexed in the composition has 4-10, 4-6, or more than 5, glutamyl groups. In some embodiments, greater than 30%, 40%, 50%, 60%, 70%, 80% or 90%, of the polyglutamated pemetrexed in a provided liposomal composition is tetraglutamated. In some embodiments, greater than 30%, 40%, 50%, 60%, 70%, 80% or 90%, of the polyglutamated pemetrexed in a provided liposomal composition is pentaglutamated. In some embodiments, greater than 30%, 40%, 50%, 60%, 70%, 80% or 90%, of the polyglutamated pemetrexed in a provided liposomal composition is hexaglutamated.

In some embodiments, the alpha polyglutamated pemetrexed compositions (e.g., polyglutamates and delivery vehicles such as liposomes containing the polyglutamates) are in an aqueous solution. In some embodiments, the αPPMX composition is administered in a liposomal composition at a dose of between 0.005 and 5000 mg of αPPMX per square meter ($m^2$) of body surface area, or any range therein between. In further embodiments, the αPPMX composition is administered in a liposomal composition at a dose of between 0.1 and 1000 mg αPPMX/meter squared of body surface area, or any range therein between.

(1) Liposome Composition

The lipids and other components of the liposomes contained in the liposomal compositions can be any lipid, lipid combination and ratio, or combination of lipids and other liposome components and their respective ratios known in the art. However, it will be understood by one skilled in the art that liposomal encapsulation of any particular drug, such as, and without limitation, the alpha polyglutamated PMX discussed herein, may involve substantial routine experimentation to achieve a useful and functional liposomal formulation. In general, the provided liposomes may have any liposome structure, e.g., structures having an inner space sequestered from the outer medium by one or more lipid bilayers, or any microcapsule that has a semi-permeable membrane with a lipophilic central part where the membrane sequesters an interior. The lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward the sheet while hydrophilic moieties are oriented outward. Amphiphilic molecules forming the provided liposomes can be any known or later discovered amphiphilic molecules, e.g., lipids of synthetic or natural origin or biocompatible lipids. The liposomes can also be formed by amphiphilic polymers and surfactants, e.g., polymerosomes and niosomes. For the purpose of this disclosure, without limitation, these liposome-forming materials also are referred to as "lipids".

The liposome composition formulations provided herein can be in liquid or dry form such as a dry powder or dry cake. The dry powder or dry cake may have undergone primary drying under, for example, lyophilization conditions or optionally, the dry cake or dry powder may have undergone both primary drying only or both primary drying and secondary drying. In the dry form, the powder or cake may, for example, have between 1% to 6% moisture, for example, such as between 2% to 5% moisture or between 2% to 4% moisture. One example method of drying is lyophilization (also called freeze-drying, or cyrodessication). Any of the compositions and methods of the disclosure may include liposomes, lyophilized liposomes or liposomes reconstituted from lyophilized liposomes. In some embodiments, the disclosed compositions and methods include one or more lyoprotectants or cryoprotectants. These protectants are typically polyhydroxy compounds such as sugars (mono-, di-, and polysaccharides), polyalcohols, and their derivatives, glycerol, or polyethyleneglycol, trehalose, maltose, sucrose, glucose, lactose, dextran, glycerol, or aminoglycosides. In further embodiments, the lyoprotectants or cryoprotectants comprise up to 10% or up to 20% of a solution outside the liposome, inside the liposome, or both outside and inside the liposome.

In some embodiments, the liposomes include a steric stabilizer that increases their longevity in circulation. One or more steric stabilizers such as a hydrophilic polymer (Polyethylene glycol (PEG)), a glycolipid (monosialoganglioside (GM1)) or others occupies the space immediately adjacent to the liposome surface and excludes other macromolecules from this space. Consequently, access and binding of blood plasma opsonins to the liposome surface are hindered, and thus interactions of macrophages with such liposomes, or any other clearing mechanism, are inhibited and longevity of the liposome in circulation is enhanced. In some embodiments, the steric stabilizer or the population of steric stabilizers is a PEG or a combination comprising PEG. In further embodiments, the steric stabilizer is a PEG or a combination comprising PEG with a number average molecular weight (Mn) of 200 to 5000 daltons. These PEG(s) can be of any structure such as linear, branched, star or comb structure and are commercially available.

The diameter of the disclosed liposomes is not particularly limited. In some embodiments, the liposomes have a diameter in the range of for example, 30-150 nm (nanometer). In other embodiments, the liposomes have a diameter in the range of 40-70 nm.

The properties of liposomes are influenced by the nature of lipids used to make the liposomes. A wide variety of lipids have been used to make liposomes. These include cationic, anionic and neutral lipids. In some embodiments, the liposomes comprising the alpha polyglutamated pemetrexed are anionic or neutral. In other embodiments, the provided liposomes are cationic. The determination of the charge (e.g., anionic, neutral or cationic) can routinely be determined by measuring the zeta potential of the liposome. The zeta potential of the liposome can be positive, zero or negative. In some embodiments, the zeta potential of the liposome is less than or equal to zero. In some embodiments, the zeta potential of the liposome is in a range of 0 to −150 mV. In another embodiment, the zeta potential of the liposome is in the range of −30 to −50 mV.

In some embodiments, cationic lipids are used to make cationic liposomes which are commonly used as gene transfection agents. The positive charge on cationic liposomes enables interaction with the negative charge on cell surfaces. Following binding of the cationic liposomes to the cell, the liposome is transported inside the cell through endocytosis.

In some preferred embodiments, a neutral to anionic liposome is used. In a preferred embodiment, an anionic liposome is used. Using a mixture of, for example, neutral lipids such as HSPC and anionic lipids such as PEG-DSPE results in the formation of anionic liposomes which are less likely to non-specifically bind to normal cells. Specific binding to tumor cells can be achieved by using a tumor targeting antibody such as, for example, a folate receptor antibody, including, for example, folate receptor alpha antibody, folate receptor beta antibody and/or folate receptor delta antibody.

As an example, at least one (or some) of the lipids is/are amphipathic lipids, defined as having a hydrophilic and a hydrophobic portions (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer). The hydrophilic portion can comprise polar or charged groups such as carbohydrates, phosphate, carboxylic, sulfato, amino, sulfhydryl, nitro, hydroxy and other like groups. The hydrophobic portion can comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

Typically, for example, the lipids are phospholipids. Phospholipids include without limitation phosphatidylcholine, phosphatidylethanolamine, phosphatidylglycerol, phosphatidylinositol, phosphatidylserine, and the like. It is to be understood that other lipid membrane components, such as cholesterol, sphingomyelin, and cardiolipin, can be used.

The lipids comprising the liposomes provided herein can be anionic and neutral (including zwitterionic and polar) lipids including anionic and neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphos-phatidylcholine (DMPC), and dioleoylphosphatidylserine (DOPS). Anionic lipids are negatively charged at physiological pH. These lipids include without limitation phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphospha-tidylglycerols, palmitoyloleyolphos-phatidylglycerol (POPG), and other anionic modifying groups joined to neutral lipids.

Collectively, anionic and neutral lipids are referred to herein as non-cationic lipids. Such lipids may contain phosphorus but they are not so limited. Examples of non-cationic lipids include lecithin, lysolecithin, phosphatidylethanolamine, lysophosphatidylethan-olamine, dioleoylphosphati-dylethanolamine (DOPE), dipalmitoyl phosphatidyl ethanol-amine (DPPE), dimyristoylphosphoethanolamine (DMPE), distearoyl-phosphatidy 1-ethan-olamine (DSPE), palmitoyloleoyl-phosphatidylethanolamine (POPE) palmitoyl-oleoylphosphatidylcholine (POPC), egg phosphatidylcholine (EPC), distearoylphosphat-idylcholine (DSPC), dioleoylphosphatidylcholine (DOPC), dipalmitoylphosphatidylcholine (DPPC), dioleoylphosphatidylglycerol (DOPG), dipalmitoylphospha-tidylglycerol (DPPG), palmitoyl-oleyolphosphatidylglycerol (POPG), 16-0-monomethyl PE, 16-0-dimethyl PE, 18-1-trans PE, palmitoyloleoyl-phosphatidyletanolamine (POPE), 1-stearoyl-2-oleoylphospha-tidyethanol-amine (SOPE), phosphatidylserine, phosphatidyl-inositol, sphingomyelin, cephalin, cardiolipin, phosphatidic acid, cerebrosides, dicetyl-phosphate, and cholesterol.

The liposomes may be assembled using any liposomal assembly method using liposomal components (also referred to as liposome components) known in the art. Liposomal components include, for example, lipids such as DSPE, HSPC, cholesterol and derivatives of these components. Other suitable lipids are commercially available for example, by Avanti Polar Lipids, Inc. (Alabaster, Alabama, USA). A partial listing of available negatively or neutrally charged lipids suitable for making anionic liposomes, can be, for example, at least one of the following: DLPC, DMPC, DPPC, DSPC, DOPC, DMPE, DPPE, DOPE, DMPA·Na, DPPA·Na, DOPA·Na, DMPG·Na, DPPG·Na, DOPG·Na, DMPS·Na, DPPS·Na, DOPS·Na, DOPE-Glutaryl·(Na)2, Tetramyristoyl Cardiolipin·(Na)2, DSPE-mPEG-2000·Na, DSPE-mPEG-5000·Na, and DSPE-Maleimide PEG-2000·Na.

In some embodiments, the αPPMX compositions provided herein are formulated in a liposome comprising a cationic lipid. In one embodiment, the cationic lipid is selected from, but not limited to, a cationic lipid described in Intl. Appl. Publ. Nos. WO2012/040184, WO2011/153120, WO2011/149733, WO2011/090965, WO2011/043913, WO2011/022460, WO2012/061259, WO2012/054365, WO2012/044638, WO2010/080724, WO2010/21865 and WO2008/103276, U.S. Pat. Nos. 7,893,302, 7,404,969 and 8,283,333 and US Appl. Publ. Nos. US20100036115 and US20120202871; each of which is herein incorporated by reference in their entirety. In another embodiment, the cationic lipid may be selected from, but not limited to, formula A described in Intl. Appl. Publ. Nos. WO2012/040184, WO2011/153120, WO2011/1149733, WO2011/090965, WO2011/043913, WO2011/022460, WO2012/061259, WO2012/054365 and WO2012/044638; each of which is herein incorporated by reference in their entirety. In yet another embodiment, the cationic lipid may be selected from, but not limited to, formula CLI-CLXXIX of International Publication No. WO2008103276, formula CLI-CLXIX of U.S. Pat. No. 7,893,302, formula CLI-CLXXXII of U.S. Pat. No. 7,404,969 and formula I-VI of US Patent Publication No. US20100036115; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemyl-hexa-cosa-17,20-dien-9-amine, (1Z,19Z)—N5N-dimethylpentacosa-16, 19-dien-8-amine, (13Z,16Z)—N,N-dimethyldocosa-13,16-dien-5-amine, (12Z,15Z)—N,N-dimethyl-henicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyl-tricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexa-cosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyl-triaconta-21,24-dien-9-amine, (18Z)—N,N-dimethylheptacos-18-en-10-amine, (17Z)—N,N-dimethylhexacos-17-en-9-amine, (19Z,22Z)—N,N-dimethyloctacosa-19,22-dien-7-amine, N,N-dimethyl-heptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethyl-heptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpenta-cos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclo-propyl] eptadecan-8-amine, 1-[(1S,2R)-2-hexylcyclopropyl]-N,N-dimethyl nonadecan-10-amine, N,N-dimethyl-1-[(1S,2R)-2-octylcyclopropyl]-nonadecan-10-amine, N,N-dimethyl-21-[R1S,2R)-2-octylcyclopropyl] henicosan-10-amine, N,N-dimethyl-1-[(1S,2S)-2-{[(1R,2R)-2-pentylcyclopropyl]methyl}cyclopropyl] nonadecan-10-amine, N,N-dimethyl-1-[(1S,2R)-2-octylcyclopropyl]hexadecan-8-amine, N,N-dimethyl-[(1R,2S)-2-undecyl-cyclopropyl] tetradecan-5-amine, N,N-dimethyl-3-{7-[(1S,2R)-2-octylcyclopropyl] heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethyl-penta-decan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{12-[(9Z,12Z)-octadeca-9,12-dien-1-yloxy]-1-[(octyloxy)methyl]ethyl}pyrrolidine, (2S)-1-N,N-dimethyl-1-[(9Z,12Z)-octadeca-9,12-dien-1-yloxy]-3-[(5Z-)-oct-5-en-1-yloxy] propan-2-amine, 1-{2-[(9Z,12Z)-octadeca-9,12-dien-1-yloxy]-1-[(octyloxy)methyl] ethyl} azetidine, (2S)-1-(hexyloxy)-N,N-dimethyl-3-[(9Z,12Z)-octadeca-9,12-dien-1-ylo-xy]propan-2-amine, (2S)-1-(heptyloxy)-N,N-dimethyl-3-[(9Z,12Z)-octadeca-9,12-dien-1-yloxy]pr-opan-2-amine, N,N-dimethyl-1-(nonyloxy)-3-[(9Z,12Z)-octadeca-9,12-dien-1-yloxy] propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)pro-pan-2-amine, (2S)-1-(hexyloxy)-3-[(11Z,14Z)-icosa-11,14-dien-1-yloxy]-N,N-dimethylprop-an-2-amine, 1-[(11Z,14Z)-icosa-11,14-dien-1-yloxy]-N,N-dimethyl 1-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dime-thyl-propan-2-amine, (2S)-1-[(13Z)-docos-13-en-1-yloxy]-3-(hexyloxy)-N,N-dimethyl propan-2-amine, 1-[(13Z)-docos-13-en-1-yloxy]-N,N-dimethyl-3-(octyloxy) propan-2-amine, 1-[(9Z)-hexadec-9-en-1-yloxy]-N,N-dimethyl-3-(octyloxy) propan-2-amine, (2R)—N,N-dimethyl-H(1-metoyloctyl)oxy]-3-[(9Z,12Z)-octa-deca-9,12-dien-1-yloxy]propan-2-amine, (2R)-1-[(3,7-dimethyloctyl)oxy]-N,N-dimethyl-3-R9Z,12Z)-octadeca-9,12-die-n-1-yloxylpropan-2-amine, N,N-dimethyl-1-(octyloxy)-3-({8-[(1S,2S)-2-{[(1R,2R)-2-pentylcyclopropyl]-methyl}cyclopropyl] octyl} oxy) propan-2-amine, N,N-dimethyl-1-1[{-(2-oclylcyclopropyl)octyl]oxy}-3-(octyloxy) propan-2-amine and (11E,20Z,23Z)—N,N- dimethylnonacosa-11,20,2-trien-10-amine or a pharmaceutically acceptable salt or acid or stereoisomer thereof.

In one embodiment, the lipid may be a cleavable lipid such as those described in in Intl. Publ. No. WO2012/170889, which is herein incorporated by reference in its entirety The cationic lipid can routinely be synthesized using methods known in the art and/or as described in Intl. Publ. Nos. WO2012/040184, WO2011/153120, WO2011/149733, WO2011/090965, WO201/1043913, WO2011/022460, WO2012/061259, WO2012/054365, WO2012/044638, WO2010/080724 and WO2010/21865; each of which is herein incorporated by reference in its entirety.

Lipid derivatives can include, for example, at least, the bonding (preferably covalent bonding) of one or more steric stabilizers and/or functional groups to the liposomal component after which the steric stabilizers and/or functional groups should be considered part of the liposomal components. Functional groups comprises groups that can be used to attach a liposomal component to another moiety such as a protein. Such functional groups include, at least, maleimide. These steric stabilizers include at least one from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxy-propyl) methacrylamide]; amphiphilic poly-N-vinylpyrrolidones; L-amino-acid-based polymer; and polyvinyl alcohol.

In some embodiments, the αPPMX compositions are formulated in a lipid-polycation complex. The formation of the lipid-polycation complex may be accomplished using methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012/013326; herein incorporated by reference in its entirety. In another embodiment, the αPPMX is formulated in a lipid-polycation complex which further includes a neutral lipid such as, but not limited to, cholesterol or dioleoyl phosphatidylethanolamine (DOPE).

Since the components of a liposome can include any molecule(s) (i.e., chemical/reagent/protein) that is bound to it, in some embodiments, the components of the provided liposomes include, at least, a member selected from the group: DSPE, DSPE-PEG, DSPE-maleimide, HSPC; HSPC-PEG; HSPC-maleimide; cholesterol; cholesterol-PEG; and cholesterol-maleimide. In some embodiments, the components of the provided liposomes include DSPE, DSPE-PEG, DSPE-maleimide, HSPC; HSPC-PEG; HSPC-maleimide; cholesterol; cholesterol-PEG; and cholesterol-maleimide. In a preferred embodiment, the liposomal components that make up the liposome comprises DSPE; DSPE-FITC; DSPE-maleimide; cholesterol; and HSPC.

In additional embodiments, the liposomes of the liposome compositions provided herein comprise oxidized phospholipids. In some embodiments, the liposomes comprise an oxidize phospholipid of a member selected from the group consisting of phosphatidylserines, phosphatidylinositols, phosphatidylethanolamines, phosphatidylcholines and 1-palmytoyl-2-arachidonoyl-sn-glycero-2-phosphate. In some embodiments, the phospholipids have unsaturated bonds. In some embodiments, the phospholipids are arachidonic acid containing phospholipids. In additional embodiments, the phospholipids are sn-2-oxygenated. In additional embodiments, the phospholipids are not fragmented.

In some embodiments, the liposomes of the disclosed liposome compositions comprise oxidized 1-palmitoyl-2-arachidonoyl-sn-glycero-3-phosphorylcholine (OxPAPC). The term "oxPAPC", as used herein, refers to lipids generated by the oxidation of 1-palmitoyl-2-arachidonyl-sn-glycero-3-phosphorylcholine (PAPC), which results in a mixture of oxidized phospholipids containing either fragmented or full length oxygenated sn-2 residues. Well-characterized oxidatively fragmented species contain a five-carbon sn-2 residue bearing omega-aldehyde or omega-carboxyl groups. Oxidation of arachidonic acid residue also produces phospholipids containing esterified isoprostanes. oxPAPC includes HOdiA-PC, KOdiA-PC, HOOA-PC and KOOA-PC species, among other oxidized products present in oxPAPC. In further embodiments, the oxPAPCs are epoxy-isoprostane-containing phospholipids. In further embodiments, the oxPAPC is 1-palmitoyl-2-(5,6-epoxyisoprostane E2)-sn-glycero-3-phosphocholine (5,6-PEIPC), 1-palmitoyl-2-(epoxy-cyclo-pentenone)-sn-glycero-3-phosphorylcholine (PECPC) and/or 1-palmitoyl-2-(epoxy-isoprostane E2)-sn-glycero-4-phosphocholine (PEIPC). In some embodiments, the phospholipids have unsaturated bonds. In some embodiments, the phospholipids are arachidonic acid containing phospholipids. In additional embodiments, the phospholipids are sn-2-oxygenated. In additional embodiments, the phospholipids are not fragmented.

In some embodiments, the liposomal alpha polyglutamated pemetrexed composition is pegylated (i.e., a pegylated liposomal alpha polyglutamated (e.g., pentaglutamated or hexaglutamated) antifolate (PLp-αPPMX or PLp-αPPMX)). In some embodiments, the PLp-αPPMX or PLp-αPPMX is water soluble. That is, the PLp-αPPMX or PLp-αPPMX is in the form an aqueous solution.

In some embodiments, the liposomes of the disclosed liposome compositions comprise a lipid selected from: 1-palmitoyl-2-glutaroyl-sn-glycero-3-phosphocholine (PGPC); 1-palmitoyl-2-(9'oxo-nonanoyl)-sn-glycero-3-phosphocholine; 1-palmitoyl-2-arachinodoyl-sn-glycero-3-phosphocholine; 1-palmitoyl-2-myristoyl-sn-glycero-3-phosphocholine; 1-palmitoyl-2-hexadecyl-sn-glycero-3-phosphocholine; 1-palmitoyl-2-azelaoyl-sn-glycero-3-phosphocholine; and 1-palmitoyl-2-acetoyl-sn-glycero-3-phospho-choline. In further embodiments, the liposome comprises PGPC.

In some embodiments, the pH of solutions comprising the liposome composition is from pH 2 to 8, or any range therein between. In some embodiments, the pH of solutions comprising the liposome composition is from pH 5 to 8, or any range therein between. In some embodiments, the pH of solutions comprising the liposome composition is from pH 6 to 7, or any range therein between. In some embodiments, the pH of solutions comprising the liposome composition is from 6 to 7.5, from 6.5 to 7.5, from 6.7 to 7.5, or from 6.3 to 7.0, or any range therein between.

In some embodiments, at least one component of the liposome lipid bilayer is functionalized (or reactive). As used herein, a functionalized component is a component that comprises a reactive group that can be used to crosslink reagents and moieties to the lipid. If the lipid is functionalized, any liposome that it forms is also functionalized. In some embodiments, the reactive group is one that will react with a crosslinker (or other moiety) to form crosslinks. The reactive group in the liposome lipid bilayer is located anywhere on the lipid that allows it to contact a crosslinker and be crosslinked to another moiety (e.g., a steric stabilizer or targeting moiety). In some embodiments, the reactive group is in the head group of the lipid, including for example a phospholipid. In some embodiments, the reactive group is a maleimide group. Maleimide groups can be crosslinked to each other in the presence of dithiol crosslinkers including but not limited to dithiolthrietol (DTT).

It is to be understood that the use of other functionalized lipids, other reactive groups, and other crosslinkers beyond those described above is further contemplated. In addition to the maleimide groups, other examples of contemplated reactive groups include but are not limited to other thiol reactive groups, amino groups such as primary and secondary amines, carboxyl groups, hydroxyl groups, aldehyde groups, alkyne groups, azide groups, carbonyls, halo acetyl (e.g., iodoacetyl) groups, imidoester groups, N-hydroxysuccinimide esters, sulfhydryl groups, and pyridyl disulfide groups.

Functionalized and non-functionalized lipids are available from a number of commercial sources including Avanti Polar Lipids (Alabaster, AL) and Lipoid LLC (Newark, NJ).

(2) Liposome Interior Space

In further non-limiting embodiments, the provided liposomes enclose an interior space. In some embodiments, the interior space comprises, but is not limited to, an aqueous solution. In some embodiments, the interior space comprises an alpha polyglutamated pemetrexed as provided herein. In additional embodiments, the interior space of the liposome comprises a tonicity agent. In some embodiments. In some embodiments, the concentration (weight percent) of the tonicity agent is 0.1-20%, 1-20%, 0.5-15%, 1-15%, or 1-50%, or any range therein between. In some embodiments, the interior space of the liposome includes a sugar (e.g., trehalose, maltose, sucrose, lactose, mannose, mannitol, glycerol, dextrose, fructose, etc.). In further embodiments, the concentration (weight percent) of the sugar is 0.1-20%, 1-20%, 0.5-15%, 1%-15%, or 1-50%, or any range therein between. In some embodiments, the pH of the interior space of the liposome is from pH 2 to 8, or any range therein between. In some embodiments, the pH of solutions comprising the liposome composition is from pH 5 to 8, or any range therein between. In some embodiments, the pH of solutions comprising the liposome composition is from pH 6 to 7, or any range therein between. In some embodiments, the pH of solutions comprising the liposome composition is from 6 to 7.5, from 6.5 to 7.5, from 6.7 to 7.5, or from 6.3 to 7.0, or any range therein between. In some embodiments, the interior space comprises buffer. In further embodiments, the buffer a buffer selected from HEPES, citrate, or sodium phosphate (e.g., monobasic and/or dibasic sodium phosphate). In some embodiments, the buffer is HEPES. In some embodiments, the buffer is citrate. In some embodiments, the buffer is sodium phosphate (e.g., monobasic and/or dibasic sodium phosphate). In some embodiments, the buffer is at a concentration of 15 to 200 mM, or any range therein between. In yet further embodiments, the buffer is at a concentration of between 5 to 200 mM, 15-200, between 5 to 100 mM, between 15 to 100 mM, between 5 to 50 mM, between 15 to 50 mM, between 5 to 25 mM, between 5 to 20 mM, between 5 to 15 mM, or any range therein between. In some embodiments, the buffer is HEPES at a concentration of 15 to 200 mM, or any range therein between. In some embodiments, the buffer is citrate at a concentration of 15 to 200 mM, or any range therein between. In some embodiments, the buffer is sodium phosphate at a concentration of 15 to 200 mM, or any range therein between. In some embodiments, the interior space of the liposome comprises a total concentration of sodium acetate and calcium acetate of between 5 mM to 500 mM, or 50 mM to 500 mM, or any range therein between.

In some embodiments, the interior space of the liposome includes trehalose. In further embodiments, the concentration weight percent of trehalose is 0.1-20%, 1-20%, 0.5-15%, 1%-15%, 5-20%, or 1-50%, or any range therein between. In yet further embodiments, the concentration (weight percent) of trehalose is 1-15%, or any range therein between. In an additional embodiment, the trehalose is present at about 5% to 20% weight percent of trehalose or any combination of one or more lyoprotectants or cryoprotectants at a total concentration of 5% to 20%. In some embodiments, the pH of solutions comprising the liposome composition is from 6 to 7.5, from 6.5 to 7.5, from 6.7 to 7.5, or from 6.3 to 7.0, or any range therein between. In some embodiments, the interior space comprises buffer. In some embodiments, the buffer is selected from HEPES, citrate, or sodium phosphate (e.g., monobasic and/or dibasic sodium phosphate). In some embodiments, the buffer is HEPES. In some embodiments, the buffer is citrate. In some embodiments, the buffer is sodium phosphate (e.g., monobasic and/or dibasic sodium phosphate). In some embodiments, the buffer is at a concentration of 15 to 200 mM, or any range therein between. In yet further embodiments, the buffer is at a concentration of between 5 to 200 mM, 15-200, between 5 to 100 mM, between 15 to 100 mM, between 5 to 50 mM, between 15 to 50 mM, between 5 to 25 mM, between 5 to 20 mM, between 5 to 15 mM, or any range therein between. In some embodiments, the buffer is HEPES at a concentration of 15 to 200 mM, or any range therein between. In some embodiments, the buffer is citrate at a concentration of 15 to 200 mM, or any range therein between. In some embodiments, the buffer is sodium phosphate at a concentration of 15 to 200 mM, or any range therein between. In additional embodiments, the interior space of the liposome comprises sodium acetate and/or calcium acetate. In some embodiments, the interior space of the liposome comprises a total concentration of sodium acetate and calcium acetate of between 5 mM to 500 mM, or 50 mM to 500 mM, or any range therein between.

In some embodiments, the interior space of the liposome includes dextrose. In further embodiments, the concentration weight percent of dextrose is 0.1-20%, 1-20%, 0.5-15%, 1-15%, 5-20%, or 1-50%, or any range therein between. In yet further embodiments, the concentration (weight percent) of dextrose is 1-15%, or any range therein between. In an additional embodiment, the dextrose is present at about 5% to 20% weight percent of dextrose or any combination of one or more lyoprotectants or cryoprotectants at a total concentration of 5% to 20%. In some embodiments, the pH of solutions comprising the liposome composition is from 6 to 7.5, from 6.5 to 7.5, from 6.7 to 7.5, or from 6.3 to 7.0, or any range therein between. In some embodiments, the interior space comprises buffer. In some embodiments, the buffer is selected from HEPES, citrate, or sodium phosphate (e.g., monobasic and/or dibasic sodium phosphate). In some embodiments, the buffer is HEPES. In some embodiments, the buffer is citrate. In some embodiments, the buffer is sodium phosphate (e.g., monobasic and/or dibasic sodium phosphate). In some embodiments, the buffer is at a concentration of 15 to 200 mM, or any range therein between. In yet further embodiments, the buffer is at a concentration of between 5 to 200 mM, 15-200, between 5 to 100 mM, between 15 to 100 mM, between 5 to 50 mM, between 15 to 50 mM, between 5 to 25 mM, between 5 to 20 mM, between 5 to 15 mM, or any range therein between. In some embodiments, the buffer is HEPES at a concentration of 15 to 200 mM, or any range therein between. In some embodiments, the buffer is citrate at a concentration of 15 to 200 mM, or any range therein between. In some embodiments, the buffer is sodium phosphate at a concentration of 15 to 200 mM, or any range therein between. In additional embodiments, the interior space of the liposome comprises sodium acetate and/or calcium acetate. In some embodiments, the interior space of the liposome comprises a total concentration of sodium acetate and calcium acetate of between 5 mM to 500 mM, or 50 mM to 500 mM, or any range therein between.

In additional embodiments, the disclosure provides liposomal compositions that comprise a liposome encapsulating (i.e., filled with) an alpha polyglutamated pemetrexed e.g., an αPPMX disclosed herein). In some embodiments, a liposome in the liposomal composition comprises a αPPMX containing 4, 5, 6, 2-10, 4-6, or more than 5, glutamyl groups (including the glutamyl group in pemetrexed). In some embodiments, the alpha polyglutamated pemetrexed in the Lp-αPPMX comprises two or more glutamyl groups in the L-form. In other embodiments, the alpha polyglutamated pemetrexed in the Lp-αPPMX comprises a glutamyl group in the D-form. In further embodiments, the alpha polyglutamated pemetrexed in the Lp-αPPMX comprises a glutamyl group in the D-form and two or more glutamyl groups in the L-form. In additional embodiments, the alpha polyglutamated pemetrexed in the Lp-αPPMX comprises two or more glutamyl groups that have a gamma carboxyl linkage. In some embodiments, the liposomal composition comprises a liposome comprising an α pentaglutamated PMX. In further embodiments, the liposome comprises an L-α pentaglutamated PMX, a D-α pentaglutamated PMX, or an L- and D-α pentaglutamated PMX. In some embodiments, the liposomal composition comprises a liposome comprising an α hexaglutamated PMX (Lp-αPPMX). In further embodiments, the liposome comprises an L-α hexaglutamated PMX, a D-α hexaglutamated PMX, or an L- and D-α hexaglutamated PMX.

In some embodiments, the targeted pegylated liposomal alpha polyglutamated (e.g., pentaglutamated or hexaglutamated) pemetrexed comprises a medium comprising a liposome including an interior space; an aqueous alpha polyglutamated pemetrexed disposed within the interior space; and a targeting moiety comprising a protein with specific affinity for at least one folate receptor, and wherein the targeting moiety disposed at the exterior of the liposome. In some embodiments, the medium is an aqueous solution. In some embodiments, the interior space, the exterior space (e.g., the medium), or both the interior space and the medium contains one or more lyoprotectants or cryoprotectants which are listed above. In some embodiments, the cryoprotectant is mannitol, trehalose, sorbitol, or sucrose.

In some embodiments, the liposome encapsulating alpha polyglutamated pemetrexed (i.e., Lp-αPPMX, including PLp-αPPMX, TPLp-αPPMX, TLp-αPPMX, and NTLp-αPPMX) has an interior space that contains less than 500,000 or less than 200,000 molecules of alpha polyglutamated pemetrexed. In some embodiments, the liposome interior space contains between 10 to 100,000 molecules of alpha polyglutamated pemetrexed, or any range therein between. In some embodiments, the liposome interior space contains between 10,000 to 100,000 molecules of alpha polyglutamated pemetrexed, or any range therein between. In some embodiments, the liposome is unpegylated and has an interior space that contains less than 500,000 or less than 200,000 molecules of alpha polyglutamated pemetrexed. In some embodiments, the liposome is unpegylated and the interior space of the liposome contains between 10 to 100,000 molecules of alpha polyglutamated pemetrexed, or any range therein between. In further embodiments, the liposome is unpegylated and the interior space of the liposome contains between 10,000 to 100,000 molecules of alpha polyglutamated pemetrexed, or any range therein between. In some embodiments, the liposome is targeted and unpegylated (TLp-αPPMX) and has an interior space that contains less than 500,000 or less than 200,000 molecules of alpha polyglutamated pemetrexed. In some embodiments, the liposome is targeted and unpegylated and the interior space of the liposome contains between 10 to 100,000 molecules of alpha polyglutamated pemetrexed, or any range therein between. In further embodiments, the liposome is targeted and unpegylated and the interior space of the liposome contains between 10,000 to 100,000 molecules of alpha polyglutamated pemetrexed, or any range therein between. In some embodiments, the liposome is non-targeted and unpegylated (NTLp-αPPMX) and has an interior space that contains less than 500,000 or less than 200,000 molecules of alpha polyglutamated pemetrexed. In some embodiments, the liposome is non-targeted and unpegylated and the interior space of the liposome contains between 10 to 100,000 molecules of alpha polyglutamated pemetrexed, or any range therein between. In further embodiments, the liposome is non-targeted and unpegylated and the interior space of the liposome contains between 10,000 to 100,000 molecules of alpha polyglutamated pemetrexed, or any range therein between.

In some embodiments, the liposome encapsulates alpha polyglutamated containing 2-10 glutamyl groups (i.e., Lp-αPPMX, including PLp-αPPMX, TPLp-αPPMX, TLp-αPPMX, and NTLp-αPPMX) and has an interior space that contains less than 500,000 or 200,000 molecules of alpha polyglutamated pemetrexed containing 2-10 glutamyl groups. In some embodiments, the liposome interior space contains between 10 to 100,000 molecules of alpha polyglutamated pemetrexed containing 2-10 glutamyl groups, or any range therein between. In further embodiments, the liposome interior space contains between 10,000 to 100,000 molecules of alpha polyglutamated pemetrexed containing 2-10 glutamyl groups, or any range therein between. In some embodiments, the liposome is unpegylated and has an interior space that contains less than 500,000 or 200,000 molecules of alpha polyglutamated pemetrexed containing 2-10 glutamyl groups. In some embodiments, the liposome is unpegylated and the interior space of the liposome contains between 10 to 100,000 molecules of alpha polyglutamated pemetrexed containing 2-10 glutamyl groups, or any range therein between. In further embodiments, the liposome is unpegylated and the interior space of the liposome contains between 10,000 to 100,000 molecules of alpha polyglutamated pemetrexed containing 2-10 glutamyl groups, or any range therein between. In some embodiments, the liposome is targeted and unpegylated (TLp-αPPMX) and has an interior space that contains less than 500,000 or 200,000 molecules of alpha polyglutamated pemetrexed containing 2-10 glutamyl groups. In some embodiments, the liposome is targeted and unpegylated and the interior space of the liposome contains between 10 to 100,000 molecules alpha polyglutamated pemetrexed containing 2-10 glutamyl groups, or any range therein between. In further embodiments, the liposome is targeted and unpegylated and the interior space of the liposome contains between 10,000 to 100,000 molecules alpha polyglutamated pemetrexed containing 2-10 glutamyl groups, or any range therein between.

In some embodiments, the liposome is non-targeted and unpegylated (NTLp-αPPMX) and has an interior space that contains less than 500,000 or 200,000 molecules of alpha polyglutamated pemetrexed containing 2-10 glutamyl groups. In some embodiments, the liposome is non-targeted and unpegylated and the interior space of the liposome contains between 10 to 100,000 molecules of alpha polyglutamated pemetrexed containing 2-10 glutamyl groups, or any range therein between. In further embodiments, the liposome is non-targeted and unpegylated and the interior space of the liposome contains between 10,000 to 100,000 molecules of alpha polyglutamated pemetrexed containing 2-10 glutamyl groups, or any range therein between.

In some embodiments, the liposome encapsulates alpha tetraglutamated pemetrexed (i.e., Lp-αPPMX, including PLp-αPPMX, TPLp-αPPMX, TLp-αPPMX, and NTLp-αPPMX) and has an interior space that contains less than 500,000 or 200,000 molecules of alpha tetraglutamated pemetrexed. In some embodiments, the liposome interior space contains between 10 to 100,000 molecules of alpha tetraglutamated pemetrexed, or any range therein between. In some embodiments, the liposome interior space contains between 10,000 to 100,000 molecules of alpha tetraglutamated pemetrexed, or any range therein between. In some embodiments, the liposome is unpegylated and has an interior space that contains less than 500,000 or 200,000 molecules of alpha tetraglutamated pemetrexed. In some embodiments, the liposome is unpegylated and the interior space of the liposome contains between 10 to 100,000 molecules of alpha tetraglutamated pemetrexed, or any range therein between. In further embodiments, the liposome is unpegylated and the interior space of the liposome contains between 10,000 to 100,000 molecules of alpha tetraglutamated pemetrexed, or any range therein between. In some embodiments, the liposome is targeted and unpegylated (TLp-αPPMX) and has an interior space that contains less than 500,000 or 200,000 molecules of alpha tetraglutamated pemetrexed. In some embodiments, the liposome is targeted and unpegylated and the interior space of the liposome contains between 10 to 100,000 molecules of alpha tetraglutamated pemetrexed, or any range therein between. In further embodiments, the liposome is targeted and unpegylated and the interior space of the liposome contains between 10,000 to 100,000 molecules of alpha tetraglutamated pemetrexed, or any range therein between. In some embodiments, the liposome is non-targeted and unpegylated (NTLp-αPPMX) and has an interior space that contains less than 500,000 or 200,000 molecules of alpha tetraglutamated pemetrexed. In some embodiments, the liposome is non-targeted and unpegylated and the interior space of the liposome contains between 10 to 100,000 molecules of alpha tetraglutamated pemetrexed, or any range therein between. In further embodiments, the liposome is non-targeted and unpegylated and the interior space of the liposome contains between 10,000 to 100,000 molecules of alpha tetraglutamated pemetrexed, or any range therein between.

In some embodiments, the liposome encapsulates alpha pentaglutamated pemetrexed (i.e., Lp-αPPMX, including PLp-αPPMX, TPLp-αPPMX, TLp-αPPMX, and NTLp-αPPMX) and has an interior space that contains less than 500,000 or 200,000 molecules of alpha pentaglutamated pemetrexed. In some embodiments, the liposome interior space contains between 10 to 100,000 molecules of alpha pentaglutamated pemetrexed, or any range therein between. In some embodiments, the liposome interior space contains between 10,000 to 100,000 molecules of alpha pentaglutamated pemetrexed, or any range therein between. In some embodiments, the liposome is unpegylated and has an interior space that contains less than 500,000 or 200,000 molecules of alpha pentaglutamated pemetrexed. In some embodiments, the liposome is unpegylated and the interior space of the liposome contains between 10 to 100,000 molecules of alpha pentaglutamated pemetrexed, or any range therein between. In further embodiments, the liposome is unpegylated and the interior space of the liposome contains between 10,000 to 100,000 molecules of alpha pentaglutamated pemetrexed, or any range therein between. In some embodiments, the liposome is targeted and unpegylated (TLp-αPPMX) and has an interior space that contains less than 500,000 or 200,000 molecules of alpha pentaglutamated pemetrexed. In some embodiments, the liposome is targeted and unpegylated and the interior space of the liposome contains between 10 to 100,000 molecules of alpha pentaglutamated pemetrexed, or any range therein between. In further embodiments, the liposome is targeted and unpegylated and the interior space of the liposome contains between 10,000 to 100,000 molecules of alpha pentaglutamated pemetrexed, or any range therein between. In some embodiments, the liposome is non-targeted and unpegylated (NTLp-αPPMX) and has an interior space that contains less than 500,000 or 200,000 molecules of alpha pentaglutamated pemetrexed. In some embodiments, the liposome is non-targeted and unpegylated and the interior space of the liposome contains between 10 to 100,000 molecules of alpha pentaglutamated pemetrexed, or any range therein between. In further embodiments, the liposome is non-targeted and unpegylated and the interior space of the liposome contains between 10,000 to 100,000 molecules of alpha pentaglutamated pemetrexed, or any range therein between.

In some embodiments, the liposome encapsulates alpha hexaglutamated pemetrexed (i.e., Lp-αPPMX, including PLp-αPPMX, TPLp-αPPMX, TLp-αPPMX, and NTLp-αPPMX) and has an interior space that contains less than 500,000 or 200,000 molecules of alpha hexaglutamated pemetrexed. In some embodiments, the liposome interior space contains between 10 to 100,000 molecules of alpha hexaglutamated pemetrexed, or any range therein between. In further embodiments, the liposome interior space contains between 10,000 to 100,000 molecules of alpha hexaglutamated pemetrexed, or any range therein between. In some embodiments, the liposome is unpegylated and has an interior space that contains less than 500,000 or 200,000 molecules of alpha hexaglutamated pemetrexed. In some embodiments, the liposome is unpegylated and the interior space of the liposome contains between 10 to 100,000 molecules of alpha hexaglutamated pemetrexed, or any range therein between. In further embodiments, the liposome is unpegylated and the interior space of the liposome contains between 10,000 to 100,000 molecules of alpha hexaglutamated pemetrexed, or any range therein between. In some embodiments, the liposome is targeted and unpegylated (TLp-αPPMX) and has an interior space that contains less than 500,000 or 200,000 molecules of alpha hexaglutamated pemetrexed. In some embodiments, the liposome is targeted and unpegylated and the interior space of the liposome contains between 10 to 100,000 molecules of alpha hexaglutamated pemetrexed, or any range therein between. In further embodiments, the liposome is targeted and unpegylated and the interior space of the liposome contains between 10,000 to 100,000 molecules of alpha hexaglutamated pemetrexed, or any range therein between. In some embodiments, the liposome is non-targeted and unpegylated (NTLp-αPPMX) and has an interior space that contains less than 500,000 or 200,000 molecules of alpha hexaglutamated pemetrexed. In some embodiments, the liposome is non-targeted and unpegylated and the interior space of the liposome contains between 10 to 100,000 molecules of alpha hexaglutamated pemetrexed, or any range therein between. In further embodiments, the liposome is non-targeted and unpegylated and the interior space of the liposome contains between 10,000 to 100,000 molecules of alpha hexaglutamated pemetrexed, or any range therein between.

In some embodiments, the disclosure provides a liposomal alpha polyglutamated pemetrexed composition wherein the liposome encapsulates alpha polyglutamated pemetrexed or a salt or acid thereof, and one or more aqueous pharmaceutically acceptable carriers. In some embodiments, the liposome interior space contains trehalose. In some embodiments, the liposome interior space contains 1% to 50% weight of trehalose. In some embodiments, the liposome interior space contains HBS at a concentration of between 1 to 200 mM and a pH of between 2 to 8. In some embodiments, liposome interior space has a pH 5-8, or any range therein between. In some embodiments, liposome interior space has a pH 6-7, or any range therein between. In some embodiments, the liposome interior space has a total concentration of sodium acetate and calcium acetate of between 50 mM to 500 mM, or any range therein between.

A Non-Polyglutamated Polyglutamatable Antifolates

In some embodiments, the liposome alpha polyglutamated pemetrexed (i.e., Lp-αPPMX, including PLp-αPPMX, TPLp-αPPMX, TLp-αPPMX, and NTLp-αPPMX) compositions comprise alpha polyglutamated pemetrexed e.g., an αPPMX disclosed herein) and one or more non-polyglutamated, polyglutamatable antifolate compositions.

In some embodiments, the Lp-αPPMX (e.g., PLp-αPPMX, TPLp-αPPMX, TLp-αPPMX, and NTLp-αPPMX) comprises alpha polyglutamated pemetrexed (e.g., an αPPMX disclosed herein) and pemetrexed (PMX). In some embodiments, the Lp-αPPMX (i.e., liposome alpha polyglutamated pemetrexed) comprises alpha polyglutamated pemetrexed and a polyglutamatable antifolate selected from the group consisting of: pemetrexed (PMX), methotrexate (MTX), lometrexol (LMX), raltitrexed (RTX), pralatrexate, AG2034, GW1843, aminopterin, and LY309887. In some embodiments, the Lp-αPPMX comprises alpha polyglutamated pemetrexed and lometrexol. In some embodiments, the Lp-αPPMX comprises alpha polyglutamated pemetrexed and pemetrexed. In some embodiments, the Lp-αPPMX comprises alpha polyglutamated pemetrexed and leucovorin. In some embodiments, the Lp-αPPMX comprises alpha polyglutamated pemetrexed and a triazine antifolate derivative (e.g., a sulphonyl fluoride triazine such as NSC 127755). In some embodiments, the Lp-αPPMX comprises alpha polyglutamated pemetrexed and a serine hydroxymethyltransferase (SHMT2) inhibitor. In some embodiments, the SHMT2 inhibitor is an antifolate (e.g., a polyglutamatable or nonpolyglutamatable antifolate). In some embodiments, the SHMT2 inhibitor is an antifolate.

B Non-Polyglutamatable Antifolates

In some embodiments, the Lp-αPPMX (e.g., PLp-αPPMX, TPLp-αPPMX, TLp-αPPMX, and NTLp-αPPMX) comprises an alpha polyglutamated pemetrexed (e.g., an αPPMX disclosed herein) and a so-called "non-polyglutamatable" antifolate. In some embodiments, the liposome comprises an alpha polyglutamated pemetrexed and a non-polyglutamatable antifolate that inhibits one or more enzymes in the folate cycle metabolic pathway. In further embodiments, the non-polyglutamatable antifolate inhibits one or more enzymes selected from: thymidylate synthase (TS), dihydrofolate reductase (DHFR), glycinamide ribonucleotide (GAR) transformylase, and aminoimidazole carboxamide ribonucleotide (AICAR) transformylase. In some embodiments, the liposome comprises an alpha polyglutamated pemetrexed and a non-polyglutamatable antifolate that inhibits DHFR. In some embodiments, the liposome comprises an alpha polyglutamated pemetrexed and a non-polyglutamatable antifolate that inhibits TS. In some embodiments, the liposome comprises an alpha polyglutamated pemetrexed and a non-polyglutamatable antifolate that inhibits GAR or AICAR transformylase. In further embodiments, the non-polyglutamatable antifolate is selected from the group consisting of: trimetrexate (TMQ), piritrexim (BW301U), and talotrexin (PT523). In further embodiments, the non-polyglutamatable antifolate is selected from the group consisting of: nolatrexed (AG337), plevitrexed (ZD9331, BGC9331), and BGC 945 (ONX 0801).

C Platinums

In some embodiments, the liposome comprises an alpha polyglutamated pemetrexed (Lp-αPPMX, such as e.g., PLp-αPPMX, TPLp-αPPMX, TLp-αPPMX, and NTLp-αPPMX) comprises an alpha polyglutamated pemetrexed (e.g., an αPPMX disclosed herein) and a platinum-based chemotherapeutic agent or a salt or acid, thereof. In some embodiments, the liposome contains an alpha polyglutamated pemetrexed/platinum based agent complex (e.g., as described in Section IIC).

In some embodiments, the Lp-αPPMX comprises a platinum-based chemotherapeutic agent selected from the group consisting of: cisplatin, carboplatin, and oxaliplatin, or a salt or acid thereof. In other embodiments, the Lp-αPPMX comprises an analog of a platinum-based chemotherapeutic agent selected from the group consisting of: cisplatin, carboplatin, or oxaliplatin, or a salt or acid thereof.

In some embodiments, the Lp-αPPMX comprises an alpha polyglutamated pemetrexed and cisplatin or a salt or acid thereof. In some embodiments, the Lp-αPPMX comprises an alpha polyglutamated pemetrexed and a cisplatin analog, or a salt or acid thereof.

In some embodiments, the Lp-αPPMX comprises an alpha polyglutamated pemetrexed and carboplatin, or a salt or acid thereof. In some embodiments, the liposome comprises an alpha polyglutamated pemetrexed and carboplatin analog, or a salt or acid thereof.

In some embodiments, the Lp-αPPMX comprises an alpha polyglutamated pemetrexed and oxaliplatin, or a salt or acid thereof. In some embodiments, the liposome comprises an alpha polyglutamated pemetrexed and an oxaliplatin analog, or a salt or acid thereof.

In some embodiments, the liposome comprises an alpha polyglutamated pemetrexed (e.g., an αPPMX disclosed herein) and a platinum-based chemotherapeutic agent selected from the group consisting of: nedaplatin, heptaplatin, and lobaplatin, nedaplatin, heptaplatin, and lobaplatin or a salt or acid thereof. In some embodiments, the Lp-αPPMX comprises an alpha polyglutamated pemetrexed and an analog of a platinum-based chemotherapeutic agent selected from the group consisting of: nedaplatin, heptaplatin, and lobaplatin, or a salt or acid thereof.

In some embodiments, the Lp-αPPMX comprises an alpha polyglutamated pemetrexed and a platinum-based chemotherapeutic agent selected from the group consisting of: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin, or a salt or acid thereof. In some embodiments, the Lp-αPPMX comprises an alpha polyglutamated pemetrexed and an analog of a platinum-based chemotherapeutic agent selected from the group consisting of: stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM-216, 254-S, NK 121, CI-973, DWA 2114R, NDDP, and dedaplatin, or a salt or acid thereof.

In some embodiments, the liposome composition comprises liposomes that further contain one or more of an immunostimulatory agent, a detectable marker and a maleimide disposed on at least one of the PEG and the exterior of the liposome.

D Cyclodextrins

In additional embodiments, the αPPMX liposome comprise a αPPMX (e.g., a αPPMX disclosed herein) and a cyclodextrin (e.g., a cyclodextrin in Section IIC, herein).

In some embodiments, the αPPMX liposome comprises a complex formed by a cyclodextrin and a therapeutic agent. In some embodiments, the therapeutic agent is a cytotoxic compound or a salt or acid thereof. In a further embodiment, the therapeutic agent is a chemotherapeutic agent or a salt or acid thereof. In another embodiment, the therapeutic agent is a platinum-based drug. In another embodiment, the therapeutic agent is a taxane-based drug. In further embodiments, the therapeutic agent of the cyclodextrin/therapeutic agent complex is a member selected from the group consisting of: gemcitabine, a gemcitabine-based therapeutic agent, doxorubicin, an antifolate, an antifolate-based chemotherapeutic, or a salt or acid, acid or free base form thereof. In additional embodiments, the molar ratio of cyclodextrin/therapeutic agent in the complex is in the range 1-10:1. In some embodiments, the molar ratio of αPPMX/therapeutic agent in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of cyclodextrin/therapeutic agent in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1.

In some embodiments, the αPPMX liposome comprises αPPMX and a cyclodextrin/platinum-based chemotherapeutic agent complex. In some embodiments, the platinum-based chemotherapeutic agent is selected from the group consisting of: cisplatin, carboplatin, and oxaliplatin, or a salt or acid thereof. In other embodiments, the cyclodextrin/platinum-based chemotherapeutic agent complex comprises an analog of a cisplatin, carboplatin, oxaliplatin, or a salt or acid thereof. In some embodiments, the molar ratio of cyclodextrin/platinum-based agent in the complex is in the range 1-10:1. In some embodiments, the molar ratio of cyclodextrin/platinum-based agent in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/platinum-based agent in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1.

In some embodiments, the platinum-based chemotherapeutic agent is selected from the group consisting of: cisplatin, carboplatin, and oxaliplatin, or a salt or acid thereof. In other embodiments, the cyclodextrin/platinum-based chemotherapeutic agent complex comprises an analog of a cisplatin, carboplatin, oxaliplatin, or a salt or acid thereof. In some embodiments, the molar ratio of cyclodextrin/platinum-based agent in the complex is in the range 1-10:1. In some embodiments, the molar ratio of cyclodextrin/platinum-based agent in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/platinum-based chemotherapeutic agent in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1.

In additional embodiments, the cyclodextrin//platinum-based agent complex is encapsulated in a liposome (e.g., as described herein or otherwise known in the art).

In further embodiments, the disclosure provides a complex containing cyclodextrin and cisplatin or a salt or acid thereof. In some embodiments, the molar ratio of cyclodextrin/cisplatin (or cisplatin salt or acid) in the complex is in the range 1-10:1. In some embodiments, the molar ratio of cyclodextrin/cisplatin (or cisplatin salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/cisplatin (or cisplatin salt or acid) in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin//cisplatin (or cisplatin salt or acid) complex is encapsulated in a liposome (e.g., as described herein or otherwise known in the art).

In another embodiment, the disclosure provides a complex containing cyclodextrin and carboplatin or a salt or acid thereof. In some embodiments, the molar ratio of cyclodextrin/carboplatin (or carboplatin salt or acid) in the complex is in the range 1-10:1. In some embodiments, the molar ratio of cyclodextrin/carboplatin (or carboplatin salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/carboplatin (or carboplatin salt or acid) in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/carboplatin (or carboplatin salt or acid) complex is encapsulated in a liposome (e.g., as described herein or otherwise known in the art).

In another embodiment, the disclosure provides a complex containing cyclodextrin and oxaliplatin, or a salt or acid thereof. In some embodiments, the molar ratio of cyclodextrin/oxaliplatin (or oxaliplatin salt or acid) in the complex is in the range 1-10:1. In some embodiments, the molar ratio of cyclodextrin/oxaliplatin (or oxaliplatin salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/oxaliplatin (or oxaliplatin salt or acid) in the complex is: 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/oxaliplatin (or oxaliplatin salt or acid) complex is encapsulated in a liposome (e.g., as described herein or otherwise known in the art).

In additional embodiments, the disclosure provides a complex comprising cyclodextrin and a platinum-based chemotherapeutic agent selected from the group consisting of:

nedaplatin, heptaplatin, lobaplatin, stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM216, NK121, C1973, DWA 2114R, NDDP, and dedaplatin, or a salt or acid thereof. In other embodiments, the cyclodextrin/platinum-based chemotherapeutic agent complex comprises an analog of nedaplatin, heptaplatin, lobaplatin, stratoplatin, paraplatin, platinol, cycloplatin, dexormaplatin, spiroplatin, picoplatin, triplatin, tetraplatin, iproplatin, ormaplatin, zeniplatin, platinum-triamine, traplatin, enloplatin, JM216, NK121, CI973, DWA 2114R, NDDP, or dedaplatin, or a salt or acid thereof. In some embodiments, the molar ratio of cyclodextrin/oxaliplatin (or oxaliplatin salt or acid) in the complex is in the range 1-10:1. In some embodiments, the molar ratio of cyclodextrin/platinum-based chemotherapeutic agent (or salt or acid or analog thereof) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/platinum-based chemotherapeutic agent (or salt or acid or analog thereof) in the complex is: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/platinum-based chemotherapeutic agent (or salt or acid or analog thereof) complex is encapsulated in a liposome (e.g., as described herein or otherwise known in the art).

In some embodiments, the disclosure provides a composition comprising a cyclodextrin/taxane-based chemotherapeutic agent complex. In some embodiments, the taxane-based chemotherapeutic agent is selected from the group consisting of: paclitaxel (PTX), docetaxel (DTX), larotaxel (LTX), and cabazitaxel (CTX), or a salt or acid thereof. In some embodiments, the molar ratio of cyclodextrin/taxane-based agent in the complex is in the range 1-10:1. In some embodiments, the molar ratio of cyclodextrin/taxane-based agent in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/taxane-based agent in the complex is: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/taxane-based agent complex is encapsulated in a liposome (e.g., as described herein or otherwise known in the art).

In additional embodiments, the disclosure provides a complex comprising cyclodextrin and paclitaxel (PTX), or a salt or acid thereof. In other embodiments, the cyclodextrin/taxane-based chemotherapeutic agent complex comprises an analog of paclitaxel (PTX), or a salt or acid thereof. In some embodiments, the molar ratio of cyclodextrin/paclitaxel (or paclitaxel salt or acid) in the complex is in the range 1-10:1. In some embodiments, the molar ratio of cyclodextrin/paclitaxel (or paclitaxel salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/paclitaxel (or paclitaxel salt or acid) in the complex is: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/paclitaxel (or paclitaxel salt or acid) complex is encapsulated in a liposome (e.g., as described herein or otherwise known in the art).

In additional embodiments, the disclosure provides a complex comprising cyclodextrin and docetaxel (DTX), or a salt or acid thereof. In other embodiments, the cyclodextrin/taxane-based chemotherapeutic agent complex comprises an analog of docetaxel (DTX), or a salt or acid thereof. In some embodiments, the molar ratio of cyclodextrin/docetaxel (or docetaxel salt or acid) in the complex is in the range 1-10:1. In some embodiments, the molar ratio of cyclodextrin/docetaxel (or docetaxel salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/docetaxel (or docetaxel salt or acid) in the complex is: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/docetaxel (or docetaxel salt or acid) complex is encapsulated in a liposome (e.g., as described herein or otherwise known in the art).

In additional embodiments, the disclosure provides a complex comprising cyclodextrin and larotaxel (LTX), or a salt or acid thereof. In other embodiments, the cyclodextrin/taxane-based chemotherapeutic agent complex comprises an analog of larotaxel (LTX), or a salt or acid thereof. In some embodiments, the molar ratio of cyclodextrin/larotaxel (or larotaxel salt or acid) in the complex is in the range 1-10:1. In some embodiments, the molar ratio of cyclodextrin/larotaxel (or larotaxel salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/larotaxel (or larotaxel salt or acid) in the complex is: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/larotaxel (or larotaxel salt or acid) complex is encapsulated in a liposome (e.g., as described herein or otherwise known in the art).

In additional embodiments, the disclosure provides a complex comprising cyclodextrin and cabazitaxel (CTX), or a salt or acid thereof. In other embodiments, the cyclodextrin/taxane-based chemotherapeutic agent complex comprises an analog of cabazitaxel (CTX), or a salt or acid thereof. In some embodiments, the molar ratio of cyclodextrin/cabazitaxel (or cabazitaxel salt or acid) in the complex is in the range 1-10:1. In some embodiments, the molar ratio of cyclodextrin/cabazitaxel (or cabazitaxel salt or acid) in the complex is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:(21-50), or 1:>50. In some embodiments, the molar ratio of αPPMX/cabazitaxel (or cabazitaxel salt or acid) in the complex is: 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, (21-50):1, or >50:1. In additional embodiments, the cyclodextrin/cabazitaxel (or cabazitaxel salt or acid) complex is encapsulated in a liposome (e.g., as described herein or otherwise known in the art).

The cyclodextrin of the cyclodextrin/therapeutic agent complex can be derivatized or underivatized. In some embodiments, the cyclodextrin is derivatized. In further embodiments, the cyclodextrin is a derivatized beta-cyclodextrin (e.g., a hydroxypropyl beta-cyclodextrin (HP-beta-CD), and a sulfobutyl ether beta-CD (SBE)-beta-cyclodextrin). In some embodiments, the cyclodextrin of the cyclodextrin/therapeutic agent complex is a derivatized beta-cyclodextrin comprising: 1, 2, 3, 4, 5, 6, 7, 8, 9, 10, or more 2-hydroxylpropyl-3-group substitutions of hydroxy groups; or 1, 2, 3, 4, 5, 6, 7, 8, 9, 10, or more sulfoalkyl ether group substitutions of hydroxy groups. In further embodiments, the cyclodextrin of the cyclodextrin/therapeutic agent complex is a derivatized beta-cyclodextrin comprising: 1, 2, 3, 4, 5, 6, 7, 8, 9, 10, or more sulfobutyl ether group substitutions of hydroxy groups.

In some embodiments, the cyclodextrin of the cyclodextrin/therapeutic agent complex contained in the αPPMX liposome composition is a derivatized cyclodextrin of Formula I:

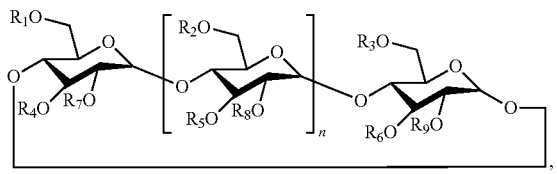

wherein: n is 4, 5, or 6; and wherein $R_1$, $R_2$, $R_3$, $R_4$, $R_5$, $R_6$, $R_7$, $R_8$, and $R_9$ are each, independently, —H, a straight chain or branched $C_1$-$C_8$-alkylene group, a 2-hydroxylpropyl-3- group; or an optionally substituted straight-chain or branched $C_1$-$C_6$ group, wherein at least one of $R_1$, $R_2$, $R_3$, $R_4$, $R_5$, $R_6$, $R_7$, $R_8$ and $R_9$ is a straight-chain or branched $C_1$-$C_8$-alkylene group or a 2-hydroxylpropyl-3- group.

In some embodiments, the cyclodextrin of the cyclodextrin/therapeutic agent complex contained in the αPPMX liposome composition is a derivatized cyclodextrin of Formula II:

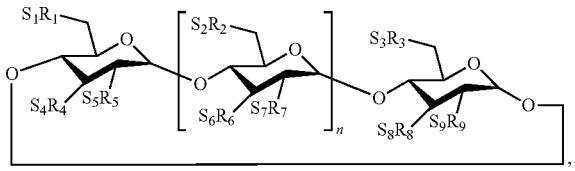

wherein: n is 4, 5, or 6; and wherein $R_1$, $R_2$, $R_3$, $R_4$, $R_5$, $R_6$, $R_7$, $R_8$, and $R_9$ are each, independently, —O— or a —O—($C_2$-$C_6$ alkylene)-$SO_3^-$ group; wherein at least one of $R_1$ and $R_2$ is independently a —O—($C_2$-$C_6$ alkylene)-$SO_3^-$ group; and $S_1$, $S_2$, $S_3$, $S_4$, $S_5$, $S_6$, $S_7$, $S_8$, and $S_9$ are each, independently, a —H or a H or a pharmaceutically acceptable cation. In further embodiments, the wherein the pharmaceutically acceptable cation is selected from: an alkali metal such as $Li^+$, $Na^+$, or $K^+$; an alkaline earth metal such as $Ca^{+2}$, or $Mg^{+2}$, and ammonium ions and amine cations such as the cations of (C1-C6)-alkylamines, piperidine, pyrazine, (C1-C6)-alkanolamine and (C4-C8)-cycloalkanolamine.

In some embodiments, the αPPMX liposome comprises between 100 to 100,000 of the cyclodextrin/therapeutic agent complexes.

In some embodiments, a cyclodextrin derivative of the αPPMX/cyclodextrin complex and/or cyclodextrin/therapeutic agent complex is a cyclodextrin disclosed in U.S. Pat. Nos. 6,133,248, 5,874,418, 6,046,177, 5,376,645, 5,134,127, 7,034,013, 6,869,939; and Intl. Appl. Publ. No. WO 02005/117911, the contents each of which is herein incorporated by reference in its priority.

In some embodiments, the cyclodextrin derivative of the cyclodextrin/therapeutic agent complex is a sulfoalkyl ether cyclodextrin. In some embodiments, the cyclodextrin derivative of complex is a sulfobutyl ether-3-cyclodextrin such as CAPTISOL® (CyDex Pharma. Inc., Lenexa, Kansas. Methods for preparing sulfobutyl ether-3-cyclodextrin and other sulfoalkyl ether cyclodextrins are known in the art.

In some embodiments, the cyclodextrin derivative of the cyclodextrin/therapeutic agent complex is a compound of Formula III:

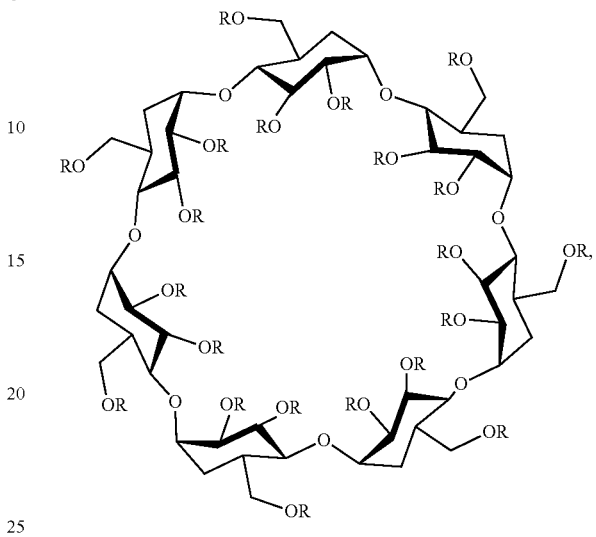

wherein R equals:
(a) $(H)_{21-x}$ or (—$(CH_2)_4$—$SO_3Na$)x, and x=1.0-10.0, 1.0-5.0, 6.0-7.0, or 8.0-10.0;
(b) $(H)_{21-x}$ or (—$CH_2CH(OH)CH_3$)x, and x=1.0-10.0, 1.0-5.0, 6.0-7.0, or 8.0-10.0;
(c) $(H)_{21}$-x or (sulfoalkyl ethers)x, and x=1.0-10.0, 1.0-5.0, 6.0-7.0, or 8.0-10.0; or
(d) $(H)_{21-x}$ or (—$(CH_2)_4$—$SO_3Na$)x, and x=1.0-10.0, 1.0-5.0, 6.0-7.0, or 8.0-10.0.

Additional cyclodextrins and cyclodextrin/platinum-based therapeutic complexes that can be contained in the αPPMX liposomes and used according to the disclosed methods is disclosed in U.S. Appl. No. 62/583,432, the contents of which is herein incorporated by reference it its entirety.

In some embodiments, the αPPMX liposome comprises a complex of a cyclodextrin and a platinum-based chemotherapeutic agent, or a salt thereof. In some embodiments, the platinum-based chemotherapeutic agent is cisplatin or a cisplatin analog. In some embodiments, the platinum-based chemotherapeutic agent is carboplatin. In additional embodiments, the liposome composition comprises a platinum-based chemotherapeutic agent is a member selected from the group consisting of: carboplatin, cisplatin, oxaliplatin, satraplatin, picoplatin, nedaplatin, triplatin, tetraplatin, lipoylation, lobaplatin, ormaplatin, zeniplatin, platinum-triamine, traplatin, enloplatin, JM-216, 254-S, NK 121, CI-973, DWA 2114R, NDDP, and dedaplatin. In some embodiments, the αPPMX liposome comprises between 100 to 100,000 platinum-based chemotherapeutic agent/CD complexes. In additional embodiments, the liposome composition comprises liposomes that have a diameter in the range of 20 nm to 500 nm, or 20 nm to 200 nm, or any range therein between. In some embodiments, liposomes in the composition comprise between 100 to 100,000 platinum.

(3) Targeted Liposomes

In some embodiments, the disclosure provides a liposomal alpha polyglutamated pemetrexed composition wherein the liposome comprises an alpha polyglutamated pemetrexed and a targeting moiety attached to one or both of a PEG and the exterior of the liposome, and wherein the targeting moiety has a specific affinity for a surface antigen on a target cell of interest. Such liposomes may generally be referred to herein as "targeted liposomes," e.g., liposomes including one or more targeting moieties or biodistribution modifiers on the surface of, or otherwise attached to, the liposomes. The targeting moiety of the targeted liposomes can be any moiety or agent that is capable of specifically binding a desired target (e.g., an antigen target expressed on the surface of a target cell of interest). In one embodiment, the targeted liposome specifically and preferentially binds to a target on the surface of a target cell of interest that internalizes the targeted liposome into which the liposome encapsulated alpha polyglutamated pemetrexed (e.g., alpha pentaglutamated PMX or alpha hexaglutamated PMX) exerts its cytotoxic effect. In further embodiments, the target cell is a cancer cell, a tumor cell or a metastatic cell. In some embodiments, the targeted liposome is pegylated.

The term "attach" or "attached" refers, for example, to any type of bonding such as covalent bonding, ionic bonding (e.g., avidin-biotin) bonding by hydrophobic interactions, and bonding via functional groups such as maleimide, or linkers such as PEG. For example, a detectable marker, a steric stabilizer, a liposome, a liposomal component, an immunostimulating agent may be attached to each other directly, by a maleimide functional group, or by a PEG-malemide group.

The composition and origination of the targeting moiety is non-limiting to the scope of this disclosure. In some embodiments, the targeting moiety attached to the liposome is a polypeptide or peptidomimetic ligand. Peptide and peptidomimetic targeting moieties include those having naturally occurring or modified peptides, e.g., D or L peptides; alpha, beta, or gamma peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic is a molecule capable of folding into a defined three-dimensional structure similar to a natural peptide. In some embodiments, the peptide or peptidomimetic targeting moiety is 2-50 amino acids long, e.g., about 5, 10, 15, 20, 25, 30, 35, 40, 45, or 50 amino acids long In some embodiments, the targeting moiety polypeptide is at least 40 amino acid residues in length. In other embodiments, the targeting moiety polypeptide is at least 50, 60, 75, 100, 125, 150, 175, 200, 250, or 300 amino acid residues in length.

In additional embodiments, the targeting moiety polypeptide such as an antibody or an antigen-binding antibody fragment that binds a target antigen with an equilibrium dissociation constant (Kd) in a range of $0.5 \times 10^{-10}$ to $10 \times 10^{-6}$ as determined using BIACORE® analysis.

In some embodiments, the targeting moiety is an antibody or an antibody derivative. In other embodiments, the binding domain of the targeting moiety polypeptide is not derived from the antigen binding domain of an antibody. In some embodiments, the targeting moiety is a polypeptide derived from a binding scaffold selected from the group consisting of a DARPin, affilin, and armadillo repeat, D domain (see, e.g., WO 2016/164308), Z-domain (Affibody), adnectin, lipocalin, affilin, anticalin, knottin, fynomer, atrimer, kunitz domain (see, e.g., WO 2004/063337), CTLA4, or avimer (see, e.g., U.S. Publ. Nos. 2004/0175756, 2005/0053973, 2005/0048512, and 2006/0008844).

In additional embodiments, the targeting moiety is an antibody or a derivative of the antigen binding domain of an antibody that has specific affinity for an epitope on a cell surface antigen of interest expressed on the surface of a target cell. In some embodiments, the targeting moiety is a full-length antibody. In some embodiments, the targeting moiety is an antigen binding portion of an antibody. In some embodiments, the targeting moiety is an scFv. In other embodiments, the targeting moiety is a Fab. In some embodiments, the targeting moiety comprises a binding domain derived from the antigen binding domain of an antibody (e.g., an scFv, Fab, Fab', F(ab')$_2$, an Fv fragment, a disulfide-linked Fv (sdFv), a Fd fragment consisting of VH and CH1 domains, an scFv, a minibody, a BiTE, a Tandab, a diabody ((VL-VH)$_2$ or (VH-VL)$_2$), a single domain antibody (e.g., an sdAb such as a nanobody (either VL or VH)), and a camelid VHH domain). In some embodiments, the targeting moiety comprises one or more complementarity determining regions (CDRs) of antibody origin. Examples of suitable antibody-based targeting moieties for the disclosed targeted liposomes include a full-length human antibody, a humanized antibody, a chimeric antibody, an antigen binding fragment of an antibody, a single chain antibody, a single-domain antibody, a bi-specific antibody, a synthetic antibody, a pegylated antibody and a multimeric antibody. The antibody of the provided targeted liposomes can have a combination of the above characteristics. For example, a humanized antibody can be an antigen binding fragment and can be pegylated and multimerized as well.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, and hamster) that have the desired specificity, affinity, and capability (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

In further embodiments, the targeting moiety has specific affinity for an epitope on a surface antigen of a target cell of interest. In some embodiments, the target cell is a cancer cell. In some embodiments, the target cell is a tumor cell. In other embodiments, the target cell is an immune cell.

In some embodiments, the targeting moiety has specific affinity for an epitope expressed on a tumor cell surface antigen. The term "tumor cell surface antigen" refers to an antigen that is common to a specific hyperproliferative disorder such as cancer. In some embodiments, the targeting moiety has specific affinity for an epitope of a tumor cell surface antigen that is a tumor associated antigen (TAA). A TAA is an antigen that is found on both tumor and some normal cells. A TAA may be expressed on normal cells during fetal development when the immune system is immature and unable to respond or may be normally present at extremely low levels on normal cells but which are expressed at much higher levels on tumor cells. Because of the dynamic nature of tumors, in some instances, tumor cells may express unique antigens at certain stages, and at others also express antigens that are also expressed on non-tumor cells. Thus, inclusion of a certain marker as a TAA does not preclude it being considered a tumor specific antigen. In some embodiments, the targeting moiety has specific affinity for an epitope of a tumor cell surface antigen that is a tumor specific antigen (TSA). A TSA is an antigen that is unique to tumor cells and does not occur on other cells in the body. In some embodiments, the targeting moiety has specific affinity for an epitope of a tumor cell surface antigen expressed on the surface of a cancer including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer, mesothelioma, and adenocarcinomas such as breast cancer, prostate cancer, ovarian cancer, pancreatic cancer, colon cancer and other cancers known in the art. In some embodiments, the targeting moiety has specific affinity for an epitope of a cell surface antigen expressed on the surface of a cell in the tumor microenvironment (e.g., and antigen such as VEGFR and TIE1, or TIE2 expressed on endothelial cells and macrophage, respectively, or an antigen expressed on tumor stromal cells such as cancer-associated fibroblasts (CAFs) tumor infiltrating T cells and other leukocytes, and myeloid cells including mast cells, eosinophils, and tumor-associated macrophages (TAM).

In some embodiments, the targeted liposome αPPMX composition (e.g., TLp-αPPMX or TPLp-αPPMX) comprises a targeting moiety that has specific affinity for an epitope of a cancer or tumor cell surface antigen that is preferentially/differentially expressed on a target cell such as a cancer cell or tumor cell, compared to normal or non-tumor cells, that is present on a tumor cell but absent or inaccessible on a non-tumor cell. For example, in some situations, the tumor antigen is on the surface of both normal cells and malignant cancer cells but the tumor epitope is only exposed in a cancer cell. As a further example, a tumor cell surface antigen may experience a confirmation change in a cancerous state that causes a cancer cell specific epitope to be present. A targeting moiety with specific affinity to an epitope on a targetable tumor cell surface antigen described herein or otherwise known in the art is useful and is encompassed by the disclosed compositions and methods. In some embodiments, the tumor cell with the tumor cell surface antigen is a cancer cell. Examples of such tumor cell surface antigens include, without limitation folate receptor alpha, folate receptor beta and folate receptor delta.

In further embodiments, the targeting moiety comprises a polypeptide targeting moiety such as an antibody or an antigen-binding antibody fragment and the targeting moiety has binding specificity for a folate receptor. In some embodiments, the targeting moiety binds a folate receptor with an equilibrium dissociation constant (Kd) in a range of $0.5 \times 10^{-10}$ to $10 \times 10^{-6}$ as determined using BIACORE® analysis. In some embodiments, the folate receptor bound by the targeting moiety is one or more folate receptors selected from the group consisting of: folate receptor alpha (FR-α), folate receptor beta (FR-β), and folate receptor delta (FR-δ). In a further embodiment, the targeting moiety has specific affinity for at least two antigens selected from the group consisting of folate receptor alpha, folate receptor beta, and folate receptor delta. In another embodiment, the targeting moiety has specific affinity for folate receptor alpha; folate receptor beta; and folate receptor delta.

In some embodiments, the targeting moiety has a specific affinity for an epitope of a cell surface antigen that internalizes the targeting moiety upon binding. Numerous cell surface antigens that internalize binding partners such as antibodies upon binding are known in the art and are envisioned to be binding targets for the targeting moieties expressed on the targeted liposome αPPMX compositions (e.g., TLp-αPPMX or TPLp-αPPMX) disclosed herein.

In some embodiments, the targeting moiety has a specific affinity for an epitope of a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK.

In some embodiments, the targeting moiety has a specific affinity for a cell surface antigen(s) derived, from or determined to be expressed on, a specific subject's cancer (e.g., tumor) such as a neoantigen.

In some embodiments, the targeting moiety has a specific affinity for an epitope of a cell surface antigen selected from the group consisting of mannose-6-phosphate receptor, transferrin receptor, and a cell adhesion molecule (CAM). In further embodiments, the targeting moiety has a specific affinity for an epitope of a CAM is selected from the group consist of: intercellular adhesion molecule (ICAM), platelet-endothelial cell adhesion molecule (PECAM), activated leukocyte cell adhesion molecule (ALCAM), B-lymphocyte cell adhesion molecule (BL-CAM), vascular cell adhesion molecule (VCAM), mucosal vascular addressin cell adhesion molecule (MAdCAM), CD44, LFA-2, LFA-3, and basigin.

A discussed herein, folate receptors (FRs) are distinct from reduced folate carriers (RFCs) and exploit different pathways for bringing folates and antifolates into cells. In some embodiments, the targeting moiety specifically binds a folate receptor. In further embodiments, the targeting moiety specifically binds a folate receptor selected from folate receptor alpha, folate receptor beta and folate receptor delta. Antibodies to folate receptor alpha can routinely be generated using techniques known in the art. Moreover, the sequences of numerous anti-folate receptor antibodies are in the public domain and/or commercially available and are readily obtainable.

Murine antibodies against folate receptor are examples of antibodies that can be used as targeting moieties of the disclosed targeted liposome is a murine antibody against folate receptor. The sequence of these antibodies are known and are described, for example, in U.S. Pat. Nos. 5,646,253; 8,388,972; 8,871,206; and 9,133,275, and Intl. Appl. Nos. PCT/US2011/056966, and PCT/US2012/046672. For example, based on the sequences already in the public domain, the gene for the antibodies can be synthesized and placed into a transient expression vector and the antibody was produced in HEK-293 transient expression system. The antibody can be a complete antibody, a Fab, or any of the various antibody variations discussed herein or otherwise known in the art.

In some embodiments, the targeted liposome (e.g., TL-αPPMX or TPL-αPPMX) contains from 1 to 1,000, or more than 1,000, targeting moieties on its surface. In some embodiments, the targeted liposome contains from 30 to 1,000, 30 to 500, 30 to 250 or 30-200, targeting moieties, or any range therein between. In some embodiments, the targeted liposome contains less than 220 targeting moieties, less than 200 targeting moieties, or less than 175 targeting moieties. In some embodiments, the targeting moiety is non-covalently bonded to the outside of the liposome (e.g., via ionic interaction or a GPI anchor).

In some embodiments, the molecules on the outside of the targeted liposome (e.g., TL-αPPMX or TPL-αPPMX) include a lipid, a targeting moiety, a steric stabilizer (e.g., a PEG), a maleimide, and a cholesterol. In some embodiments, the targeting moiety is covalently bound via a maleimide functional group. In some embodiments, the targeting moiety is covalently bound to a liposomal component or a steric stabilizer such as a PEG molecule. In some embodiments, all the targeting moieties of the liposome are bound to one component of the liposome such as a PEG. In other embodiments, the targeting moieties of the targeted liposome are bound to different components of the liposome. For example, some targeting moieties may be bound to the lipid components or cholesterol, some targeting moieties may be bound to the steric stabilizer (e.g., PEG) and still other targeting moieties may be bound to a detectable marker or to another targeting moiety. In some embodiments, the outside of the targeted liposome (e.g., TL-αPPMX or TPL-αPPMX) further comprises one or more of an immunostimulatory agent, a detectable marker and a maleimide disposed on at least one of the PEG and the exterior of the liposome.

In some embodiments, the targeted liposome (e.g., TL-αPPMX or TPL-αPPMX) is anionic or neutral. In some embodiments, the targeted anionic or neutral liposome has a diameter in the range of 20 nm to 500 nm or 20 nm to 200 nm, or any range therein between. In further embodiments, the targeted anionic or neutral liposome has a diameter in the range of 80 nm to 120 nm, or any range therein between.

In other embodiments, the targeted liposome (e.g., TL-αPPMX or TPL-αPPMX) is cationic. In some embodiments, the targeted anionic or neutral liposome has a diameter in the range of 20 nm to 500 nm or 20 nm to 200 nm, or any range therein between. In further embodiments, the targeted anionic or neutral liposome has a diameter in the range of 80 nm to 120 nm, or any range therein between.

In some embodiments, the targeted liposomes comprise at least 1%, 5%, 10%, 15%, 20%, 25%, 30%, 35, 40%, 45%, 50%, 55%, 60%, 65%, 70%, 75%, or more than 75%, w/w of the alpha polyglutamated PMX. In some embodiments, during the process of preparing the targeted liposomes, at least 1%, 5%, 10%, 15%, 20%, 25%, 30%, 35%, 40%, 45%, 50%, 55%, 60%, 65%, 70%, 75%, or more than 75%, of the starting material of alpha polyglutamated PMX is encapsulated (entrapped) in the targeted liposomes.

In some embodiments, the targeted liposomal compositions comprise 30-70%, 30-60%, or 30-50%, w/w of the alpha tetraglutamated PMX, or any range therein between In some embodiments, the targeted liposomes comprise at least 1%, 5%, 10%, 15%, 20%, 25%, 30%, 35, 40%, 45%, 50%, 55%, 60%, 65%, 70%, 75%, or more than 75%, w/w of the alpha tetraglutamated PMX. In some embodiments, during the process of preparing the targeted liposomes, at least 1%, 5%, 10%, 15%, 20%, 25%, 30%, 35%, 40%, 45%, 50%, 55%, 60%, 65%, 70%, 75%, or more than 75%, of the starting material of alpha tetraglutamated PMX is encapsulated (entrapped) in the targeted liposomes.

In some embodiments, the targeted liposomal compositions comprise 30-70%, 30-60%, or 30-50%, w/w of the alpha pentaglutamated PMX, or any range therein between In some embodiments, the targeted liposomes comprise at least 1%, 5%, 10%, 15%, 20%, 25%, 30%, 35, 40%, 45%, 50%, 55%, 60%, 65%, 70%, 75%, or more than 75%, w/w of the alpha pentaglutamated PMX. In some embodiments, during the process of preparing the targeted liposomes, at least 1%, 5%, 10%, 15%, 20%, 25%, 30%, 35%, 40%, 45%, 50%, 55%, 60%, 65%, 70%, 75%, or more than 75%, of the starting material of alpha pentaglutamated PMX is encapsulated (entrapped) in the targeted liposomes.

In some embodiments, the targeted liposomal compositions comprise 30-70%, 30-60%, or 30-50%, w/w of the alpha hexaglutamated PMX, or any range therein between In some embodiments, the targeted liposomes comprise at least 1%, 5%, 10%, 15%, 20%, 25%, 30%, 35, 40%, 45%, 50%, 55%, 60%, 65%, 70%, 75%, or more than 75%, w/w of the alpha hexaglutamated PMX. In some embodiments, during the process of preparing the targeted liposomes, at least 1%, 5%, 10%, 15%, 20%, 25%, 30%, 35%, 40%, 45%, 50%, 55%, 60%, 65%, 70%, 75%, or more than 75%, of the starting material of alpha hexaglutamated PMX is encapsulated (entrapped) in the targeted liposomes.

Methods and techniques for covalently associating polypeptide targeting moieties with a liposome surface molecule are known in the art and can readily be applied to prepare the TL-αPPMX or TPL-αPPMX liposome compositions.

Chemical binding of non-proteinaceous targeting moieties and other compositions to the liposomal surface may be employed. Thus, a non-proteinaceous moiety, may be covalently or non-covalently linked to, embedded or adsorbed onto the liposome using any linking or binding method and/or any suitable chemical linker known in the art. The exact type and chemical nature of such cross-linkers and cross linking methods is preferably adapted to the type of affinity group used and the nature of the liposome. Methods for binding or adsorbing or linking the targeting moiety are also well known in the art. For example, in some embodiments, the targeting moiety may be attached to a group at the interface via, but not limited to, polar groups such as amino, SH, hydroxyl, aldehyde, formyl, carboxyl, His-tag or other polypeptides. In addition, the targeting moiety may be attached via, but not limited to, active groups such as succinimidyl succinate, cyanuric chloride, tosyl activated groups, imidazole groups, CNBr, NHS, Activated CH, ECH, EAH, Epoxy, Thiopropyl, Activated Thiol, etc., Moreover, the targeting moiety may be attached via, but not limited to, hydrophobic bonds (Van Der Waals) or electrostatic interactions that may or may not include cross-linking agents (e.g., bivalent anions, poly-anions, poly-cations etc.).

(4) Manufacture of Liposomes

In some embodiments, the disclosure provides a method of making a liposomal composition disclosed herein. In one embodiment, the method includes forming a mixture comprising: (1) a liposomal component; and (2) an alpha polyglutamated (e.g., pentaglutamated or hexaglutamated) pemetrexed in aqueous solution. In further embodiments, the mixture comprises a pegylated liposomal component. The mixture is then homogenized to form liposomes in the aqueous solution. Further, the mixture can be extruded through a membrane to form liposomes enclosing the alpha polyglutamated pemetrexed in an aqueous solution. It is understood the liposomal components of this disclosure can comprise any lipid (including cholesterol) including functionalized lipids and lipids attached to targeting moieties, detectable labels, and steric stabilizers, or any subset of all of these. It is further noted that the bioactive alpha polyglutamated pemetrexed in aqueous solution can comprise any reagents and chemicals discussed herein or otherwise known in the art for the interior or exterior of the liposome including, for example, buffers, salts, and cryoprotectants.

In some embodiments, the disclosure provides a method of making a targeted pegylated liposomal alpha polyglutamated pemetrexed (targeted-PLp-αPPMX) or non-targeted PLp-αPPMX disclosed herein. In one embodiment, the method includes forming a mixture comprising: (1) a liposomal component; (2) an alpha polyglutamated (e.g., pentaglutamated or hexaglutamated) pemetrexed in aqueous solution; and (3) the targeting moiety. The mixture is then homogenized to form liposomes in the aqueous solution. Further, the mixture may be extruded through a membrane to form liposomes enclosing the targeted alpha polyglutamated pemetrexed in an aqueous solution. It is understood that the targeted pegylated liposomal components can comprise any lipid (including cholesterol) including functionalized lipids and lipids attached to targeting moieties, detectable labels, and steric stabilizers, or any subset of all of these. It is further noted that the targeted pegylated liposome can comprise any reagents and chemicals discussed herein or otherwise known in the art for the interior or exterior of the liposome including, for example, buffers, salts, and cryoprotectants.

The above methods optionally further comprise the step of lyophilizing the composition after the removing step (discussed below) to form a lyophilized composition. As stated above, targeted-PTPLA or non-targeted-PTPLA in aqueous solution may comprise a cryoprotectant described herein or otherwise known in the art. If the composition is to be lyophilized, a cryoprotectant may be preferred.

Additionally, after the lyophilizing step, the method optionally further comprises the step of reconstituting the lyophilized composition by dissolving the composition in a solvent after the lyophilizing step. Methods of reconstitution are known in the art. One preferred solvent is water. Other preferred solvents include saline solutions and buffered solutions.

While certain exemplary embodiments, are discussed herein, it is understood that liposomes can be made by any method that is known in the art. See, for example, G. Gregoriadis (editor), Liposome Technology, vol. 1-3, 1st edition, 1983; 2nd edition, 1993, CRC Press, 45 Boca Raton, Fla. Examples of methods suitable for making liposome compositions include extrusion, reverse phase evaporation, sonication, solvent (e.g., ethanol) injection, microfluidization, detergent dialysis, ether injection, and dehydration/rehydration. The size of liposomes can routinely be controlled by controlling the pore size of membranes used for low pressure extrusions or the pressure and number of passes utilized in microfluidization or any other suitable methods known in the art.

In general, the alpha polyglutamated pemetrexed is contained inside, that is, in the inner (interior) space of the liposomes. In one embodiment, polyglutamated pemetrexed is partially or substantially completely removed from the outer medium surrounding the liposomes. Such removal can be accomplished by any suitable means known in the art (e.g., dilution, ion exchange chromatography, size exclusion chromatography, dialysis, ultrafiltration, and precipitation). Accordingly, the methods of making liposomal compositions set forth above or otherwise known in the art can optionally further comprise the step of removing alpha polyglutamated pemetrexed in aqueous solution outside of the liposomes after forming the liposomes, for example, by the homogenization or by the extruding step.

In other embodiments, the disclosure provides a targeted pegylated liposomal alpha polyglutamated pemetrexed (PLp-αPPMX) that selectively targets folate receptors comprising: a liposome including an interior space, an alpha polyglutamated pemetrexed disposed within the interior space, a steric stabilizer molecule attached to an exterior of the liposome, and a targeting moiety comprising a protein with specific affinity for at least one folate receptor, said targeting moiety attached to at least one of the steric stabilizer and the exterior of the liposome. The components of this embodiment, may be the same as described for other embodiments, of this disclosure. For example, the targeted pegylated liposomal alpha polyglutamated pemetrexed and the steric stabilizer which may be PEG, are as described in other parts of this disclosure.

In some embodiments, the disclosure provides a method of preparing a targeted composition comprising a pegylated liposome including an entrapped and/or encapsulated alpha polyglutamated pemetrexed; a targeting moiety an amino acid chain, the amino acid chain comprising a plurality of amino acids, the targeting moiety having a specific affinity for at least one type of folate receptor, the specific affinity being defined to include an equilibrium dissociation constant (Kd) in a range of $0.5 \times 10^{-10}$ to $10 \times 10^{-6}$ moles [0.05 nM to 10 μM] for at least one type folate receptor, the targeting moiety attached to one or both of a PEG and an exterior of the liposome, the method comprising: forming a mixture comprising: liposomal components and alpha polyglutamated pemetrexed in solution; homogenizing the mixture to form liposomes in the solution; processing the mixture to form liposomes entrapping and/or encapsulating alpha polyglutamated pemetrexed; and providing the targeting moiety on a surface of the liposomes entrapping and/or encapsulating the alpha polyglutamated pemetrexed, the targeting moiety having the specific affinity for at least one of folate receptor alpha (FR-α), folate receptor beta (FR-β) and folate receptor delta (FR-δ). In some embodiments, the method comprising: forming a mixture comprising: liposomal components and alpha polyglutamated pemetrexed in solution; forming liposomes entrapping and/or encapsulating alpha polyglutamated pemetrexed, for example by homogenizing or otherwise processing the mixture to form liposomes; and providing the targeting moiety on a surface of the liposomes entrapping and/or encapsulating the alpha polyglutamated pemetrexed, the targeting moiety having the specific affinity for at least one of folate receptor alpha (FR-α), folate receptor beta (FR-β) and folate receptor delta (FR-δ). In some embodiments, the processing includes one or more of: thin film hydration, extrusion, in-line mixing, ethanol injection technique, freezing-and-thawing technique, reverse-phase evaporation, dynamic high pressure microfluidization, microfluidic mixing, double emulsion, freeze-dried double emulsion, 3D printing, membrane contactor method, and stirring, and once the particles have been formed, the particles can have their sizes further modified by one or more of extrusion and sonication. In some embodiments, during the process of preparing the liposomes at least 1%, 5%, 10%, 15%, 20%, 25%, 30%, 35%, 40%, 45%, 50%, 55%, 60%, 65%, 70%, 75%, or more than 75%, of the starting material of alpha polyglutamated PMX is encapsulated (entrapped) in the targeted liposomes. In some embodiments, the liposomes are anionic or neutral. In some embodiments, the targeting moiety has the specific affinity for one or more of: folate receptor alpha (FR-α), folate receptor beta (FR-β) and folate receptor delta (FR-δ). In further embodiments, the targeting moiety has the specific affinity for folate receptor alpha (FR-α) and folate receptor beta (FR-β). In additional embodiments, the targeting moiety has the specific affinity for an epitope on a tumor cell surface antigen that is present on a tumor cell but absent or inaccessible on a non-tumor cell.

Liposomes can also be prepared to target particular cells, organs, or cell organelles by varying phospholipid composition or by inserting receptors or counter-receptors into the liposomes. For example, liposomes, prepared with a high content of a nonionic surfactant, have been used to target the liver. (See, e.g., Japanese Patent 04-244,018 to Hayakawa et al.; Kato et al., Biol. Pharm. Bull. 16:960, (1993).) A liposomal formulation of dipalmitoylphosphatidylcholine (DPPC) with a soybean-derived sterylglucoside mixture (SG) and cholesterol (Ch) has also been shown to target the liver. (See Shimizu et al., Biol. Pharm. Bull. 20:881, 1997.)

B. Antibody Delivery Vehicles

In additional embodiments, the disclosure provides an antibody delivery vehicle (e.g., ADC). In some embodiments, the disclosure provides an immunoconjugate having the formula (A)-(L)-(αPPMX), wherein: (A) is an antibody or antigen binding fragment of an antibody; (L) is a linker; and (αPPMX) is a αPPMX composition described herein; and wherein said linker (L) links (A) to (αPPMX).

In some embodiments, the antibody or antigen binding antibody fragment has specific affinity for an epitope of a cell surface antigen on a cell of interest (e.g., an epitope and/or antigen described herein). In certain embodiments, the antibody binds to an antigen target that is expressed in or on the cell membrane (e.g., on the cell surface) of a cancer/tumor and the antibody is internalized by the cell after binding to the (antigen) target, after which the αPPMX is released intracellularly. In some embodiments, the antibody is a full length antibody.

The antibody or antigen binding antibody fragment of the (A)-(L)-(αPPMX) immunoconjugate can be an IgA, IgD, IgE, IgG or IgM antibody. The different classes of immunoglobulins have different and well known subunit structures and three-dimensional configurations. In certain embodiments, the antibody is an IgG antibody. In some embodiments, the antibody is an IgG1, IgG2, IgG3 or IgG4 antibody. In certain embodiments, the antibody is an IgG1 antibody.

In some embodiments, (A) is an antigen binding fragment of an antibody. In some embodiments, (A) is an antigen binding fragment of an antibody.

A "linker" is any chemical moiety that is capable of linking a compound, usually a drug, such as a αPPMX, to an antibody or antigen binding fragment of an antibody in a stable, covalent manner. The linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are known in the art and include, for example, disulfide groups, thioether groups, acid labile groups, photolabile groups, peptidase labile groups and esterase labile groups. Linkers also include charged linkers, and hydrophilic forms thereof.

In some embodiments, the linker is selected from the group consisting of a cleavable linker, a non-cleavable linker, a hydrophilic linker, and a dicarboxylic acid based linker. In another embodiment, the linker is a non-cleavable linker. In another embodiment, the linker is selected from the group consisting: N-succinimidyl 4-(2-pyridyldithio) pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexane-carboxylate (SMCC); N-sulfosuccinimidyl 4-(maleimidomethyl)cyclohex-anecarboxylate (sulfoSMCC); N-succinimidyl-4-(iodoacetyl)-aminobenzoate (SIAB); and N-succinimidyl-[(N-maleimido-propionamido)-tetraethyleneglycol]ester (NHS-PEG4-maleimide). In a further embodiment, the linker is N-succinimidyl-[(N-maleimido-propionamido)-tetraethyleneglycol]ester(NHS-PEG4-maleimide).

In some embodiments, the α polyglutamated PMX is attached (coupled) to the antibody or antigen binding antibody fragment of the immunoconjugate directly, or through a linker using techniques known in the art. Such attachment of one or more αPPMX can include many chemical mechanisms, such as covalent binding, affinity binding, intercalation, coordinate binding and complexation. Covalent binding of the αPPMX and antibody or antigen binding antibody fragment can be achieved by direct condensation of existing side chains or by the incorporation of external bridging molecules. Many bivalent or polyvalent agents are useful in associating polypeptides to other proteins with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents. In some embodiments, the antibody or antigen binding antibody fragment is derivatized and then attached to the α polyglutamated PMX. Alternatively, the αPPMX can be derivatized and attached to the antibody or antigen binding antibody fragment using techniques known in the art.

In some embodiments, the immunoconjugate comprises an antibody or an antigen-binding fragment of an antibody and αPPMX containing 4, 5, 6, 2-10, 4-6, or more than 5, glutamyl groups (including the glutamyl group in pemetrexed). In some embodiments, the immunoconjugate comprises alpha polyglutamated pemetrexed that comprises two or more glutamyl groups in the L-form. In other embodiments, the immunoconjugate comprises alpha polyglutamated pemetrexed that comprises a glutamyl group in the D-form. In further embodiments, the immunoconjugate comprises alpha polyglutamated pemetrexed that comprises a glutamyl group in the D-form and two or more glutamyl groups in the L-form. In additional embodiments, the immunoconjugate comprises alpha polyglutamated pemetrexed that comprises two or more glutamyl groups that have a gamma carboxyl linkage. In some embodiments, the immunoconjugate comprises a pentaglutamated PMX. In further embodiments, the immunoconjugate comprises L-α pentaglutamated PMX, a D-α pentaglutamated PMX, or an L- and D-α pentaglutamated PMX. In some embodiments, the immunoconjugate comprises an α hexaglutamated PMX (Lp-αPPMX). In further embodiments, the immunoconjugate comprises an L-α hexaglutamated PMX, a D-α hexaglutamated PMX, or an L- and D-α hexaglutamated PMX.

In some embodiments, the antibody delivery vehicle composition comprises an alpha polyglutamated pemetrexed and an antibody or an antigen binding antibody fragment that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle comprises a targeting moiety that has specific affinity for an epitope on a cell surface antigen derived from, or determined to be expressed on, a specific subject's cancer (tumor) such as a neoantigen.

In some embodiments, the antibody delivery vehicle composition comprises an alpha polyglutamated pemetrexed and an antibody or an antigen binding antibody fragment that has specific affinity for an epitope on an antigen selected from the group consisting of mannose-6-phosphate receptor, transferrin receptor, and a cell adhesion molecule (CAM). In further embodiments, the targeting moiety has a specific affinity for an epitope of a CAM is selected from the group consist of: intercellular adhesion molecule (ICAM), platelet-endothelial cell adhesion molecule (PECAM), activated leukocyte cell adhesion molecule (ALCAM), B-lymphocyte cell adhesion molecule (BL-CAM), vascular cell adhesion molecule (VCAM), mucosal vascular addressin cell adhesion molecule (MAdCAM), CD44, LFA-2, LFA-3, and basigin In some embodiments, the antibody delivery vehicle composition comprises 1, 2, 3, 4, 5, 5-10, or greater than 10 α polyglutamated PMX. In some embodiments, the antibody delivery vehicle composition comprises 1, 2, 3, 4, 5, 5-10, or greater than 10, a pentaglutamated PMX. In some embodiments, the antibody delivery vehicle composition comprises 1, 2, 3, 4, 5, 5-10, or greater than 10, a hexaglutamated PMX.

IV. Pharmaceutical Compositions and Administration

In some embodiments, the liposome composition is provided as a pharmaceutical composition containing the liposome and a carrier, e.g., a pharmaceutically acceptable carrier. Examples of pharmaceutically acceptable carriers contained in the provided pharmaceutical compositions include normal saline, isotonic dextrose, isotonic sucrose, Ringer's solution, and Hanks' solution. In some embodiments, a buffer substance is added to maintain an optimal pH for storage stability of the pharmaceutical composition. In some embodiments, the pH of the pharmaceutical composition is between 6.0 and 7.5. In some embodiments, the pH is between 6.3 and 7.0. In further embodiments, the pH is 6.5. Ideally the pH of the pharmaceutical composition allows for both stability of liposome membrane lipids and retention of the entrapped entities. Histidine, hydroxyethylpiperazine-ethylsulfonate (HEPES), morpholipoethylsulfonate (MES), succinate, tartrate, and citrate, typically at 2-20 mM concentration, are exemplary buffer substances. Other suitable carriers include, e.g., water, buffered aqueous solution, 0.4% NaCl, and 0.3% glycine. Protein, carbohydrate, or polymeric stabilizers and tonicity adjusters can be added, e.g., gelatin, albumin, dextran, or polyvinylpyrrolidone. The tonicity of the composition can be adjusted to the physiological level of 0.25-0.35 mol/kg with glucose or a more inert compound such as lactose, sucrose, mannitol, or dextrin. These compositions can routinely be sterilized using conventional, sterilization techniques known in the art (e.g., by filtration). The resulting aqueous solutions can be packaged for use or filtered under aseptic conditions and lyophilized, the lyophilized preparation being combined with a sterile aqueous medium prior to administration.

The provided pharmaceutical liposome compositions can also contain other pharmaceutically acceptable auxiliary substances as required to approximate physiological conditions, such as pH adjusting and buffering agents, and tonicity adjusting agents, for example, sodium acetate, sodium lactate, sodium chloride, potassium chloride, and calcium chloride. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The liposome concentration in the provided fluid pharmaceutical formulations can vary widely depending upon need, e.g., from less than about 0.05% usually or at least about 2-10% to as much as 30-50% by weight and will be selected primarily by fluid volumes, and viscosities, in accordance with the particular mode of administration selected. For example, the concentration may be increased to lower the fluid load associated with treatment. This may be particularly desirable in patients having atherosclerosis-associated congestive heart failure or severe hypertension. Alternatively, liposome pharmaceutical compositions composed of irritating lipids may be diluted to low concentrations to lessen inflammation at the site of administration.

Some embodiments, relate to a method of delivering a targeted pegylated liposomal formulation of alpha polyglutamated pemetrexed, to a tumor expressing folate receptor on its surface. An exemplary method comprises the step of administering a liposome pharmaceutical composition provided herein in an amount to deliver a therapeutically effective dose of the targeted pegylated liposomal alpha polyglutamated pemetrexed to the tumor.

The amount of liposome pharmaceutical composition administered will depend upon the particular alpha polyglutamated pemetrexed entrapped inside the liposomes, the disease state being treated, the type of liposomes being used, and the judgment of the clinician. Generally the amount of liposome pharmaceutical composition administered will be sufficient to deliver a therapeutically effective dose of the particular therapeutic entity.

The quantity of liposome pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, LWW, 2003. Therapeutically effective dosages for various therapeutic compositions are known to those skilled in the art. In some embodiments, a therapeutic entity delivered via the pharmaceutical liposome composition and provides at least the same or higher activity than the activity obtained by administering the same amount of the therapeutic entity in its routine non-liposome formulation. Typically the dosages for the liposome pharmaceutical composition is in a range for example, between about 0.005 and about 5000 mg of the therapeutic entity per square meter of body surface area most often, between about 0.1 and about 1000 mg therapeutic entity per square meter of body surface area.

For example, if the subject has a tumor, an effective amount may be that amount of the agent (e.g., alpha polyglutamated pemetrexed composition) that reduces the tumor volume or load (as for example determined by imaging the tumor). Effective amounts can also routinely be assessed by the presence and/or frequency of cancer cells in the blood or other body fluid or tissue (e.g., a biopsy). If the tumor is impacting the normal functioning of a tissue or organ, then the effective amount can routinely be assessed by measuring the normal functioning of the tissue or organ. In some instances the effective amount is the amount required to lessen or eliminate one or more, and preferably all, symptoms.

Pharmaceutical compositions comprising the alpha polyglutamated pemetrexed compositions (e.g., liposomes containing a pentaglutamated or hexaglutamated pemetrexed) are also provided. Pharmaceutical compositions are sterile compositions that comprise a sample liposome and preferably alpha polyglutamated pemetrexed, preferably in a pharmaceutically-acceptable carrier.

Unless otherwise stated herein, a variety of administration routes are available. The particular mode selected will depend, upon the particular active agent selected, the particular condition being treated and the dosage required for therapeutic efficacy. The provided methods can be practiced using any known mode of administration that is medically acceptable and in accordance with good medical practice. In some embodiments, the administration route is an injection. In further embodiments, the injection is by a parenteral route elected from an intramuscular, subcutaneous, intravenous, intraarterial, intraperitoneal, intraarticular, intraepidural, intrathecal, intravenous, intramuscular, or intra sternal injection. In some embodiments, the administration route is an infusion. In additional embodiments, the administration route is oral, nasal, mucosal, sublingual, intratracheal, ophthalmic, rectal, vaginal, ocular, topical, transdermal, pulmonary, or inhalation.

Therapeutic compositions containing αPPMX compositions such as the liposomal αPPMX compositions described herein can be conventionally administered intravenously, as by injection of a unit dose, for example. The term "unit dose" when used in reference to a therapeutic composition provided herein refers to physically discrete units suitable as unitary dosage for the subject, each unit containing a predetermined quantity of active material calculated to produce the desired therapeutic effect in association with the required diluent; e.g., carrier, or vehicle. In a specific embodiment, therapeutic compositions containing an Adapter are administered subcutaneously.

In some embodiments, the α-PPMX composition is administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The αPPMX composition are formulated, dosed, and administered in a fashion consistent with good medical practice. Factors for consideration in this context include the particular disorder being treated, the particular patient being treated, the clinical condition of the individual patient, the cause of the disorder, the site of delivery of the agent, the method of administration, the scheduling of administration, and other factors known to medical practitioners. The dosage ranges for the administration of αPPMX composition are those large enough to produce the desired effect in which the disease symptoms mediated by the target molecule are ameliorated. The dosage should not be so large as to cause adverse side effects, such as, hyperviscosity syndromes, pulmonary edema, congestive heart failure, and other adverse side effects known in the art. Generally, the dosage will vary with the age, weight, height, body surface area, state of health (e.g., renal and liver function), condition, sex and extent of the disease in the patient and can routinely be determined by one of ordinary skill in the art. The dosage can be adjusted by the individual physician in the event of any complication.

The dosage schedule and amounts effective for therapeutic and prophylactic uses, i.e., the "dosing regimen," will depend upon a variety of factors, including the cause, stage and severity of the disease or disorder, the health, physical status, age of the subject being treated, and the site and mode of the delivery of the αPPMX composition. Therapeutic efficacy and toxicity of the αPPMX composition can be determined by standard pharmaceutical, pharmacological, and toxicological procedures in cell cultures or experimental animals. Data obtained from these procedures can likewise be used in formulating a range of dosages for human use. Moreover, therapeutic index (i.e., the dose therapeutically effective in 50 percent of the population divided by the dose lethal to 50 percent of the population (ED50/LD50)) can readily be determined using known procedures. The dosage is preferably within a range of concentrations that includes the ED50 with little or no toxicity, and may vary within this range depending on the dosage form employed, sensitivity of the patient, and the route of administration.

The dosage regimen also takes into consideration pharmacokinetics parameters known in the art, such as, drug absorption rate, bioavailability, metabolism and clearance (see, e.g., Hidalgo-Aragones, J. Steroid Biochem. Mol. Biol. 58:611-617 (1996); Groning et al., Pharmazie 51:337-341 (1996); Fotherby, Contraception 54:59-69 (1996); and Johnson et al., J. Pharm. Sci. 84:1144-1146 (1995)). It is well within the state of the art for the clinician to determine the dosage regimen for each subject being treated. Moreover, single or multiple administrations of the αPPMX composition can be administered depending on the dosage and frequency as required and tolerated by the subject. The duration of prophylactic and therapeutic treatment will vary depending on the particular disease or condition being treated. Some diseases are amenable to acute treatment whereas others require long-term, chronic therapy. The αPPMX composition can be administered serially, or simultaneously with the additional therapeutic agent.

In some embodiments, the αPPMX composition is administered in a liposomal composition at a dose of between 0.005 and 5000 mg of αPPMX per square meter of body surface area, or any range therein between. In further embodiments, the αPPMX composition is administered in a liposomal composition at a dose of between 0.1 and 1000 mg αPPMX/meter squared of body surface area, or any range therein between.

In some embodiments, the αPPMX composition is administered in an immunoconjugate composition at a dose of 1 mg/kg to 500 mg/kg, 1 mg/kg to 250 mg/kg, 1 mg/kg to 200 mg/kg, 1 mg/kg to 150 mg/kg, 1 mg/kg to 100 mg/kg, 1 mg/kg to 50 mg/kg, 1 mg/kg to 25 mg/kg, 1 mg/kg to 20 mg/kg, 1 mg/kg to 15 mg/kg, 1 mg/kg to 10 mg/kg, or 1 mg/kg to 5 mg/kg, or any range therein between.

In another embodiment, the αPPMX composition is administered in combination with one or more additional therapeutics.

In some embodiment, the PLp-αPPMX and/or targeted-PLp-αPPMX is prepared as an infusion composition, an injection composition, a parenteral composition, or a topical composition. In further embodiments, the injection includes one or more of: intraperitoneal injection, direct intratumor injection, intra-arterial injection, and intravenous injection, subcutaneous injection, intramuscular injection, delivery via transcutaneous and intranasal route. In a further embodiment, the PLp-αPPMX and/or targeted-PLp-αPPMX is a liquid solution or a suspension. However, solid forms suitable for solution in, or suspension in, liquid vehicles prior to injection are also provided herein. In some embodiments, the targeted pegylated liposomal alpha polyglutamated pemetrexed composition is formulated as an enteric-coated tablet or gel capsule according to methods known in the art.

In some embodiments, the targeted pegylated liposomal alpha polyglutamated pemetrexed formulations are administered to a tumor of the central nervous system using a slow, sustained intracranial infusion of the liposomes directly into the tumor (e.g., a convection-enhanced delivery (CED)). See, Saito et al., Cancer Research 64:2572-2579 (2004); Mamot et al., J. Neuro-Oncology 68:1-9 (2004). In other embodiments, the formulations are directly applied to tissue surfaces. Sustained release, pH dependent release, and other specific chemical or environmental condition-mediated release administration of the pegylated liposomal alpha polyglutamated pemetrexed formulations (e.g., depot injections and erodible implants) are also provided. Examples of such release-mediating compositions are further described herein or otherwise known in the art.

For administration by inhalation, the compositions can be conveniently delivered in the form of an aerosol spray presentation from pressurized packs or a nebulizer, with the use of a suitable propellant, e.g., dichlorodifluoromethane, trichlorofluoromethane, ichlorotetra-fluoroethane, carbon dioxide or other suitable gas. In the case of a pressurized aerosol, the dosage unit can be determined by providing a valve to deliver a metered amount.

When it is desirable to deliver the compositions systemically, they can formulated for parenteral administration by injection, e.g., by bolus injection or continuous infusion. Formulations for injection can be presented in unit dosage form, e.g., in ampoules or in multi-dose containers. Pharmaceutical parenteral formulations include aqueous solutions of the ingredients. Aqueous injection suspensions can contain substances which increase the viscosity of the suspension, such as sodium carboxymethyl cellulose, sorbitol, or dextran. Alternatively, suspensions of liposomes can be prepared as oil-based suspensions. Suitable lipophilic solvents or vehicles include fatty oils such as sesame oil, or synthetic fatty acid esters, such as ethyl oleate or triglycerides.

Alternatively, the non-targeted or targeted pegylated liposomal alpha polyglutamated pemetrexed can be in powder form or lyophilized form for constitution with a suitable vehicle, e.g., sterile pyrogen-free water, before use.

The provided compositions (e.g., alpha polyglutamated pemetrexed and liposomes containing the alpha polyglutamated pemetrexed) can also be formulated in rectal or vaginal compositions such as suppositories or retention enemas, e.g., containing conventional suppository bases such as cocoa butter or other glycerides.

Methods of Use and Treatment

In additional embodiments, the disclosure provides methods of using alpha polyglutamated pemetrexed (αPPMX) compositions. In some embodiments, the alpha αPPMX compositions are used to treat a disease or disorder.

In some embodiments, the disclosure provides a method of killing a cell that comprises contacting the cell with a composition comprising an alpha polyglutamated pemetrexed (e.g., an αPPMX disclosed herein). In some embodiments, the contacted cell is a mammalian cell. In further embodiments, the contacted cell is a human cell. In some embodiments, the contacted cell is a hyperproliferative cell. In further embodiments, the hyperproliferative cell is a cancer cell. In yet further embodiments, the cancer cell is a primary cell or a cell from a cell line obtained/derived from a cancer selected from the group consisting of: a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. In some embodiments, the cancer cell is a primary cell or a cell from a cell line obtained/derived from lung cancer (e.g., NSCLC or mesothelioma). In some embodiments, the cancer cell is a primary cell or a cell from a cell line obtained/derived from breast cancer (e.g., HER2++ or triple negative breast cancer). In some embodiments, the cancer cell is a primary cell or a cell from a cell line obtained/derived from colorectal cancer. In some embodiments, the cancer cell is a primary cell or a cell from a cell line obtained/derived from ovarian cancer. In some embodiments, the cancer cell is a primary cell or a cell from a cell line obtained/derived from endometrial cancer. In some embodiments, the cancer cell is a primary cell or a cell from a cell line obtained/derived from pancreatic cancer. In some embodiments, the cancer cell is a primary cell or a cell from a cell line obtained/derived from liver cancer. In some embodiments, the cancer cell is a primary cell or a cell from a cell line obtained/derived from head and neck cancer. In some embodiments, the 1 the cancer cell is a primary cell or a cell from a cell line obtained/derived from osteosarcoma. In some embodiments, the method is performed in vivo. In other embodiments, the method is performed in vitro. In some embodiments, the αPPMX composition contains 4, 5, 6, 2-10, 4-6, or more than 5, glutamyl groups. In some embodiments, the αPPMX composition comprises alpha pentaglutamated pemetrexed. In some embodiments, the αPPMX composition comprises alpha hexaglutamated pemetrexed. In some embodiments, the αPPMX composition comprises L alpha polyglutamated pemetrexed. In some embodiments, the αPPMX composition comprises D alpha polyglutamated pemetrexed. In some embodiments, the αPPMX composition comprises L and D alpha polyglutamated pemetrexed.

In additional embodiments, the disclosure provides a method of killing a cell that comprises contacting the cell with a liposome containing alpha polyglutamated pemetrexed (e.g., an Lp-αPPMX such as, PLp-αPPMX, NTLp-αPPMX, NTPLp-αPPMX, TLp-αPPMX or TPLp-αPPMX disclosed herein). In some embodiments, the liposome is pegylated (e.g., PLp-αPPMX and NTPLp-αPPMX). In some embodiments, the liposome comprises a targeting moiety on its surface that has specific affinity for an epitope of a antigen on the surface of the cell (e.g., TLp-αPPMX and TPLp-αPPMX). In further embodiments, the liposome is pegylated and comprises a targeting moiety on its surface that specifically binds an antigen on the surface of the cell (e.g., TPLp-αPPMX). In some embodiments, the contacted cell is a mammalian cell. In further embodiments, the contacted cell is a human cell. In additional embodiments, the contacted cell is a hyperproliferative cell. In further embodiments, the hyperproliferative cell is a cancer cell. In further embodiments, the contacted cancer cell is a primary cell or a cell from a cell line obtained/derived from a cancer selected from the group consisting of: lung cancer (e.g., non-small cell), pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, myeloma, a leukemia and a lymphoma. In some embodiments, the contacted cancer cell is a primary cell or a cell from a cell line obtained/derived from lung cancer (e.g., NSCLC or mesothelioma). In some embodiments, the contacted cancer cell is a primary cell or a cell from a cell line obtained/derived from breast cancer (e.g., HER2++ or triple negative breast cancer). In some embodiments, the contacted cancer cell is a primary cell or a cell from a cell line obtained/derived from colorectal cancer. In some embodiments, the contacted cancer cell is a primary cell or a cell from a cell line obtained/derived from ovarian cancer. In some embodiments, the contacted cancerell is a primary cell or a cell from a cell line obtained/derived from endometrial cancer. In some embodiments, the contacted cancer cell is a primary cell or a cell from a cell line obtained/derived from pancreatic cancer. In some embodiments, the contacted cancerell is a primary cell or a cell from a cell line obtained/derived from liver cancer. In some embodiments, the contacted cancer cell is a primary cell or a cell from a cell line obtained/derived from head and neck cancer. In some embodiments, the contacted cancer cell is a primary cell or a cell from a cell line obtained/derived from osteosarcoma. In some embodiments, the method is performed in vivo. In other embodiments, the method is performed in vitro. In some embodiments, the liposome contains an αPPMX containing 4, 5, 6, 2-10, 4-6, or more than 5, glutamyl groups. In some embodiments, the liposome comprises L alpha polyglutamated pemetrexed. In some embodiments, the liposome comprises D alpha polyglutamated pemetrexed. In some embodiments, the liposome comprises L and D alpha polyglutamated pemetrexed.

In some embodiments, the disclosure provides a method of killing a hyperproliferative cell that comprises contacting a hyperproliferative cell with a delivery vehicle (e.g., a liposome or antibody) comprising alpha polyglutamated pemetrexed (e.g., an αPPMX disclosed herein). In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the delivery vehicle is non-targeted. In other embodiments, the delivery vehicle is targeted and comprises a targeting moiety on its surface that has specific affinity for an epitope on an antigen on the surface of the hyperproliferative cell. In further embodiments, the delivery vehicle comprises a targeting moiety that has specific affinity for an epitope on an antigen on the surface of the hyperproliferative cell selected from the group consisting of GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle comprises a targeting moiety that specifically binds a cell surface antigen(s) derived from, or determined to be expressed on, a specific subject's cancer (tumor) such as a neoantigen. In some embodiments, the method is performed in vivo. In some embodiments, the method is performed in vitro. In some embodiments, the delivery vehicle comprises an αPPMX consisting of 4, 5, 6, 2-10, 4-6, or more than 5, glutamyl groups. In some embodiments, the delivery vehicle comprises alpha pentaglutamated pemetrexed. In other embodiments, the delivery vehicle comprises alpha hexaglutamated pemetrexed. In some embodiments, the delivery vehicle comprises L alpha polyglutamated pemetrexed. In some embodiments, the delivery vehicle comprises D alpha polyglutamated pemetrexed. In some embodiments, the delivery vehicle comprises L and D alpha polyglutamated pemetrexed.

In particular embodiments, the method of a killing a hyperproliferative cell is performed using a liposome delivery vehicle that comprises alpha polyglutamated pemetrexed (e.g., an Lp-αPPMX such as, PLp-αPPMX, NTLp-αPPMX, NTPLp-αPPMX, TLp-αPPMX or TPLp-αPPMX disclosed herein). In some embodiments, the delivery vehicle is an non-targeted liposome. In some embodiments, the delivery vehicle comprises a targeting moiety on its surface that has specific affinity for an epitope on an antigen on the surface of the hyperproliferative cell (e.g., TLp-αPPMX and TPLp-αPPMX). In some embodiments, the delivery vehicle is a liposome comprising a targeting moiety on its surface that has specific affinity for an epitope on an antigen on the surface of the hyperproliferative cell. In further embodiments, the targeting moiety has specific affinity for an epitope on an antigen selected from the group consisting of GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the liposome comprises a targeting moiety that specifically binds a cell surface antigen(s) derived from, or determined to be expressed on, a specific subject's cancer (tumor) such as a neoantigen. In some embodiments, the liposome is pegylated (e.g., PLp-αPPMX, and NTPLp-αPPMX). In further embodiments, the liposome is pegylated and comprises a targeting moiety on its surface that has specific affinity for an epitope on an antigen on the surface of the hyperproliferative cell (e.g., TPLp-αPPMX). In other embodiments, the embodiments, the liposome is unpegylated. In some embodiments, the liposome is unpegylated and the liposome comprises a targeting moiety on its surface that has specific affinity for an epitope on an antigen on the surface of the hyperproliferative cell (e.g., TPLp-αPPMX). In some embodiments, the liposome comprises an αPPMX consisting of 4, 5, 6, 2-10, 4-6, or more than 5, glutamyl groups. In some embodiments, the liposome comprises alpha tetraglutamated pemetrexed. In some embodiments, the liposome comprises alpha pentaglutamated pemetrexed. In other embodiments, the liposome comprises alpha hexaglutamated pemetrexed. In some embodiments, the liposome comprises L alpha polyglutamated pemetrexed. In some embodiments, the liposome comprises D alpha polyglutamated pemetrexed. In some embodiments, the liposome comprises L and D alpha polyglutamated pemetrexed.

In additional embodiments, the disclosure provides a method of inhibiting the proliferation of a cancer cell that comprises contacting the cancer cell with a delivery vehicle (e.g., a liposome or antibody) comprising alpha polyglutamated pemetrexed (e.g., an αPPMX disclosed herein). In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the delivery vehicle is non-targeted. In some embodiments, the delivery vehicle is targeted and comprises a targeting moiety on its surface that has specific affinity for an epitope on an antigen on the surface of the cancer cell. In further embodiments, the delivery vehicle comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrign αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle is an antibody that has specific affinity for an epitope on an antigen on the surface of the cancer cell. In some embodiments, the contacted cancer cell is a mammalian cell. In further embodiments, the contacted cancer cell is a human cell. In additional embodiments, the contacted cancerell is a primary cell or a cell from a cell line obtained/derived from a cancer selected from the group consisting of: lung cancer (e.g., non-small cell), pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, myeloma, a leukemia and a lymphoma. In some embodiments, the contacted cancer cell is a primary cell or a cell from a cell line obtained/derived from lung cancer (e.g., NSCLC or mesothelioma). In some embodiments, the contacted cancer cell is a primary cell or a cell from a cell line obtained/derived from breast cancer (e.g., HER2++ or triple negative breast cancer). In some embodiments, the contacted cancer cell is a primary cell or a cell from a cell line obtained/derived from colorectal cancer. In some embodiments, the contacted cancer cell is a primary cell or a cell from a cell line obtained/derived from ovarian cancer. In some embodiments, the contacted cancerell is a primary cell or a cell from a cell line obtained/derived from endometrial cancer. In some embodiments, the contacted cancer cell is a primary cell or a cell from a cell line obtained/derived from pancreatic cancer. In some embodiments, the contacted cancerell is a primary cell or a cell from a cell line obtained/derived from liver cancer. In some embodiments, the contacted cancer cell is a primary cell or a cell from a cell line obtained/derived from head and neck cancer. In some embodiments, the contacted cancer cell is a primary cell or a cell from a cell line obtained/derived from osteosarcoma.

In some embodiments, the method is performed in vivo. In some embodiments, the method is performed in vitro. In some embodiments, the delivery vehicle is an antibody that has specific affinity for an epitope on one of the above-listed cell surface antigens. In other embodiments, the targeting vehicle is a liposome that comprises a targeting moiety that has specific affinity for an epitope on the surface of the cancer cell. In other embodiments, the targeting vehicle is a liposome that comprises a targeting moiety that has specific affinity for an epitope on one of the above-listed cell surface antigens. In some embodiments, the delivery vehicle is a liposome that is pegylated. In other embodiments, the delivery vehicle is a liposome that is unpegylated. In some embodiments, the delivery vehicle comprises a αPPMX composition containing 4, 5, 6, 2-10, 4-6, or more than 5, glutamyl groups. In some embodiments, the delivery vehicle comprises alpha pentaglutamated pemetrexed. In other embodiments, the delivery vehicle comprises alpha hexaglutamated pemetrexed. In some embodiments, the delivery vehicle comprises L alpha polyglutamated pemetrexed. In some embodiments, the delivery vehicle comprises D alpha polyglutamated pemetrexed. In some embodiments, the delivery vehicle comprises L and D alpha polyglutamated pemetrexed.

In further embodiments, the disclosure provides a method of inhibiting the proliferation of a cancer cell that comprises contacting the cancer cell with a liposome comprising alpha polyglutamated pemetrexed (e.g., an αPPMX disclosed herein). In some embodiments, the liposome is non-targeted. In some embodiments, the liposome is targeted and comprises a targeting moiety on its surface that has specific affinity for an epitope on an antigen on the surface of the cancer cell. In further embodiments, the liposome comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle comprises a targeting moiety that specifically binds a cell surface antigen(s) derived from, or determined to be expressed on, a specific subject's cancer (tumor) such as a neoantigen. In some embodiments, the contacted cancer cell is a mammalian cell. In further embodiments, the contacted cancer cell is a human cell. In additional embodiments, the contacted cancerell is a primary cell or a cell from a cell line obtained/derived from a cancer selected from the group consisting of: lung cancer (e.g., non-small cell), pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, myeloma, a leukemia and a lymphoma. In some embodiments, the contacted cancer cell is a primary cell or a cell from a cell line obtained/derived from lung cancer (e.g., NSCLC or mesothelioma). In some embodiments, the contacted cancer cell is a primary cell or a cell from a cell line obtained/derived from breast cancer (e.g., HER2++ or triple negative breast cancer). In some embodiments, the contacted cancer cell is a primary cell or a cell from a cell line obtained/derived from colorectal cancer. In some embodiments, the contacted cancer cell is a primary cell or a cell from a cell line obtained/derived from ovarian cancer. In some embodiments, the contacted cancerell is a primary cell or a cell from a cell line obtained/derived from endometrial cancer. In some embodiments, the contacted cancer cell is a primary cell or a cell from a cell line obtained/ derived from pancreatic cancer. In some embodiments, the contacted cancerell is a primary cell or a cell from a cell line obtained/derived from liver cancer. In some embodiments, the contacted cancer cell is a primary cell or a cell from a cell line obtained/derived from head and neck cancer. In some embodiments, the contacted cancer cell is a primary cell or a cell from a cell line obtained/derived from osteosarcoma. In some embodiments, the method is performed in vivo. In some embodiments, the method is performed in vitro. In other embodiments, the targeting vehicle is a liposome that comprises a targeting moiety that has specific affinity for an epitope on one of the above-listed cell surface antigens. In some embodiments, the liposome is pegylated. In other embodiments, the liposome that is unpegylated. In some embodiments, the liposome comprises a αPPMX composition containing 4, 5, 6, 2-10, 4-6, or more than 5, glutamyl groups. In some embodiments, the liposome comprises alpha tetraglutamated pemetrexed. In some embodiments, the liposome comprises alpha pentaglutamated pemetrexed. In other embodiments, the liposome comprises alpha hexaglutamated pemetrexed. In some embodiments, the liposome comprises L alpha polyglutamated pemetrexed. In some embodiments, the liposome comprises D alpha polyglutamated pemetrexed. In some embodiments, the liposome comprises L and D alpha polyglutamated pemetrexed.

In additional embodiments, the disclosure provides a method for treating a hyperproliferative disorder that comprises administering an effective amount of a delivery vehicle (e.g., antibody or liposome) comprising alpha polyglutamated pemetrexed (e.g., an αPPMX disclosed herein) to a subject having or at risk of having a hyperproliferative disorder. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the administered delivery vehicle is pegylated. In some embodiments, the administered delivery vehicle is not pegylated. In additional embodiments, the administered delivery vehicle comprises a targeting moiety that has a specific affinity for an epitope of antigen on the surface of the hyperproliferative cell. In additional embodiments, the delivery vehicle comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle comprises a targeting moiety that specifically binds (i.e., has specific affinity for) an epitope on a cell surface antigen a cell surface antigen(s) derived from, or determined to be expressed on, a specific subject's cancer (tumor) such as a neoantigen. In some embodiments, the targeting moiety is an antibody or an antigen binding antibody fragment. In some embodiments, the administered delivery vehicle does not comprise a targeting moiety that has a specific affinity for an epitope on a cell surface antigen of the hyperproliferative cell. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed. In some embodiments, the hyperproliferative disorder is cancer. In some embodiments, the hyperproliferative disorder is an autoimmune disease (e.g., rheumatoid arthritis). In some embodiments, the hyperproliferative disorder is a benign or malignant tumor; leukemia, hematological, or lymphoid malignancy. In other embodiments, the hyperproliferative disorder selected from the group consisting of a: neuronal, glial, astrocytal, hypothalamic, glandular, macrophagal, epithelial, stromal, blastocoelic, inflammatory, angiogenic and immunologic disorder, including an autoimmune disease.

In additional embodiments, the disclosure provides a method for treating a hyperproliferative disorder that comprises administering an effective amount of a liposome comprising alpha polyglutamated pemetrexed (e.g., an Lp-αPPMX such as, PLp-αPPMX, NTLp-αPPMX, NTPLp-αPPMX, TLp-αPPMX, or TPLp-αPPMX) to a subject having or at risk of having a hyperproliferative disorder. In some embodiments, the liposome is pegylated. In some embodiments, the liposome is not pegylated. In additional embodiments, the liposome comprises a targeting moiety that has a specific affinity for an epitope of antigen on the surface of the hyperproliferative cell. In additional embodiments, the liposome comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the liposome comprises a targeting moiety that has specific affinity for an epitope on a cell surface antigen(s) derived from, or determined to be expressed on, a specific subject's cancer (tumor) such as a neoantigen. In some embodiments, the targeting moiety is an antibody or an antigen binding antibody fragment. In some embodiments, the liposome does not comprise a targeting moiety that has a specific affinity for an epitope on a cell surface antigen of the hyperproliferative cell. In some embodiments, the liposome comprises αPPMX containing 4, 5, 6, 2-10, 4-6, or more than 5, glutamyl groups. In some embodiments, the liposome comprises alpha tetraglutamated pemetrexed. In some embodiments, the liposome comprises alpha pentaglutamated pemetrexed. In other embodiments, the liposome comprises alpha hexaglutamated pemetrexed. In some embodiments, the liposome comprises L alpha polyglutamated pemetrexed. In some embodiments, liposome comprises D alpha polyglutamated pemetrexed. In some embodiments, the liposome comprises L and D alpha polyglutamated pemetrexed. In some embodiments, the hyperproliferative disorder is cancer. In some embodiments, the hyperproliferative disorder is an autoimmune disease (e.g., rheumatoid arthritis). In some embodiments, the hyperproliferative disorder is a benign or malignant tumor; leukemia, hematological, or lymphoid malignancy. In other embodiments, the hyperproliferative disorder is selected from the group consisting of a neuronal, glial, astrocytal, hypothalamic, glandular, macrophagal, epithelial, stromal, blastocoelic, inflammatory, angiogenic or an immunologic disorder, including an autoimmune disease.

Exemplary hyperproliferative disorders that can be treated according to the disclosed methods include, but are not limited to, disorders associated with benign, pre-malignant, and malignant cellular proliferation, including but not limited to, neoplasms and tumors (e.g., histiocytoma, glioma, astrocytoma, osteoma), cancers (e.g., lung cancer, small cell lung cancer, gastrointestinal cancer, bowel cancer, colorectal cancer, breast carcinoma, ovarian carcinoma, prostate cancer, testicular cancer, liver cancer, kidney cancer, bladder cancer, pancreatic cancer, brain cancer, sarcoma (e.g., osteosarcoma, Kaposi's sarcoma), and melanoma), leukemias, psoriasis, bone diseases, fibroproliferative disorders (e.g., of connective tissues), and atherosclerosis.

In additional embodiments, the disclosure provides a method for treating cancer that comprises administering an effective amount of a delivery vehicle (e.g., antibody or liposome) comprising alpha polyglutamated pemetrexed (e.g., an αPPMX disclosed herein) to a subject having or at risk of having cancer. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX). In some embodiments, the administered delivery vehicle is pegylated. In some embodiments, the administered delivery vehicle is not pegylated. In additional embodiments, the administered delivery vehicle comprises a targeting moiety that has a specific affinity for an epitope of antigen on the surface of a cancer cell. In additional embodiments, the delivery vehicle comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrign αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the delivery vehicle comprises a targeting moiety that has specific affinity for an epitope on a cell surface antigen(s) derived from, or determined to be expressed on, a specific subject's cancer (tumor) such as a neoantigen. In some embodiments, the targeting moiety is an antibody or an antigen binding antibody fragment. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the admin-istered delivery vehicle comprises D alpha polyglutamated pemetrexed. In some embodiments, the administered delivery vehicle comprises L and D alpha polyglutamated pemetrexed. In some embodiments, the cancer is selected from the group consisting of: lung (e.g., non-small lung cancer), pancreatic, breast cancer, ovarian, lung, prostate, head and neck, gastric, gastrointestinal, colon, esophageal, cervical, kidney, biliary duct, gallbladder, and a hematologic malignancy (e.g., a leukemia or lymphoma). In some embodiments, the cancer is lung cancer (e.g., NSCLC or mesothelioma). In some embodiments, the cancer is breast cancer (e.g., HER2++ or triple negative breast cancer). In some embodiments, the cancer is colorectal cancer. In some embodiments, the cancer is ovarian cancer. In some embodiments, the cancer is endometrial cancer. In some embodiments, the cancer is pancreatic cancer. In some embodiments, the cancer is liver cancer. In some embodiments, the cancer is head and neck cancer. In some embodiments, the cancer is osteosarcoma.

In additional embodiments, the disclosure provides a method for treating cancer that comprises administering an effective amount of a liposome comprising alpha polyglutamated pemetrexed (e.g., an Lp-αPPMX such as, PLp-αPPMX, NTLp-αPPMX, NTPLp-αPPMX, TLp-αPPMX, or TPLp-αPPMX) to a subject having or at risk of having cancer. In some embodiments, the liposome is pegylated. In some embodiments, the liposome is not pegylated. In additional embodiments, the liposome comprises a targeting moiety that has a specific affinity for an epitope of antigen on the surface of a cancer cell. In additional embodiments, the liposome comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the liposome comprises a targeting moiety that has specific affinity for an epitope on a cell surface antigen(s) derived from, or determined to be expressed on, a specific subject's cancer (tumor) such as a neoantigen. In some embodiments, the targeting moiety is an antibody or an antigen binding antibody fragment. In some embodiments, the liposome comprises αPPMX containing 4, 5, 6, 2-10, 4-6, or more than 5, glutamyl groups. In some embodiments, the liposome comprises alpha tetraglutamated pemetrexed. In some embodiments, the liposome comprises alpha pentaglutamated pemetrexed. In other embodiments, the liposome comprises alpha hexaglutamated pemetrexed. In some embodiments, the liposome comprises L alpha polyglutamated pemetrexed. In some embodiments, liposome comprises D alpha polyglutamated pemetrexed. In some embodiments, the liposome comprises L and D alpha polyglutamated pemetrexed. In some embodiments, the cancer is selected from the group consisting of: lung (e.g., non-small lung cancer), pancreatic, breast cancer, ovarian, lung, prostate, head and neck, gastric, gastrointestinal, colon, esophageal, cervical, kidney, biliary duct, gallbladder, and a hematologic malignancy (e.g., a leukemia or lymphoma). In some embodiments, the cancer is lung cancer (e.g., NSCLC or mesothelioma). In some embodiments, the cancer is breast cancer (e.g., HER2++ or triple negative breast cancer). In some embodiments, the cancer is colorectal cancer. In some embodiments, the cancer is ovarian cancer. In some embodiments, the cancer is endometrial cancer. In some embodiments, the cancer is pancreatic cancer. In some embodiments, the cancer is liver cancer. In some embodiments, the cancer is head and neck cancer. In some embodiments, the cancer is osteosarcoma.

In additional embodiments, the disclosure provides a method for treating cancer that comprises administering to a subject having or at risk of having cancer, an effective amount of a liposomal composition containing a liposome that comprises alpha polyglutamated pemetrexed and a targeting moiety that has a specific affinity for an epitope of antigen on the surface of the cancer. In some embodiments, the liposome comprises a targeting moiety that has specific affinity for an epitope on a cell surface antigen selected from the group consisting: of GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the liposome comprises a targeting moiety that has specific affinity for an epitope on a cell surface antigen(s) derived from, or determined to be expressed on, a specific subject's cancer (tumor) such as a neoantigen. In some embodiments, the administered liposomal composition comprises pegylated liposomes (e.g., TPLp-αPPMX). In some embodiments, the administered liposomal composition comprises liposomes that are not pegylated. In some embodiments, liposomes of the administered liposomal composition comprises αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprises alpha hexaglutamated pemetrexed. In some embodiments, the liposomal composition is administered to treat a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma.

In some embodiments, the liposome comprises a targeting moiety that has specific affinity for an epitope of a tumor specific antigen (TSA) or tumor associated antigen (TAA). In some embodiments, the liposome comprises a targeting moiety that has specific affinity for an epitope of an antigen selected from the group consisting of: a tumor differentiation antigen (e.g., MART1/MelanA, gp100 (Pmel 17), tyrosinase, TRP1, and TRP2), a tumor-specific multilineage antigen (e.g., MAGE1, MAGE3, BAGE, GAGE1, GAGE2, and p15), an overexpressed embryonic antigen (e.g., carcinoembryonic antigen (CEA)), an overexpressed oncogene or mutated tumor-suppressor gene product (e.g., p53, Ras, and HER2/neu), a unique tumor antigen resulting from chromosomal translocations (e.g., BCR-ABL, E2A-PRL, H4-RET, IGH-IGK, and MYL-RAR), a viral antigen (e.g., Epstein Barr virus antigen EBVA, human papillomavirus (HPV) antigen E6 or E7), GP 100), prostatic acid phosphatase (PAP), prostate-specific antigen (PSA), PTGER4, ITGA4, CD37, CD52, CD62L (L-selectin), CXCR4, CD69, EVI2B (CD361), SLC39A8, MICB, LRRC70, CLELC2B, HMHA1, LST1, and CMTM6 (CKLFSF6).

In some embodiments, the liposome comprises a targeting moiety that has specific affinity for an epitope of a hematologic tumor antigen. In further embodiments, the targeting moiety has specific affinity for an epitope of a hematologic tumor antigen selected from the group consisting of: CD19, CD20, CD22, CD30, CD138, CD33 CD34, CD38, CD123, CS1, ROR1, Lewis$^Y$, Ig kappa light chain, TCR, BCMA, TACI, BAFFR (CD268), CALLA, and a NKG2DL ligand). In some embodiments, the liposome comprises a targeting moiety that has specific affinity for an epitope of a B-cell lymphoma-specific idiotype immunoglobulin, or a B-cell differentiation antigen (e.g., CD19, CD20, and CD37). In some embodiments, the liposome comprises a targeting moiety that has specific affinity for an epitope of an antigen on a multiple myeloma cell (e.g., CS-1, CD38, CD138, MUC1, HM1.24, CYP1B1, SP17, PRAME, Wilms' tumor 1

(WT1), and heat shock protein gp96) or an antigen on myeloid cells (e.g., TSLPR and IL-7R).

In some embodiments, the liposome comprises a targeting moiety that has specific affinity for an epitope of a solid tumor antigen. In further embodiments, the targeting moiety has specific affinity for an epitope of a hematologic tumor antigen selected from the group consisting of: disialoganglioside (GD2), o-acetyl GD2, EGFRvIII, ErbB2, VEGFR2, FAP, mesothelin, IL13Ra2 (glioma), cMET, PSMA, L1CAM, CEA, and EGFR. In some embodiments, the liposome comprises a targeting moiety that has specific affinity for an epitope of an antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the liposome comprises a targeting moiety that has specific affinity for an epitope of an antigen selected from the group consisting of: CD137, PDL1, CTLA4, CD47, KIR, TNFRSF10B (DR5), TIM3, PD1, cMet, Glycolipid F77, EGFRvIII, HLAA2 (NY-ESO-1), LAG3, CD134 (OX40), HVEM, BTLA, TNFRSF25 (DR3), CD133, MAGE A3, PSCA, MUC1, CD44v6, CD44v6/7, CD44v7/8, IL11Ra, ephA2, CAIX, MNCAIX, CSPG4, MUC16, EPCAM (EGP2), TAG72, EGP40, ErbB receptor family, ErbB2 (HER2), ErbB3/4, RAGE1, GD3, FAR, Lewis$^Y$, NCAM, HLAA1/MAGE1, MAGEA1, MAGEA3, MAGE-A4, B7H3, WT1, MelanA (MART1), HPVE6, HPVE7, thyroglobulin, tyrosinase, PSA, CLL1GD3, Tn Ag, FLT3, KIT, PRSS21, CD24, PDGFR-beta, SSEA4, prostase, PAP, ELF2M, ephB2, IGF1, IGFII, IGFI receptor, LMP2, gp100, bcr-abl, Fucosyl GM1, sLe, GM3, TGS5, folate receptor beta, TEM1 (CD248), TEM7R, CLDN6, TSHR, GPRC5D, CXORF61, CD97, CD7a, HLE, CD179a, ALK, Plysialic acid, PLAC1, GloboH, NY-BR-1, UPK2, HAVCR1, ADRB3, PANX3, GPR20, LY6K, OR51E2, TARP, LAGE1a, legumain, E7, ETV6-AML, sperm protein 17, XAGE1, Tie 2, MAD-CT1, MAD-CT2, Fos-related antigen 1, p53, p53 mutant, prostein, survivin, telomerase, PCTA1 (Galectin 8), Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP2, CYP1B1, BORIS, SART3, PAX5, OY-TES1, LCK, AKAP4, SSX2, reverse transcriptase, RU1, RU2, intestinal carboxyl esterase, neutrophil elastase, muthsp70-2, CD79a, CD79b, CD72, LAIR1, FCAR, LILRA2, CD300LF, CLEC12A, BST2, EMR2, LY75, GPC3, FCRLS, IGLL1, TSP-180, MAGE4, MAGE5, MAGE6, VEGFR1, IGF1R, hepatocyte growth factorreceptor, pl85ErbB2, pl80ErbB-3, nm-23H1, CA 19-9, CA 72-4, CAM 17.1, NuMa, K-ras, beta-Catenin, CDK4, Mum1, p15, p16, 43-9F, 5T4, 791Tgp72, -human chorionic gonadotropin, BCA225, BTAA, CA125, CA15-3, CA 27.29 (BCAA), CA195, CA242, CA-50, CAM43, CD68, CO-029, FGF5, G250, HTgp-175, M344, MA50, MG7-Ag, MOV18, NB/70K, NY-CO1, RCAS1, SDCCAG16, M2BP, TAAL6, TLP, and TPS, glioma-associated antigen, alpha-fetoprotein (AFP), p26 fragment of AFP, lectin-reactive AFP, and TLR4.

In some embodiments, the liposome comprises a targeting moiety that has specific affinity for an epitope of an antigen selected from the group consisting of: PDGFRA, VEGFR1, VEGFR3, neuropilin 1 (NRP1), neuropilin 2 (NRP2), betacellulin, PLGF, RET (rearranged during transfection), TIE1, TIE2 (TEK), CA125, CD3, CD4, CD7, CD10, CD13, CD25 CD32, CD32b, CD44 (e.g., CD44v6), CD47, CD49e (integrin alpha 5), CD54 (ICAM), CD55, CD64, CD74, CD80, CD90, CD200, CD147, CD166, CD200, ESA, SHH, DHH, IHH, patched 1 (PTCH1), smoothened (SMO), WNT1, WNT2B, WNT3A, WNT4, WNT4A, WNT5A, WNT5B, WNT7B, WNT8A, WNT10A, WNT10B, WNT16B, LKP5, LRP5, LRP6, FZD1, FZD2, FZD4, FZD5, FZD6, FZD7, FZD8, Notch, Notch1, Notch3, Notch4, DLL4, Jagged, Jagged1, Jagged2, Jagged3, TNFRSF1A (TNFR1, p55, p60), TNFRSF1B (TNFR2), TNFRSF6 (Fas, CD95), TNFRSF6B (DcR3), TNFRSF7 (CD27), TNFSF9 (41BB Ligand), TNFRSF8 (CD30), TNFRSF10A (TRAILR1, DR4), TNFRSF11A (RANK), TNFRSF12 (TWEAKR), TNFRSF19L (KELT), TNFRSF19 (TROY), TNFRSF21 (DR6), IL1RI, 1L1R$_2$, IL2R, IL5R, IL6R, 1L8R, IL10R, IL12R, IL13R, IL15R, IL18R, IL19R, IL21R, IL23R, XAG1, XAG3, REGIV, FGFR1, FGFR2, FGFR3, ALK, ALK1, ALK7, ALCAM, Ax1, TGFb, TGFb2, TGFb3, TGFBR1, IGFIIR, BMPRI, N-cadherin, E-cadherin, VE-cadherin, ganglioside GM2, ganglioside GD3, PSGR, DCC, CDCP1, CXCR2, CXCR7, CCR3, CCR4, CCR5, CCR7, CCR10, Claudin1, Claudin2, Claudin3, Claudin4, TMEFF2, neuregulin, MCSF, CSF, CSFR (fms), GCSF, GCSFR, BCAM, BRCA1, BRCA2, HLA-DR, ABCC3, ABCB5, HM 1.24, LFA1, LYNX, S100A8, S100A9, SCF, Von Willebrand factor, Lewis Y6 receptor, CA G250 (CA9), CRYPTO, VLA5, HLADR, MUC18, mucin CanAg, EGFL7, integrin avb3, integrin α5β activin B1 alpha, leukotriene B4 receptor (LTB4R), neurotensin NT receptor (NTR), 5T4 oncofetal antigen, Tenascin C, MMP, MMP2, MMP7, MMP9, MMP12, MMP14, MMP26, cathepsin G, SULF1, SULF2, MET, CA9, TM4SF1, syndecan (SDC1), Ephrin B4, TEM1, TGFbeta 1, and TGFBRII.

In some embodiments, the liposome comprises a targeting moiety that has specific affinity for an epitope of an antigen associated with a disorder of the immune system (e.g., an autoimmune disorder and an inflammatory disorder), or is associated with regulating an immune response. In some embodiments, the targeting moiety has specific affinity for an epitope of a cell surface antigen expressed on the surface of a macrophage (expressing CD44).

In some embodiments, the liposome comprises a targeting moiety that has specific affinity for an epitope of an immunoinhibitory target. In another embodiment, the AD is an epitope of an immunoinhibitory target selected from the group consisting of: IL1Ra, IL6R, CD26L, CD28, CD80, FcGamma RIIB. In another embodiment, the AD in the Adapter is an epitope of an immunostimulatory target selected from: CD25, CD28, CTLA4, PD1, B7H1 (PDL1), B7H4 TGFbeta, TNFRSF4 (OX40), TNFRSF5 (CD40), TNFRSF9 (41BB, CD137), TNFRSF14 (HVEM), TNFRSF25 (DR3), and TNFRSF18 (GITR).

In some embodiments, the liposome comprises a targeting moiety that has specific affinity for an epitope of an antigen selected from the group consisting of: IL1Rb, $C_3AR$, $C_5AR$, CXCR1, CXCR2, CCR1, CCR3, CCR7, CCR8, CCR9, CCR10, ChemR23, MPL, GP130, TLR2, TLR3, TLR4, TLR5, TLR7, TLR8, TLR9, TREM1, TREM2, CD49a (integrin alpha 1), integrin a5b3, alpha4 integrin subunit, A4B7 integrin, cathepsin G, TNFRSF3 (LTBR), TNFRSF6 (Fas, CD95), TNFRSF6B (DcR3), TNFRSF8 (CD30), TNFRSF11A (RANK), TNFRSF16 (NGFR), TNFRSF19L (RELT), TNFRSF19 (TROY), TNFRSF21 (DR6), CD14, CD23, CD36, CD36L, CD39, CD91, CD153, CD164, CD200, CD200R, B71 (CD80), B72 (CD86), B7h, B7DC (PDL2), ICOS, ICOSL, MHC, CD, B7H2, B7H3, B7x, SLAM, KIM1, SLAMF2, SLAMF3, SLAMF4, SLAMF5, SLAMF6, SLAMF7, TNFRSF1A (TNFR1, p55, p60), TNFRSF1B (TNFR2), TNFRSF7 (CD27), TNFRSF12 (TWEAKR), TNFRSF5 (CD40), IL1R, IL2R, IL4Ra, IL5R, IL6RIL15R, IL17R, IL17Rb, IL17RC, IL22RA, IL23R, TSLPR, B7RP1, cKit, GMCSF, GMCSFR, CD2, CD4, CD11a, CD18, CD30, CD40, CD86, CXCR3, CCR2, CCR4, CCR5, CCR8, RhD, IgE, and Rh.

In additional embodiments, the disclosure provides a method for treating cancer that comprises administering an effective amount of a liposomal composition to a subject having or at risk of having a cancer that expresses folate receptor on its cell surface, wherein the liposomal composition comprises liposomes that comprise (a) alpha polyglutamated pemetrexed (αPPMX) and (b) a targeting moiety that has specific binding affinity for a folate receptor. In some embodiments, the targeting moiety has specific binding affinity for folate receptor alpha (FR-α), folate receptor beta (FR-β), and/or folate receptor delta (FR-δ). In some embodiments, the targeting moiety has a specific binding affinity for folate receptor alpha (FR-α), folate receptor beta (FR-β), and/or folate receptor delta (FR-δ). In some embodiments, the targeting moiety has a specific binding affinity for folate receptor alpha (FR-α) and folate receptor beta (FR-β). In some embodiments, the administered liposomal composition comprises pegylated liposomes (e.g., TPLp-αPPMX). In some embodiments, the administered liposomal composition comprises liposomes that are not pegylated. In some embodiments, liposomes of the administered liposomal composition comprises αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprises alpha hexaglutamated pemetrexed. In some embodiments, the liposomal composition is administered to treat an epithelial tissue malignancy. In some embodiments, the liposomal composition is administered to treat a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma.

In some embodiments, the disclosure provides a method for treating lung cancer (e.g., non-small lung cancer) that comprises administering an effective amount of a delivery vehicle (e.g., an antibody or liposome) comprising alpha polyglutamated pemetrexed (e.g., an αPPMX disclosed herein) to a subject having or at risk of having lung cancer. In particular embodiments, the, the cancer is non-small cell lung cancer. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the administered delivery vehicle is pegylated. In some embodiments, the administered delivery vehicle is not pegylated. In additional embodiments, the delivery vehicle comprises a targeting moiety on its surface that has specific affinity for an epitope on an antigen on the surface of a lung cancer (e.g., non-small cell lung cancer) cell. In further embodiments, the delivery vehicle comprises a targeting moiety that has specific affinity for an epitope on an antigen selected from the group consisting of Mucin 1, Nectin 4, NaPi2b, CD56, EGFR, and SC-16. In some embodiments, the targeting moiety is an antibody or a fragment of an antibody. In additional embodiments, the delivery vehicle is a liposome, and the liposome comprises a targeting moiety that has specific affinity for an epitope on an antigen selected from the group consisting of Mucin 1, Nectin 4, NaPi2b, CD56, EGFR, and SC-16. In further embodiments, the delivery vehicle is a pegylated liposome that comprises a targeting moiety that has specific affinity for an epitope on an antigen selected from consisting of Mucin 1, Nectin 4, NaPi2b, CD56, EGFR, and SC-16. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed.

In some embodiments, the disclosure provides a method for treating pancreatic cancer that comprises administering an effective amount of a delivery vehicle (e.g., an antibody (ADC) or liposome) comprising alpha polyglutamated pemetrexed (e.g., an αPPMX disclosed herein) to a subject having or at risk of having pancreatic cancer. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the administered delivery vehicle is pegylated. In some embodiments, the administered delivery vehicle is not pegylated. In additional embodiments, the delivery vehicle comprises a targeting moiety on its surface that has specific affinity for an epitope on an antigen on the surface of a pancreatic cancer cell. In further embodiments, the delivery vehicle comprises a targeting moiety that has specific affinity for an epitope on an antigen selected from the group consisting of TACSTD2 (TROP2), Mucin 1, mesothelin, Guanylyl cyclase C (GCC), SLC44A4, and Nectin 4. In further embodiments, the delivery vehicle is a liposome, and the liposome comprises a targeting moiety has specific affinity for an epitope on an antigen selected from the group consisting of TACSTD2 (TROP2), Mucin 1, Mesothelin, Guanylyl cyclase C (GCC), SLC44A4, and Nectin 4. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed.

In additional embodiments, the disclosure provides a method for treating breast cancer (e.g., triple negative breast cancer (estrogen receptor-, progesterone receptor-, and HER2)) that comprises administering an effective amount of a delivery vehicle (e.g., an antibody or liposome) comprising alpha polyglutamated pemetrexed (e.g., an αPPMX disclosed herein) to a subject having or at risk of having breast cancer. In some embodiments, the administered delivery vehicle is a liposome that comprises alpha polyglutamated pemetrexed. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the administered delivery vehicle is pegylated. In some embodiments, the administered delivery vehicle is not pegylated. In additional embodiments, the delivery vehicle comprises a targeting moiety on its surface that has specific affinity for an epitope on an antigen on the surface of a breast cancer cell. In further embodiments, the delivery vehicle comprises a targeting moiety that has specific affinity for an epitope on an antigen selected from the group consisting of: LIV-1 (ZIP6), EGFR, HER2, HER3, Mucin 1, GONMB, and Nectin 4. In some embodiments, the targeting moiety is an antibody or a fragment of an antibody. In additional embodiments, the delivery vehicle is a liposome, and the liposome comprises a targeting moiety that has specific affinity for an epitope on an antigen selected from the group consisting of: LIV-1 (ZIP6), EGFR, HER2, HER3, Mucin 1, GONMB, and Nectin 4. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed.

In some embodiments, the disclosure provides a method for treating a hematological cancer that comprises administering an effective amount of a delivery vehicle (e.g., an antibody or liposome) comprising alpha polyglutamated pemetrexed (e.g., an αPPMX disclosed herein) to a subject having or at risk of having a hematological cancer. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX)). In some embodiments, the administered delivery vehicle is pegylated. In some embodiments, the administered delivery vehicle is not pegylated. In additional embodiments, the delivery vehicle comprises a targeting moiety on its surface that has specific affinity for an epitope on an antigen on the surface of a hematological cancer cell. In further embodiments, the delivery vehicle comprises a targeting moiety that has specific affinity for an epitope on an antigen selected from the group consisting of: CD30, CD79b, CD19, CD138, CD74, CD37, CD19, CD22, CD33, CD34, and CD98. In further embodiments, the delivery vehicle is a liposome, and the liposome comprises a targeting moiety has specific affinity for an epitope on an antigen selected from the group consisting of: CD30, CD79b, CD19, CD138, CD74, CD37, CD19, CD22, CD33, CD34, and CD98. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed In some embodiments, the disclosure provides a method for treating a subject having or at risk of having a cancer that is distinguishable by the expression of an antigen on its cell surface. Thus, in some embodiments, the disclosure provides a method for treating cancer that comprises administering to a subject having or at risk of having a cancer, an effective amount of a delivery vehicle (e.g., an antibody or liposome) comprising a targeting moiety that has specific affinity for an epitope on a surface antigen of the cancer and alpha polyglutamated pemetrexed (e.g., an αPPMX disclosed herein). In some embodiments, the administered delivery vehicle is pegylated. In some embodiments, the targeting moiety is an antibody or a fragment of an antibody. In additional embodiments, the delivery vehicle is a liposome. In some embodiments, the administered delivery vehicle comprises αPPMX consisting of 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed.

In some embodiments, the disclosed compositions (e.g., liposomes containing alpha polyglutamated pemetrexed) are administered to subjects having or at risk of having a cancer, a solid tumor, and/or a metastasis that is distinguishable by the expression of a tumor specific antigen or tumor associated antigen on its cell surface. Thus, in some embodiments, the disclosure provides a method for treating cancer that comprises administering an effective amount of a delivery vehicle (e.g., liposome) comprising a targeting moiety and alpha polyglutamated pemetrexed (e.g., an αPPMX disclosed herein) to a subject having or at risk of having a cancer, solid tumor, and/or metastasis that is distinguishable by the expression of a tumor specific antigen or tumor associated antigen on its cell surface cancer, and wherein the targeting moiety has specific binding affinity for an epitope on an tumor specific antigen or tumor associated antigen. In some embodiments, the administered delivery vehicle is a liposome. In further embodiments, the liposome is pegylated. In additional embodiments, the delivery vehicle comprises a targeting moiety that has specific affinity for an epitope on a cell surface antigen expressed on the surface of a cancer, a solid tumor, and/or a metastatic cell. In additional embodiments, the targeting moiety has specific affinity for an epitope on an antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK.

In further embodiments, the delivery vehicle is a liposome, and the liposome comprises a targeting moiety has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed.

In further embodiments, the disclosure provides a method for treating cancer that comprises administering an effective amount of a delivery vehicle (e.g., an antibody or liposome) comprising a targeting moiety on its surface that has specific affinity for an epitope on an folate receptor, and an alpha polyglutamated pemetrexed (e.g., an αPPMX disclosed herein) to a subject having or at risk of having a cancer that contains cells expressing the folate receptor on their cell surface. In some embodiments, the targeting moiety is an antibody, or an antigen binding fragment of an antibody. In further embodiments, the targeting moiety has specific affinity for folate receptor alpha, folate receptor beta or folate receptor delta. As disclosed herein, the folate receptor targeted pegylated liposomes containing alpha polyglutamated pemetrexed are able to deliver high quantities of alpha polyglutamated pemetrexed to cancer cells and particularly cancer cells that express folate receptors, compared to normal cells (i.e., cells that unlike cancer cells do not actively take up liposomes, and/or do not express folate receptors). Any cancers that express folate receptors may be treated according to the disclosed methods. It should be noted that some cancers may express folate receptors in an early stage while the majority of cancers may express folate receptors at late stages. In some embodiments, the administered delivery vehicle is a liposome. In further embodiments, the liposome is pegylated. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed In additional embodiments, the disclosure provides a method for cancer maintenance therapy that comprises administering an effective amount of a liposomal composition comprising liposomes that contain alpha polyglutamated pemetrexed (e.g., an αPPMX disclosed herein) to a subject that is undergoing or has undergone cancer therapy. In some embodiments, the administered liposomal composition is a PLp-αPPMX, NTLp-αPPMX, NTPLp-αPPMX, TLp-αPPMX or TPLp-αPPMX. In some embodiments, the administered liposomal composition comprises pegylated liposomes (e.g., PLp-αPPMX, NTPLp-αPPMX, or TPLp-αPPMX). In some embodiments, the administered liposomal composition comprises a targeting moiety that has specific affinity for an epitope on a surface antigen of a cancer cell (e.g., TLp-αPPMX or TPLp-αPPMX). In some embodiments, the administered liposomal composition comprises liposomes that are pegylated and targeted (e.g., TPLp-αPPMX). In some embodiments, the administered liposomal composition comprises liposomes that are targeted and liposomes that are not targeted. In some embodiments, the administered liposomal composition comprises liposomes that are pegylated and liposomes that are not pegylated. In some embodiments, liposomes of the administered liposomal composition comprise alpha polyglutamated pemetrexed that contains 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprise alpha hexaglutamated pemetrexed.

In some embodiments, the cancer treated by one or more of the methods disclosed herein is a solid tumor lymphoma. Examples of solid tumor lymphoma include Hodgkin's lymphoma, Non-Hodgkin's lymphoma, and B cell lymphoma.

In some embodiments, the cancer treated by one or more of the methods disclosed herein is bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, prostate cancer, retinoblastoma, or rhabdomyosarcoma. In some embodiments, the cancer is lung cancer (e.g., NSCLC or mesothelioma). In some embodiments, the cancer is breast cancer (e.g., HER2++ or triple negative breast cancer). In some embodiments, the cancer is colorectal cancer. In some embodiments, the cancer is ovarian cancer. In some embodiments, the cancer is endometrial cancer. In some embodiments, the cancer is pancreatic cancer. In some embodiments, the cancer is liver cancer. In some embodiments, the cancer is head and neck cancer. In some embodiments, the cancer is osteosarcoma.

In some embodiments, the disclosure provides a method for treating cancer that comprises administering an effective amount of a composition comprising a delivery vehicle and alpha polyglutamated pemetrexed to a subject having or at risk of having cancer. In some embodiments, the administered composition comprises a pegylated delivery vehicle. In some embodiments, the administered composition comprises a targeting moiety that has a specific affinity for an epitope of antigen on the surface of a target cell of interest such as a cancer cell. In some embodiments, the delivery vehicle comprises an antibody or an antigen binding antibody fragment. In some embodiments, the composition is administered to treat a cancer selected from the group consisting of: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, myeloma, a leukemia and a lymphoma. In some embodiments, the composition is administered to treat colorectal cancer. In some embodiments, the composition is administered to treat ovarian cancer. In some embodiments, the composition is administered to treat endometrial cancer. In some embodiments, the composition is administered to treat pancreatic cancer. In some embodiments, the composition is administered to treat liver cancer. In some embodiments, the composition is administered to treat head and neck cancer. In some embodiments, the composition is administered to treat osteosarcoma.

In some embodiments, the administered composition contains 4, 5, 6, 2-10, 4-6, or more than 5, glutamyl groups. In some embodiments, the administered composition comprises alpha tetraglutamated pemetrexed. In some embodiments, the administered composition comprises alpha pentaglutamated pemetrexed. In other embodiments, the administered composition comprises alpha hexaglutamated pemetrexed In additional embodiments, the disclosure provides a method for treating cancer that comprises administering an effective amount of a liposomal composition comprising liposomes that contain alpha polyglutamated pemetrexed (e.g., Lp-αPPMX, PLp-αPPMX, NTLp-αPPMX, NTPLp-αPPMX, TLp-αPPMX or TPLp-αPPMX) to a subject having or at risk of having cancer. In some embodiments, the liposomal composition is administered to treat a cancer selected from the group consisting of: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, myeloma, a leukemia and a lymphoma. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma. In some embodiments, the administered liposomal composition comprises pegylated liposomes (e.g., PLp-αPPMX, NTPLp-αPPMX, or TPLp-αPPMX). In some embodiments, liposomes of the administered liposomal composition comprise an αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprises alpha hexaglutamated pemetrexed.

In additional embodiments, the disclosure provides a method for treating cancer that comprises administering an effective amount of a liposomal composition that comprises targeted liposomes (e.g., TLp-αPPMX or TPLp-αPPMX) to a subject having or at risk of having cancer, wherein the liposomal composition comprises liposomes that comprise alpha polyglutamated pemetrexed (Lp-αPPMX) and further comprise a targeting moiety having a specific affinity for a surface antigen (epitope) on the cancer. In some embodiments, the liposomal composition is administered to treat a cancer selected from the group consisting of: lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, melanoma, myeloma, a leukemia and a lymphoma. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma. In some embodiments, the administered liposomal composition comprises pegylated liposomes (e.g., TPLp-αPPMX). In some embodiments, liposomes of the administered liposomal composition comprise an αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprises alpha hexaglutamated pemetrexed.

In further embodiments, the disclosure provides a method for treating cancer that comprises administering an effective amount of a liposomal composition that contains targeted liposomes (e.g., TLp-αPPMX or TPLp-αPPMX) to a subject having or at risk of having a cancer that expresses folate receptor on its cell surface, wherein the liposomal composition comprises liposomes that comprise (a) alpha polyglutamated pemetrexed (αPPMX) and (b) a targeting moiety that has specific binding affinity for the folate receptor. In some embodiments, the administered liposomal composition comprises pegylated liposomes (e.g., TPLp-αPPMX). In some embodiments, the targeting moiety has a specific binding affinity for folate receptor alpha (FR-α), folate receptor beta (FR-β), and/or folate receptor delta (FR-δ). In some embodiments, the targeting moiety has a specific binding affinity for folate receptor alpha (FR-α), folate receptor beta (FR-β), and/or folate receptor delta (FR-δ). In some embodiments, the targeting moiety has a specific binding affinity for folate receptor alpha (FR-α) and folate receptor beta (FR-β). In some embodiments, the liposomal composition is administered to treat a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy. In some embodiments, the liposomal composition is administered to treat lung cancer (e.g., NSCLC or mesothelioma). In some embodiments, the liposomal composition is administered to treat breast cancer (e.g., HER2++ or triple negative breast cancer). In some embodiments, the liposomal composition is administered to treat colorectal cancer. In some embodiments, the liposomal composition is administered to treat ovarian cancer. In some embodiments, the liposomal composition is administered to treat endometrial cancer. In some embodiments, the liposomal composition is administered to treat pancreatic cancer. In some embodiments, the liposomal composition is administered to treat liver cancer. In some embodiments, the liposomal composition is administered to treat head and neck cancer. In some embodiments, the liposomal composition is administered to treat osteosarcoma. In some embodiments, liposomes of the administered liposomal composition comprise an αPPMX containing 4, 5, 6, 2-10, 4-6, or more than 5, glutamyl groups. In some embodiments, liposomes of the administered liposomal composition comprise alpha tetraglutamated pemetrexed. In some embodiments, liposomes of the administered liposomal composition comprise alpha pentaglutamated pemetrexed. In other embodiments, liposomes of the administered liposomal composition comprises alpha hexaglutamated pemetrexed.

In some embodiments, the disclosure provides a method for treating a disorder of the immune system (e.g., an autoimmune disease such as rheumatoid arthritis) that comprises administering an effective amount of a delivery vehicle (e.g., antibody or liposome) comprising alpha polyglutamated pemetrexed (e.g., an αPPMX disclosed herein) to a subject having or at risk of having a disorder of the immune system. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX). In some embodiments, the administered delivery vehicle is pegylated. In some embodiments, the administered delivery vehicle is not pegylated. In additional embodiments, the administered delivery vehicle comprises a targeting moiety that has a specific affinity for an epitope of antigen on the surface of an immune cell associated with a disorder of the immune system. In some embodiments, the targeting moiety is an antibody or an antigen binding antibody fragment. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed. In some embodiments, the autoimmune disease is rheumatoid arthritis.

In some embodiments, the disclosure provides a method for treating an infectious disease (e.g., HIV) that comprises administering an effective amount of a delivery vehicle (e.g., antibody or liposome) comprising alpha polyglutamated pemetrexed (e.g., an αPPMX disclosed herein) to a subject having or at risk of having an infectious disease. In some embodiments, the delivery vehicle is an antibody (e.g., a full-length IgG antibody, a bispecific antibody, or a scFv). In some embodiments, the delivery vehicle is a liposome (e.g., an Lp-αPPMX such as, PLp-αPPMX, NTLp-αPPMX, NTPLp-αPPMX, TLp-αPPMX, or TPLp-αPPMX). In some embodiments, the administered delivery vehicle is pegylated. In some embodiments, the administered delivery vehicle is not pegylated. In additional embodiments, the administered delivery vehicle comprises a targeting moiety that has a specific affinity for an epitope of antigen on the surface of a pathogen associated with an infectious disease. In some embodiments, the targeting moiety is an antibody or an antigen binding antibody fragment. In some embodiments, the administered delivery vehicle comprises αPPMX containing 4, 5, 6, 2-10, 4-6, or more than 5, glutamyl groups. In some embodiments, the administered delivery vehicle comprises alpha pentaglutamated pemetrexed. In other embodiments, the administered delivery vehicle comprises alpha hexaglutamated pemetrexed. In some embodiments, the administered delivery vehicle comprises L alpha polyglutamated pemetrexed. In some embodiments, the administered delivery vehicle comprises D alpha polyglutamated pemetrexed. In some embodiments, the administered delivery vehicle comprises L and D alpha polyglutamated pemetrexed.

In some embodiments, the administered delivery vehicle is a liposome. In further embodiments, the liposome is pegylated. In additional embodiments, the delivery vehicle comprises a targeting moiety on its surface that has specific affinity for an epitope on the surface of a target cell of interest. In further embodiments, the delivery vehicle comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK.

In further embodiments, the delivery vehicle is a liposome, and the liposome comprises a targeting moiety that has specific affinity for an epitope on a cell surface antigen selected from the group consisting of: GONMB, TACSTD2 (TROP2), CEACAM5, EPCAM, a folate receptor (e.g., folate receptor-α, folate receptor-β or folate receptor-δ), Mucin 1 (MUC-1), MUC-6, STEAP1, mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P Cadherin, Fibronectin Extra-domain B (ED-B), VEGFR2 (CD309), Tenascin, Collagen IV, Periostin, endothelin receptor, HER2, HER3, ErbB4, EGFR, EGFRvIII, FGFR1, FGFR2, FGFR3, FGFR4, FGFR6, IGFR-1, FZD1, FZD2, FZD3, FZD4, FZD5, FZD6, FZD7, FZD8, FZD9, FZD10, SMO, CD2, CD3, CD4, CD5, CD6, CD8, CD11, CD11a, CD15, CD18, CD19, CD20, CD22, CD26, CD27L, CD28, CD30, CD33, CD34, CD37, CD38, CD40, CD44, CD56, CD70, CD74, CD79, CD79b, CD98, CD105, CD133, CD138, cripto, IGF-1R, IGF-2R, EphA1 an EphA receptor, an EphB receptor, EphA2, EphA3, EphA4, EphA5, EphA6, EphA7, EphA8, EphA1, EphB1, EphB2, EphB3, EphB4, EphB6, an integrin (e.g., integrin αvβ3, αvβ5, or αvβ6), a C242 antigen, Apo2, PSGR, NGEP, PSCA, TMEFF2, endoglin, PSMA, CanAg, CALLA, c-Met, VEGFR-1, VEGFR-2, DDR1, PDGFR alpha., PDGFR beta, TrkA, TrkB, TrkC, UFO, LTK, ALK, Tie1, Tie2, PTK7, Ryk, TCR, NMDAR, LNGFR, and MuSK.

In some embodiments, the disclosure provides for the use of a composition comprising an alpha polyglutamated pemetrexed for manufacture of a medicament for treatment of a hyperproliferative disease. In some embodiments, the alpha polyglutamated pemetrexed comprise 5 or more glutamyl groups. In some embodiments, the alpha polyglutamated pemetrexed is pentaglutamated or hexaglutamated. In some embodiments, the alpha polyglutamated pemetrexed is polyglutamated pemetrexed (PMX), pemetrexed (PMX). In some embodiments, the alpha polyglutamated pemetrexed is in a liposome. In some embodiments, the hyperproliferative disease is cancer. In some embodiments, the cancer is selected from the group consisting of: lung (e.g., non-small lung cancer), pancreatic, breast cancer, ovarian, lung, prostate, head and neck, gastric, gastrointestinal, colon, esophageal, cervical, kidney, biliary duct, gallbladder, and a hematologic malignancy. In some embodiments, the cancer is lung cancer (e.g., NSCLC or mesothelioma). In some embodiments, the cancer is breast cancer (e.g., HER2++ or triple negative breast cancer). In some embodiments, the cancer is colorectal cancer. In some embodiments, the cancer is ovarian cancer. In some embodiments, the cancer is endometrial cancer. In some embodiments, the cancer is pancreatic cancer. In some embodiments, the cancer is liver cancer. In some embodiments, the cancer is head and neck cancer. In some embodiments, the cancer is osteosarcoma. In some embodiments, the cancer is leukemia or lymphoma. In some embodiments, the hyperproliferative disease is an autoimmune disease. In some embodiments, the hyperproliferative disease is rheumatoid arthritis.

The disclosed methods can practiced in any subject that is likely to benefit from delivery of compositions contemplated herein (e.g., alpha polyglutamated pemetrexed compositions such as liposome containing a pentaglutamated or hexaglutamated PMX). Mammalian subjects, and in particular, human subjects are preferred. In some embodiments, the subjects also include animals such as household pets (e.g., dogs, cats, rabbits, and ferrets), livestock or farm animals (e.g., cows, pigs, sheep, chickens and other poultry), horses such as thoroughbred horses, laboratory animals (e.g., mice, rats, and rabbits), and other mammals. In other embodiments, the subjects include fish and other aquatic species.

The subjects to whom the agents are delivered may be normal subjects. Alternatively the subject may have or be at risk of developing a condition that can be diagnosed or that can benefit from delivery of one or more of the provided compositions. In some embodiments, such conditions include cancer (e.g., solid tumor cancers or non-solid cancer such as leukemias). In some embodiments, these conditions (e.g., cancers) involve cells that express an antigen that can be specifically bound by a targeted pegylated liposomal alpha polyglutamated pemetrexed disclosed herein. In further embodiments, these antigens specifically bind and internalize the targeted pegylated liposomal alpha polyglutamated pemetrexed into the cell. In some embodiments, the targeted pegylated liposomal alpha polyglutamated pemetrexed specifically binds a folate receptor (e.g., folate receptor alpha (FR-α), folate receptor beta (FR-β) and folate receptor delta (FR-S)) expressed on the surface of the cancer cell.

Tests for diagnosing the conditions that can be treated with the provided compositions are known in the art and will be familiar to the medical practitioner. The determination of whether a cell type expresses folate receptors can be made using commercially available antibodies. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, and serologic tests. The medical practitioner will generally also take a full history and conduct a complete physical examination in addition to running the laboratory tests listed above.

A subject having a cancer can, for example, be a subject that has detectable cancer cells. A subject at risk of developing a cancer can, for example, be a subject that has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission.

In some embodiments, the disclosure provides methods for selectively deliver a folate receptor targeted pegylated liposomal alpha polyglutamated pemetrexed to a tumor cell expressing a folate receptor on its surface at a rate that is higher (e.g., at least two-fold greater, at least three-fold greater, at least four-fold greater, or at least five-fold greater, than α cell not expressing folate receptor on its cell surface). In some embodiments, the delivered pegylated liposome comprises alpha polyglutamated PMX. In some embodiments, the delivered pegylated liposome comprises L-alpha polyglutamated PMX. In some embodiments, the delivered pegylated liposome comprises D-alpha polyglutamated PMX.

i. Combination Therapy

In certain embodiments, in addition to administering alpha polyglutamated PMX composition described herein, the method or treatment further comprises administering at least one additional therapeutic agent. An additional therapeutic agent can be administered prior to, concurrently with, and/or subsequently to, administration of the alpha polyglutamated PMX composition. The additional therapeutic agent can be associated with an alpha polyglutamated PMX delivery vehicle (e.g., coencapsulated with alpha polyglutamated PMX in a liposome), present in a solution containing an alpha polyglutamated PMX delivery vehicle, or in a separate formulation from the composition containing the alpha polyglutamated PMX composition. Pharmaceutical compositions comprising a polypeptide or agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the polypeptide or agent (s). Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments, of the methods described herein, the combination of a αPPMX composition described herein and at least one additional therapeutic agent results in additive or synergistic results. In some embodiments, the combination therapy results in an increase in the therapeutic index of the αPPMX or agent. In some embodiments, the combination therapy results in an increase in the therapeutic index of the additional therapeutic agent(s). In some embodiments, the combination therapy results in a decrease in the toxicity and/or side effects of the αPPMX or agent. In some embodiments, the combination therapy results in a decrease in the toxicity and/or side effects of the additional therapeutic agent(s).

In some embodiments, the disclosure provides a method for treating cancer that comprises administering an effective amount of a αPPMX composition disclosed herein and a biologic. In some embodiments, the alpha polyglutamated Antifolate is administered in combination with a therapeutic antibody. In further embodiments, the αPPMX composition is administered in combination with an anti-CD antibody (e.g., rituximab) or an antibody that binds an immune checkpoint protein (e.g., CTLA4, PD1, PDL1, and TIM3). In further embodiments, the αPPMX composition is administered in combination with an fc-fusion protein (e.g., entanercept).

In some embodiments, in addition to administering alpha polyglutamated PMX compositions described herein, the methods or treatments described herein further comprise administering at least one additional therapeutic agent selected from: an anti-tubulin agent, an auristatin, a DNA minor groove binder, a DNA replication inhibitor, an alkylating agent (e.g., platinum complexes such as cisplatin, mono(platinum), bis(platinum) and tri-nuclear platinum complexes and carboplatin), an anthracycline, an antibiotic, an anti-folate (e.g., a polyglutamatable antifolate or a non polyglutamatable anti-folate), an antimitotic (e.g., a, a vinca alkaloid, such as vincristine, vinblastine, vinorelbine, or vindesine), radiation sensitizer, a steroid, a taxane, a topoisomerase inhibitor (e.g., doxorubicin HCl, daunorubicin citrate, mitoxantrone HCl, actinomycin D, etoposide, topotecan HCl, teniposide (VM-26), and irinotecan), an antimetabolite, a chemotherapy sensitizer, a duocarmycin, an etoposide, a fluorinated pyrimidine, an ionophore, a lexitropsin, a nitrosourea, a platinol, a purine antimetabolite, a PARP inhibitor, and a puromycin. In certain embodiments, the second therapeutic agent is an alkylating agent, an antimetabolite, an antimitotic, a topoisomerase inhibitor, or an angiogenesis inhibitor.

Therapeutic agents that may be administered in combination with the αPPMX compositions described herein include chemotherapeutic agents. Thus, in some embodiments, the methods or treatments described herein further comprise administering at least one involves the administration of a αPPMX composition described herein in combination with a chemotherapeutic agent or in combination with a cocktail of chemotherapeutic agents. Treatment with a αPPMX composition can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4.sup.th Edition, 2008, M. C. Perry, Editor, Lippincott, Williams & Wilkins, Philadelphia, Pa.

Chemotherapeutic agents useful in the present invention include, but are not limited to, alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, such as paclitaxel (TAXOL®) and docetaxel (TAXOTERE®); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA®); anti-hormonal agents such as, tamoxifen, raloxifene, aromatase inhibiting 4(5)-imidazoles, 4-hydroxytamoxifen, trioxifene, keoxifene, LY117018, onapristone, and toremifene (FARESTON®); anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin. In other embodiments, the additional therapeutic agent is oxaloplatin.

Additional therapeutic agents that may be administered in combination with the αPPMX compositions described herein include one or more immunotherapeutic agents.

In some embodiments αPPMX is administered in combination with an immunotherapeutic agent that inhibits one or more T cell-associated inhibitory molecules (e.g., CTLA4, PD1, Lymphocyte activation gene-3 (LAG-3, CD223), T cell immunoglobulin-3 (TIM-3), T cell immunoglobulin and ITIM domain (TIGIT), V-domain Ig suppressor of T cell activation (VISTA), B7 homolog 3 (B7-H3, CD276), B and T cell lymphocyte attenuator (BTLA, CD272), or Adenosine A2a receptor (A2aR) or CD73). In some embodiments, the αPPMX composition is administered separately from the immunotherapeutic agent. In some embodiments, the αPPMX composition is administered at the same time (e.g., concurrently or serially) as the immunotherapeutic agent. In some embodiments, the αPPMX and the immunotherapeutic agent are encapsulated in or otherwise associated with the same liposome.

In some embodiments, treatment methods provided herein comprise administering a αPPMX composition described herein in combination with a PD1 inhibitor. In some embodiments, the αPPMX composition is administered in combination with pembroluzumab. In some embodiments, the αPPMX composition is administered in combination with nivolumab. In some embodiments, the αPPMX composition is administered separately from the PD1 inhibitor. In some embodiments, the αPPMX composition is administered at the same time (e.g., concurrently or serially) as the PD1 inhibitor. In some embodiments, the αPPMX and the PD1 inhibitor are encapsulated in or otherwise associated with the same liposome.

In other embodiments, the αPPMX composition is administered in combination with a PDL1 inhibitor. In some embodiments, the αPPMX composition is administered in combination with atezolizumab. In some embodiments, the αPPMX composition is administered in combination with avelumab. In some embodiments, the αPPMX composition is administered in combination with durvalumab. In some embodiments, the αPPMX composition is administered in combination with PDR001. In some embodiments, the αPPMX composition is administered separately from the PDL-1 inhibitor. In some embodiments, the αPPMX composition is administered at the same time (e.g., concurrently or serially) as the PDL-1 inhibitor. In some embodiments, the αPPMX and the PDL-1 inhibitor are encapsulated in or otherwise associated with the same liposome.

In some embodiments, treatment methods provided herein comprise administering a αPPMX composition in combination with a therapeutic agent that inhibits activity of CTLA4 LAG3, TIM-3, TIGIT, VISTA, B7-H3, BTLA, A2aR or CD73. In some embodiments, treatment methods provided herein comprise administering a αPPMX composition described herein in combination with a CTLA4 inhibitor. In further embodiments, the αPPMX composition is administered in combination with ipilimumab. In some embodiments, treatment methods provided herein comprise administering a αPPMX composition in combination with a LAG3 inhibitor. In further embodiments, the αPPMX composition is administered in combination with TSR-033, MK-4280, LAG525, BMS-986106, or MGD013. In some embodiments, treatment methods provided herein comprise administering a αPPMX composition in combination with a TIM-3 inhibitor. In further embodiments, the αPPMX composition is administered in combination with MBG453 or MEDI9447. In some embodiments, treatment methods provided herein comprise administering a αPPMX composition in combination with a TIGIT inhibitor. In further embodiments, the αPPMX composition is administered in combination with BMS-986207 or OMP-31M32. In some embodiments, treatment methods provided herein comprise administering a αPPMX composition in combination with a VISTA inhibitor. In further embodiments, the αPPMX composition is administered in combination with JNJ-61610588 or CA-170. In some embodiments, treatment methods provided herein comprise administering a αPPMX composition in combination with a B7-H3 inhibitor. In further embodiments, the αPPMX composition is administered in combination with neoblituzumab, enoblituzumab, MGD009, or 8H9. In some embodiments, treatment methods provided herein comprise administering a αPPMX composition in combination with a BTLA inhibitor. In some embodiments, treatment methods provided herein comprise administering a αPPMX composition in combination with an A2aR or CD73 inhibitor. In further embodiments, the αPPMX composition is administered in combination with CPI444. In some embodiments, the αPPMX composition is administered separately from the immunotherapeutic agent. In some embodiments, the αPPMX composition is administered at the same time (e.g., concurrently or serially) as the immunotherapeutic agent. In some embodiments, the αPPMX and the immunotherapeutic agent are encapsulated in or otherwise associated with the same liposome.

In some embodiments, treatment methods provided herein comprise administering a αPPMX composition in combination with a therapeutic agent that inhibits activity of transforming growth factor (TGF)-β, phosphoinositide 3-kinase gamma (PI3Kγ), Killer immunoglobulin-like receptors (KIR, CD158), CD47, or Indoleamine 2,3-dioxygenase (IDO). In some embodiments, treatment methods provided herein comprise administering a αPPMX composition described herein in combination with a TGFβ antagonist. In further embodiments, the αPPMX composition is administered in combination with M7824 or Galusertinib (LY2157299). In some embodiments, treatment methods provided herein comprise administering a αPPMX composition described herein in combination with a PI3Kγ antagonist. In further embodiments, the αPPMX composition is administered in combination with IPI-549. In some embodiments, treatment methods provided herein comprise administering a αPPMX composition described herein in combination with a KIR antagonist. In further embodiments, the αPPMX composition is administered in combination with IPH4102 or lirilumab. In some embodiments, treatment methods provided herein comprise administering a αPPMX composition described herein in combination with a CD47 antagonist. In further embodiments, the αPPMX composition is administered in combination with Hu5F9-G4 or TTI-621. In some embodiments, treatment methods provided herein comprise administering a αPPMX composition described herein in combination with an IDO antagonist. In further embodiments, the αPPMX composition is administered in combination with BMS-986205, indoximod, or epacadostat. In some embodiments, the αPPMX composition is administered separately from the therapeutic agent. In some embodiments, the αPPMX composition is administered at the same time (e.g., concurrently or serially) as the therapeutic agent. In some embodiments, the αPPMX and the therapeutic agent are encapsulated in or otherwise associated with the same liposome.

In some embodiments, treatment methods provided herein comprise administering a αPPMX composition in combination with a therapeutic agent that is an agonist of OX40 (CD134), inducible co-stimulator (ICOS), Glucocorticoid-induced TNF receptor family-related protein (GITR), 4-1BB (CD137), CD40, CD27-CD70, or a Toll-like receptor (TLR). In some embodiments, treatment methods provided herein comprise administering a αPPMX composition described herein in combination with an OX40 agonist. In further embodiments, the αPPMX composition is administered in combination with GSK3174998, MOXR0916, 9B12, PF-04518600 (PF-8600), MEDI6383, MEDI0562, INCAGN01949, or GSK3174998. In some embodiments, treatment methods provided herein comprise administering a αPPMX composition described herein in combination with an ICOS agonist. In further embodiments, the αPPMX composition is administered in combination with JTX-2011, GSK3359609, or MEDI-570. In some embodiments, treatment methods provided herein comprise administering a αPPMX composition described herein in combination with a GITR agonist. In further embodiments, the αPPMX composition is administered in combination with TRX-518, AMG 228, BMS-986156, MEDI1873, MK-4166, INCAGN01876, or GWN32. In some embodiments, treatment methods provided herein comprise administering a αPPMX composition described herein in combination with a 4-1BB agonist. In further embodiments, the αPPMX composition is administered in combination with utomilumab or urelumab (PF-05082566). In some embodiments, treatment methods provided herein comprise administering a αPPMX composition described herein in combination with a CD40 agonist. In further embodiments, the αPPMX composition is administered in combination with CP-870893, APX005M, ADC-1013, lucatumumab, Chi Lob 7/4, dacetuzumab, SEA-CD40, or R07009789. In some embodiments, treatment methods provided herein comprise administering a αPPMX composition described herein in combination with a CD27-CD70 agonist. In further embodiments, the αPPMX composition is administered in combination with ARGX-110, or BMS-936561 (MDX-1203). In some embodiments, treatment methods provided herein comprise administering a αPPMX composition described herein in combination with a TLR agonist. In further embodiments, the αPPMX composition is administered in combination with MEDI9197, PG545 (pixatimod, pINN), or poly-ICLC. In some embodiments, the αPPMX composition is administered separately from the therapeutic agent. In some embodiments, the αPPMX composition is administered at the same time (e.g., concurrently or serially) as the therapeutic agent. In some embodiments, the αPPMX and the therapeutic agent are encapsulated in or otherwise associated with the same liposome.

Kits Comprising αPPMX Compositions

The disclosure also provides kits that comprise the αPPMX compositions described herein and that can be used to perform the methods described herein. In certain embodiments, a kit comprises at least one purified αPPMX composition in one or more containers.

In some embodiments the kits include a dosage amount (e.g., as used for therapy or diagnosis) of at least one αPPMX compositions (e.g., a αPPMX liposome), or pharmaceutical formulation thereof, as disclosed herein. Kits may further comprise suitable packaging and/or instructions for use of the composition. Kits may also comprise a means for the delivery for the composition, or pharmaceutical formulation thereof, such as a syringe for injection or other device as described herein and known to those of skill in the art. One of skill in the art will readily recognize that the disclosed αPPMX compositions can be readily incorporated into one of the established kit formats which are well known in the art.

Further provided are kits that comprise a αPPMX compositions as well as at least one additional therapeutic agent. In certain embodiments, the second (or more) therapeutic agent is an anti-metabolite. In certain embodiments, the second (or more) therapeutic agent is a chemotherapeutic agent.

The following examples are intended to illustrate but not to limit the disclosure in any manner, shape, or form, either explicitly or implicitly. While they are typical of those that might be used, other procedures, methodologies, or techniques known to those skilled in the art may alternatively be used without departing from the scope of the present disclosure.

FIGS. 1B-1N show chemical formula of exemplary alpha polyglutamates encompassed by the disclosure.

EXAMPLES

Example 1: Liposomal Alpha Polyglutamated Pemetrexed Compositions

Methods

Production of Alpha Hexaglutamated Pemetrexed (αHgPMX) Liposomes

Briefly L alpha hexaglutamated pemetrexed (aG6) and D alpha hexaglutamated pemetrexed (aDG6) were encapsulated in liposomes by the following procedure. First, the lipid components of the liposome membrane were weighed out and combined as a concentrated solution in ethanol at a temperature of around 65° C. In this example, the lipids used were hydrogenated soy phosphatidylcholine, cholesterol, and DSPE-PEG-2000 (1,2-distearoyl-sn-glycero-3-phosphoethanolamine-N-[methoxy (poly-ethylene glycol)-2000]). The molar ratio of HSPC:Cholesterol:PEG-DSPE was approximately 3:2:0.15. Next, the aG6 or aDG6 was dissolved in 5% dextrose at a concentration of 150 mg/ml with a pH of 6.5-6.9. The drug solution was heated up to 65° C. The ethanolic lipid solution was injected into the aG6 or aDG6 solution using a small-bore needle. During this step the drug solution was well stirred using a magnetic stirrer. The mixing was performed at an elevated temperature (63° C.-72° C.) to ensure that the lipids were in the liquid crystalline state (as opposed to the gel state that they attain at temperatures below the lipid transition temperature Tm=51° C.-54° C.). As a result, the lipids were hydrated and form multiple bilayer (multilamellar) vesicles (MLV) containing aG6 or aDG6 in the aqueous core.

Downsizing of MLV's Using Filter Extrusion

The MLVs were fragmented into unilamellar (single bilayer) vesicles of the desired size by high-pressure extrusion using three passes through stacked (track-etched polycarbonate) membranes. The first pass was performed through stacked membranes consisting of two layers with a pore size of 200 nm. The remaining two passes were through the stacked membranes consisting of three layers with a pore size of 100 nm. During extrusion, the temperature was maintained above the Tm to ensure plasticity of the lipid membranes. As a result of the extrusion, large and heterogeneous in size and lamellarity MLVs turned into small, homogenous (90-125 nm) unilamellar vesicles (ULV) that sequestered the drug in their interior. A Malvern Zetasizer Nano ZS instrument (Southborough, MA) with back scattering detector (90°) was used for measuring the hydrodynamic size (diameter) at 25° C. in a quartz micro cuvette. The samples were diluted 50-fold in formulation matrix before analysis.

Purification of Liposomes

After the ULV's containing aG6 or aDG6 had been produced, the extra-liposomal gG6 was removed using columns for small volume or tangential flow diafiltration against a suitable buffer for large volume. Although any buffer solution can be used, in this example the buffer used was 5 mM HEPES, 145 mM Sodium Chloride, pH 6.7. Upon completion of purification, filter sterilization was performed using a 0.22 micron filter. The typical characteristics of liposomal derivatives are shown in the table below.

|  | Starting con. | Encapsulation efficiency | Final con. | Drug/Lipid Ratio | Diameter | PDI | Zeta potential |
| --- | --- | --- | --- | --- | --- | --- | --- |
| Lps aDG6 | 1 mg/ml | 4.75% | 0.031 mg/ml | 25-30 g/mM lipids | 122.8 nm | 0.021 | −1.14 mV |
| Lps aG6 | 1 mg/ml | 5.90% | 0.039 mg/ml | 25-30 g/mM lipids | 100.2 nm | 0.018 | −1.90 mV |
| LpS aG6 | 150 mg/ml | 36% | 8.0 mg/ml | 230-260 g/mM Lipids | 104 nm | 0.04 | −2.73 mV |

Dose Response Study of Alpha HGP (Hexaglutamated Pemetrexed) and Liposomes

Cell viability was determined by CellTiter-Glo® (CTG) luminescent cell viability assay on Day 3 (48 hour) and Day 4 (72 hour). This assay determines the number of viable cells in culture based on quantifying ATP that is present within, which in turn signals the presence of metabolically active cells. The CTG assay uses luciferase as a readout. To assess cell viability Dose response inhibition of pemetrexed, HGP and liposomes on different cancer cell growth were investigated using CellTiter-Glo® luminescent cell viability assay. Human cancer cells were harvested, counted and plated at a same cell density on Day 0. A series of 8 dilutions of each test article were added to the cells on Day 1. Dose response curve were generated and fit using GraphPad Prism and IC50 of each test article were calculated. A lower the IC50 is, the more potent the test article is in term of cancer cell growth inhibition.

Cells were seeded into 96-well plate at a cell density of $5 \times 10^4$ cells per well in 100 µl of fresh media on Day 0. Eight serial 2-fold dilutions of each test article in culture medium were generated and added to cells in triplicate on Day 1. In addition, three wells of cells were treated with vehicle (HBS for free drug or empty liposome for liposomal HGP) alone as a control.

On Days 3 and 4, 100 µl of CellTiterGlo® Reagent were added to each well and incubated at room temperature for 15 minutes. Luciferase luminescence were recorded for each well. In addition, 8 serial 2-fold dilutions of the vehicle (HBS or empty liposome) in culture medium were added into empty wells and included in the assay to generate the background luminescence signals. Luciferase signals were normalized by subtracting the background luminescence signal out of the read-outs respectively.

Human Normal Primary Bone Marrow CD34+ Cells were obtained from ATCC. (ATCC Catalog Number PCS-800-012). Cells were thawed at 37° C. for 1 minute and then placed on ice. The cells were then resuspended in StemSpan SFEM (Stem Cell Tech Catalog Number 9650) plus 10% heat inactivated fetal bovine serum (Corning 35-015-CV). The cells were plated into 96 well culture plates at a density of $2.5 \times 10^4$ cells/well. The following day, live cells were collected via centrifugation and resuspended in neutrophil growth media (StemSpan SFEM plus 10% Heat Inactivated fetal bovine serum plus 100 ng/ml human stem cell factor (Sigma Catalog Number H8416), 20 ng/ml human granulocyte colony-stimulation factor (Sigma Catalog Number H5541), and 10 ng/ml human recombinant IL3 (Sigma SRP3090) at a density of $2.5 \times 10^4$ cells/well. Cells were incubated at 37° C. for 10 days. Fresh media was added every two days. Mature neutrophils were then collected and plated in 96 well plates at a density of $1 \times 10^4$ cells/well and incubated at 37° C. overnight. The next day, test article or vehicle was resuspended in neutrophil growth media and added to the plates. The cells were then incubated for either 48 hours or 72 hours at 37° C. and then assayed at each time point using the Cell Titer Glo Assay (Promega Catalog #G7572).

Methodologies used for cell line AML12 (non-cancerous liver cells) and CCD841 (non-cancerous colon epithelial cells) are similar to the methods used for cancer cells.

Results

Figure 2:
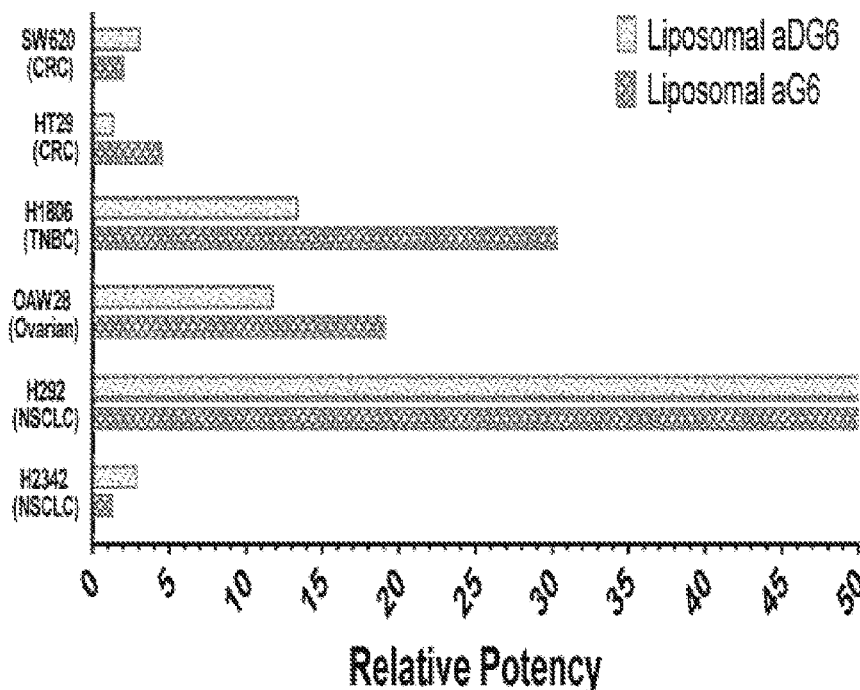

In a set of dose response experiments, 6 cell lines representing different types of cancers, namely HT-29 (colon cancer), H2342 (NSCLC, adenocarcinoma subtype), H292 (NSCLC, adenocarcinoma subtype), SW620 (CRC), H1806 (triple negative breast cancer) and OAW28 (ovarian cancer), were studied (FIG. 2). Treatment consisted of exposure for 48 hours using 2 different encapsulated derivatives of liposomal alpha pemetrexed hexaglutamate, namely liposomal alpha L hexaglutamate (liposomal aG6) and its mirror image, liposomal alpha D hexaglutamate (liposomal aDG6) also referred to as its corresponding enantiomer.

The relative potency of the above mentioned derivatives as compared to pemetrexed, following exposure over 48 hours, is represented in FIG. 2. The relative potency of treatment using the various derivatives, as shown in this figure was calculated by dividing the IC50 of pemetrexed by the IC50 of the liposomal alpha pemetrexed hexaglutamate for each cell line. As shown in this figure, in all cell lines, the potency of liposomal alpha pemetrexed hexaglutamate well exceeded that of pemetrexed. By way of example, consider the NSCLC cell line H292. As shown in the figure, the potency of liposomal alpha pemetrexed hexaglutamate was >50-fold that of pemetrexed. This suggests that a 2% or lower dose of the liposomal alpha pemetrexed hexaglutamate could have the same treatment effect as a 100% dose of pemetrexed.

Figure 3:
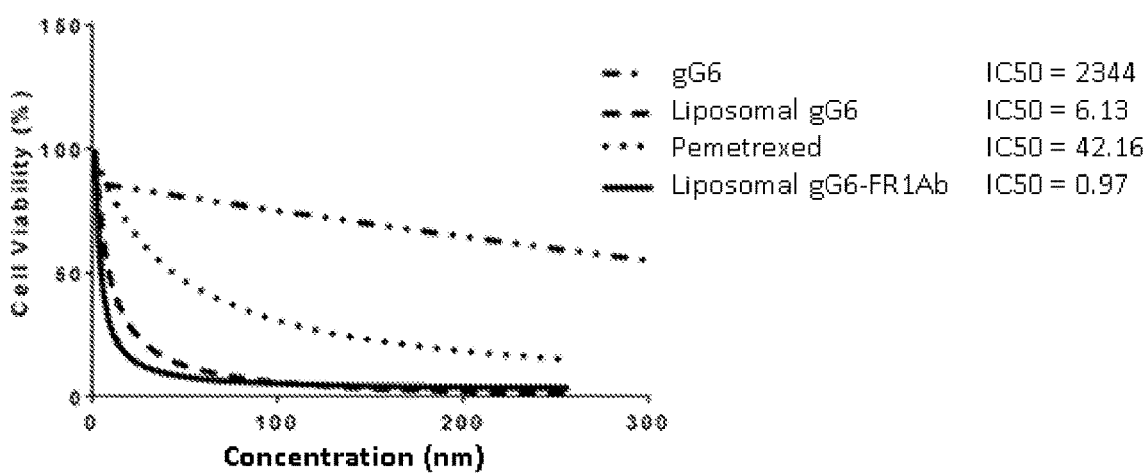
Figure 4:
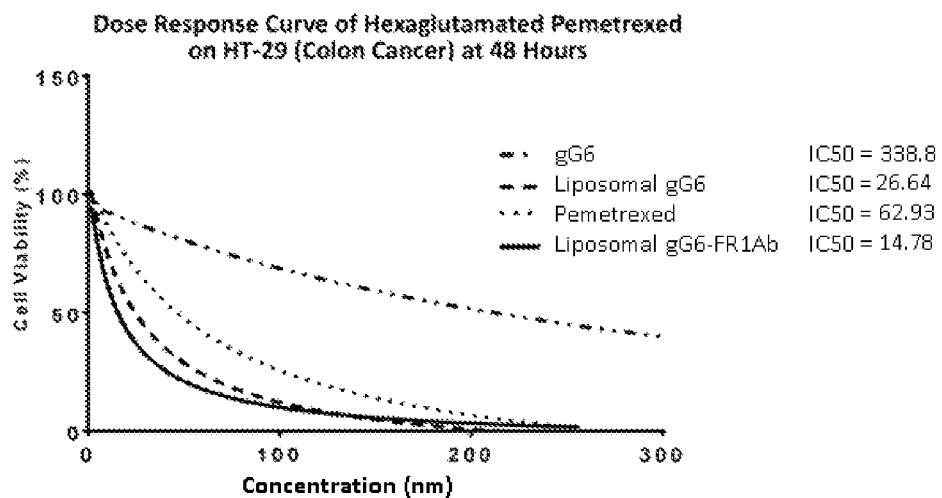

As stated in some instances increased uptake of payload can be achieved by targeting the liposomal delivery vehicle using antibody such as Folate Receptor Alpha. By way of example in the next two experiments Liposomal L Gamma G6/Lps Hexa gG6 was encapsulated using the methods previously described above. Subsequently, pemetrexed, liposomal gamma pemetrexed hexaglutamate derivatives (Liposomal L gamma G6/Lps Hexa gG6) and Folate Receptor Alpha Targeted Liposomal L Gamma G6 (Liposomal gG6-FR1Ab), Free (unencapsulated) L gamma G6 were tested for cytotoxic activity on representative cell lines in non-small cell lung cancer cells (NCI-H2342) and colorectal cancer cells (HT-29) as shown in FIG. 3 and FIG. 4 respectively. These data show that both liposomal L gamma pemetrexed hexaglutamate and Folate Receptor Alpha Targeting liposomal L gamma pemetrexed hexaglutamate are more potent than pemetrexed in both cell lines. In general Folate Receptor Alpha Antibody targeting liposomes show the highest potency. By contrast free L gamma G6 has the lowest potency due to its inability to traffic across cell membranes effectively.

Figure 5:
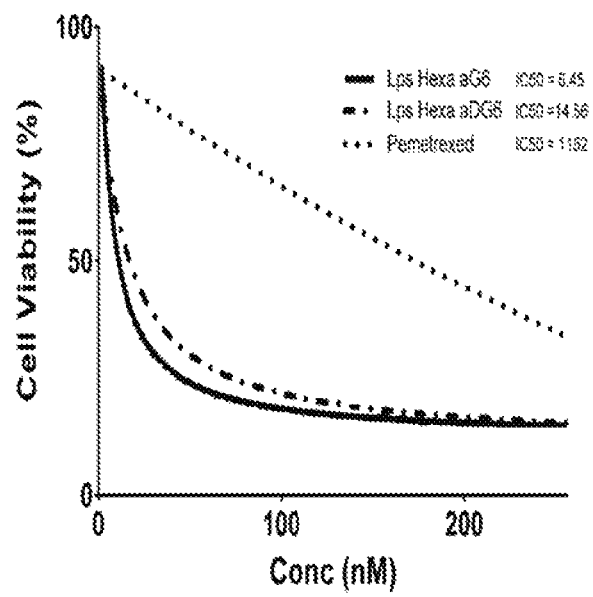
Figure 6:
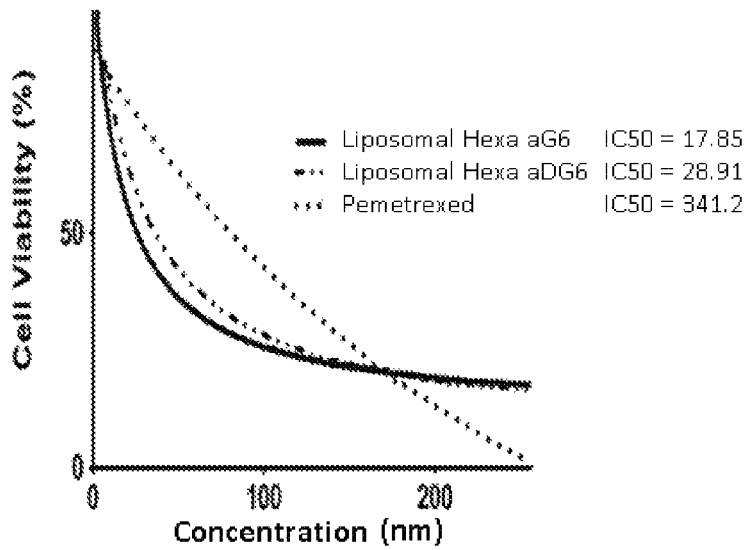
Figure 7:
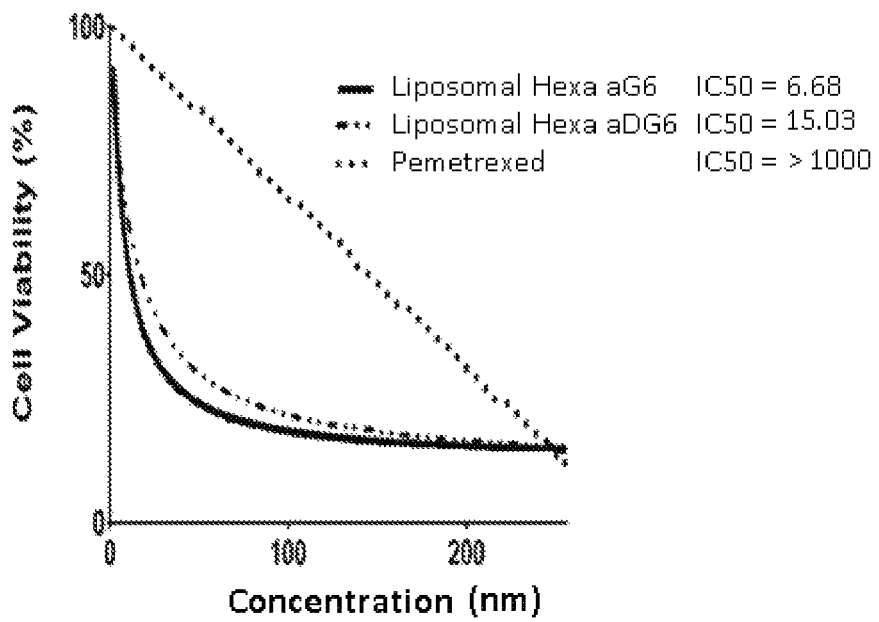
Figure 8:
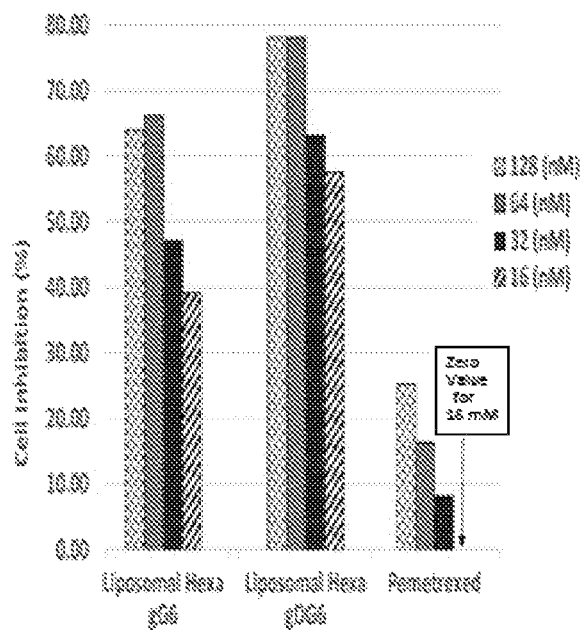
Figure 9:
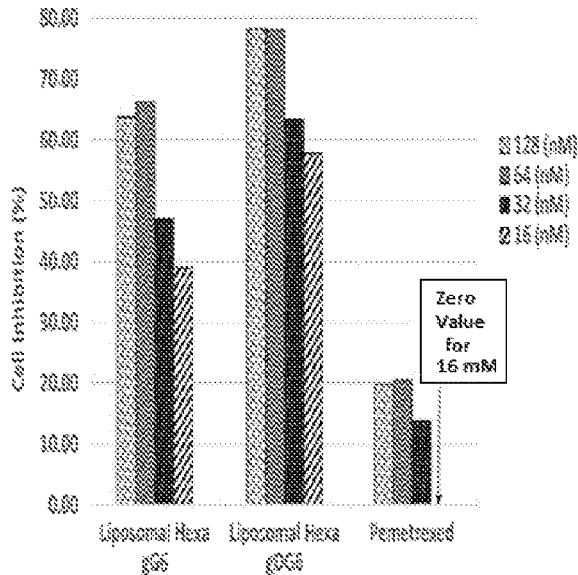
Figure 10:
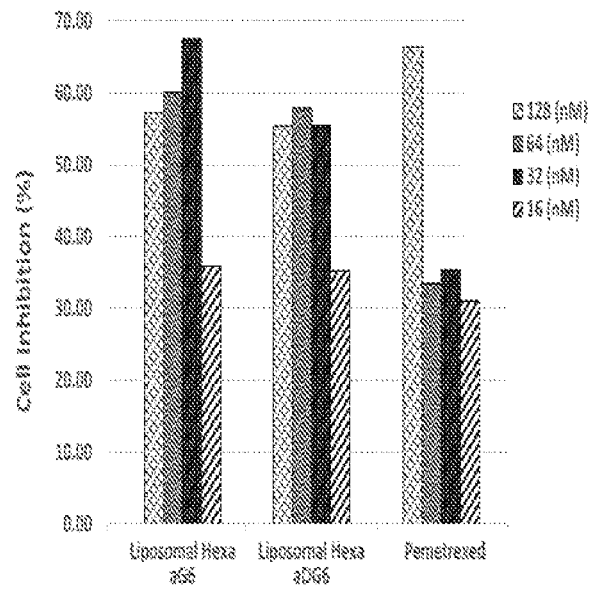

Cancer cell viability studies comparing the liposomal alpha pemetrexed hexaglutamate derivatives (liposomal L alphaG6/Lps Hexa aG6 and liposomal D alphaG6/Lps Hexa aDG6) and pemetrexed for cytotoxic activity on representative cell lines in breast, lung and ovarian cancer are shown in FIGS. 5-7. These data show that both liposomal alpha L pemetrexed hexaglutamate and liposomal alpha D pemetrexed hexaglutamate are more potent than pemetrexed. Further, as an indicator of efficacy, the results of the experiments on the same cell lines depicted at various dose levels ranging from 16 to 128 nM in FIGS. 8-10. As shown in these figures, at each of these dose ranges, liposomal alpha L pemetrexed hexaglutamate and liposomal alpha D pemetrexed hexaglutamate are superior to pemetrexed in terms of inhibiting cancer cells for the lung and breast cancer cell lines. In the ovarian cancer cell line, pemetrexed at the dose of 128 nM, appears to be equally effective as liposomal alpha pemetrexed hexaglutamate, whereas the liposomal alpha pemetrexed hexaglutamate at the dose of 32 nM and 64 nM has a better treatment effect than pemetrexed; at 16 nM the treatment effect is lower and similar in magnitude for liposomal alpha pemetrexed hexaglutamate and pemetrexed.

As shown in FIGS. 21A-F, each of liposomal pemetrexed alpha-L tetraglutamate (Liposomal aG4), liposomal pemetrexed alpha-L hexaglutamate (Liposomal aG6), liposomal pemetrexed alpha-L octaglutamate (Liposomal aG8), and liposomal pemetrexed alpha-L tridecaglutamate (Liposomal aG13), demonstrate a dose dependent effect in treating H2342 (NSCLC, adenocarcinoma subtype) cells, H292 (NSCLC, adenocarcinoma subtype) cells, HT-29 (colon cancer) cells, HCC1806 (triple negative breast cancer) cells, MCF7 (ER+ breast cancer) cells, and OAW28 (ovarian cancer) cells, respectively, over 48 hours.

Figure 11:
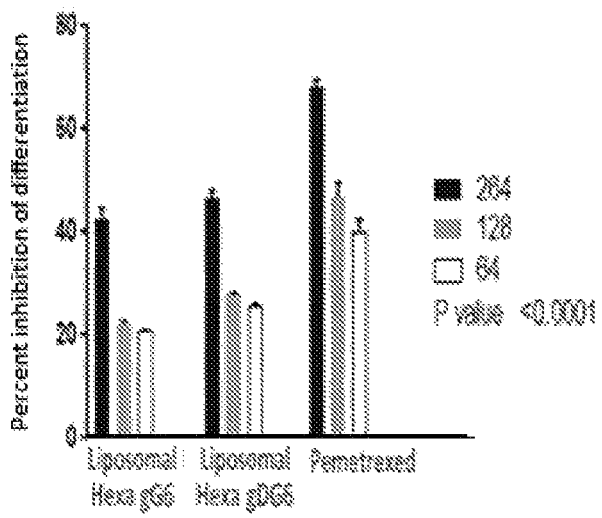
FIG. 11 shows the toxicity of liposomal pemetrexed alpha-L hexaglutamate (Liposomal aG6), liposomal pemetrexed alpha-D hexaglutamate (Liposomal aDG6), and pemetrexed on differentiating human neutrophils at 64 nM, 128 nM, and 264 nM. The figure demonstrates that liposomal pemetrexed aG6 is significantly less toxic to differentiating human neutrophils than pemetrexed.
Figure 12:
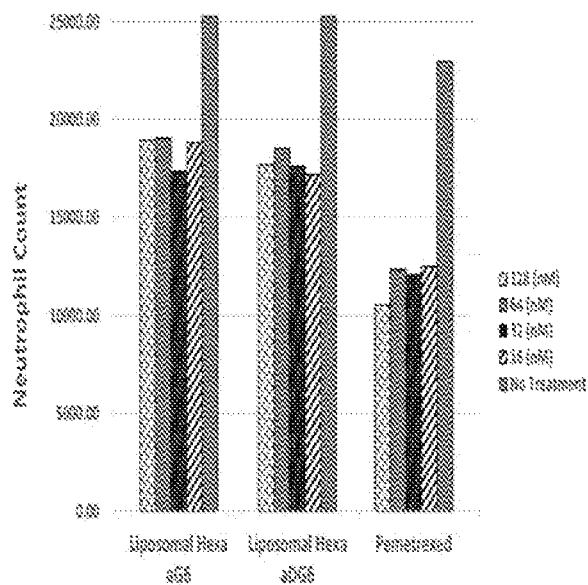
FIG. 12 shows the effect of liposomal pemetrexed alpha-L hexaglutamate (liposomal aG6), liposomal alpha-D hexaglutamate (liposomal aDG6), and pemetrexed on neutrophils (differentiated from CD34+ cells) following exposure of various dose levels ranging from 16 to 128 nM of the corresponding agent over 48 hours.

The major toxicities seen in patients treated with pemetrexed is bone marrow suppression which manifests as a decrease in blood counts including neutrophil counts (a type of white blood cells). There is also some adverse effect on the lining of the mouth and gut that manifests as diarrhea and mucositis, as well as an adverse effect on the liver in some instances. To assess the above-mentioned toxicities, treatment of the liposomal alpha pemetrexed hexaglutamate derivatives (L and D) and pemetrexed was measured at 48 hours on CD34+ cells that were differentiated into neutrophils, CCD841 colon epithelium cells and AML12 liver cells. As shown in FIG. 11, liposomal alpha pemetrexed hexaglutamate is significantly less toxic to differentiating human neutrophils in contrast to pemetrexed. This is also supported by neutrophil counts that are better preserved following treatment with the liposomal alpha L pemetrexed hexaglutamate or liposomal alpha D pemetrexed hexaglutamate compared to pemetrexed, at dose ranges from 16 nM to 128 nM (FIG. 12). Strikingly, there does not appear to be any toxicity to the liver cells following treatment with liposomal L alpha pemetrexed hexaglutamate or liposomal alpha D pemetrexed hexaglutamate at the dose levels studied (FIG. 13). In contrast, pemetrexed at all doses studied is leading to a reduction in the liver cell counts of approximately 40%. And finally, the same trend is seen following treatment of epithelial colon cells (FIG. 14). As shown in this figure, pemetrexed at all doses studied is leading to approximately a ≥50% decrease in the number of cells compared to approximately a 20% or less decrease after treatment with liposomal alpha L pemetrexed hexaglutamate and liposomal alpha D pemetrexed hexaglutamate.

Example 2: Polyglutamated Antifolate-Cisplatin Complexes (PGPD)

Methods

Folate Analogues also known as antifolate have been an important anticancer treatment for the last 70 years. Used in this setting this class of anti-cancer drugs interferes with various enzymes in the important folate metabolic pathway. This can result in impaired pyrimidine and purine (DNA and RNA) synthesis, impaired amino acid glycine and serine metabolism, impaired redox response and impaired methylation processes within the cell.

In in clinical practice, antifolates such as pemetrexed and methotrexate are often used in combination with platinum agents such as cisplatin and carboplatin. The combinations result in enhanced efficacy. In this context, we set out to coencapsulated the polyglutamates with platinum agents in a specific ratio to facilitate controlled delivery of a predetermined ratio of the two anticancer drugs namely a polyglutamated antifolate and a platinum analogue. We surprisingly discovered that long forms of polyglutamate antifolate (e.g., pentaglutamated antifolate) forms a complex with cisplatin that is stable at high pH, and that this complex disassociates into polyglutamate and cisplatin at low pH. Low pH is believed to be occur in many tumor cells and the tumor cell environment, particularly in hypoxic settings. Application of this discovery provides the ability to facilitate the delivery of combinations of αPPMX and therapeutic agents such as cisplatin to target cells such as tumor cells and to release the drugs from the complex in physiologically relevant low pH conditions.

Production of Polyglutamated Antifolates-DDAP (Cisplatin) Complexes (PGPD)

To produce (Polyglutamated antifolates-cisplatin DDAP Complex), alpha hexaglutamate (aG6) and Diammine dicarboxylic acid platinum (DDAP) was used. The process of complexation was dependent on the presence of Chlorinated platinum compound and pH conditions. The complexation was achieved by a nucleophilic attack on one or two carboxyl groups of glutamate by the platinate derivative. Briefly the complex was formed by the following procedure. First, the active compound DDAP was weighed and dissolved in 5% dextrose. After the DDAP dissolution step, aG6 was weighed out and added to the DDAP-Captisol® (solution and allowed to stir for 1 hour at 45-55° C. The pH of the solution was adjusted to 6.5-7.0 using 1N NaOH and the solution was stirred for 1-2 hour. The formation of complex was confirmed visually. However when the pH is adjusted to acidic pH of 3-5, the color reverted back to its original, indicating the decomplexatoin of the polyglutamated antifolate and cisplatin. FIG. 15 depicts a schematic providing possible scenarios explaining the observed pH dependent complex formation between the polyglutamated antifolate and cisplatin.

Complex formation was confirmed using HPLC which showed two distinct peaks that merge into 1 large peak at high pH of 6.5 to 7.5 and then reappear at low pH of 3-5. Repeating the experiment without Captisol showed that complex formation was independent of Captisol®

Production of Pentaglutamated Pemetrexed-DDAP Complex (PGPD) Liposomes

Briefly PGPD was encapsulated in liposomes by the following procedure. First, the lipid components of the liposome membrane was weighed out and combined as a concentrated solution in ethanol at a temperature of around 65° C. In this example, the lipids used were hydrogenated soy phosphatidylcholine, cholesterol, and DSPE-PEG-2000 (1,2-distearoyl-sn-glycero-3-phosphoethanolamine-N-[methoxy(polyethylene glycol)-2000]). The molar ratio of HSPC:Cholesterol:PEG-DSPE was approximately 3:2:0.15. Next, PGPD was prepared as described above. The PGPD drug solution was heated up to 65° C. The ethanolic lipid solution was injected into the PGPD solution using a small-bore needle. During this step the drug solution was well stirred using a magnetic stirrer. The mixing was performed at an elevated temperature (63° C.-72° C.) to ensure that the lipids were in the liquid crystalline state (as opposed to the gel state that they attain at temperatures below the lipid transition temperature Tm=51° C.-54° C.). As a result, the lipids were hydrated and formed multiple bilayer (multilamellar) vesicles (MLV) containing PGPD in the aqueous core.

Downsizing of MLV's Using Filter Extrusion

The MLVs were fragmented into unilamellar (single bilayer) vesicles of the desired size by high-pressure extrusion using two passes through stacked (track-etched polycarbonate) membranes. The stacked membranes have two layers with a pore size of 200 nm and six layers with a pore size of 100 nm. During extrusion, the temperature was maintained above the Tm to ensure plasticity of the lipid membranes. Because of the extrusion, large and heterogeneous in size and lamellarity MLVs turn into small, homogenous (100-120 nm) unilamellar vesicles (ULV) that sequester the drug in their interior. A Malvern Zetasizer Nano ZS instrument (Southborough, MA) with back scattering detector (90°) was used for measuring the hydrodynamic size (diameter) at 25° C. in a quartz micro cuvette. The samples were diluted 50-fold in formulation matrix before analysis.

Purification of Liposomes:

After the ULV's containing PGPD had been produced, the extra-liposomal PGPD was removed using columns for small volume or tangential flow diafiltration against a suitable buffer for large volume. Although many different buffers known in the art could have been used, in this example the buffer used was 5 mM HEPES, 145 mM Sodium Chloride, pH 6.7. Upon completion of purification, filter sterilization was performed using a 0.22-micron filter. The liposomes prepared according to the above procedures were determined to have a diameter of 116.6 nm, a PDI of 0.083, and a zeta potentials of −2.05 mV.

Example 3: Targeted Liposome Polyglutamated Pemetrexed Cell Delivery

Methods
Production of Targeted Gamma Hexaglutamated Pemetrexed (HGP) Liposomes

Gamma HGP (gG6) was encapsulated in liposomes and the liposomes were downsized and purified according to procedures essentially as set forth above in Example 1.

Antibody Conjugation

Activated liposomes were prepared by adding DSPE-PEG-maleimide to the lipid composition. The liposomes contain four different lipids: hydrogenated soy phosphatidylcholine (HSPC), cholesterol, 1,2-distearoyl-sn-glycero-3-phosphoethanolamine-N-[methoxy(polyethylene glycol)-2000](DSPE-PEG-2000), and 1,2-distearoyl-sn-glycero-3-phosphoethanolamine-N-[maleimide(polyethylene glycol)-2000](DSPE-PEG-maleimide), in ratios of 3:2:0.1125:0.0375.

Antibody thiolation was accomplished through use of Traut's reagent (2-iminothiolane) to attach a sulfhydryl group onto primary amines. Antibody was suspended in PBS at a concentration of 0.9-1.6 mg/ml. Traut's reagent (14 mM) was added to antibody solution at a final concentration of 1-5 mM and then removed through dialysis after one-hour incubation at room temperature. Thiolated antibody was added to activated liposome at a ratio of 60 g/mol phosphate lipids, and the reaction mixture was incubated for one hour at room temperature and over-night at 4 uL-cysteine was used to terminate the reaction and unconjugated antibody was removed through dialysis.

Exemplary direct and post insertion antibody-liposome conjugation methods are provided below.

Exemplary Antibody Conjugation Method 1: Direct Conjugation

Antibody or its fragments, such as Fab or scFv, can be conjugated directly onto thiol-reactive liposome. Thiol-reactive liposomes are prepared by adding DSPE-PEG-maleimide to the lipid composition. The liposomes contain four different lipids: hydrogenated soy phosphatidylcholine (HSPC), cholesterol, 1,2-distearoyl-sn-glycero-3-phosphoethan-olamine-N-[methoxy(polyethylene glycol)-2000] (DSPE-PEG-2000), and 1,2-distearoyl-sn-glycero-3-phosphoethanolamine-N-[maleimide (polyethylene glycol)-2000] (DSPE-PEG-maleimide), in ratios of 3:2:0.1125:0.0375.

Antibody (or its fragments, such as Fab or scFv) thiolation is accomplished through use of Traut's reagent (2-iminothiolane) to attach a sulfhydryl group onto primary amines. Antibody (or its fragment) is suspended in PBS at a concentration of 0.9-1.6 mg/ml. Traut's reagent (14 mM) is added to antibody (or its fragment) solution at a final concentration of 1-5 mM and then removed through dialysis after one-hour incubation at room temperature. Thiolated antibody (or its fragment) is added to thiol-reactive liposome at a ratio of 60 g/mol phosphate lipids, and the reaction mixture is incubated for one hour at room temperature and over-night at 4° C. L-cysteine is used to terminate the reaction and unconjugated antibody (or its fragment) is removed through dialysis.

Antibody or its fragments, such as Fab or scFv, which contains a cysteine residue at the C-terminal can be conjugated directly onto the liposome by incubating a reduced antibody (or its fragment) with thiol-reactive liposome. Antibody (or its fragment) with a cysteine tail is dissolved and reduced by a 10-20 mM reducing reagent (such as 2-mercaptoethylamine, cysteine, or dithioerythritol) at pH <7. The excess reducing reagent is removed thoroughly by size exclusion chromatography or dialysis. The purified and reduced antibody (or its fragment) can be directly conjugated to the thiol-reactive liposome.

Exemplary Antibody Conjugation Method 2: Post Insertion

Antibody or its fragments, such as Fab or scFv, which contains a cysteine residue at the C-terminal can be conjugated and incorporated into the liposome through a "post insertion" method. Micelles of thiol-reactive lipopolymer (such as DSPE-PEG-maleimide) is prepared by dissolving in an aqueous solution at 10 mg/ml. Antibody (or its fragment) with a cysteine tail is dissolved and reduced by a 10-20 mM reducing reagent (such as 2-mercaptoethylamine, cysteine, or dithioerythritol) at pH <7. The excess reducing reagent is removed thoroughly by size exclusion chromatography or dialysis. The purified and reduced antibody (or its fragment) is then incubated with the micelles of thiol-reactive lipopolymers at a molar ratio of 1:4. At the end of the reaction, the excess maleimide groups are quenched by a small amount of cysteine (1 mM) or mercaptoethanol. Unconjugated antibody (or its fragment) is removed by size exclusion chromatography. Purified conjugated micelles is then incubated with liposome at 37° C. or elevated temperature.

Physical Characteristics of the Nanoparticles

|  | Starting con. | Encapsulation efficiency | Final con. | Drug/Lipid Ratio | Diameter | PDI | Zeta potential |
|---|---|---|---|---|---|---|---|
| Lps gG6 | 20 mg/ml | 10.60% | 1.39 mg/ml | 35-50 g/mM lipids | 114.9 nm | 0.035 | −1.76 mV |

Dose Response Study of HGP (Pentaglutamated Pemetrexed) and Liposomes.

Cell viability was determined by CellTiter-Glo® (CTG) luminescent cell viability assay on Day 3 (48 hour) and Day 4 (72 hour). This assay determines the number of viable cells in culture based on quantifying ATP that was present within, which in turn signals the presence of metabolically active cells. The CTG assay uses luciferase as a readout. To assess cell viability Dose response inhibition of pemetrexed, HGP and liposomes on different cancer cell growth were investigated using CellTiter-Glo® luminescent cell viability assay. Human cancer cells were harvested, counted and plated at a same cell density on Day 0. A series of 8 dilutions of each test article were added to the cells on Day 1. Dose response curve were generated and fit using GraphPad Prism and IC50 of each test article were calculated. A lower the IC50 is, the more potent the test article was in term of cancer cell growth inhibition.

Cells were seeded into 96-well plate at a cell density of $5 \times 10^4$ cells per well in 100 µl of fresh media on Day 0. Eight serial 2-fold dilutions of each test article in culture medium were generated and added to cells in triplicate on Day 1. In addition, three wells of cells were treated with vehicle (HBS for free drug or empty liposome for liposomal HGP) alone as a control.

On Days 3 and 4, 100 µl of CellTiterGlo® Reagent were added to each well and incubated at room temperature for 15 minutes. Luciferase luminescence were recorded for each well. In addition, 8 serial 2-fold dilutions of the vehicle (HBS or empty liposome) in culture medium were added into empty wells and included in the assay to generate the background luminescence signals. Luciferase signals were normalized by subtracting the background luminescence signal out of the read-outs respectively.

Human Normal Primary Bone Marrow CD34+ Cells were obtained from ATCC. (ATCC Catalog Number PCS-800-012). Cells were thawed at 37° C. for 1 minute and then placed on ice. The cells were then resuspended in StemSpan SFEM (Stem Cell Tech Catalog Number 9650) plus 10% heat inactivated fetal bovine serum (Corning 35-015-CV). The cells were plated into 96 well culture plates at a density of $2.5 \times 10^4$ cells/well. The following day, live cells were collected via centrifugation and resuspended in neutrophil growth media (StemSpan SFEM plus 10% Heat Inactivated fetal bovine serum plus 100 ng/ml human stem cell factor (Sigma Catalog Number H8416), 20 ng/ml human granulocyte colony-stimulation factor (Sigma Catalog Number H5541), and 10 ng/ml human recombinant IL3 (Sigma SRP3090) at a density of $2.5 \times 10^4$ cells/well. Cells were incubated at 37° C. for 10 days. Fresh media was added every two days. Mature neutrophils were then collected and plated in 96 well plates at a density of $1 \times 10^4$ cells/well and incubated at 37° C. overnight. The next day, test article or vehicle was resuspended in neutrophil growth media and added to the plates. The cells were then incubated for either 48 hours or 72 hours at 37° C. and then assayed at each time point using the Cell Titer Glo Assay (Promega Catalog #G7572).

Methodologies used for cell line AML12 (non-cancerous liver cells) and CCD841 (non-cancerous colon epithelial cells) are similar to the methods used for cancer cells.

Results

The dose response relationship of free pemetrexed gamma hexaglutamate (gG6), (non-targeted) liposomal gamma hexaglutamate (liposomal gG6), pemetrexed and folate receptor alpha targeting antibody (FR1Ab) liposomal pemetrexed gamma hexaglutamate (liposomal gG6-FR1Ab), in the NCI H2342 non-small cell lung cancer (NSCLC), adenocarcinoma subtype is shown in FIG. 3. The output is percentage of viable cells after 48 hours of treatment as measured by luciferase luminescence. As shown in this FIG. 3, the free pemetrexed gG6 appears to be the least potent as measured by IC50. Both the liposomal pemetrexed gG6 and the liposomal pemetrexed gG6-FR1Ab are 7-fold and 40-fold more potent, respectively, than free pemetrexed.

Similar data is shown for the HT-29 colon cancer cell line in FIG. 4 that depict cell viability expressed as a percentage. As shown in this figure, free pemetrexed gG6 appears to be the least potent. In this instance, the liposomal pemetrexed gG6 is twice as potent as pemetrexed and the liposomal pemetrexed gG6-FR1Ab is 5-fold more potent than free pemetrexed.

Example 4: In Vivo Studies

Methods
Safety Studies in Mice

Because some of the major toxicities associated with a pemetrexed based treatment are hematologic and hepatic, it is important to evaluate the effect of Liposomal alpha G6 (Lp-aG6) in an in-vivo (murine) model and compare the changes in hematologic and the liver serum chemistry panel following treatment. To obtain this data an initial dose ranging study was conducted using healthy female BALB/c mice (6-8 weeks old) which were purchased from The Jackson Laboratory (Bar Harbor, ME). Prior to the study, animals were weighed, randomized by weight, observed for clinical abnormalities, and distributed into groups (5 mice per group). Doses from 10 mg/kg up to 200 mg/kg were investigated to identify a tolerable dose in mice. Treatments were administrated intravenously once a week for four weeks. Body weight and detailed clinical observation were recorded daily. At the end of study, Day 28, mice were euthanized, and blood and tissue were harvested from untreated Control mice and for the mice treated with Liposomal aG6 40 mg/kg and Liposomal aG6 80 mg/kg. Whole blood was collected into K2-EDTA anticoagulant tubes for comprehensive complete blood count (CBC) and serum was isolated for comprehensive chemistry and was sent to IDEXX (Westbrook, ME) on the day of collection.

Results

In general, treatment with once weekly liposomal aG6 at two dose levels of 40 mg/kg and 80 mg/kg for 4 weeks was well tolerated and there were no major differences in weight compared to untreated controls. To assess some of the effects on hematologic parameters, white blood cell (WBC) counts, neutrophil counts as well as platelet counts were measured after treatment with liposomal aG6 at two dose levels of 40 mg/kg and 80 mg/kg both given once weekly for 4 weeks. As can be seen in FIG. 16, there were no appreciable decreases in mean neutrophil, mean white blood cell and mean platelet counts, after four weeks of treatment with Liposomal aG6 in treated animals compared to untreated control animals. Hemoglobin and reticulocyte indices were measured to assess the impact on red blood cell. As shown in FIG. 17, there was a minimal decrease in mean hemoglobin concentrations at the higher dose level. In parallel there is a slight increase in mean reticulocytosis indices which suggests a bone marrow's response to treatment by increasing red blood cell production. Altogether this effect seems minor as the mice hemoglobin levels are maintained after 4 weeks of treatment. Taken together these data suggest that at these dose levels, 40 mg/kg and 80 mg/kg once-weekly, there is little impact on the bone marrow and related hematologic indices.

Another concern with pemetrexed is hepatic toxicity that has been observed in some patients treated with pemetrexed based therapy. To assess hepatic well being in mice serum chemistries including serum aspartate transaminase (AST) and serum alanine transaminase (ALT) along with serum albumin were measured. As shown in FIG. 18, there were no appreciable increases in liver transaminases mean AST and mean ALT levels at 4 weeks following treatment with Liposomal aG6 at the two dose levels of 40 mg/kg and 80 mg/kg both given once weekly for 4 weeks when compared to untreated controls. There was no change in mean albumin levels either. Taken together these data suggest a favorable safety profile for Liposomal aG6.

Pilot Efficacy Study in Mice Xenografts

To assess whether there was any tumor control following treatment with liposomal alpha G6 (Lp-aG6) the pilot study was conducted. In this study immunodeficient female Nude mice (Nu/J; 6-8 weeks old) were purchased from The Jackson Laboratory (Bar Harbor, ME). NCI-H292 (Non-Small Cell Lung Cancer) cells were cultured in RPMI media supplemented with 10% Fetal Bovine Serum in a 37° C., 5% $CO_2$ incubator. $1\times10^6$ cells were inoculated subcutaneously into the dorsal hind flank of each mouse. Tumor volume and body weight were monitored twice every week. Tumor-bearing mice were randomized by tumor volume on Day 0 and distributed into groups (5 mice per group): Control, pemetrexed, and Liposomal aG6. Pemetrexed was given intravenously at 167 mg/kg once every three weeks. This murine dose of 167 mg/kg every three weeks is equivalent to the FDA/EMA approved human dose and schedule of 500 mg/m$^2$ every three weeks. Liposomal aG6 was dosed intravenously at 80 mg/kg once a week for four weeks. Tumor size was measured with a caliper and tumor burden is calculated using the following equations: tumor volume=0.5×(tumor length)×(tumor width)$^2$; Relative tumor volume=(tumor volume/tumor volume on Day 0)×100%. The preliminary data for this study are shown in FIG. 19. In this figure, relative tumor volume is displayed following treatment with Liposomal aG6 and pemetrexed. As can be seen from these preliminary data, liposomal aG6 provides better tumor control when compared to pemetrexed.

In a parallel study, the survival of mice (10) dosed intravenously with 90 mg/kg Liposomal aG6 once a week for four weeks (90 mg/kg intravenously one a week for 6 weeks), mice (10) dosed with pemetrexed (167 mg/kg intravenously every three weeks for 6 weeks) was studied in the NSCLC (H292) xenograft model. The results of this study are presented in FIG. 20 and the table provide below. As indicated in the table presented below, the median survival following treatment with Liposomal aG6 was longer than that following treatment with pemetrexed. Also, 50% of the mice treated with Liposomal aG6 were alive at 60 days post dosing, whereas none of mice treated with pemetrexed survived to 60 days.

|  | Median Survival (days) | 60 Day Survival |
| --- | --- | --- |
| Control | 28.5 | 0% |
| Pemetrexed | 39.0 | 0% |
| Liposomal aG6 | 58.5 | 50% |

Further Embodiments

In a non-limiting embodiment, of this disclosure, there is provided a composition comprising alpha polyglutamated pemetrexed.

In the composition of the immediately preceding paragraph, the composition may comprise pentaglutamated or hexaglutamated pemetrexed.

In the composition of any of the preceding two paragraphs, the composition may comprise alpha polyglutamated pemetrexed which may include pentaglutamated or hexaglutamated pemetrexed.

A non-limiting example liposomal alpha polyglutamated pemetrexed (L-αPPMX) composition may comprise a composition of any of the preceding three paragraphs and the liposome may be optionally pegylated (PL-αPPMX).

In the L-αPPMX or PL-αPPMX composition of the immediately preceding paragraph, the alpha polyglutamated pemetrexed may include pentaglutamated or hexaglutamated pemetrexed.

In the L-αPPMX or PL-αPPMX composition of any of the preceding two paragraphs, the liposome may be anionic or neutral.

In the L-αPPMX or PL-αPPMX composition of any of the preceding three paragraphs, a targeting moiety may be attached to one or both of a PEG and the exterior of the liposome, and the targeting moiety may have a specific affinity for a surface antigen on a target cell of interest (TL-αPPMX or TPL-αPPMX).

In the L-αPPMX or PL-αPPMX composition of any of the preceding four paragraphs, a targeting moiety may be attached to one or both of a PEG and the exterior of the liposome and may be a polypeptide.

In the L-αPPMX or PL-αPPMX composition of any of the preceding five paragraphs, a targeting moiety may be attached to one or both a PEG and the exterior of the liposome and may be an antibody or a fragment of an antibody.

In the L-αPPMX or PL-αPPMX composition of any of the preceding six paragraphs, one or more of an immunostimulatory agent, a detectable marker and a maleimide may be disposed on at least one of a PEG and the exterior of the liposome.

In the L-αPPMX or PL-αPPMX composition of any of the preceding seven paragraphs, a polypeptide may bind an antigen with an equilibrium dissociation constant (Kd) in a range of $0.5\times10^{-10}$ to $10\times10^{-6}$ as determined using BIACORE® analysis.

In the L-αPPMX or PL-αPPMX composition of any of the preceding eight paragraphs, a polypeptide may specifically bind one or more folate receptors selected from the group consisting of: folate receptor alpha (FR-α), folate receptor beta (FR-β), and folate receptor delta (FR-δ).

A non-limiting exemplary method of killing a hyperproliferative cell that includes contacting a hyperproliferative cell with a liposomal alpha polyglutamated pemetrexed composition of any of the preceding nine paragraphs.

In the method of the immediately preceding paragraph, the hyperproliferative cell is a cancer cell.

A non-limiting example method for treating cancer comprises administering an effective amount of the alpha polyglutamated pemetrexed composition of any of preceding paragraphs from preceding paragraph eleven to preceding paragraph three, to a subject having or at risk of having cancer.

In the method of the immediately preceding paragraph, the cancer may be one or more selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy.

A non-limiting example maintenance therapy for subjects that are undergoing or have undergone cancer therapy includes administering an effective amount of the alpha polyglutamated pemetrexed composition of any of preceding paragraphs from preceding paragraph thirteen to preceding paragraph five, to a subject that is undergoing or has undergone cancer therapy.

A non-limiting example pharmaceutical composition may include any alpha polyglutamated pemetrexed composition of Section IV.

A non-limiting example method for treating a disorder of the immune system may include administering an effective amount of the of the alpha polyglutamated pemetrexed composition of any of preceding paragraphs from preceding paragraph fourteen to preceding paragraph six, to a subject having or at risk of having a disorder of the immune system.

A non-limiting example method for treating an infectious may include comprises administering an effective amount of the of the alpha polyglutamated pemetrexed composition of any of preceding paragraphs from preceding paragraph fifteen to preceding paragraph seven, to a subject having or at risk of having an infectious disease.

A non-limiting example method of delivering alpha polyglutamated pemetrexed to a tumor expressing a folate receptor on its surface may include administering a polyglutamated pemetrexed composition of any of preceding paragraphs from preceding paragraph sixteen to preceding paragraph eight, to a subject having the tumor in an amount to deliver a therapeutically effective dose of the alpha polyglutamated pemetrexed to the tumor.

A non-limiting example method of preparing a liposomal alpha polyglutamated pemetrexed composition which includes alpha polyglutamated pemetrexed composition of any of preceding paragraphs from preceding paragraph seventeen to preceding paragraph nine includes forming a mixture comprising: liposomal components; alpha polyglutamated pemetrexed in solution; homogenizing the mixture to form liposomes in the solution; and processing the mixture to form liposomes containing the polyglutamated pemetrexed.

A non-limiting example pharmaceutical composition includes an alpha polyglutamated pemetrexed composition of any of preceding paragraphs from preceding paragraph eighteen to preceding paragraph ten.

Although the disclosure has been described with reference to various some embodiments, it should be understood that various modifications can be made without departing from the spirit of the disclosure. Accordingly, the scope of the disclosure should be determined with reference to the appended claims, along with the full scope of equivalents to which such claims are entitled. Throughout this application, various publications are referenced by author name and date, or by Patent No. or Patent Publication No. The disclosure of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Various new chemical entities, methods and equipment for making these chemical entities are set forth below in the appended claims.

It is to be appreciated that the Detailed Description section, and not the Summary and Abstract sections, is intended to be used to interpret the claims. The Summary and Abstract sections may set forth one or more but not all exemplary embodiments, of the present invention as contemplated by the inventor(s), and thus, are not intended to limit the present invention and the appended claims in any way.

The disclosure of each of U.S. Appl. No. 62/627,703, filed Feb. 7, 2018; U.S. Appl. No. 62/627,714, filed Feb. 7, 2018; U.S. Appl. No. 62/627,716, filed Feb. 7, 2018; U.S. Appl. No. 62/627,731, filed Feb. 7, 2018; U.S. Appl. No. 62/627,741, filed Feb. 7, 2018; U.S. Appl. No. 62/630,629, filed Feb. 14, 2018; U.S. Appl. No. 62/630,634, filed Feb. 14, 2018; U.S. Appl. No. 62/630,637, filed Feb. 14, 2018; U.S. Appl. No. 62/630,671, filed Feb. 14, 2018; U.S. Appl. No. 62/630,713, filed Feb. 14, 2018; U.S. Appl. No. 62/630,728, filed Feb. 14, 2018; U.S. Appl. No. 62/630,744, filed Feb. 14, 2018; U.S. Appl. No. 62/630,820, filed Feb. 14, 2018; U.S. Appl. No. 62/630,825, filed Feb. 14, 2018; U.S. Appl. No. 62/636,294, filed Feb. 28, 2018; U.S. Appl. No. 62/662,374, filed Apr. 25, 2018; U.S. Appl. No. 62/702,732, filed Jul. 24, 2018; U.S. Appl. No. 62/702,561, filed Jul. 24, 2018; U.S. Appl. No. 62/764,943, filed Aug. 17, 2018; and U.S. Appl. No. 62/764,955.

What is claimed is:

1. A liposomal composition comprising a polyglutamated pemetrexed encapsulated by a liposome, wherein the polyglutamated pemetrexed comprises 4, 5, or 6 glutamyl groups in the D-form that have an alpha carboxyl group linkage.

2. The liposomal composition of claim 1, wherein the liposome comprises 4 glutamyl groups in the D-form that have an alpha carboxyl group linkage.

3. The liposomal composition of claim 1, wherein the liposome comprises 5 glutamyl groups in the D-form that have an alpha carboxyl group linkage.

4. The liposomal composition of claim 1, wherein the liposome comprises 6 glutamyl groups in the D-form that have an alpha carboxyl group linkage.

5. The liposomal composition of claim 1, wherein the liposome is pegylated.

6. The composition of claim 1, wherein the liposome is not pegylated.

7. The liposomal composition of claim 1, wherein the liposome has a diameter in the range of 20 nm to 200 nm or 80 nm to 120 nm.

8. The liposomal composition of claim 1, wherein the liposome comprises at least one steric stabilizer selected from: polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L amino-acid-based polymer; oligoglycerol, copolymer containing polyethylene glycol and polypropylene oxide; Poloxamer 188; and polyvinyl alcohol.

9. The liposomal composition of claim 8, wherein the steric stabilizer is PEG and the PEG has a number average molecular weight (Mn) of 200 to 5000 daltons.

10. The liposomal composition of claim 1, wherein the liposome is anionic or neutral.

11. The liposomal composition of claim 1, wherein the liposome has a zeta potential that is between 0 to −150 mV or between −30 to −50 mV.

12. The liposomal composition of claim 1, wherein the liposome is cationic.

13. The liposomal composition of claim 1, wherein the liposome has an interior space comprising the polyglutamated pemetrexed and an aqueous pharmaceutically acceptable carrier comprising:
   a tonicity agent at a concentration of greater than 1%;
   1% to 50% trehalose;
   1% to 50% dextrose;
   5% dextrose suspended in an HEPES buffered solution; or
   a total concentration of sodium acetate and calcium acetate of between 50 mM to 500 mM.

14. The liposomal composition of claim 13, wherein the interior space of the liposome has a pH of 5-8.

15. The liposomal composition of claim 1, wherein the liposome comprises 10 to 500,000 molecules of the polyglutamated pemetrexed.

16. The liposomal composition of claim 1, which further comprises a targeting moiety and wherein the targeting moiety has a specific affinity for a surface antigen on a target cell of interest.

17. The liposomal composition of claim 16, wherein the targeting moiety is attached to one or both of a PEG and the exterior of the liposome, optionally wherein targeting moiety is attached to one or both of the PEG and the exterior of the liposome by a covalent bond.

18. The liposomal composition of claim 16, wherein the targeting moiety is a polypeptide, an antibody or an antigen binding fragment of an antibody.

19. The liposomal composition of claim 16, wherein the targeting moiety binds the surface antigen with an equilibrium dissociation constant (Kd) in a range of $0.5 \times 10^{-10}$ to $10 \times 10^{-6}$ as determined using surface plasmon analysis.

20. The liposomal composition of claim 16, wherein the targeting moiety specifically binds one or more folate receptors selected from: folate receptor alpha (FR-α), folate receptor beta (FR-β), and folate receptor delta (FR-δ).

21. The liposomal composition of claim 16, wherein the targeting moiety comprises one or more selected from: an antibody, a humanized antibody, an antigen binding fragment of an antibody, a single chain antibody, a single-domain antibody, a bi-specific antibody, a synthetic antibody, a pegylated antibody, and a multimeric antibody.

22. The liposomal composition of claim 17, wherein the liposome is pegylated and comprises from 1 to 1000 or 30-200 targeting moieties.

23. The liposomal composition of claim 5, further comprising one or more of an immunostimulatory agent, a detectable marker and a maleimide, wherein the immunostimulatory agent, the detectable marker or the maleimide is attached to said PEG or the exterior of the liposome.

24. The liposomal composition of claim 23, wherein the immunostimulatory agent is at least one selected from: a fluorescein; a fluorescein isothiocyanate (FITC); a DNP; a beta glucan; a beta-1,3-glucan; a beta-1,6-glucan; a resolvin (e.g., a Resolvin D such as Dn-6DPA or Dn-3DPA, a Resolvin E, or a T series resolvin); and a Toll-like receptor (TLR) modulating agent.

25. The liposomal composition of claim 1, which further comprises at least one cryoprotectant selected from mannitol; trehalose; sorbitol; and sucrose.

26. The liposomal composition of claim 1, which further comprises carboplatin or pembroluzumab.

27. A pharmaceutical composition comprising the liposomal composition of claim 1.

28. The liposomal composition of claim 1, wherein the liposome is pegylated, has a diameter in the range of 20 nm to 200 nm, and a zeta potential between 0 to −150 mV.

29. The liposomal composition of claim 2, wherein the liposome is pegylated, has a diameter in the range of 20 nm to 200 nm, and a zeta potential between 0 to −150 mV.

30. The liposomal composition of claim 3, wherein the liposome is pegylated, has a diameter in the range of 20 nm to 200 nm, and a zeta potential between 0 to −150 mV.

31. The liposomal composition of claim 4, wherein the liposome is pegylated, has a diameter in the range of 20 nm to 200 nm, and a zeta potential between 0 to −150 mV.

32. A pharmaceutical composition comprising the liposomal composition of claim 2.

33. A pharmaceutical composition comprising the liposomal composition of claim 3.

34. A pharmaceutical composition comprising the liposomal composition of claim 4.

35. A pharmaceutical composition comprising the liposomal composition of claim 28.

36. A pharmaceutical composition comprising the liposomal composition of claim 29.

37. A pharmaceutical composition comprising the liposomal composition of claim 30.

38. A pharmaceutical composition comprising the liposomal composition of claim 31.

* * * * *